US007250171B1

(12) United States Patent
Tao et al.

(10) Patent No.: US 7,250,171 B1
(45) Date of Patent: *Jul. 31, 2007

(54) CONSTRUCTION AND USE OF RECOMBINANT PARAINFLUENZA VIRUSES EXPRESSING A CHIMERIC GLYCOPROTEIN

(75) Inventors: Tao Tao, Bethesda, MD (US); Mario H. Skiadopoulos, Potomac, MD (US); Peter L. Collins, Rockville, MD (US); Brian R. Murphy, Bethesda, MD (US)

(73) Assignee: United States of America as Represented by the Dept. of Health & Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/459,062

(22) Filed: Dec. 10, 1999

Related U.S. Application Data

(63) Continuation-in-part of application No. 09/083,793, filed on May 22, 1998.

(60) Provisional application No. 60/047,575, filed on May 23, 1997, provisional application No. 60/059,385, filed on Sep. 19, 1997.

(51) Int. Cl.
*A61K 31/155* (2006.01)
*C12N 15/00* (2006.01)

(52) U.S. Cl. .............................. 424/211.1; 424/184.1; 424/204.1; 424/205.1; 424/212.1; 536/23.1; 435/320.1

(58) Field of Classification Search ............. 424/184.1, 424/204.1, 205.1, 211.1, 212.1, 93.2; 536/23.1; 514/44; 435/320.1
See application file for complete search history.

(56) References Cited

U.S. PATENT DOCUMENTS

| 5,716,821 A | 2/1998 | Wertz et al. | 435/235.1 |
| 5,789,229 A | 8/1998 | Wertz et al. | 435/235.1 |
| 5,869,036 A | 2/1999 | Belshe et al. | 424/93.2 |
| 6,033,886 A | 3/2000 | Conzelmann | 435/172.3 |
| 6,264,957 B1 * | 7/2001 | Collins et al. | 424/211.1 |

FOREIGN PATENT DOCUMENTS

| EP | 0 440 219 A1 | 8/1991 |
| EP | 0 702 085 A1 | 3/1996 |
| WO | WO 93/14207 | 7/1993 |
| WO | WO 97/06270 | 2/1997 |
| WO | WO 97/11093 | 3/1997 |
| WO | WO 97/20468 | 6/1997 |
| WO | WO 98/02530 | 1/1998 |
| WO | WO 98/43668 | 10/1998 |
| WO | WO 98/53078 | 11/1998 |
| WO | WO 99/02657 | 1/1999 |
| WO | WO 99/15631 | 4/1999 |

OTHER PUBLICATIONS

Baron et al., "Rescue of Rinderpest Virus from Cloned cDNA," *J. Virol.* 71:1265-1271, 1997.

Belshe et al., "Cold Adaptation of Parainfluenza Virus Type 3: Induction of Three Phenotypic Markers," *J. Med. Virol.* 10:235-42, 1982.

Blumberg et al., "Measles Virus L Protein Evidences Elements of Ancestral RNA Polymerase,"*Virology* 164:487-497, 1988.

Buchholz et al., "Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Promoter," *J. Virol.* 73:251-259, 1999.

Bukreyev, et al., "Recovery of Infectious Respiratory Syncytial Virus Expressing an Additional, Foreign Gene," *J. Virol.* 70:6634-41, 1996.

Bukreyev, et al., "Interferon γ Expressed by a Recombinant Respiratory Syncytial Virus Attenuates Virus Replication in Mice Without Compromissing Immunogenicity," *Proc. Nat. Acad. Sci. USA* 96:2367-2372, 1999.

Cadd et al., "The Sendai Paramyxiovirus Accessory C Proteins Inhibit Viral Genome Amplification in Promoter-Specific Fashion," *J. Virol.* 70:5067-74, 1996.

Collins, et al., "Production of Infectious Human Respiratory Syncytial Virus from Cloned cDNA Confirms an Essential Role of the Transcription Elongation Factor from the 5' Proximal Open Reading Frame of the M2 mRNA in Gene Expression and Provides a Capability for Vaccine Development," *Proc Nat. Acad. Sci. USA* 92:11563-11567, 1995.

(Continued)

*Primary Examiner*—Stacy B. Chen
(74) *Attorney, Agent, or Firm*—Birch Stewart Kolasch & Birch, LLP

(57) ABSTRACT

Chimeric parainfluenza viruses (PIVs) are provided that incorporate a PIV vector genome or antigenome modified to encode a chimeric glycoprotein incorporating one or more heterologous antigenic domains, fragments, or epitopes of a second, antigenically distinct HPIV. These chimeric viruses are infectious and attenuated in humans and other mammals and are useful in vaccine formulations for eliciting an immune responses against one or more PIVs, and, optionally against respiratory syncytial virus (RSV). Also provided are isolated polynucleotide molecules and vectors incorporating a chimeric PIV genome or antigenome which includes a HPIV vector genome or antigenome combined or integrated with one or more heterologous genome segment(s) encoding one or more antigenic determinant(s) of a heterologous PIV to encode a chimeric glycoprotein. In preferred aspects of the invention, the chimeric virus is attenuated for use as a vaccine agent by additional mutations or nucleotide modifications introduced into the chimeric genome or antigenome.

70 Claims, 12 Drawing Sheets

OTHER PUBLICATIONS

Collins et al., "Parainfluenza Viruses", in *Fields Virology*, B. N. Fields (Knipe et al., eds.), 3rd ed., vol. 1, p. 1205-1243, Lippincott-Raven Publishers, Philadelphia, 1996.

Conzelmann et al., "Rescue of Synthetic Genomic RNA Analogs of Rabies Virus by Plasmid-Encoded Proteins," *J. Virol.* 68:713-719, 1994.

Conzelmann, "Genetic Manipulation on Non-Segmented Negative-strand RNA Viruses," *J. Gen. Virol.* 77:381-389, 1996.

Curran, et al., "Sendai Virus P Gene Produces Multiple Proteins from Overlapping Open Reading Frames," *Enzyme* 44:244-249, 1990.

Curran, et al., "The Sendai Virus Nonstructural C Proteins Specifically Inhibit Viral mRNA Synthesis," *Virology* 189:647-656, 1992.

Delenda, et al., "Normal Cellular Replication of Sendai Virus Without the *trans*-Frame, Nonstructural V Protein," *Virology* 228:55-62, 1997.

Delenda et al., "Sendai Viruses with Altered P, V, and W Protein Expression," *Virology* 242:327-337, 1998.

Dimock, et al., "Rescue of Synthetic Analogs of Genomic RNA and Replicative-Intermediate RNA of Human Parainfluenza Virus Type 3," *J. Virol.* 67: 2772-2778, 1993.

Durbin et al., "Minimum Protein Requirements for Transcription and RNA Replication of a Minigenome of Human Parainfluenza Virus Type 3 and Evaluation of the Rule of Six," *Virology* 234:74-83, 1997.

Durbin et al., "Recovery of Infectious Human Parainfluenza Virus Type 3 from cDNA," *Virology* 235:323-332, 1997.

Finke et al. "Ambisense Gene Expression for Recombinant Rabies Virus: Random Packaging of Positive- and Negative-Strand Ribonucleoprotein Complexes into Rabies Virions," *J. Virol.* 71:7281-7288, 1997.

Galinski et al., "Molecular Cloning and Sequence Analysis of the Human Parainfluenza 3 Virus mRNA Encoding the P and C Proteins," *Virology* 155:46-60, 1986.

Galinski et al., "Molecular Cloning and Sequence Analysis of the Human Parainfluenza 3 Virus Gene Encoding the L Protein," *Virology* 165:499-510, 1988.

Galinski et al., "RNA Editing in the Phosphoprotein Gene of the Human Parainfluenza Virus Type 3," *Virology* 186:543-550, 1992.

Garcin et al., "A Highly Recombinogenic System for the Recovery of Infectious Sendai Paramyxovirus from cDNA: Generation of a Novel Copy-back Nondefective Interfering Virus," *EMBO J.* 14:6087-6094, 1995.

Garcin et al., "A Point Mutation in the Sendai Virus Accessory C Proteins Attenuates Virulence for Mice, But Not Virus Growth in Cell Culture," *Virology* 238:424-431, 1997.

Grosfeld et al., "RNA Replication by Respiratory Syncytial Virus (RSV) Is Directed by the N, P, and L Proteins; Transcription Also Occurs under These Conditions but Requires RSV Superinfection for Efficient Synthesis of Full-Length mRNA," *J. Virol.* 69: 5677-5686, 1995.

Hall et al., "Cold-passaged Human Parainfluenza Type 3 Viruses Contain *ts* and Non-*ts* Mutations Leading to Attenuation in Rhesus Monkeys," *Virus Res.* 22:173-184, 1992.

Hasan et al., "Creation of an Infectious Recombinant Sendai Virus Expressing the Firefly Luciferase Gene from the 3' Proximal First Locus," *J. Gen. Virol.* 78:2813-20, 1997.

He et al., "Recovery of Infectious SV5 from Cloned DNA and Expression of a Foreign Gene," *Virology* 237:249-260, 1997.

Hoffman et al., "An Infectious Clone of Human Parainfluenza Virus Type 3," *J. Virol.* 71:4272-4277, 1997.

Itoh et al., "Isolation of an Avirulent Mutant of Sendai Virus with Two Amino Acid Mutations from a Highly Virulent Field Strain Through Adaption to LLC-MK$_2$ Cells," *J. Gen. Virol.* 78:3207-3215, 1997.

Jin et al., "Recombinant Human Respiratory Syncytial Virus (RSV) from cDNA and Construction of Subgroup A and B Chimeric RSV," *Virology* 251:206-214, 1998.

Johnson et al., "Specific Targeting to CD4+ Cells of Recombinant Vesicular Stomatitis Viruses Encoding Human Immunodeficiency Virus Envelope Proteins," *J. Virol.* 71:5060-5068, 1997.

Juhasz et al., "The Temperature-Sensitive (*ts*) Phenotype of a Cold-Passage (*cp*) Live Attenuated Respiratory Syncytial Virus Vaccine Candidate, Designated *cpts*530, Results from a Single Amino Acid Substitution in the L Protein," *J. Virol.* 71:5814-5819, 1997.

Kahn et al., "Recombinant Vesicular Stomatitis Virus Expressing Respiratory Syncytial Virus (RSV) Glycoproteins: RSV Fusion Protein Can Mediate Infection and Cell Fusion," *Virology* 254:81-91, 1999.

Karron et al., "A Live Attenuated Bovine Parainfluenza Virus Type 3 Vaccine is Safe, Infectious, Immunogenic, and Phenotypically Stable in Infants and Children," *J. Inf. Dis.* 171:1107-1114, 1995.

Karron et al., "A Live Human Parainfluenza Type 3 Virus Vaccine Is Attenuated and Immunogenic in Healthy Infants and Children," *J. Inf. Dis.* 172:1445-1450, 1995.

Kato et al., "Initiation of Sendai Virus Multiplication from Transfected cDNA or RNA with Negative or Positive Sense," *Genes to Cells* 1:569-579, 1996.

Kato et al., "The Paramyxovirus, Sendai Virus, V Protein Encodes a Luxury Function Required for Viral Pathogenesis," *EMBO. J.* 16:578-587, 1997.

Kato et al., "Importance of the Cysteine-Rich Carboxyl-Terminal Half of V Protein for Sendai Virus Pathogenesis," *J. Virol.* 71:7266-7272, 1997.

Kretzchmar et al., "Normal Replication of Vesicular Stomatitis Virus Without C Proteins," *Virology* 216:309-316, 1996.

Kretzschmar et al., "High-Efficiency Incorporation of Functional Influenza Virus Glycoproteins into Recombinant Vesicular Stomatitis Viruses," *J. Virol.* 71:5982-5989, 1997.

Kuo et al., "Effect of Mutations in the Gene-Start and Gene-End Sequence Motifs on Transcription of Monocistronic and Dicistronic Minigenomes of Respiratory Syncytial Virus," *J. Virol.* 70:6892-6901, 1996.

Kurotani et al., "Sendai Virus C Proteins are Categorically Nonessential Gene Products but Silencing Their Expression Severely Impairs Viral Replication and Pathogenesis," *Genes to Cells.* 3:111-124, 1998.

Latorre et al., "The Various Sendai Virus C Proteins Are Not Functionally Equivalent and Exert both Positive and Negative Effects on Viral FNA Accumulation During the Course of Infection," *J. Virol.* 72:5984-5993, 1998.

Lawson et al., "Recombinant Vesicular Stomatitis Viruses from DNA," *Proc. Natl. Acad. Sci. USA* 92:4477-4481, 1995.

Matsuoka et al., "The P Gene of Human Parainfluenza Virus Type 1 Encodes P and C Proteins but not a Cysteine-Rich V Protein," *J. Virol.* 65:3406-3410, 1991.

Mebatsion et al., "Highly Stable Expression of a Foreign Gene from Rabies Virus Vectors," *Proc. Natl. Acad. Sci. U S A* 93:7310-7314, 1996.

Moriya et al., "Large Quantity Production with Extreme Convenience of Human SDF-1α by a Sendai Virus Vector," *FEBS Lett.* 425:105-111, 1998.

Murphy et al., "Current Approaches to the Development of Vaccines Effective Against Parainfluenza and Respiratory Syncytial Viruses," *Virus Res* 11:1-15, 1988.

Murphy et al., "Enhanced Pulmonary Histopathology Is Observed In Cotton Rats Immunized With Formalin-Inactivated Respiratory Syncytial Virus (RSV) Or Purified F Glycoprotein And Challenged With RSV 3-6 Months After Immunization," *Vaccine* 8:497-502, 1990.

Palese et al., "Negative-Strand RNA Viruses: Genetic Engineering and Applications," *Proc. Natl. Acad. Sci. USA* 93:11354-11358, 1996.

Peeters et al., "Rescue of Newcastle Disease Virus from Cloned cDNA:Evidence that Cleavability of the Fusion Protein is a Major Determinant for Virulence," *J. Virol.* 73:5001-5009, 1999.

Pelet et al., "The P Gene of Bovine Parainfluenza Virus 3 Expresses all Three Reading Frames from a Single mRNA Editing Site," *EMBO J* 10:443-448, 1991.

Radecke et al., "Rescue of Measles Viruses from Cloned DNA," *EMBO J.* 14:5773-5784, 1995.

Ray et al., "Human Parainfluenza virus Induces a Type-Specific Protective Immune Response," *J. Infect. Dis.* 162:746, 1990.

Ray et al., "Temperature-Sensitive Phenotype of the Human Parainfluenza Virus Type 3 Candidate Vaccine Strain (cp45) Correlates with a Defect in the L Gene," *J. Virol.* 70:580-584, 1996.

Roberts et al., "Attenuated Vesicular Stomatitis Viruses as Vaccine Vectors," *J. Virol.* 73:3723-3732, 1999.

Roberts et al., "Vaccination with a Recombinant Vesicular Stomatitis Virus Expressing an Influenza Virus Hamagglutinin Provides Complete Protection from Influenza Virus Challenge," *J. Virol.* 72:4704-4711, 1998.

Roberts et al., "Recovery of Negative-Strand RNA Viruses from Plasmid DNAs: A Positive Approach Revitalizes a Negative Field," *Virology* 247:1-6, 1998.

Sakaguchi et al., "Expression of the HN, F, NP and M Proteins of Sendai Virus By Recombinant Vaccinia Viruses and Their Contribution to Protective Immunity Against Sendai Virus Infections in Mice," *J. Gen. Virol.* 74:479-484, 1993.

Sakai et al., "Accommodation Of Foreign Genes Into The Sendai Virus Genome: Sizes Of Inserted Genes And Viral Replication," *FEBS Letters* 456:221-226, 1999.

Sanchez et al., "Cloning and Gene Assignment of mRNAs of Human Parainfluenza Virus 3," *Virology* 147:177-186, 1985.

Schnell et al., "Infectious Rabies Viruses from Cloned cDNA," *EMBO J.* 13:4195-4203, 1994.

Schnell et al., "The Minimal Conserved Transcription Stop-Start Signal Promotes Stable Expression of a Foreign Gene in Vesicular Stomatitis Virus," *J. Virol.* 70:2318-2323, 1996.

Schell et al., "Foreign Glycoproteins Expressed from Recombinant Vesicular Stomatitis Viruses are Incorporated Efficiently into Virus Particles," *Proc. Natl. Acad. Sci. USA* 93:11359-11365, 1996.

Schnell et al., "Construction of a Novel Virus that Targets HIV-1-Infected Cells and Controls HIV-1 Infection," *Cell* 90:849-857, 1997.

Singh et al., "A Recombinant Measles Virus Expressing Biologically Active Human Interleukin-12," *J. Gen. Virol.* 80:101-106, 1999.

Singh et al., "A Recombinant Measles Virus expressing Hepatitis B Virus Surface Antigen Induces Humoral Immune Responses in Genetically Modified Mice," *J. Virol.* 73:4823-4828, 1999.

Skiadopoulos et al., "Three Amino Acid Substitutions in the L Protein of the Human Parainfluenza Virus Type 3 cp45 Live Attenuated Vaccine Candidate Contribute to Its Temperature-Sensitive and Attenuation Phenotypes," *J. Virol* 72:1762-1768, 1998.

Skiadopoulos et al., "Identification of Mutations Contributing to the Temperature-Sensitive, Cold-Adapted, and Attenuation Phenotypes of the Live-Attenuated Cold-Passage 45 (*cp*45) Human Parainfluenza Virus 3 Candidate Vaccine," *J. Virol.* 73:1374-1381, 1999.

Skiadopoulos et al., "Generation of Parainfluenza Virus Type 1 Vaccine Candidate by Replacing the HN and F Glycoproteins of the Live-Attenuated PIV3 *cp*45 Vaccine Virus with Their PIVI Counterparts," *Vaccine* 18:503-510, 1999.

Spielhofer et al., "Chimeric Measles Viruses with a Foreign Envelope," *J. Virol.* 72:2150-2159, 1998.

Spriggs et al., "Sequence Analysis of the P and C Protein Genes of Human Parainfluenza Virus Type 3: Patterns of Amino Acid Sequence Homology Among Paramyxovirus Proteins," *J. Gen. Virol.* 67:2705-2719, 1986.

Stokes et al., "The Complete Nucleotide Sequence of the JS Strain of Human Parainfluenza Virus Type 3: Comparison with the Wash/47885/57 Prototype Strain," *Virus Res.* 25:91-103, 1992.

Stokes et al., "The Complete Nucleotide Sequence of Two Cold-Adapted, Temperature-Sensitive Attenuated Mutant Vaccine Viruses (*cp*12 and *cp*45) Derived from the JS Strain and Human Parainfluenza Virus Type 3 (PIV3)," *Virus Res.* 30:43-52, 1993.

Tanabayashi, K. and Compans, R.W., "Functional Interaction of Paramyxovirus Glycoproteins: Identification of a Domain in Sendai Virus HN Which Promotes Cell Fusion," *J. Virol.* 70:6112-6118, 1996.

Tao et al., "Recovery of a Fully Viable Chimeric Human Parainfluenza Virus (PIV) Type 3 in Which the Hemagglutinin-Neuraminidase and Fusion Glycoproteins Have Been Replaced by Those of PIV Type 1," *J. Virol.* 72:2955-2961, 1998.

Tao et al., "A Live Attenuated Recombinant Chimeric Parainfluenza Virus (PIV) Candidate Vaccine Containing the Hemagglutinin-Neuraminidase and Fusion Glycoproteins of PIV1 and the Remaining Proteins from PIV3 Induces Resistance to PIV1 Even in Animals Immune to PIV3" *Vaccine* 17:1101-1108, 1999.

van Wyke Coelingh et al., "Antigenic Variation in the Hemagglutinin-Neuraminidase Protein of Human Parainfluenza Type 3 Virus," 143:569-582, 1985.

van Wyke Coelingh et al., "Antigenic and Structural Properties of the Hemagglutinin-Neuraminidase Glycoprotein of Human Parainfluenza Virus Type 3: Sequence Analysis of Variants Selected with Monoclonal Antibodies Which Inhibit Infectivity, Hemagglutination, and Neuraminidase Activities," *J. Virol.* 61:1473-1477, 1987.

Vidal et al., "Editing of the Sendai Virus P/C mRNA by G Insertion Occurs during mRNA Synthesis via a Virus-Encoded Activity," *J. Virol.* 64:239-246, 1990.

Wathen et al., "Characterization of a Novel Human Respiratory Syncytial Virus Chimeric FG Glycoprotein Expressed Using a Baculovirus Vector," *J. Gen. Virol.* 70:2625-2635, 1989.

Whelan et al., "Efficient Recovery Of Infectious Vesicular Stomatitis Virus Entirely From CDNA Clones," *Proc. Natl. Acad. Sci. USA* 92:8388-8392, 1995.

Whitehead et al., "A Single Nucleotide Substitution in the Transcription Start Signal of the M2 Gene of Respiratory Syncytial Virus Vaccine Candidate *cpts*248/404 is the Major Determinant of the Temperature-Sensitive and Attenuation Phenotypes," *Virology* 247:232-239, 1998a.

Whitehead et al., "Recombinant Respiratory Syncytial Virus (RSV) Bearing a Set of Mutations from cold-Passaged RSV is Attenuated in Chimpanzees," *J. Virol.* 72:4467-4471, 1998b.

Whitehead et al., "Recombinant Respiratory Syncytial Virus Bearing a Deletion of Either the NS2 or SH Gene is Attenuated in Chimpanzees," *J. Virol.* 73:3438-3442, 1999.

Yu et al., "Sendai Virus-Based Expression of HIV-1 gp120: Reinforcement by the V(-) Version," *Genes to Cells* 2:457-466, 1997.

Bailly et al., "A Recombinant Human Parainfluenza Virus Type 3 (PIV3) in Which the Nucleocapsid N Protein Has Been Replaced by That of Bovine PIV3 Is Attenuated in Primates," *J. Virol.* 74(7):3188-3195, 2000.

Bukreyev et al., "Interferon γ expressed by recombinant respiratory syncytial virus attenuates virus replication in mice without compromising immunogenicity," *Proc. Natl. Acad. Sci. USA* 96:2367-2372, 1999.
Tao, "A live attenuated chimeric recombinant parainfluenza virus (PIV) encoding the internal proteins of PIV type 3 and the surface glycoproteins of PIV type 1 induces complete resistance to PIV1 challenge and partial resistance of PIV3 challenge," *Vaccine* 17:1100-1108, 1999,
van Wyke Coelingh et al., "Attenuation of Bovine Parainfluenza Virus Type 3 in Nonhuman Primates and Its Ability to Confer Immunity Parainfluenza Virus Type 3 Challenge," *J. Infect. Dis.* 157(4):655-661, 1988.
U.S. Appl. No. 09/083,793, filed May 22, 1998, by Murphy et al.
U.S. Appl. No. 60/129,006, filed Apr. 13, 1999, by Murphy et al.
U.S. Appl. No. 09/350,821, filed Jul. 9, 1999, by Durbin et al.
U.S. Appl. No. 09/424,628, filed Nov. 23, 1999, by Murphy et al.
U.S. Appl. No. 60/170,195, filed Dec. 10, 1999, by Murphy et al.
U.S. Appl. No. 09/458,813, filed Dec. 10, 1999, by Murphy et al.
U.S. Appl. No. 09/586,479, filed Jun. 1, 2000, by Schmidt et al.
U.S. Appl. No. 60/215,809, filed Jul. 5, 2000, by Skiadopoulos et al.

* cited by examiner

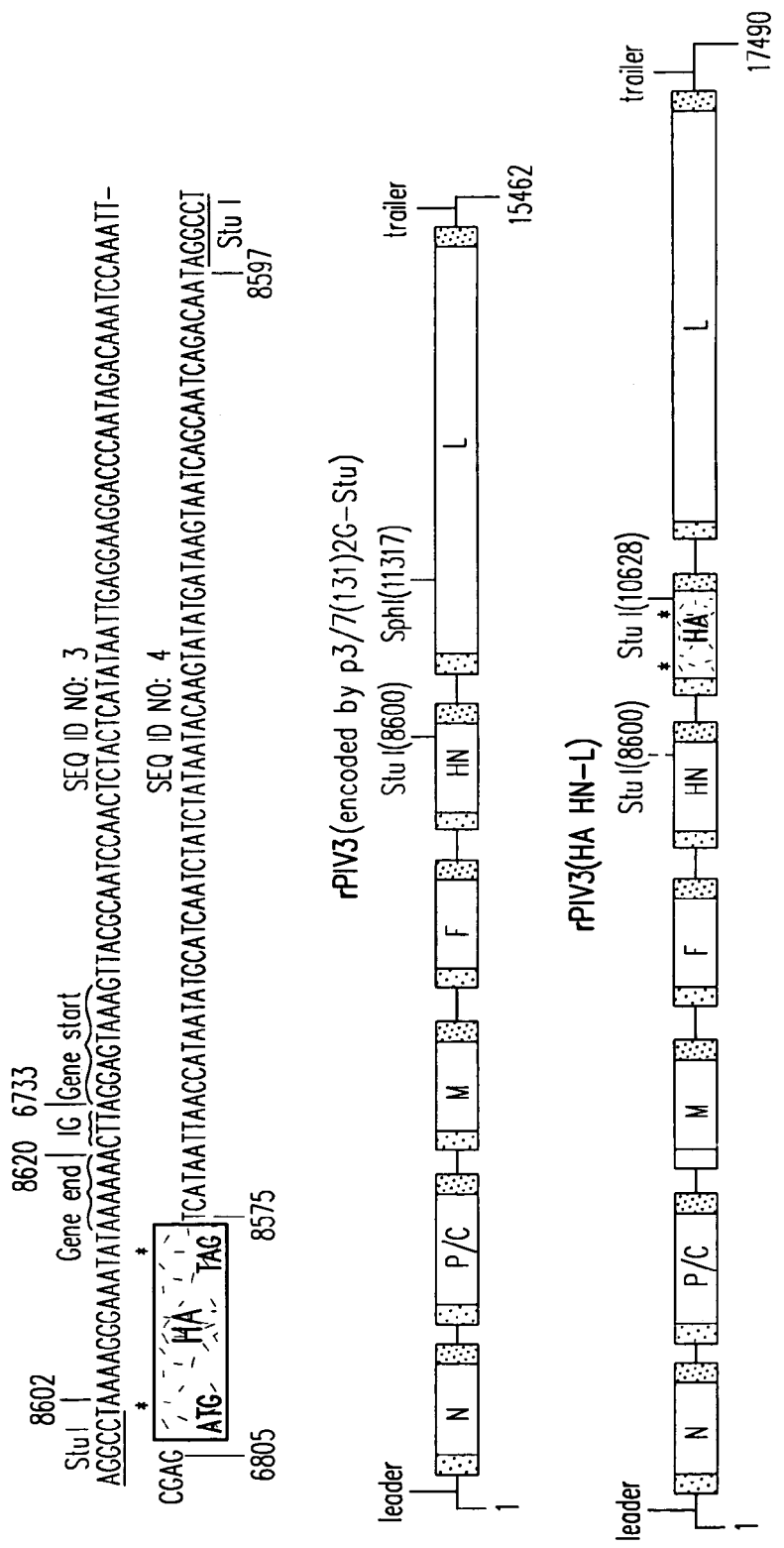

SEQUENCE LISTING

<160> NUMBER OF SEQ ID NOS: 57

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Flanking
      sequence of measles HA gene insert for N-P and P-M
      junctions.

```
<400> SEQUENCE: 1
cttaagaata tacaaataag aaaaacttag gattaaagag cg                         42

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Flanking
      sequence of measles HA gene insert for N-P and P-M
      junctions.

<400> SEQUENCE: 2
gatccaacaa agaaacgaca ccgaacaaac cttaag                                36

<210> SEQ ID NO 3
<211> LENGTH: 101
<212> TYPE: DNA
<213> ORGANISM: Artificial Sequence
<220> FEATURE:
<223> OTHER INFORMATION: Description of Artificial Sequence: Flanking
      sequence of measles HA gene insert for HN-L
      junction.

<400> SEQUENCE: 3
aggcctaaaa gggaaatata aaaaacttag gagtaaagtt acgcaatcca actctactca      60
tataattgag gaaggaccca atagacaaat ccaaattcga g                         101

<210> SEQ ID NO 4
<211> LENGTH: 79
<212> TYPE: DNA
<213> ORGANISM: Artificial Sequence
<220> FEATURE:
<223> OTHER INFORMATION: Description of Artificial Sequence: Flanking
      sequence of measles HA gene insert for HN-L
      junction.

<400> SEQUENCE: 4
tcataattaa ccataatatg catcaatcta tctataatac aagtatatga taagtaatca      60
gcaatcagac aataggcct                                                   79

<210> SEQ ID NO 5
<211> LENGTH: 83
<212> TYPE: DNA
<213> ORGANISM: Artificial Sequence
<220> FEATURE:
<223> OTHER INFORMATION: Description of Artificial Sequence: Forward
      primer for PCR of measles HA gene insert for N-P and P-M
      junction.

<400> SEQUENCE: 5
ttaatcttaa gaatatacaa ataagaaaaa cttaggatta agagcgatg tcaccacaac       60 gagaccggat aaatgccttc tac                                              83

<210> SEQ ID NO 6
<211> LENGTH: 67
<212> TYPE: DNA
<213> ORGANISM: Artificial Sequence
<220> FEATURE:
<223> OTHER INFORMATION: Description of Artificial Sequence: Reverse
      primer for PCR of measles HA gene insert for N-P and P-M
      junctions.

<400> SEQUENCE: 6
attattgctt aaggtttgtt cggtgtcgtt tctttgttgg atcctatctg cgattggttc      60
```

```
catcttc                                                             67

<210> SEQ ID NO 7
<211> LENGTH: 55
<212> TYPE: DNA
<213> ORGANISM: Artificial Sequence
<220> FEATURE:
<223> OTHER INFORMATION: Description of Artificial Sequence: Forward
      primer for PCR of measles HA gene insert for HN-L
      junction.

<400> SEQUENCE: 7
gacaataggc ctaaaaggga aatataaaaa acttaggagt aaagttacgc aatcc         55

<210> SEQ ID NO 8
<211> LENGTH: 68
<212> TYPE: DNA
<213> ORGANISM: Artificial Sequence
<220> FEATURE:
<223> OTHER INFORMATION: Description of Artificial Sequence:
      Reverse/Forward primer for PCR of measles HA gene
      insert for HN-L junction.

<400> SEQUENCE: 8
gtagaacgcg tttatccggt ctcgttgtgg tgacatctcg aatttggatt tgtctattgg    60
gtccttcc                                                            68

<210> SEQ ID NO 9
<211> LENGTH: 77
<212> TYPE: DNA
<213> ORGANISM: Artificial Sequence
<220> FEATURE:
<223> OTHER INFORMATION: Description of Artificial Sequence: Forward
      primer for PCR of measles HA gene insert for HN-L
      junction.

<400> SEQUENCE: 9
cagtcacccg ggaagatgga accaatcgca gatagtcata attaaccata atatgcatca    60
atctatctat aatacaa                                                  77

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Reverse
      primer for PCR of measles HA gene insert for HN-L
      junction.

<400> SEQUENCE: 10
ccatgtaatt gaatccccca acactagc                                      28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:
      Forward/Reverse primer for PCR of measles HA gene
      insert for HN-L junction.

<400> SEQUENCE: 11
cggataaacg cgttctacaa agataacc                                      28

<210> SEQ ID NO 12
```

-continued

<211> LENGTH: 25
<212> TYPE: DNA
<213> ORGANISM: Artificial Sequence
<220> FEATURE:
<223> OTHER INFORMATION: Description of Artificial Sequence: Reverse
primer for PCR of measles HA gene for N-P and M-P
junctions.

<400> SEQUENCE: 12
ccatcttccc gggtgactgt gcagc 25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Upstream
HPIV2 HN primer.

<400> SEQUENCE: 13
gggccatgga agattacagc aat 23

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Downstream
HPIV2 HN primer.

<400> SEQUENCE: 14
caataagctt aaagcattag ttccc 25

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Upstream
HPIV2 HN primer.

<400> SEQUENCE: 15
gcgatgggcc cgaggaagga cccaatagac a 31

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Downstream
HPIV2 HN primer.

<400> SEQUENCE: 16
cccgggtcct gatttcccga gcacgctttg 30

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: HPIV1 HN
primer.

<400> SEQUENCE: 17
agtggctaat tgcattgcat ccacat 26

<210> SEQ ID NO 18

-continued

```
<211> LENGTH: 24
<212> TYPE: DNA
<213> ORGANISM: Artificial Sequence
<220> FEATURE:
<223> OTHER INFORMATION: Description of Artificial Sequence: HPIV1 HN
      primer.

<400> SEQUENCE: 18
gccgtctgca tggtgaatag caat                                            24

<210> SEQ ID NO 19
<211> LENGTH: 15492
<212> TYPE: DNA
<213> ORGANISM: Artificial Sequence
<220> FEATURE:
<223> OTHER INFORMATION: Description of Artificial Sequence: Sequence of
      pFLC.PIV32, 15492 bp in sense orientation.

<400> SEQUENCE: 19
accaaacaag agaagaaact tgtctgggaa tataaattta actttaaatt aacttaggat        60
taaagacatt gactagaagg tcaagaaaag ggaactctat aatttcaaaa atgttgagcc       120
tatttgatac atttaatgca cgtaggcaag aaaacataac aaaatcagcc ggtggagcta       180
tcattcctgg acagaaaaat actgtctcta tattcgccct tggaccgaca ataactgatg       240
ataatgagaa aatgacatta gctcttctat ttctatctca ttcactagat aatgagaaac       300
aacatgcaca aagggcaggg ttcttggtgt ctttattgtc aatggcttat gccaatccag       360
agctctacct aacaacaaat ggaagtaatg cagatgtcaa gtatgtcata tacatgattg       420
agaaagatct aaaacggcaa agtatggag gatttgtggt taagacgaga gagatgatat       480
atgaaaagac aactgattgg atatttggaa gtgacctgga ttatgatcag gaaactatgt       540
tgcagaacgg caggaacaat tcaacaattg aagaccttgt ccacacattt gggtatccat       600
catgtttagg agctcttata atacagatct ggatagttct ggtcaaagct atcactagta       660
tctcagggtt aagaaaaggc ttttcaccc gattggaagc tttcagacaa gatggaacag       720
tgcaggcagg gctggtattg agcggtgaca cagtggatca gattgggtca atcatgcggt       780
ctcaacagag cttggtaact cttatggttg aaacattaat aacaatgaat accagcagaa       840
atgacctcac aaccatagaa aagaatatac aaattgttgg caactacata agagatgcag       900
gtctcgcttc attcttcaat acaatcagat atggaattga gaccagaatg gcagctttga       960
ctctatccac tctcagacca gatatcaata gattaaaagc tttgatggaa ctgtatttat      1020
caaagggacc acgcgctcct ttcatctgta tcctcagaga tcctatacat ggtgagttcg      1080
caccaggcaa ctatcctgcc atatggagct atgcaatggg ggtggcagtt gtacaaaata      1140
gagccatgca acagtatgtg acgggaagat catatctaga cattgatatg ttccagctag      1200
gacaagcagt agcacgtgat gccgaagctc aaatgagctc aacactggaa gatgaacttg      1260
gagtgacaca cgaatctaaa gaaagcttga gagacatat aaggaacata aacagttcag      1320
agacatcttt ccacaaaccg acaggtggat cagccataga gatggcaata gatgaagagc      1380
cagaacaatt cgaacataga gcagatcaag aacaaaatgg agaacctcaa tcatccataa      1440
ttcaatatgc ctgggcagaa ggaaatagaa gcgatgatca gactgagcaa gctacagaat      1500
ctgacaatat caagaccgaa caacaaaaca tcagagacac actaaacaag agactcaacg      1560
acaagaagaa acaaagcagt caaccaccca ctaatccac aaacagaaca accaggacg       1620 aaatagatga tctgttttaac gcatttggaa gcaactaatc gaatcaacat tttaatctaa      1680
atcaataata aataagaaaa acttaggatt aaagaatcct atcataccgg aatataggt       1740
```

-continued

```
ggtaaattta gagtctgctt gaaactcaat caatagagag ttgatggaaa gcgatgctaa    1800
aaactatcaa atcatggatt cttgggaaga ggaatcaaga gataaatcaa ctaatatctc    1860
ctcggccctc aacatcattg aattcatact cagcaccgac ccccaagaag acttatcgga    1920
aaacgacaca atcaacacaa gaacccagca actcagtgcc accatctgtc aaccagaaat    1980
caaaccaaca gaaacaagtg agaaagatag tggatcaact gacaaaaata gacagtccgg    2040
gtcatcacac gaatgtacaa cagaagcaaa agatagaaat attgatcagg aaactgtaca    2100
gagaggacct gggagaagaa gcagctcaga tagtagagct gagactgtgg tctctggagg    2160
aatccccaga agcatcacag attctaaaaa tggaacccaa aacacggagg atattgatct    2220
caatgaaatt agaaagatgg ataaggactc tattgagggg aaaatgcgac aatctgcaaa    2280
tgttccaagc gagatatcag gaagtgatga catatttaca acagaacaaa gtagaaacag    2340
tgatcatgga agaagcctgg aatctatcag tacacctgat acaagatcaa taagtgttgt    2400
tactgctgca acaccagatg atgaagaaga aatactaatg aaaaatagta ggacaaagaa    2460
aagttcttca acacatcaag aagatgacaa agaattaaaa aaggggggaa aagggaaaga    2520
ctggtttaag aaatcaaaag ataccgacaa ccagatacca acatcagact acagatccac    2580
atcaaaaggg cagaagaaaa tctcaaagac aacaaccacc aacaccgaca caaaggggca    2640
aacagaaata cagacagaat catcagaaac acaatcctca tcatggaatc tcatcatcga    2700
caacaacacc gaccggaacg aacagacaag cacaactcct ccaacaacaa cttccagatc    2760
aacttataca aagaatcga tccgaacaaa ctctgaatcc aaacccaaga cacaaaagac    2820
aaatggaaag gaaaggaagg atacagaaga gagcaatcga tttacagaga gggcaattac    2880
tctattgcag aatcttggtg taattcaatc cacatcaaaa ctagatttat atcaagacaa    2940
acgagttgta tgtgtagcaa atgtactaaa caatgtagat actgcatcaa agatagattt    3000
cctggcagga ttagtcatag gggttttcaat ggacaacgac acaaaattaa cacagataca    3060
aaatgaaatg ctaaacctca aagcagatct aaagaaaatg gacgaatcac atagaagatt    3120
gatagaaaat caaagagaac aactgtcatt gatcacgtca ctaatttcaa atctcaaaat    3180
tatgactgag agaggaggaa agaaagacca aaatgaatcc aatgagagag tatccatgat    3240
caaaacaaaa ttgaaagaag aaaagatcaa gaagaccagg tttgacccac ttatggaggc    3300
acaaggcatt gacaagaata tacccgatct atatcgacat gcaggagata cactagagaa    3360
cgatgtacaa gttaaatcag agatattaag ttcatacaat gagtcaaatg caacaagact    3420
aatacccaaa aaagtgagca gtacaatgag atcactagtt gcagtcatca acaacagcaa    3480
tctctcacaa agcacaaaac aatcatacat aaacgaactc aaacgttgca aaaatgatga    3540
agaagtatct gaattaatgg acatgttcaa tgaagatgtc aacaattgcc aatgatccaa    3600
caaagaaacg acaccgaaca acagacaag aacaacagt agatcaaaac ctgtcaacac    3660
acacaaaatc aagcagaatg aaacaacaga tatcaatcaa tatacaaata agaaaaactt    3720
aggattaaag aataaattaa tccttgtcca aaatgagtat aactaactct gcaatataca    3780
cattcccaga atcatcattc tctgaaaatg gtcatataga accattacca ctcaaagtca    3840
atgaacagag gaaagcagta ccccacatta gagttgccaa gatcggaaat ccaccaaaac    3900
acggatcccg gtatttagat gtcttcttac tcggcttctt cgagatggaa cgaatcaaag    3960
acaaatacgg gagtgtgaat gatctcgaca gtgaccgag ttacaaagtt tgtggctctg    4020
gatcattacc aatcggattg ctaagtaca ctgggaatga ccaggaattg ttacaagccg    4080
```

```
caaccaaact ggatatagaa gtgagaagaa cagtcaaagc gaaagagatg gttgtttaca    4140
cggtacaaaa tataaaacca gaactgtacc catggtccaa tagactaaga aaaggaatgc    4200
tgttcgatgc caacaaagtt gctcttgctc ctcaatgtct tccactagat aggagcataa    4260
aatttagagt aatcttcgtg aattgtacgg caattggatc aataaccttg ttcaaaattc    4320
ctaagtcaat ggcatcacta tctctaccca acacaatatc aatcaatctg caggtacaca    4380
taaaaacagg ggttcagact gattctaaag ggatagttca aattttggat gagaaaggcg    4440
aaaaatcact gaatttcatg gtccatctcg gattgatcaa agaaaagta ggcagaatgt    4500 actctgttga atactgtaaa cagaaaatcg agaaatgag attgatatt tctttaggac     4560 tagttggagg aatcagtctt catgtcaatg caactgggtc catatcaaaa acactagcaa    4620
gtcagctggt attcaaaaga gagatttgtt atcctttaat ggatctaaat ccgcatctca    4680
atctagttat ctgggcttca tcagtagaga ttacaagagt ggatgcaatt ttccaacctt    4740 cttttacctgg cgagttcaga tactatccta atattattgc aaaaggagtt gggaaaatca   4800
aacaatggaa ctagtaatct ctattttagt ccggacgtat ctattaagcc gaagcaaata    4860
aaggataatc aaaaacttag gacaaaagag gtcaatacca acaactatta gcagtcacac    4920
tcgcaagaat aagagagaag ggaccaaaaa agtcaaatag gagaaatcaa acaaaaggt    4980 acagaacacc agaacaacaa aatcaaaaca tccaactcac tcaaaacaaa aattccaaaa    5040
gagaccggca acacaacaag cactgaacac catggatcac ctgcatccaa tgatagtatg    5100 cattttttgtt atgtacactg gaattgtagg ttcagatgcc attgctggag atcaactcct    5160
caatgtaggg gtcattcaat caaagataag atcactcatg tactacactg atggtggcgc    5220
tagctttatt gttgtaaaat tactacccaa tcttcccccca agcaatggaa catgcaacat    5280
caccagtcta gatgcatata atgttaccct atttaagttg ctaacacccc tgattgagaa    5340
cctgagcaaa atttctgctg ttacagatac caaaccccgc cgagaacgat ttgcaggagt    5400
cgttattggg cttgctgcac taggagtagc tacagctgca caaataaccg cagctgtagc    5460
aatagtaaaa gccaatgcaa atgctgctgc gataaacaat cttgcatctt caattcaatc    5520
caccaacaag gcagtatccg atgtgataac tgcatcaaga acaattgcaa ccgcagttca    5580
agcgattcag gatcacatca atggagccat tgtcaacggg ataacatctg catcatgccg    5640
tgcccatgat gcactaattg ggtcaatatt aaatttgtat ctcactgagc ttactacaat    5700
atttcataat caaataacaa accctgcgct gacaccactt tccatccaag ctttaagaat    5760
cctcctcggt agcaccttgc caattgtcat tgaatccaaa ctcaacacaa aactcaacac    5820
agcagagctg ctcagtagcg gactgttaac tggtcaaata atttccattt ccccaatgta    5880
catgcaaatg ctaattcaaa tcaatgttcc gacatttata atgcaacccg gtgcgaaggt    5940
aattgatcta attgctatct ctgcaaacca taaattacaa gaagtagttg tacaagttcc    6000
taatagaatt ctagaatatg caaatgaact acaaaactac ccagccaatg attgtttcgt    6060
gacaccaaac tctgtatttt gtagatacaa tgagggttcc ccgatccctg aatcacaata    6120
tcaatgctta aggggaatc ttaattcttg cacttttacc cctattatcg ggaactttct     6180
caagcgattc gcatttgcca atggtgtgct ctatgccaac tgcaaatctt gctatgtaa     6240 gtgtgccgac cctccccatg ttgtgtctca agatgacaac caaggcatca gcataattga    6300
tattaagagg tgctctgaga tgatgcttga cactttttca tttaggatca catctacatt    6360
caatgctaca tacgtgacag acttctcaat gattaatgca aatattgtac atctaagtcc    6420
tctagacttg tcaaatcaaa tcaattcaat aaacaaatct cttaaaagtg ctgaggattg    6480
```

```
gattgcagat agcaacttct tcgctaatca agccagaaca gccaagacac tttattcact   6540
aagtgcaatc gcattaatac tatcagtgat tactttggtt gttgtgggat tgctgattgc   6600
ctacatcatc aagctggttt ctcaaatcca tcaattcaga gcactagctg ctacaacaat   6660
gttccacagg gagaatcctg ccgtcttttc caagaacaat catggaaaca tatatgggat   6720
atcttaggat ccctcagat cattagatat taaaattata aaaaacttag gagtaaagtt   6780
acgcaatcca actctactca tataattgag gaaggaccca atagacaaat ccaaatccat   6840
ggaagattac agcaatctat ctcttaaatc aattcctaaa aggacatgta gaatcatttt   6900
ccgaactgcc acaattcttg gcatatgcac attaattgtg ctatgttcaa gtattcttca   6960
tgagataatt catcttgatg tttcctctgg tcttatgaat tctgatgagt cacagcaagg   7020
cattattcag cctatcatag aatcattaaa atcattgatt gctttggcca accagattct   7080
atataatgtt gcaatagtaa ttcctcttaa aattgacagt atcgaaactg taatactctc   7140
tgctttaaaa gatatgcaca ccgggagtat gtccaatgcc aactgcacgc caggaaatct   7200
gcttctgcat gatgcagcat acatcaatgg aataaacaaa ttccttgtac ttgaatcata   7260
caatgggacg cctaaatatg gacctctcct aaatatacc agctttatcc cctcagcaac   7320
atctccccat gggtgtacta gaataccatc attttcactc atcaagaccc attggtgtta   7380
cactcacaat gtaatgcttg gagattgtct tgatttcacg gcatctaacc agtatttatc   7440
aatggggata atacaacaat ctgctgcagg gtttccaatt ttcaggacta tgaaaaccat   7500
ttacctaagt gatggaatca atcgcaaaag ctgttcagtc actgctatac caggaggttg   7560
tgtcttgtat tgctatgtag ctacaaggtc tgaaaaagaa gattatgcca cgactgatct   7620
agctgaactg agacttgctt tctattatta taatgatacc tttattgaaa gagtcatatc   7680
tcttccaaat acaacagggc agtgggccac aatcaaccct gcagtcggaa gcgggatcta   7740
tcatctaggc tttatcttat ttcctgtata tggtggtctc ataaatggga ctacttctta   7800
caatgagcag tcctcacgct atttatccc aaaacatccc aacataactt gtgccggtaa   7860
ctccagcaaa caggctgcaa tagcacggag ttcctatgtc atccgttatc actcaaacag   7920
gttaattcag agtgctgttc ttatttgtcc attgtctgac atgcatacag aagagtgtaa   7980
tctagttatg tttaacaatt cccaagtcat gatgggtgca gaaggtaggc tctatgttat   8040
tggtaataat ttgtattatt atcaacgcag ttcctcttgg tggtctgcat cgctcttta   8100 caggatcaat acagatttt ctaaaggaat tcctccgatc attgaggctc aatgggtacc   8160
gtcctatcaa gttcctcgtc ctggagtcat gccatgcaat gcaacaagtt tttgccctgc   8220
taattgcatc acagggtgt acgcagatgt gtggccgctt aatgatccag aactcatgtc   8280
acgtaatgct ctgaacccca actatcgatt tgctggagcc tttctcaaaa atgagtccaa   8340
ccgaactaat cccacattct acactgcatc ggctaactcc ctcttaaata ctaccggatt   8400
caacaacacc aatcacaaag cagcatatac atcttcaacc tgctttaaaa acactggaac   8460
ccaaaaaatt tattgtttaa taataattga aatgggctca tctcttttag gggagttcca   8520
aataatacca tttttaaggg aactaatgct ttaagcttaa ttaaccataa tatgcatcaa   8580
tctatctata atacaagtat atgataagta atctgcaatc agacaataga caaaagggaa   8640
atataaaaaa cttaggagca aagcgtgctc gggaaatgga cactgaatct aacaatggca   8700
ctgtatctga catactctat cctgagtgtc accttaactc tcctatcgtt aaaggtaaaa   8760
tagcacaatt acacactatt atgagtctac ctcagcctta tgatatggat gacgactcaa   8820
```

```
tactagttat cactagacag aaaataaaac ttaataaatt ggataaaaga caacgatcta   8880
ttagaagatt aaaattaata ttaactgaaa aagtgaatga cttaggaaaa tacacattta   8940
tcagatatcc agaaatgtca aaagaaatgt tcaaattata tatacctggt attaacagta   9000
aagtgactga attattactt aaagcagata gaacatatag tcaaatgact gatggattaa   9060
gagatctatg gattaatgtg ctatcaaaat tagcctcaaa aaatgatgga agcaattatg   9120
atcttaatga agaaattaat aatatatcga aagttcacac aacctataaa tcagataaat   9180
ggtataatcc attcaaaaca tggtttacta tcaagtatga tatgagaaga ttacaaaaag   9240
ctcgaaatga gatcactttt aatgtttggga aggattataa cttgttagaa gaccagaaga   9300
atttcttatt gatacatcca gaattggttt tgatattaga taaacaaaac tataatggtt   9360
atctaattac tcctgaatta gtattgatgt attgtgacgt agtcgaaggc cgatggaata   9420
taagtgcatg tgctaagtta gatccaaaat tacaatctat gtatcagaaa ggtaataacc   9480
tgtgggaagt gatagataaa ttgttttcaa ttatgggaga aaagacattt gatgtgtatat   9540
cgttattaga accacttgca ttatccttaa ttcaaactca tgatcctgtt aaacaactaa   9600
gaggagcttt tttaaatcat gtgttatccg agatggaatt aatatttgaa tctagagaat   9660
cgattaagga atttctgagt gtagattaca ttgataaaat tttagatata tttaataagt   9720
ctacaataga tgaaatagca gagattttct cttttttttag aacatttggg catcctccat   9780
tagaagctag tattgcagca gaaaaggtta gaaaatatat gtatattgga aaacaattaa   9840
aatttgacac tattaataaa tgtcatgcta tcttctgtac aataataatt aacggatata   9900
gagagaggca tggtggacag tggcctcctg tgacattacc tgatcatgca cacgaattca   9960
tcataaatgc ttacggttca aactctgcga tatcatatga aaatgctgtt gattattacc  10020
agagctttat aggaataaaa ttcaataaat tcatagagcc tcagttagat gaggatttga  10080
caatttatat gaaagataaa gcattatctc caaaaaaatc aaattgggac acagtttatc  10140
ctgcatctaa tttactgtac cgtactaacg catccaacga atcacgaaga ttagttgaag  10200
tatttatagc agatagtaaa tttgatcctc atcagatatt ggattatgta gaatctgggg  10260
actggttaga tgatccagaa tttaatatttt cttatagtct taaagaaaaa gagatcaaac  10320
aggaaggtag actctttgca aaaatgacat acaaaatgag agctacacaa gttttatcag  10380
agaccctact tgcaaataac ataggaaaat tctttcaaga aaatgggatg gtgaagggag  10440
agattgaatt acttaagaga ttaacaacca tatcaatatc aggagttcca cggtataatg  10500
aagtgtacaa taattctaaa agccatacag atgaccttaa aacctacaat aaaataagta  10560
atcttaattt gtcttctaat cagaaatcaa agaaatttga attcaagtca acggatatct  10620
acaatgatgg atacgagact gtgagctgtt tcctaacaac agatctcaaa aaatactgtc  10680
ttaattggag atatgaatca acagctctat ttggagaaac ttgcaaccaa atatttggat  10740
taaataaatt gtttaattgg ttacaccctc gtccttgaagg aagtacaatc tatgtaggtg  10800
atccttactg tcctccatca gataaagaac atatatcatt agaggatcac cctgattctg  10860
gttttttacgt tcataaccca agagggggta tagaaggatt ttgtcaaaaa ttatggacac  10920
tcatatctat aagtgcaata catctagcag ctgttagaat aggcgtgagg gtgactgcaa  10980
tggttcaagg agacaatcaa gctatagctg taaccacaag agtacccaac aattatgact  11040
acagagttaa gaaggagata gtttataaag atgtagtgag attttttgat tcattaagag  11100
aagtgatgga tgatctaggt catgaactta aattaaatga aacgattata agtagcaaga  11160
tgttcatata tagcaaaaga atctattatg atgggagaat tcttcctcaa gctctaaaag  11220
```

```
cattatctag atgtgtcttc tggtcagaga cagtaataga cgaaacaaga tcagcatctt    11280
caaatttggc aacatcattt gcaaaagcaa ttgagaatgg ttattcacct gttctaggat    11340
atgcatgctc aattttaag aatattcaac aactatatat tgcccttggg atgaatatca    11400
atccaactat aacacagaat atcagagatc agtattttag gaatccaaat tggatgcaat    11460
atgcctcttt aatacctgct agtgttgggg gattcaatta catggccatg tcaagatgtt    11520
ttgtaaggaa tattggtgat ccatcagttg ccgcattggc tgatattaaa agatttatta    11580
aggcgaatct attagaccga agtgttcttt ataggattat gaatcaagaa ccaggtgagt    11640
catctttttt ggactgggct tcagatccat attcatgcaa tttaccacaa tctcaaaata    11700
taaccaccat gataaaaaat ataacagcaa ggaatgtatt acaagattca ccaaatccat    11760
tattatctgg attattcaca aatacaatga tagaagaaga tgaagaatta gctgagttcc    11820
tgatggacag gaaggtaatt ctccctagag ttgcacatga tattctagat aattctctca    11880
caggaattag aaatgccata gctggaatgt tagatacgac aaaatcacta attcgggttg    11940
gcataaatag aggaggactg acatatagtt tgttgaggaa atcagtaat tacgatctag    12000 tacaatatga aacactaagt aggactttgc gactaattgt aagtgataaa atcaagtatg    12060
aagatatgtg ttcggtagac cttgccatag cattgcgaca aaagatgtgg attcatttat    12120
caggaggaag gatgataagt ggacttgaaa cgcctgaccc attagaatta ctatctgggg    12180
tagtaataac aggatcagaa cattgtaaaa tatgttattc ttcagatggc acaaacccat    12240
atacttggat gtatttaccc ggtaatatca aaataggatc agcagaaaca ggtatatcgt    12300
cattaagagt tccttatttt ggatcagtca ctgatgaaag atctgaagca caattaggat    12360
atatcaagaa tcttagtaaa cctgcaaaag ccgcaataag aatagcaatg atatatacat    12420
gggcatttgg taatgatgag atatcttgga tggaagcctc acagatagca caaacacgtg    12480
caaattttac actagatagt ctcaaaattt taacaccggt agctacatca acaaatttat    12540
cacacagatt aaaggatact gcaactcaga tgaaattctc cagtacatca ttgatcagag    12600
tcagcagatt cataacaatg tccaatgata acatgtctat caagaagct aatgaaacca    12660 aagatactaa tcttatttat caacaaataa tgttaacagg attaagtgtt ttcgaatatt    12720
tatttagatt aaaagaaacc acaggacaca accctatagt tatgcatctg cacatagaag    12780
atgagtgttg tattaaagaa agttttaatg atgaacatat taatccagag tctacattag    12840
aattaattcg atatcctgaa agtaatgaat ttatttatga taagaccca ctcaaagatg    12900 tggacttatc aaaacttatg gttattaaag accattctta cacaattgat atgaattatt    12960
gggatgatac tgacatcata catgcaattt caatatgtac tgcaattaca atagcagata    13020
ctatgtcaca attagatcga gataatttaa aagagataat agttattgca aatgatgatg    13080
atattaatag cttaatcact gaattttga ctcttgacat acttgtattt ctcaagacat    13140
ttggtggatt attagtaaat caatttgcat acactcttta tagtctaaaa atagaaggta    13200
gggatctcat ttgggattat ataatgaaa cactgagaga tacttcccat tcaatattaa    13260
aagtattatc taatgcatta tctcatccta agtattcaa gaggttctgg gattgtggag    13320
ttttaaaccc tatttatggt cctaatactg ctagtcaaga ccagataaaa cttgccctat    13380
ctatatgtga atattcacta gatctatta tgagagaatg gttgaatggt gtatcacttg    13440
aaatatacat ttgtgacagc gatatggaag ttgcaaatga taggaaacaa gccttattt    13500 ctagacacct ttcatttgtt tgttgtttag cagaaattgc atctttcgga cctaacctgt    13560
```

```
taaacttaac atacttggag agacttgatc tattgaaaca atatcttgaa ttaaatatta      13620
aagaagaccc tactcttaaa tatgtacaaa tatctggatt attaattaaa tcgttcccat      13680
caactgtaac atacgtaaga aagactgcaa tcaaatatct aaggattcgc ggtattagtc      13740
cacctgaggt aattgatgat tgggatccgg tagaagatga aaatatgctg gataacattg      13800
tcaaaactat aaatgataac tgtaataaag ataataaagg gaataaaatt aacaatttct      13860
ggggactagc acttaagaac tatcaagtcc ttaaaatcag atctataaca agtgattctg      13920
atgataatga tagactagat gctaatacaa gtggtttgac acttcctcaa ggagggaatt      13980
atctatcgca tcaattgaga ttattcggaa tcaacgcacg tagttgtctg aaagctcttg      14040
agttatcaca aattttaatg aaggaagtca ataaagacaa ggacaggctc ttcctgggag      14100
aaggagcagg agctatgcta gcatgttatg atgccacatt aggacctgca gttaattatt      14160
ataattcagg tttgaatata acagatgtaa ttggtcaacg agaattgaaa atatttcctt      14220
cagaggtatc attagtaggt aaaaaattag gaaatgtgac acagattctt aacagggtaa      14280
aagtactgtt caatgggaat cctaattcaa catggatagg aaatatggaa tgtgagagct      14340
taatatggag tgaattaaat gataagtcca ttggattagt acattgtgat atggaaggag      14400
ctatcggtaa atcagaagaa actgttctac atgaacatta tagtgttata agaattacat      14460
acttgattgg ggatgatgat gttgttttag tttccaaaat tatacctaca atcactccga      14520
attggtctag aatactttat ctatataaat tatattggaa agatgtaagt ataatatcac      14580
tcaaaacttc taatcctgca tcaacagaat tatatctaat ttcgaaagat gcatattgta      14640
ctataatgga acctagtgaa attgttttat caaaacttaa aagattgtca ctcttggaag      14700
aaaataatct attaaaatgg atcattttat caaagaagag gaataatgaa tggttacatc      14760
atgaaatcaa agaaggagaa agagattatg gaatcatgag accatatcat atggcactac      14820
aaatctttgg atttcaaatc aatttaaatc atctggcgaa agaattttta tcaaccccag      14880
atctgactaa tatcaacaat ataatccaaa gttttcagcg aacaataaag gatgtttttat      14940 ttgaatggat taatataact catgatgata agagacataa attaggcgga agatataaca      15000
tattcccact gaaaaataag ggaaagttaa gactgctatc gagaagacta gtattaagtt      15060
ggatttcatt atcattatcg actcgattac ttacaggtcg ctttcctgat gaaaaatttg      15120
aacatagagc acagactgga tatgtatcat tagctgatac tgatttagaa tcattaaagt      15180
tattgtcgaa aaacatcatt aagaattaca gagagtgtat aggatcaata tcatattggt      15240
ttctaaccaa agaagttaaa atacttatga aattgatcgg tggtgctaaa ttattaggaa      15300
ttcccagaca atataaagaa cccgaagacc agttattaga aaactacaat caacatgatg      15360
aatttgatat cgattaaaac ataaatacaa tgaagatata tcctaaccett tatctttaag      15420 cctaggaata gacaaaaagt aagaaaaaca tgtaatatat ataccaaa cagagttctt       15480 ctcttgtttg gt                                                         15492
```

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Primer for
      construction of PIV3-2 chimeric cDNAs, PIV2 F
      (sense).

<400> SEQUENCE: 20
gtaccatgga tcacctgcat ccaat          25

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Primer for
construction of PIV3-2 chimeric cDNAs, PIV2 F
(antisense).

<400> SEQUENCE: 21
tgtggatcct aagatatccc atatatgttt c                                  31

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer for
construction of PIV3-2 chimeric cDNAs, PIV2 F
(sense).

<400> SEQUENCE: 22
atgcatcacc tgcatccaat                                               20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Primer for
construction of PIV3-2 chimeric cDNAs, PIV2
(antisense).

<400> SEQUENCE: 23
tagtgaataa agtgtcttgg ct                                            22

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Primer for
construction of PIV3-2 chimeric cDNAs, PIV2 HN
(sense).

<400> SEQUENCE: 24
catgagataa ttcatcttga tgtt                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Primer for
construction of PIV3-2 chimeric cDNAs, PIV2 HN
(antisense).

<400> SEQUENCE: 25
agcttaaagc attagttccc ttaa                                          24

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Primer for
construction of PIV3-2 chimeric cDNAs, PIV3 F (sense).

<400> SEQUENCE: 26
atcataatta ttttgataat gatcatta                                              28

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Primer for
      construction of PIV3-2 chimeric cDNAs, PIV3 F
      (antisense).

<400> SEQUENCE: 27
gttcagtgct tgttgtgtt                                                        19

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Primer for
      construction of PIV3-2 chimeric cDNAs, PIV3 HN
      (sense/antisense).

<400> SEQUENCE: 28
tcataattaa ccataatatg catcaat                                               27

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Primer for construction of PIV3-2 chimeric cDNAs, PIV3 HN (sense).

<400> SEQUENCE: 29
gatggaatta attagcacta tgat 24

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Primer for construction of PIV3-2 chimeric cDNAs, PIV2 F (antisense).

<400> SEQUENCE: 30
atgcatcacc tgcatccaat 20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Primer for construction of PIV3-2 chimeric cDNAs, PIV2 F (sense).

<400> SEQUENCE: 31
gatgatgtag gcaatcagc 19

<210> SEQ ID NO 32
<211> LENGTH: 18

```
<212> TYPE: DNA
<213> ORGANISM: Artificial Sequence
<220> FEATURE:
<223> OTHER INFORMATION: Description of Artificial Sequence: Primer for
      construction of PIV3-2 chimeric cDNAs, PIV2 HN
      (sense).

<400> SEQUENCE: 32 actgccacaa

-continued

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Primer for
      construction of PIV3-2 chimeric cDNAs, PIV3 M
      (sense).

<400> SEQUENCE: 38
gatactatcc taatattatt gc                                         22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Primer for
      construction of PIV3-2 chimeric cDNAs, PIV3 L
      (antisense).

<400> SEQUENCE: 39
gctaattttg atagcacatt                                            20

<210> SEQ ID NO 40
<211> LENGTH: 15498
<212> TYPE: DNA
<213> ORGANISM: Artificial Sequence
<220> FEATURE:
<223> OTHER INFORMATION: Description of Artificial Sequence: Sequence of
      pFLC.PIV32TM, 15498 bp in sense orientation.

<400> SEQUENCE: 40

| | | |
|---|---|---|
| accaaacaag agaagaaact tgtctgggaa tataaattta actttaaatt aacttaggat | 60 |
| taaagacatt gactagaagg tcaagaaaag ggaactctat aatttcaaaa atgttgagcc | 120 |
| tatttgatac atttaatgca cgtaggcaag aaaacataac aaaatcagcc ggtggagcta | 180 |
| tcattcctgg acagaaaaat actgtctcta tattcgccct tggaccgaca ataactgatg | 240 |
| ataatgagaa aatgacatta gctcttctat ttctatctca ttcactagat aatgagaaac | 300 |
| aacatgcaca aagggcaggg ttcttggtgt ctttattgtc aatggcttat gccaatccag | 360 |
| agctctacct aacaacaaat ggaagtaatg cagatgtcaa gtatgtcata tacatgattg | 420 |
| agaaagatct aaaacggcaa aagtatggag gatttgtggt taagacgaga gagatgatat | 480 |
| atgaaaagac aactgattgg atatttggaa gtgacctgga ttatgatcag gaaactatgt | 540 |
| tgcagaacgg caggaacaat tcaacaattg aagaccttgt ccacacattt gggtatccat | 600 |
| catgtttagg agctcttata atacagatct ggatagttct ggtcaaagct atcactagta | 660 |
| tctcagggtt aagaaaaggc ttttccaccc gattggaagc tttcagacaa gatgaaacag | 720 |
| tgcaggcagg gctggtattg agcggtgaca cagtggatca gattgggtca atcatgcggt | 780 |
| ctcaacagag cttggtaact cttatggttg aaacattaat aacaatgaat accagcagaa | 840 |
| atgacctcac aaccatagaa aagaatatac aaattgttgg caactacata agagatgcag | 900 |
| gtctcgcttc attcttcaat acaatcagat atggaattga gaccagaatg gcagctttga | 960 |
| ctctatccac tctcagacca gatatcaata gattaaaagc tttgatggaa ctgtatttat | 1020 |
| caaagggacc acgcgctcct ttcatctgta tcctcagaga tcctatacat ggtgagttcg | 1080 |
| caccaggcaa ctatcctgcc atatggagct atgcaatggg ggtggcagtt gtacaaaata | 1140 |

-continued

```
gagccatgca acagtatgtg acgggaagat catatctaga cattgatatg ttccagctag    1200
gacaagcagt agcacgtgat gccgaagctc aaatgagctc aacactggaa gatgaacttg    1260
gagtgacaca cgaatctaaa gaaagcttga agagacatat aaggaacata aacagttcag    1320
agacatcttt ccacaaaccg acaggtggat cagccataga gatggcaata gatgaagagc    1380
cagaacaatt cgaacataga gcagatcaag aacaaaatgg agaacctcaa tcatccataa    1440
ttcaatatgc ctgggcagaa ggaaatagaa gcgatgatca gactgagcaa gctacagaat    1500
ctgacaatat caagaccgaa caacaaaaca tcagagacag actaaacaag agactcaacg    1560
acaagaagaa acaaagcagt caaccaccca ctaatcccac aaacagaaca aaccaggacg    1620
aaatagatga tctgtttaac gcatttggaa gcaactaatc gaatcaacat tttaatctaa    1680
atcaataata aataagaaaa acttaggatt aaagaatcct atcataccgg aatatagggt    1740
ggtaaattta gagtctgctt gaaactcaat caatagagag ttgatggaaa gcgatgctaa    1800
aaactatcaa atcatggatt cttgggaaga ggaatcaaga gataaatcaa ctaatatctc    1860
ctcggccctc aacatcattg aattcatact cagcaccgac ccccaagaag acttatcgga    1920
aaacgacaca atcaacacaa gaacccagca actcagtgcc accatctgtc aaccagaaat    1980
caaaccaaca gaaacaagtg agaaagatag tggatcaact gacaaaaata gacagtccgg    2040
gtcatcacac gaatgtacaa cagaagcaaa agatagaaat attgatcagg aaactgtaca    2100
gagaggacct gggagaagaa gcagctcaga tagtagagct gagactgtgg tctctggagg    2160
aatccccaga agcatcacag attctaaaaa tggaacccaa aacacggagg atattgatct    2220
caatgaaatt agaaagatgg ataaggactc tattgagggg aaaatgcgac aatctgcaaa    2280
tgttccaagc gagatatcag gaagtgatga catatttaca acagaacaaa gtagaaacag    2340
tgatcatgga agaagcctgg aatctatcag tacacctgat acaagatcaa taagtgttgt    2400
tactgctgca acaccagatg atgaagaaga aatactaatg aaaaatagta ggacaaagaa    2460
aagttcttca acacatcaag aagatgacaa aagaattaaa aaggggaa aagggaaaga    2520 ctggtttaag aaatcaaaag ataccgacaa ccagatacca acatcagact acagatccac    2580
atcaaaaggg cagaagaaaa tctcaaagac aacaaccacc aacaccgaca caaaggggca    2640
aacagaaata cagacagaat catcagaaac acaatcctca tcatggaatc tcatcatcga    2700
caacaacacc gaccggaacg aacagacaag cacaactcct ccaacaacaa cttccagatc    2760
aacttataca aaagaatcga tccgaacaaa ctctgaatcc aaacccaaga cacaaaagac    2820
aaatggaaag gaaaggaagg atacagaaga gagcaatcga tttacagaga gggcaattac    2880
tctattgcag aatcttggtg taattcaatc cacatcaaaa ctagatttat atcaagacaa    2940
acgagttgta tgtgtagcaa atgtactaaa caatgtagat actgcatcaa agatagattt    3000
cctggcagga ttagtcatag gggtttcaat ggacaacgac acaaaattaa cacagataca    3060
aaatgaaatg ctaaacctca aagcagatct aagaaaatg gacgaatcac atagaagatt    3120
gatagaaaat caaagagaac aactgtcatt gatcacgtca ctaatttcaa atctcaaaat    3180
tatgactgag agaggaggaa agaaagacca aaatgaatcc aatgagagag tatccatgat    3240
caaaacaaaa ttgaaagaag aaaagatcaa gaagaccagg tttgacccac ttatggaggc    3300
acaaggcatt gacaagaata tacccgatct atatcgacat gcaggagata cactagaaaa    3360
cgatgtacaa gttaaatcag agatattaag ttcatacaat gagtcaaatg caacaagact    3420
aatacccaaa aaagtgagca gtacaatgag atcactagtt gcagtcatca acaacagcaa    3480
tctctcacaa agcacaaaac aatcatacat aaacgaactc aaacgttgca aaaatgatga    3540
```

```
agaagtatct gaattaatgg acatgttcaa tgaagatgtc aacaattgcc aatgatccaa    3600
caaagaaacg acaccgaaca acagacaag aaacaacagt agatcaaaac ctgtcaacac     3660
acacaaaatc aagcagaatg aaacaacaga tatcaatcaa tatacaaata agaaaaactt    3720
aggattaaag aataaattaa tccttgtcca aaatgagtat aactaactct gcaatataca    3780
cattcccaga atcatcattc tctgaaaatg gtcatataga accattacca ctcaaagtca    3840
atgaacagag gaaagcagta ccccacatta gagttgccaa gatcggaaat ccaccaaaac   3900
acggatcccg gtatttagat gtcttcttac tcggcttctt cgagatggaa cgaatcaaag    3960
acaaatacgg gagtgtgaat gatctcgaca gtgacccgag ttacaaagtt tgtggctctg   4020
gatcattacc aatcggattg gctaagtaca ctgggaatga ccaggaattg ttacaagccg    4080
caaccaaact ggatatagaa gtgagaagaa cagtcaaagc gaaagagatg gttgtttaca   4140
cggtacaaaa tataaaacca gaactgtacc catggtccaa tagactaaga aaaggaatgc    4200
tgttcgatgc caacaaagtt gctcttgctc ctcaatgtct tccactagat aggagcataa    4260
aatttagagt aatcttcgtg aattgtacgg caattggatc aataaccttg ttcaaaattc    4320
ctaagtcaat ggcatcacta tctctaccca acacaatatc aatcaatctg caggtacaca    4380
taaaaacagg ggttcagact gattctaaag ggatagttca aattttggat gagaaaggcg    4440
aaaaatcact gaatttcatg gtccatctcg gattgatcaa aagaaaagta ggcagaatgt    4500
actctgttga atactgtaaa cagaaaatcg agaaaatgag attgatattt tctttaggac    4560
tagttggagg aatcagtctt catgtcaatg caactgggtc catatcaaaa acactagcaa    4620
gtcagctggt attcaaaaga gagatttgtt atcctttaat ggatctaaat ccgcatctca    4680
atctagttat ctgggcttca tcagtagaga ttacaagagt ggatgcaatt ttccaacctt    4740
ctttacctgg cgagttcaga tactatccta atattattgc aaaaggagtt gggaaaatca    4800
aacaatggaa ctagtaatct ctattttagt ccggacgtat ctattaagcc gaagcaaata    4860
aaggataatc aaaaacttag gacaaaagag gtcaatacca acaactatta gcagtcacac    4920
tcgcaagaat aagagagaag ggaccaaaaa agtcaaatag gagaaatcaa acaaaaggt     4980 acagaacacc agaacaacaa aatcaaaaca tccaactcac tcaaaacaaa aattccaaaa    5040
gagaccggca acacaacaag cactgaacat gcatccaaaag catccaatga tagtatgcat   5100 tttttgttatg tacactggaa ttgtaggttc agatgccatt gctggagatc aactcctcaa    5160
tgtaggggtc attcaatcaa agataagatc actcatgtac tacactgatg gtggcgctag    5220
ctttattgtt gtaaaattac tacccaatct tcccccaagc aatggaacat gcaacatcac    5280
cagtctagat gcatataatg ttaccctatt taagttgcta acacccctga ttgagaacct    5340
gagcaaaatt tctgctgtta cagataccaa accccgccga gaacgatttg caggagtcgt    5400
tattgggctt gctgcactag gagtagctac agctgcacaa ataaccgcag ctgtagcaat    5460
agtaaaagcc aatgcaaatg ctgctgcgat aaacaatctt gcatcttcaa ttcaatccac    5520
caacaaggca gtatccgatg tgataactgc atcaagaaca attgcaaccg cagttcaagc    5580
gattcaggat cacatcaatg gagccattgt caacgggata acatctgcat catgccgtgc    5640
ccatgatgca ctaattgggt caatattaaa tttgtatctc actgagctta ctacaatatt    5700
tcataatcaa ataacaaacc ctgcgctgac accacttttc atccaagctt taagaatcct    5760
cctcggtagc accttgccaa ttgtcattga atccaaactc aacacaaaac tcaacacagc    5820
agagctgctc agtagcggac tgttaactgg tcaaataatt ccatttccc caatgtacat     5880
```

```
gcaaatgcta attcaaatca atgttccgac atttataatg caacccggtg cgaaggtaat    5940
tgatctaatt gctatctctg caaaccataa attacaagaa gtagttgtac aagttcctaa    6000
tagaattcta gaatatgcaa atgaactaca aaactaccca gccaatgatt gtttcgtgac    6060
accaaactct gtattttgta gatacaatga gggttccccg atccctgaat cacaatatca    6120
atgcttaagg gggaatctta attcttgcac ttttacccct attatcggga actttctcaa    6180
gcgattcgca tttgccaatg gtgtgctcta tgccaactgc aaatctttgc tatgtaagtg    6240
tgccgaccct ccccatgttg tgtctcaaga tgacaaccaa ggcatcagca taattgatat    6300
taagaggtgc tctgagatga tgcttgacac ttttttcattt aggatcacat ctacattcaa    6360
tgctacatac gtgacagact tctcaatgat taatgcaaat attgtacatc taagtcctct    6420
agacttgtca aatcaaatca attcaataaa caaatctctt aaaagtgctg aggattggat    6480
tgcagatagc aacttcttcg ctaatcaagc cagaacagcc aagacacttt attcactaat    6540
cataattatt ttgataatga tcattatatt gtttataatt aatataacga taattacaat    6600
tgcaattaag tattacagaa ttcaaaagag aaatcgagtg gatcaaaatg acaagccata    6660
tgtactaaca aacaaataac atatctacag atcattagat attaaaatta taaaaaactt    6720
aggagtaaag ttacgcaatc caactctact catataattg aggaaggacc caatagacaa    6780
atccaaattc gagatggaat actggaagca taccaatcac ggaaaggatg ctggtaatga    6840
gctggagacg tctatggcta ctcatggcaa caagctcact aataagataa tatacatatt    6900
atggacaata atcctggtgt tattatcaat agtcttcatc atagtgctaa ttaattccat    6960
ccatgagata attcatcttg atgtttcctc tggtcttatg aattctgatg agtcacagca    7020
aggcattatt cagcctatca tagaatcatt aaaatcattg attgctttgg ccaaccagat    7080
tctatataat gttgcaatag taattcctct taaaattgac agtatcgaaa ctgtaatact    7140
ctctgcttta aaagatatgc acaccgggag tatgtccaat gccaactgca cgccaggaaa    7200
tctgcttctg catgatgcag catacatcaa tggaataaac aaattccttg tacttgaatc    7260
atacaatggg acgcctaaat atggacctct cctaaatata cccagcttta tccctcagc    7320 aacatctccc catgggtgta ctagaatacc atcattttca ctcatcaaga cccattggtg    7380
ttacactcac aatgtaatgc ttggagattg tcttgatttc acggcatcta accagtattt    7440
atcaatgggg ataatacaac aatctgctgc agggtttcca attttcagga ctatgaaaac    7500
catttaccta agtgatggaa tcaatcgcaa aagctgttca gtcactgcta taccaggagg    7560
ttgtgtcttg tattgctatg tagctacaag gtctgaaaaa gaagattatg ccacgactga    7620
tctagctgaa ctgagacttg cttttctatta ttataatgat accttttattg aaagagtcat    7680 atctcttcca aatacaacag ggcagtgggc cacaatcaac cctgcagtcg gaagcgggat    7740
ctatcatcta ggctttatct tatttcctgt atatggtggt ctcataaatg ggactacttc    7800
ttacaatgag cagtcctcac gctatttat cccaaaacat cccaacataa cttgtgccgg    7860
taactccagc aaacaggctg caatagcacg gagttcctat gtcatccgtt atcactcaaa    7920
caggttaatt cagagtgctg ttcttatttg tccattgtct gacatgcata cagaagagtg    7980
taatctagtt atgtttaaca attcccaagt catgatgggt gcagaaggta ggctctatgt    8040
tattggtaat aatttgtatt attatcaacg cagttcctct tggtggtctg catcgctctt    8100
ttacaggatc aatacagatt tttctaaagg aattcctccg atcattgagg ctcaatggot    8160 accgtcctat caagttcctc gtcctggagt catgccatgc aatgcaacaa gttttttgccc    8220 tgctaattgc atcacagggg tgtacgcaga tgtgtggccg cttaatgatc cagaactcat    8280
```

-continued

```
gtcacgtaat gctctgaacc ccaactatcg atttgctgga gcctttctca aaaatgagtc    8340
caaccgaact aatcccacat tctacactgc atcggctaac tccctcttaa atactaccgg    8400
attcaacaac accaatcaca aagcagcata tacatcttca acctgcttta aaaacactgg    8460
aacccaaaaa atttattgtt taataataat tgaaatgggc tcatctcttt tagggagtt    8520 ccaaataata ccatttttaa gggaactaat gctttaagct tcataattaa ccataatatg    8580
catcaatcta tctataatac aagtatatga taagtaatca gcaatcagac aatagacaaa    8640
agggaaatat aaaaaactta ggagcaaagc gtgctcggga atggacact gaatctaaca     8700 atggcactgt atctgacata ctctatcctg agtgtcacct taactctcct atcgttaaag    8760
gtaaaatagc acaattacac actattatga gtctacctca gccttatgat atggatgacg    8820
actcaatact agttatcact agacagaaaa taaaacttaa taaattggat aaaagacaac    8880
gatctattag aagattaaaa ttaatattaa ctgaaaaagt gaatgactta ggaaaataca    8940
catttatcag atatccagaa atgtcaaaag aaatgttcaa attatatata cctggtatta    9000
acagtaaagt gactgaatta ttacttaaag cagatagaac atatagtcaa atgactgatg    9060
gattaagaga tctatggatt aatgtgctat caaaattagc ctcaaaaaat gatggaagca    9120
attatgatct taatgaagaa attaataata tatcgaaagt tcacacaacc tataaatcag    9180
ataaatggta taatccattc aaaacatggt ttactatcaa gtatgatatg agaagattac    9240
aaaaagctcg aaatgagatc acttttaatg ttgggaagga ttataacttg ttagaagacc    9300
agaagaattt cttattgata catccagaat tggttttgat attagataaa caaaactata    9360
atggttatct aattactcct gaattagtat tgatgtattg tgacgtagtc gaaggccgat    9420
ggaatataag tgcatgtgct aagttagatc caaaattaca atctatgtat cagaaaggta    9480
ataacctgtg ggaagtgata gataaattgt ttccaattat gggagaaaag acatttgatg    9540
tgatatcgtt attagaacca cttgcattat ccttaattca aactcatgat cctgttaaac    9600
aactaagagg agctttttta aatcatgtgt tatccgagat ggaattaata tttgaatcta    9660
gagaatcgat taaggaattt ctgagtgtag attacattga taaaattttta gatatattta    9720 ataagtctac aatagatgaa atagcagaga ttttctcttt ttttagaaca tttgggcatc    9780
ctccattaga agctagtatt gcagcagaaa aggttagaaa atatatgtat attggaaaac    9840
aattaaaatt tgacactatt aataaatgtc atgctatctt ctgtacaata ataattaacg    9900
gatatagaga gaggcatggt ggacagtggc tccctgtgac attacctgat catgcacacg    9960
aattcatcat aaatgcttac ggttcaaact ctgcgatatc atatgaaaat gctgttgatt   10020
attaccagag ctttatagga ataaaattca ataaattcat agagcctcag ttagatgagg   10080
atttgacaat ttatatgaaa gataaagcat tatctccaaa aaaatcaaat tgggacacag   10140
tttatcctgc atctaattta ctgtaccgta ctaacgcatc caacgaatca cgaagattag   10200
ttgaagtatt tatagcagat agtaaatttg atcctcatca gatattggat tatgtagaat   10260
ctggggactg gttagatgat ccagaattta atatttctta tagtcttaaa gaaaagaga    10320 tcaaacagga aggtagactc tttgcaaaaa tgacatacaa aatgagagct acacaagttt   10380
tatcagagac cctacttgca aataacatag gaaaattctt tcaagaaaat gggatggtga   10440
agggagagat tgaattactt aagagattaa caaccatatc aatatcagga gttccacggt   10500
ataatgaagt gtacaataat tctaaaagcc atacagatga ccttaaaacc tacaataaaa   10560
taagtaatct taatttgtct tctaatcaga aatcaaagaa atttgaattc aagtcaacgg   10620
```

-continued

```
atatctacaa tgatggatac gagactgtga gctgtttcct aacaacagat ctcaaaaaat   10680
actgtcttaa ttggagatat gaatcaacag ctctatttgg agaaacttgc aaccaaatat   10740
ttggattaaa taaattgttt aattggttac accctcgtct tgaaggaagt acaatctatg   10800
taggtgatcc ttactgtcct ccatcagata aagaacatat atcattagag gatcaccctg   10860
attctggttt ttacgttcat aacccaagag ggggtataga aggattttgt caaaaattat   10920
ggacactcat atctataagt gcaatacatc tagcagctgt tagaataggc gtgagggtga   10980
ctgcaatggt tcaaggagac aatcaagcta tagctgtaac cacaagagta cccaacaatt   11040
atgactacag agttaagaag gagatagttt ataaagatgt agtgagattt tttgattcat   11100
taagagaagt gatggatgat ctaggtcatg aacttaaatt aaatgaaacg attataagta   11160
gcaagatgtt catatatagc aaaagaatct attatgatgg gagaattctt cctcaagctc   11220
taaaagcatt atctagatgt gtcttctggt cagagacagt aatagacgaa acaagatcag   11280
catcttcaaa tttggcaaca tcatttgcaa agcaattga gaatggttat tcacctgttc    11340
taggatatgc atgctcaatt tttaagaata ttcaacaact atatattgcc cttgggatga   11400
atatcaatcc aactataaca cagaatatca gagatcagta ttttaggaat ccaaattgga   11460
tgcaatatgc ctctttaata cctgctagtg ttgggggatt caattacatg gccatgtcaa   11520
gatgttttgt aaggaatatt ggtgatccat cagttgccgc attggctgat attaaaagat   11580
ttattaaggc gaatctatta gaccgaagtg ttctttatag gattatgaat caagaaccag   11640
gtgagtcatc ttttttggac tgggcttcag atccatattc atgcaattta ccacaatctc   11700
aaaatataac caccatgata aaaaatataa cagcaaggaa tgtattacaa gattcaccaa   11760
atccattatt atctggatta ttcacaaata caatgataga agaagatgaa gaattagctg   11820
agttcctgat ggacaggaag gtaattctcc ctagagttgc acatgatatt ctagataatt   11880
ctctcacagg aattagaaat gccatagctg gaatgttaga tacgacaaaa tcactaattc   11940
ggggttggcat aaatagagga ggactgacat atagtttgtt gaggaaaatc agtaattacg   12000
atctagtaca atatgaaaca ctaagtagga ctttgcgact aattgtaagt gataaaatca   12060
agtatgaaga tatgtgttcg gtagaccttg ccatagcatt gcgacaaaag atgtggattc   12120
atttatcagg aggaaggatg ataagtggac ttgaaacgcc tgacccatta gaattactat   12180
ctgggggtagt aataacagga tcagaacatt gtaaaatatg ttattcttca gatggcacaa   12240
acccatatac ttggatgtat ttacccggta atatcaaaat aggatcagca gaaacaggta   12300
tatcgtcatt aagagttcct tattttggat cagtcactga tgaaagatct gaagcacaat   12360
taggatatat caagaatctt agtaaacctg caaaagccgc aataagaata gcaatgatat   12420
atacatgggc atttggtaat gatgagatat cttggatgga agcctcacag atagcacaaa   12480
cacgtgcaaa ttttacacta gatagtctca aaattttaac accggtagct acatcaacaa   12540
atttatcaca cagattaaag gatactgcaa ctcagatgaa attctccagt acatcattga   12600
tcagagtcag cagattcata acaatgtcca atgataacat gtctatcaaa gaagctaatg   12660
aaaccaaaga tactaatctt atttatcaac aaataatgtt aacaggatta agtgttttcg   12720
aatatttatt tagattaaaa gaaccacag acacaacccc tatagttatg catctgcaca   12780
tagaagatga gtgttgtatt aaagaaagtt ttaatgatga acatattaat ccagagtcta   12840
cattagaatt aattcgatat cctgaaagta atgaatttat ttatgataaa gacccactca   12900
aagatgtgga cttatcaaaa cttatggtta ttaaagacca ttcttacaca attgatatga   12960
attattggga tgatactgac atcatacatg caatttcaat atgtactgca attacaatag   13020
```

-continued

```
cagatactat gtcacaatta gatcgagata atttaaaaga gataatagtt attgcaaatg  13080
atgatgatat taatagctta atcactgaat ttttgactct tgacatactt gtatttctca  13140
agacatttgg tggattatta gtaaatcaat ttgcatacac tctttatagt ctaaaaatag  13200
aaggtaggga tctcatttgg gattatataa tgagaacact gagagatact tcccattcaa  13260
tattaaaagt attatctaat gcattatctc atcctaaagt attcaagagg ttctgggatt  13320
gtggagtttt aaaccctatt tatggtccta atactgctag tcaagaccag ataaaacttg  13380
ccctatctat atgtgaatat tcactagatc tatttatgag agaatggttg aatggtgtat  13440
cacttgaaat atacatttgt gacagcgata tggaagttgc aaatgatagg aaacaagcct  13500
ttatttctag acacctttca tttgtttgtt gtttagcaga aattgcatct ttcggaccta  13560
acctgttaaa cttaacatac ttggagagac ttgatctatt gaacaatat cttgaattaa  13620 atattaaaga agaccctact cttaaatatg tacaaatatc tggattatta attaaatcgt  13680
tcccatcaac tgtaacatac gtaagaaaga ctgcaatcaa atatctaagg attcgcggta  13740
ttagtccacc tgaggtaatt gatgattggg atccggtaga agatgaaaat atgctggata  13800
acattgtcaa aactataaat gataactgta ataaagataa taaagggaat aaaattaaca  13860
atttctgggg actagcactt aagaactatc aagtccttaa aatcagatct ataacaagtg  13920
attctgatga taatgataga ctagatgcta atacaagtgg tttgacactt cctcaaggag  13980
ggaattatct atcgcatcaa ttgagattat tcggaatcaa cagcactagt tgtctgaaag  14040
ctcttgagtt atcacaaatt ttaatgaagg aagtcaataa agacaaggac aggctcttcc  14100
tgggagaagg agcaggagct atgctagcat gttatgatgc cacattagga cctgcagtta  14160
attattataa ttcaggtttg aatataacag atgtaattgg tcaacgagaa ttgaaaatat  14220
ttccttcaga ggtatcatta gtaggtaaaa aattaggaaa tgtgacacag attcttaaca  14280
gggtaaaagt actgttcaat gggaatccta attcaacatg gataggaaat atggaatgtg  14340
agagcttaat atggagtgaa ttaaatgata agtccattgg attagtacat tgtgatatgg  14400
aaggagctat cggtaaatca gaagaaactg ttctacatga acattatagt gttataagaa  14460
ttacatactt gattggggat gatgatgttg ttttagtttc caaaattata cctacaatca  14520
ctccgaattg gtctagaata ctttatctat ataaattata ttggaaagat gtaagtataa  14580
tatcactcaa aacttctaat cctgcatcaa cagaattata tctaatttcg aaagatgcat  14640
attgtactat aatggaacct agtgaaattg ttttatcaaa acttaaaaga ttgtcactct  14700
tggaagaaaa taatctatta aaatggatca ttttatcaaa gaagaggaat aatgaatggt  14760
tacatcatga aatcaaagaa ggagaaagag attatgaat catgagacca tatcatatgg  14820
cactacaaat ctttggattt caaatcaatt taaatcatct ggcgaaagaa tttttatcaa  14880
ccccagatct gactaatatc aacaatataa tccaaagttt tcagcgaaca ataaggatg  14940 ttttatttga atggattaat ataactcatg atgataagag acataaatta ggcggaagat  15000
ataacatatt cccactgaaa aataagggaa agttaagact gctatcgaga agactagtat  15060
taagttggat ttcattatca ttatcgactc gattacttac aggtcgcttt cctgatgaaa  15120
aatttgaaca tagagcacag actggatatg tatcattagc tgatactgat ttagaatcat  15180
taaagttatt gtcgaaaaac atcattaaga attacagaga gtgtatagga tcaatatcat  15240 attggttttct aaccaaagaa gttaaaatac ttatgaaatt gatcggtggt gctaaattat  15300
taggaattcc cagacaatat aaagaacccg aagaccagtt attagaaaac tacaatcaac  15360
```

```
atgatgaatt tgatatcgat taaaacataa atacaatgaa gatatatcct aacctttatc    15420
tttaagccta ggaatagaca aaaagtaaga aaaacatgta atatatatat accaaacaga    15480
gttcttctct tgtttggt                                                  15498

<210> SEQ ID NO 41
<211> LENGTH: 15474
<212> TYPE: DNA
<213> ORGANISM: Artificial Sequence
<220> FEATURE:
<223> OTHER INFORMATION: Description of Artificial Sequence: Sequence of
      pFLC.PIV32CT, 15474 bp in sense orientation.

<400> SEQUENCE: 41
accaaacaag agaagaaact tgtctgggaa tataaattta actttaaatt aacttaggat      60
taaagacatt gactagaagg tcaagaaaag ggaactctat aatttcaaaa atgttgagcc    120
tatttgatac atttaatgca cgtaggcaag aaaacataac aaaatcagcc ggtggagcta    180
tcattcctgg acagaaaaat actgtctcta tattcgccct tggaccgaca ataactgatg    240
ataatgagaa aatgacatta gctcttctat ttctatctca ttcactagat aatgagaaac    300
aacatgcaca aagggcaggg ttcttggtgt ctttattgtc aatggcttat gccaatccag    360
agctctacct aacaacaaat ggaagtaatg cagatgtcaa gtatgtcata tacatgattg    420
agaaagatct aaaacggcaa aagtatggag gatttgtggt taagacgaga gagatgatat    480
atgaaaagac aactgattgg atatttggaa gtgacctgga ttatgatcag gaaactatgt    540
tgcagaacgg caggaacaat tcaacaattg aagaccttgt ccacacattt gggtatccat    600
catgtttagg agctcttata atacagatct ggatagttct ggtcaaagct atcactagta    660
tctcagggtt aagaaaaggc tttttcaccc gattggaagc tttcagacaa gatggaacag    720
tgcaggcagg gctggtattg agcggtgaca cagtggatca gattgggtca atcatgcggt    780
ctcaacagag cttggtaact cttatggttg aaacattaat aacaatgaat accagcagaa    840
atgacctcac aaccatagaa aagaatatac aaattgttgg caactacata agagatgcag    900
gtctcgcttc attcttcaat acaatcgatt atggaattga ccagaatgca gctttga    960 ctctatccac tctcagacca gatatcaata gattaaaagc tttgatggaa ctgtatttat    1020
caaagggacc acgcgctcct ttcatctgta tcctcagaga tcctatacat ggtgagttcg    1080
caccaggcaa ctatcctgcc atatggagct atgcaatggg ggtggcagtt gtacaaaata    1140
gagccatgca acagtatgtg acgggaagat catatctaga cattgatatg ttccagctag    1200
gacaagcagt agcacgtgat gccgaagctc aaatgagctc aacactggaa gatgaacttg    1260
gagtgacaca cgaatctaaa gaaagcttga agagacatat aaggaacata aacagttcag    1320
agacatcttt ccacaaaccg acaggtggat cagccataga gatggcaata gatgaagagc    1380
cagaacaatt cgaacataga gcagatcaag aacaaaatgg agaacctcaa tcatccataa    1440
ttcaatatgc ctgggcagaa ggaaatagaa gcgatgatca gactgagcaa gctacagaat    1500
ctgacaatat caagaccgaa caacaaaaca tcagagacag actaaacaag agactcaacg    1560
acaagaagaa acaaagcagt caaccaccca ctaatcccac aaacagaaca aaccaggacg    1620
aaatagatga tctgttttaac gcatttggaa gcaactaatc gaatcaacat tttaatctaa    1680
atcaataata aataagaaaa acttaggatt aaagaatcct atcataccgg aatatagggt    1740
ggtaaattta gagtctgctt gaaactcaat caatagagag ttgatggaaa gcgatgctaa    1800
aaactatcaa atcatggatt cttgggaaga ggaatcaaga gataaatcaa ctaatatctc    1860
```

-continued

```
ctcggccctc aacatcattg aattcatact cagcaccgac ccccaagaag acttatcgga    1920
aaacgacaca atcaacacaa gaacccagca actcagtgcc accatctgtc aaccagaaat    1980
caaaccaaca gaaacaagtg agaaagatag tggatcaact gacaaaaata gacagtccgg    2040
gtcatcacac gaatgtacaa cagaagcaaa agatagaaat attgatcagg aaactgtaca    2100
gagaggacct gggagaagaa gcagctcaga tagtagagct gagactgtgg tctctggagg    2160
aatccccaga agcatcacag attctaaaaa tggaacccaa aacacggagg atattgatct    2220
caatgaaatt agaaagatgg ataaggactc tattgagggg aaaatgcgac aatctgcaaa    2280
tgttccaagc gagatatcag gaagtgatga catatttaca acagaacaaa gtagaaacag    2340
tgatcatgga agaagcctgg aatctatcag tacacctgat acaagatcaa taagtgttgt    2400
tactgctgca acaccagatg atgaagaaga atactaatg aaaatagta ggacaaagaa     2460 aagttcttca acacatcaag aagatgacaa agaattaaa aaggggggaa aagggaaaga    2520
ctggtttaag aaatcaaaag ataccgacaa ccagatacca acatcagact acagatccac    2580
atcaaaaggg cagaagaaaa tctcaaagac aacaaccacc aacaccgaca caaagggggca    2640 aacagaaata cagacagaat catcagaaac acaatcctca tcatggaatc tcatcatcga    2700
caacaacacc gaccggaacg aacagacaag cacaactcct ccaacaacaa cttccagatc    2760
aacttataca aagaatcga tccgaacaaa ctctgaatcc aaacccaaga cacaaaagac     2820
aaatggaaag gaaaggaagg atacagaaga gagcaatcga tttacagaga gggcaattac    2880
tctattgcag aatcttggtg taattcaatc cacatcaaaa ctagatttat atcaagacaa    2940
acgagttgta tgtgtagcaa atgtactaaa caatgtagat actgcatcaa agatagattt    3000
cctggcagga ttagtcatag gggtttcaat ggacaacgac acaaaattaa cacagataca    3060
aaatgaaatg ctaaacctca aagcagatct aaagaaaatg gacgaatcac atagaagatt    3120
gatagaaaat caaagagaac aactgtcatt gatcacgtca ctaatttcaa atctcaaaat    3180
tatgactgag agaggaggaa agaaagacca aaatgaatcc aatgagagag tatccatgat    3240
caaaacaaaa ttgaaagaag aaaagatcaa gaagaccagg tttgacccac ttatggaggc    3300
acaaggcatt gacaagaata tacccgatct atatcgacat gcaggagata cactagagaa    3360
cgatgtacaa gttaaatcag agatattaag ttcatacaat gagtcaaatg caacaagact    3420 aataccccaaa aaagtgagca gtacaatgag atcactagtt gcagtcatca acaacagcaa    3480
tctctcacaa agcacaaaac aatcatacat aaacgaactc aaacgttgca aaaatgatga    3540
agaagtatct gaattaatgg acatgttcaa tgaagatgtc aacaattgcc aatgatccaa    3600
caaagaaacg acaccgaaca acagacaag aaacaacagt agatcaaaac ctgtcaacac     3660
acacaaaatc aagcagaatg aaacaacaga tatcaatcaa tatacaaata agaaaaactt    3720
aggattaaag aataaattaa tccttgtcca aaatgagtat aactaactct gcaatataca    3780
cattcccaga atcatcattc tctgaaaatg gtcatataga accattacca ctcaaagtca    3840
atgaacagag gaaagcagta ccccacatta gagttgccaa gatcggaaat ccaccaaaac    3900
acggatcccg gtatttagat gtcttcttac tcggcttctt cgagatggaa cgaatcaaag    3960
acaaatacgg gagtgtgaat gatctcgaca gtgacccgag ttacaaagtt tgtggctctg    4020
gatcattacc aatcggattg gctaagtaca ctgggaatga ccaggaattg ttacaagccg    4080
caaccaaact ggatatagaa gtgagaagaa cagtcaaagc gaaagagatg gttgtttaca    4140
cggtacaaaa tataaaacca gaactgtacc catggtccaa tagactaaga aaaggaatgc    4200
tgttcgatgc caacaaagtt gctcttgctc ctcaatgtct tccactagat aggagcataa    4260
```

```
aatttagagt aatcttcgtg aattgtacgg caattggatc aataaccttg ttcaaaattc    4320
ctaagtcaat ggcatcacta tctctaccca acacaatatc aatcaatctg caggtacaca    4380
taaaaacagg ggttcagact gattctaaag ggatagttca aattttggat gagaaaggcg    4440
aaaaatcact gaatttcatg gtccatctcg gattgatcaa agaaaagta ggcagaatgt     4500 actctgttga atactgtaaa cagaaaatcg agaaatgag attgatattt tctttaggac     4560
tagttggagg aatcagtctt catgtcaatg caactgggtc catatcaaaa acactagcaa    4620
gtcagctggt attcaaaaga gagatttgtt atcctttaat ggatctaaat ccgcatctca    4680
atctagttat ctgggcttca tcagtagaga ttacaagagt ggatgcaatt ttccaacctt    4740
ctttacctgg cgagttcaga tactatccta atattattgc aaaaggagtt gggaaaatca    4800
aacaatggaa ctagtaatct ctattttagt ccggacgtat ctattaagcc gaagcaaata    4860
aaggataatc aaaaacttag gacaaaagag gtcaatacca acaactatta gcagtcacac    4920
tcgcaagaat aagagagaag ggaccaaaaa agtcaaatag gagaaatcaa aacaaaaggt    4980
acagaacacc agaacaacaa aatcaaaaca tccaactcac tcaaaacaaa aattccaaaa    5040
gagaccggca acacaacaag cactgaacat gcatcacctg catccaatga tagtatgcat    5100
ttttgttatg tacactggaa ttgtaggttc agatgccatt gctggagatc aactcctcaa    5160 tgtagggggtc attcaatcaa agataagatc actcatgtac tacactgatg gtggcgctag    5220
ctttattgtt gtaaaattac tacccaatct tcccccaagc aatggaacat gcaacatcac    5280
cagtctagat gcatataatg ttaccctatt taagttgcta acaccctga ttgagaacct     5340 gagcaaaatt tctgctgtta cagataccaa accccgccga gaacgatttg caggagtcgt    5400
tattgggctt gctgcactag gagtagctac agctgcacaa ataaccgcag ctgtagcaat    5460
agtaaaagcc aatgcaaatg ctgctgcgat aaacaatctt gcatcttcaa ttcaatccac    5520
caacaaggca gtatccgatg tgataactgc atcaagaaca attgcaaccg cagttcaagc    5580
gattcaggat cacatcaatg gagccattgt caacgggata acatctgcat catgccgtgc    5640
ccatgatgca ctaattgggt caatattaaa tttgtatctc actgagctta ctacaatatt    5700
tcataatcaa ataacaaacc ctgcgctgac accactttcc atccaagctt taagaatcct    5760
cctcggtagc accttgccaa ttgtcattga atccaaactc aacacaaaac tcaacacagc    5820
agagctgctc agtagcggac tgttaactgg tcaaataatt tccatttccc caatgtacat    5880
gcaaatgcta attcaaatca atgttccgac atttataatg caacccggtg cgaaggtaat    5940
tgatctaatt gctatctctg caaaccataa attacaagaa gtagttgtac aagttcctaa    6000
tagaattcta gaatatgcaa atgaactaca aaactaccca gccaatgatt gtttcgtgac    6060
accaaactct gtattttgta gatacaatga gggttccccg atccctgaat cacaatatca    6120
atgcttaagg gggaatctta attcttgcac ttttaccct attatcggga actttctcaa    6180
gcgattcgca tttgccaatg gtgtgctcta tgccaactgc aaatctttgc tatgtaagtg    6240
tgccgaccct cccatgttg tgtctcaaga tgacaaccaa ggcatcagca taattgatat    6300
taagaggtgc tctgagatga tgcttgacac ttttttcattt aggatcacat ctacattcaa    6360
tgctacatac gtgacagact tctcaatgat taatgcaaat attgtacatc taagtcctct    6420
agacttgtca aatcaaatca attcaataaa caaatctctt aaaagtgctg aggattggat    6480
tgcagatagc aacttcttcg ctaatcaagc cagaacagcc aagacacttt attcactaag    6540
tgcaatcgca ttaatactat cagtgattac tttggttgtt gtgggattgc tgattgccta    6600
```

```
catcatcaag tattacagaa ttcaaaagag aaatcgagtg gatcaaaatg acaagccata   6660
tgtactaaca aacaaataac atatctacag atcattagat attaaaatta taaaaaactt   6720
aggagtaaag ttacgcaatc caactctact catataattg aggaaggacc caatagacaa   6780
atccaaattc gagatggaat actggaagca taccaatcac ggaaaggatg ctggtaatga   6840
gctggagacg tctatggcta ctcatggcaa caagctcact aataagactg ccacaattct   6900
tggcatatgc acattaattg tgctatgttc aagtattctt catgagataa ttcatcttga   6960
tgtttcctct ggtcttatga attctgatga gtcacagcaa ggcattattc agcctatcat   7020
agaatcatta aaatcattga ttgctttggc caaccagatt ctatataatg ttgcaatagt   7080
aattcctctt aaaattgaca gtatcgaaac tgtaatactc tctgctttaa agatatgca   7140 caccgggagt atgtccaatg ccaactgcac gccaggaaat ctgcttctgc atgatgcagc   7200
atacatcaat ggaataaaca aattccttgt acttgaatca tacaatggga cgcctaaata   7260
tggacctctc ctaaatatac ccagctttat cccctcagca acatctcccc atgggtgtac   7320
tagaatacca tcattttcac tcatcaagac ccattggtgt tacactcaca atgtaatgct   7380
tggagattgt cttgatttca cggcatctaa ccagtattta tcaatgggga taatacaaca   7440
atctgctgca gggtttccaa ttttcaggac tatgaaaacc atttacctaa gtgatggaat   7500
caatcgcaaa agctgttcag tcactgctat accaggaggt tgtgtcttgt attgctatgt   7560
agctacaagg tctgaaaaag aagattatgc cacgactgat ctagctgaac tgagacttgc   7620
tttctattat tataatgata cctttattga aagagtcata tctcttccaa atacaacagg   7680
gcagtgggcc acaatcaacc ctgcagtcgg aagcgggatc tatcatctag gctttatctt   7740
atttcctgta tatggtggtc tcataaatgg gactacttct tacaatgagc agtcctcacg   7800
ctattttatc ccaaaacatc ccaacataac ttgtgccggt aactccagca acaggctgc   7860 aatagcacgg agttcctatg tcatccgtta tcactcaaac aggttaattc agagtgctgt   7920
tcttatttgt ccattgtctg acatgcatac agaagagtgt aatctagtta tgtttaacaa   7980
ttcccaagtc atgatgggtg cagaaggtag gctctatgtt attggtaata atttgtatta   8040
ttatcaacgc agttcctctt ggtggtctgc atcgctcttt tacaggatca atacagattt   8100
ttctaaagga attcctccga tcattgaggc tcaatgggta ccgtcctatc aagttcctcg   8160
tcctggagtc atgccatgca atgcaacaag tttttgccct gctaattgca tcacagggg   8220 gtacgcagat gtgtggccgc ttaatgatcc agaactcatg tcacgtaatg ctctgaaccc   8280
caactatcga tttgctggag cctttctcaa aaatgagtcc aaccgaacta atcccacatt   8340
ctacactgca tcggctaact ccctcttaaa tactaccgga ttcaacaaca ccaatcacaa   8400
agcagcatat acatcttcaa cctgctttaa aaacactgga acccaaaaaa tttattgttt   8460
aataataatt gaaatgggct catctctttt aggggagttc caaataatac catttttaag   8520
ggaactaatg ctttaatcat aattaaccat aatatgcatc aatctatcta taatacaagt   8580
atatgataag taatcagcaa tcagacaata gacaaaggg aaatataaaa aacttaggag   8640
caaagcgtgc tcgggaaatg gacactgaat ctaacaatgg cactgtatct gacatactct   8700
atcctgagtg tcaccttaac tctcctatcg ttaaaggtaa aatagcacaa ttacacacta   8760
ttatgagtct acctcagcct tatgatatgg atgacgactc aatactagtt atcactagac   8820
agaaaataaa acttaataaa ttggataaaa gacaacgatc tattagaaga ttaaaattaa   8880
tattaactga aaagtgaat gacttaggaa aatacacatt tatcagatat ccagaaatgt   8940
caaaagaaat gttcaaatta tatatacctg gtattaacag taaagtgact gaattattac   9000
```

```
ttaaagcaga tagaacatat agtcaaatga ctgatggatt aagagatcta tggattaatg    9060
tgctatcaaa attagcctca aaaatgatg gaagcaatta tgatcttaat gaagaaatta     9120
ataatatatc gaaagttcac acaacctata atcagataa atggtataat ccattcaaaa     9180
catggtttac tatcaagtat gatatgagaa gattacaaaa agctcgaaat gagatcactt    9240
ttaatgttgg gaaggattat aacttgttag aagaccagaa gaatttctta ttgatacatc    9300
cagaattggt tttgatatta gataaacaaa actataatgg ttatctaatt actcctgaat    9360
tagtattgat gtattgtgac gtagtcgaag gccgatggaa tataagtgca tgtgctaagt    9420
tagatccaaa attacaatct atgtatcaga aaggtaataa cctgtgggaa gtgatagata    9480
aattgtttcc aattatggga gaaaagacat ttgatgtgat atcgttatta gaaccacttg    9540
cattatcctt aattcaaact catgatcctg ttaaacaact aagaggagct ttttaaatc     9600 atgtgttatc cgagatggaa ttaatatttg aatctagaga atcgattaag gaatttctga    9660
gtgtagatta cattgataaa atttagata tatttaataa gtctacaata gatgaaatag      9720
cagagatttt ctcttttttt agaacatttg ggcatcctcc attagaagct agtattgcag     9780
cagaaaaggt tagaaaatat atgtatattg gaaaacaatt aaaatttgac actattaata    9840
aatgtcatgc tatcttctgt acaataataa ttaacggata tagagagagg catggtggac     9900
agtggcctcc tgtgacatta cctgatcatg cacacgaatt catcataaat gcttacggtt    9960
caaactctgc gatatcatat gaaaatgctg ttgattatta ccagagcttt ataggaataa   10020
aattcaataa attcatagag cctcagttag atgaggattt gacaatttat atgaaagata   10080
aagcattatc tccaaaaaaa tcaaattggg acacagttta tcctgcatct aatttactgt    10140
accgtactaa cgcatccaac gaatcacgaa gattagttga agtatttata gcagatagta   10200
aatttgatcc tcatcagata ttggattatg tagaatctgg ggactggtta gatgatccag   10260
aatttaatat ttcttatagt cttaaagaaa aagagatcaa acaggaaggt agactctttg    10320
caaaaatgac atacaaaatg agagctacac aagttttatc agagacacta cttgcaaata    10380
acataggaaa attctttcaa gaaaatggga tggtgaaggg agagattgaa ttacttaaga   10440
gattaacaac catatcaata tcaggagttc cacggtataa tgaagtgtac aataattcta    10500
aaagccatac agatgacctt aaaacctaca ataaaataag taatcttaat ttgtcttcta   10560
atcagaaatc aaagaaattt gaattcaagt caacggatat ctacaatgat ggatacgaga   10620
ctgtgagctg tttcctaaca acagatctca aaaaatactg tcttaattgg agatatgaat   10680
caacagctct atttggagaa acttgcaacc aaatatttgg attaaataaa ttgtttaatt    10740
ggttacaccc tcgtcttgaa ggaagtacaa tctatgtagg tgatccttac tgtcctccat    10800
cagataaaga acatatatca ttagaggatc accctgattc tggtttttac gttcataacc   10860
caagaggggg tatagaagga ttttgtcaaa aattatggac actcatatct ataagtgcaa   10920
tacatctagc agctgttaga ataggcgtga gggtgactgc aatggttcaa ggagacaatc    10980
aagctatagc tgtaaccaca agagtaccca acaattatga ctacagagtt aagaaggaga   11040
tagtttataa agatgtagtg agatttttg attcattaag agaagtgatg gatgatctag    11100
gtcatgaact taaattaaat gaaacgatta aagtagcaa gatgttcata tatagcaaaa    11160
gaatctatta tgatgggaga attcttcctc aagctctaaa agcattatct agatgtgtct    11220
tctggtcaga gacagtaata gacgaaacaa gatcagcatc ttcaaatttg gcaacatcat    11280
ttgcaaaagc aattgagaat ggttattcac ctgttctagg atatgcatgc tcaattttta    11340
```

```
agaatattca acaactatat attgcccttg ggatgaatat caatccaact ataacacaga    11400
atatcagaga tcagtatttt aggaatccaa attggatgca atatgcctct ttaatacctg    11460
ctagtgttgg gggattcaat tacatggcca tgtcaagatg ttttgtaagg aatattggtg    11520
atccatcagt tgccgcattg gctgatatta aaagatttat taaggcgaat ctattagacc    11580
gaagtgttct ttataggatt atgaatcaag aaccaggtga gtcatctttt ttggactggg    11640
cttcagatcc atattcatgc aatttaccac aatctcaaaa tataaccacc atgataaaaa    11700
atataacagc aaggaatgta ttacaagatt caccaaatcc attattatct ggattattca    11760
caaatacaat gatagaagaa gatgaagaat tagctgagtt cctgatggac aggaaggtaa    11820
ttctccctag agttgcacat gatattctag ataattctct cacaggaatt agaaatgcca    11880
tagctggaat gttagatacg acaaaatcac taattcgggt tggcataaat agaggaggac    11940
tgacatatag tttgttgagg aaaatcagta attacgatct agtacaatat gaaacactaa    12000
gtaggacttt gcgactaatt gtaagtgata aaatcaagta tgaagatatg tgttcggtag    12060
accttgccat agcattgcga caaagatgt ggattcattt atcaggagga aggatgataa    12120
gtggacttga aacgcctgac ccattagaat tactatctgg ggtagtaata acaggatcag    12180
aacattgtaa aatatgttat tcttcagatg gcacaaaccc atatacttgg atgtatttac    12240
ccggtaatat caaaatagga tcagcagaaa caggtatatc gtcattaaga gttccttatt    12300
ttggatcagt cactgatgaa agatctgaag cacaattagg atatatcaag aatcttagta    12360
aacctgcaaa agccgcaata agaatagcaa tgatatatac atgggcattt ggtaatgatg    12420
agatatcttg gatggaagcc tcacagatag cacaaacacg tgcaaattt acactagata    12480 gtctcaaaat tttaacaccg gtagctacat caacaaattt atcacacaga ttaaaggata    12540
ctgcaactca gatgaaattc tccagtacat cattgatcag agtcagcaga ttcataacaa    12600
tgtccaatga taacatgtct atcaaagaag ctaatgaaac caaagatact aatcttattt    12660
atcaacaaat aatgttaaca ggattaagtg ttttcgaata tttatttaga ttaaaagaaa    12720
ccacaggaca caaccctata gttatgcatc tgcacataga agatgagtgt tgtattaaag    12780
aaagttttaa tgatgaacat attaatccag agtctacatt agaattaatt cgatatcctg    12840
aaagtaatga atttatttat gataaagacc cactcaaaga tgtggactta tcaaaactta    12900
tggttattaa agaccattct tacacaattg atatgaatta ttgggatgat actgacatca    12960
tacatgcaat ttcaatatgt actgcaatta caatagcaga tactatgtca caattagatc    13020
gagataattt aaaagagata atagttattg caaatgatga tgatattaat agcttaatca    13080 ctgaatttt gactcttgac atacttgtat ttctcaagac atttggtgga ttattagtaa    13140
atcaatttgc atacactctt tatagtctaa aaatagaagg tagggatctc atttgggatt    13200
atataatgag aacactgaga gatacttccc attcaatatt aaaagtatta tctaatgcat    13260
tatctcatcc taaagtattc aagaggttct gggattgtgg agttttaaac cctatttatg    13320
gtcctaatac tgctagtcaa gaccagataa aacttgccct atctatatgt gaatattcac    13380
tagatctatt tatgagagaa tggttgaatg gtgtatcact tgaaatatac atttgtgaca    13440
gcgatatgga agttgcaaat gataggaaac aagcctttat ttctagacac ctttcatttg    13500
tttgttgttt agcagaaatt gcatctttcg gacctaacct gttaaactta acatacttgg    13560
agagacttga tctattgaaa caatatcttg aattaaatat taagaagac cctactctta    13620 aatatgtaca aatatctgga ttattaatta atcgttccc atcaactgta acatacgtaa    13680
gaaagactgc aatcaaatat ctaaggattc gcggtattag tccacctgag gtaattgatg    13740
```

-continued

```
attgggatcc ggtagaagat gaaaatatgc tggataacat tgtcaaaact ataaatgata    13800
actgtaataa agataataaa gggaataaaa ttaacaattt ctggggacta gcacttaaga    13860
actatcaagt ccttaaaatc agatctataa caagtgattc tgatgataat gatagactag    13920
atgctaatac aagtggtttg acacttcctc aaggagggaa ttatctatcg catcaattga    13980
gattattcgg aatcaacagc actagttgtc tgaaagctct tgagttatca caaattttaa    14040
tgaaggaagt caataaagac aaggacaggc tcttcctggg agaaggagca ggagctatgc    14100
tagcatgtta tgatgccaca ttaggacctg cagttaatta ttataattca ggtttgaata    14160
taacagatgt aattggtcaa cgagaattga aaatatttcc ttcagaggta tcattagtag    14220
gtaaaaaatt aggaaatgtg acacagattc ttaacagggt aaaagtactg ttcaatggga    14280
atcctaattc aacatggata ggaaatatgg aatgtgagag cttaatatgg agtgaattaa    14340
atgataagtc cattggatta gtacattgtg atatggaagg agctatcggt aaatcagaag    14400
aaactgttct acatgaacat tatagtgtta taagaattac atacttgatt ggggatgatg    14460
atgttgtttt agtttccaaa attataccta caatcactcc gaattggtct agaatacttt    14520
atctatataa attatattgg aaagatgtaa gtataatatc actcaaaact tctaatcctg    14580
catcaacaga attatatcta atttcgaaag atgcatattg tactataatg gaacctagtg    14640
aaattgtttt atcaaaactt aaaagattgt cactcttgga agaaaataat ctattaaaat    14700
ggatcatttt atcaaagaag aggaataatg aatggttaca tcatgaaatc aaagaaggag    14760
aaagagatta tggaatcatg agaccatatc atatggcact acaaatcttt ggatttcaaa    14820
tcaatttaaa tcatctggcg aaagaatttt tatcaaccccc agatctgact aatatcaaca    14880
atataatcca aagttttcag cgaacaataa aggatgtttt atttgaatgg attaatataa    14940
ctcatgatga taagagacat aaattaggcg gaagatataa catattccca ctgaaaaata    15000
agggaaagtt aagactgcta tcgagaagac tagtattaag ttggatttca ttatcattat    15060
cgactcgatt acttacaggt cgctttcctg atgaaaaatt tgaacataga gcacagactg    15120
gatatgtatc attagctgat actgatttag aatcattaaa gttattgtcg aaaaacatca    15180
ttaagaatta cagagagtgt ataggatcaa tatcatattg gtttctaacc aaagaagtta    15240
aaatacttat gaaattgatc ggtggtgcta aattattagg aattcccaga caatataaag    15300
aacccgaaga ccagttatta gaaaactaca atcaacatga tgaatttgat atcgattaaa    15360
acataaatac aatgaagata tatcctaacc tttatcttta agcctaggaa tagacaaaaa    15420
gtaagaaaaa catgtaatat atatatacca aacagagttc ttctcttgtt tggt          15474
```

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Sequence
       spanning PIV3 F 5' ntr and PIV2 F ectodomain.

<400> SEQUENCE: 42
caagcactga acatgcatca cctg                                              24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Sequence

```
      spanning PIV2 F ectodomain and PIV3 F
      transmembrane/cytoplasmic domains.

<400> SEQUENCE: 43
ctttattcac taatcataat tatt                                          24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Sequence
      spanning PIV3 F transmembrane/cytoplasmic domains
      and PIV3 F 3' ntr.

<400> SEQUENCE: 44
acaaacaaat aacatatcta caga                                          24

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Terminal
      amino acids of PIV2 F ectodomain.

<400> SEQUENCE: 45

Met His His Leu
  1

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Terminal
      amino acids of PIV2 F ectodomain.

<400> SEQUENCE: 46

Leu Tyr Ser Leu Ile Ile Ile Ile
  1               5

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Sequence
      spanning PIV3 HN 5' ntr and PIV3 HN
      transmembrane/cytoplasmic domains.

<400> SEQUENCE: 47
tccaaattcg agatggaata c                                             21

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Sequence
      spanning PIV3 HN transmembrane/cytoplasmic domains
      and PIV2 HN ectodomain.

<400> SEQUENCE: 48
attaattcca tccatgagat aattcat                                       27

<210> SEQ ID NO 49
```

-continued

```
<211> LENGTH: 33
<212> TYPE: DNA
<213> ORGANISM: Artificial Sequence
<220> FEATURE:
<223> OTHER INFORMATION: Description of Artificial Sequence: Sequence
      spanning PIV2 HN ectodomain and PIV3 HN 3' ntr,
      with extra nucleotides.

<400> SEQUENCE: 49
gaactaatgc tttaagcttc ataattaacc ata                               33

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Terminal
      amino acids bridging fused PIV3 HN
      transmembrane/cytoplasmic domains and PIV2 HN
      ectodomain.

<400> SEQUENCE: 50

Ile Asn Ser Ile His Glu Leu Ile His
  1               5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Terminal
      amino acids of PIV2 HN ectodomain.

<400> SEQUENCE: 51

Glu Leu Met Leu
  1

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Sequence
      spanning PIV2 F ectodomain/transmembrane domain
      and PIV3 F cytoplasmic domain.

<400> SEQUENCE: 52
gcctacatca tcaagtatta c                                            21

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Sequence
      spanning PIV3 F cytoplasmic domain and PIV3 F3'
      ntr.

<400> SEQUENCE: 53
ataaacaaat aacatatcta caga                                         24

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Terminal
      amino acids bridging fused PIV2 F
      ectodomain/transmembrane domain and PIV3 F
```

-continued

```
      cytoplasmic domain.

<400> SEQUENCE: 54

Ala Tyr Ile Ile Lys Tyr Tyr
  1               5

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Sequence
      spanning PIV3 HN cytoplasmic domain and PIV2 HN
      transmembrane/ectodomains.

<400> SEQUENCE: 55
ctcactaata agactgccac aatt                                              24

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Sequence
      spanning PIV2 HN transmembrane/ectodomains and
      PIV3 HN 3' ntr.

<400> SEQUENCE: 56
gaactaatgc tttaatcata attaaccata                                        30

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Terminal
      amino acids bridging fused PIV3 HN cytoplasmic domain
      and PIV2 HN transmembrane/ectodomains.

<400> SEQUENCE: 57

Leu Thr Asn Lys Thr Ala Thr Ile
  1               5
```

CONSTRUCTION AND USE OF RECOMBINANT PARAINFLUENZA VIRUSES EXPRESSING A CHIMERIC GLYCOPROTEIN

RELATED APPLICATIONS

The present application is a continuation-in-part application of, and claims the benefit under Title 35 of, U.S. patent application Ser. No. 09/083,793, filed May 22, 1998 which is a continuation-in-part of U.S. Provisional Application No. 60/047,575, filed May 23, 1997, now abandoned, and U.S. Provisional Application No. 60/059,385, filed Sep. 19, 1997, now abandoned. The disclosures of each of the foregoing priority applications are incorporated herein by reference in their entirety for all purposes.

BACKGROUND OF THE INVENTION

Human parainfluenza virus type 3 (HPIV3) is a common cause of serious lower respiratory tract infection in infants and children less than one year of age. It is second only to respiratory syncytial virus (RSV) as a leading cause of hospitalization for viral lower respiratory tract disease in this age group (Collins et al., p. 1205–1243. In B. N. Fields (Knipe et al., eds), Fields Virology, 3rd ed, vol. 1. Lippincott-Raven Publishers, Philadelphia, 1996; Crowe et al., *Vaccine* 13:415–421, 1995; Marx et al., *J. Infect. Dis.* 176:1423–1427, 1997). Infections by this virus results in substantial morbidity in children less than 3 years of age. HPIV1 and HPIV2 are the principal etiologic agents of laryngotracheobronchitis (croup) and also can cause severe pneumonia and bronchiolitis (Collins et al., 3rd ed. In "*Fields Virology*," B. N. Fields, D. M. Knipe, P. M. Howley, R. M. Chanock, J. L. Melnick, T. P. Monath, B. Roizman, and S. E. Straus, Eds., Vol. 1, pp. 1205–1243. Lippincott-Raven Publishers, Philadelphia, 1996). In a long term study over a 20-year period, HPIV1, HPIV2, and HPIV3 were identified as etiologic agents for 6.0, 3.2, and 11.5%, respectively, of hospitalizations for respiratory tract disease accounting in total for 18% of the hospitalizations, and, for this reason, there is a need for an effective vaccine (Murphy et al., *Virus Res* 11, 1–15, 1988). The parainfluenza viruses have also been identified in a significant proportion of cases of virally-induced middle ear effusions in children with otitis media (Heikkinen et al., *N Eng J Med* 340:260–4, 1999). Thus, there is a need to produce a vaccine against these viruses that can prevent the serious lower respiratory tract disease and the otitis media that accompanies these HPIV infections. HPIV1, HPIV2, and HPIV3 are distinct serotypes which do not elicit significant cross-protective immunity.

Despite considerable efforts to develop effective vaccine therapies against HPIV, no approved vaccine agents have yet been achieved for any HPIV serotype, nor for ameliorating HPIV related illnesses. To date, only two live attenuated PIV vaccine candidates have received particular attention. One of these candidates is a bovine PIV (BPIV3) strain that is antigenically related to HPIV3 and which has been shown to protect animals against HPIV3. BPIV3 is attenuated, genetically stable and immunogenic in human infants and children (Karron et al., *J. Inf. Dis.* 171:1107–14 (1995a); Karron et al., *J. Inf. Dis.* 172:1445–1450, (1995b)). A second PIV3 vaccine candidate, JS cp45, is a cold-adapted mutant of the JS wildtype (wt) strain of HPIV3 (Karron et al., (1995b), supra; Belshe et al., *J. Med. Virol.* 10:235–42 (1982)). This live, attenuated, cold-passaged (cp) PIV3 vaccine candidate exhibits temperature-sensitive (ts), cold-adaptation (ca), and attenuation (att) phenotypes which are stable after viral replication in vivo. The cp45 virus is protective against human PIV3 challenge in experimental animals and is attenuated, genetically stable, and immunogenic in seronegative human infants and children (Hall et al., *Virus Res.* 22:173–184 (1992); Karron et al., (1995b), supra The most promising prospects to date are live attenuated vaccine viruses since these have been shown to be efficacious in non-human primates even in the presence of passively transferred antibodies, an experimental situation that simulates that present in the very young infant who possesses maternally acquired antibodies (Crowe et al., *Vaccine* 13:847–855, 1995; Durbin et al., *J Infect Dis* 179:1345–1351, 1999). Two live attenuated PIV3 vaccine candidates, a temperature-sensitive (ts) derivative of the wild type PIV3 JS strain (designated PIV3cp45) and a bovine PIV3 (BPIV3) strain, are undergoing clinical evaluation (Karron et al., *Pediatr Infect Dis J* 15:650–654, 1996; Karron et al., *J Infect Dis* 171:1107–1114, 1995a; Karron et al., *J Infect Dis* 172, 1445–1450, 1995b). The live attenuated PIV3cp45 vaccine candidate was derived from the JS strain of HPIV3 via serial passage in cell culture at low temperature and has been found to be protective against HPIV3 challenge in experimental animals and to be satisfactorily attenuated, genetically stable, and immunogenic in seronegative human infants and children (Belshe et al, *J. Med. Virol.* 10:235–242, 1982; Belshe et al., *Infect Immun* 37:160–5, 1982; Clements et al., *J. Clin. Microbiol.* 29:1175–82, 1991; Crookshanks et al., *J. Med. Virol.* 13:243–9, 1984; Hall et al., *Virus Res.* 22:173–184, 1992; Karron et al., *J. Infect. Dis.* 172, 1445–1450, 1995b). Because these PIV3 candidate vaccine viruses are biologically derived, there is no proven methods for adjusting the level of attenuation should this be found necessary from ongoing clinical trials.

To facilitate development of PIV vaccine candidates, recombinant DNA technology has recently made it possible to recover infectious negative-stranded RNA viruses from cDNA (for reviews, see Conzelmann, *J. Gen. Virol.* 77:381–89 (1996); Palese et al., Proc. Natl. Acad. Sci. U.S.A. 93:11354–58, (1996)). In this context, recombinant rescue has been reported for infectious respiratory syncytial virus (RSV), rabies virus (RaV), simian virus 5 (SV5), rinderpest virus, Newcastle disease virus (NDV), vesicular stomatitis virus (VSV), measles virus (MeV), and Sendai virus (SeV) from cDNA-encoded antigenomic RNA in the presence of essential viral proteins (see, e.g., Garcin et al., *EMBO J.* 14:6087–6094 (1995); Lawson et al., Proc. Natl. Acad. Sci. U.S.A. 92:4477–81 (1995); Radecke et al., *EMBO J.* 14:5773–5784 (1995); Schnell et al., *EMBO J.* 13:4195–203 (1994); Whelan et al., Proc. Natl. Acad. Sci. U.S.A. 92:8388–92 (1995); Hoffman et al., *J. Virol.* 71:4272–4277 (1997); Kato et al., *Genes to Cells* 1:569–579 (1996), Roberts et al., *Virology* 247(1), 1–6 (1998); Baron et al., *J. Virol.* 71:1265–1271 (1997); International Publication No. WO 97/06270; Collins et al., *Proc. Natl. Acad. Sci. USA* 92:11563–11567 (1995); U.S. patent application Ser. No. 08/892,403, filed Jul. 15, 1997 (corresponding to published International Application No. WO 98/02530 and priority U.S. Provisional Application No. 60/047,634, filed May 23, 1997, 60/046,141, filed May 9, 1997, and 60/021,773, filed Jul. 15, 1996); U.S. patent application Ser. No. 09/291,894, filed by Collins et al. on Apr. 13, 1999; U.S. Provisional Patent Application Ser. No. 60/129,006, filed Apr. 13, 1999; U.S. Provisional Patent Application Ser. No. 60/143,132, filed by Bucholz et al. on Jul. 9, 1999; Juhasz et al., *J. Virol.* 71(8):5814–5819 (1997); He et al. *Virology* 237:249–260

(1997); Peters et al. *J. Virol.* 73:5001–5009, 1999; Baron et al. *J. Virol.* 71:1265–1271 (1997); Whitehead et al., *Virology* 247(2):232–9 (1998a); Whitehead et al., *J. Virol.* 72(5): 4467–4471 (1998b); Jin et al. *Virology* 251:206–214 (1998); Bucholz et al. *J. Virol.* 73:251–259 (1999); and Whitehead et al., *J. Virol.* 73:(4)3438–3442 (1999), each incorporated herein by reference in its entirety for all purposes).

In more specific regard to the instant invention, a method for producing HPIV with a wt phenotype from cDNA was recently developed for recovery of infectious, recombinant HPIV3 JS strain (see, e.g., Durbin et al., *Virology* 235: 323–332, 1997; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). In addition, these disclosures allow for genetic manipulation of viral cDNA cones to determine the genetic basis of phenotypic changes in biological mutants, e.g., which mutations in the HPIV3 cp45 virus specify its ts, ca and att phenotypes, and which gene(s) or genome segment(s) of BPIV3 specify its attenuation phenotype. Additionally, these and related disclosures render it feasible to construct novel PIV vaccine candidates having a wide range of different mutations and to evaluate their level of attenuation, immunogenicity and phenotypic stability (see also, U.S. Provisional Patent Application Ser. No. 60/143,134, filed by Bailey et al. on Jul. 9, 1999; and U.S. patent application Ser. No. 09/350,821, filed by Durbin et al. on Jul. 9, 1999, each incorporated herein by reference).

Thus, infectious wild type recombinant PIV3, (r)PIV3, as well as a number of ts derivatives, have now been recovered from cDNA, and reverse genetics systems have been used to generate infectious virus bearing defined attenuating mutations and to study the genetic basis of attenuation of existing vaccine viruses. For example, the three amino acid substitutions found in the L gene of cp45, singularly or in combination, have been found to specify the ts and attenuation phenotypes. Additional ts and attenuating mutations are present in other regions of the PIV3cp45. In addition a chimeric PIV1 vaccine candidate has been generated using the PIV3 cDNA rescue system by replacing the PIV3 HN and F open reading frames (ORFs) with those of PIV1 in a PIV3 full-length cDNA that contains the three attenuating mutations in L. The recombinant chimeric virus derived from this cDNA is designated rPIV3-1.cp45L (Skiadopoulos et al., *J Virol* 72:1762–8, 1998; Tao et al., *J Virol* 72:2955–2961, 1998; Tao et al., *Vaccine* 17:1100–1108, 1999, incorporated herein by reference). rPIV3-1.cp45L was attenuated in hamsters and induced a high level of resistance to challenge with PIV1. Yet another recombinant chimeric virus, designated rPIV3-1.cp45, has been produced that contains 12 of the 15 cp45 mutations, i.e., excluding the mutations that occur in HN and F. This recombinant vaccine candidate is highly attenuated in the upper and lower respiratory tract of hamsters and induces a high level of protection against HPIV1 infection (Skiadopoulos et al., *Vaccine* In press, 18:503–510, 1999).

Recently, a number of studies have focused on the possible use of viral vectors to express foreign antigens toward the goal of developing vaccines against a pathogen for which other vaccine alternatives are not proved successful. In this context, a number of reports suggest that foreign genes may be successfully inserted into a recombinant negative strand RNA virus genome or antigenome with varying effects (Bukreyev et al., *J. Virol.* 70:6634–41, 1996; Bukreyev et al., *Proc. Natl. Acad. Sci. USA* 96:2367–72, 1999; Finke et al. *J. Virol.* 71:7281–8, 1997; Hasan et al., *J. Gen. Virol.* 78:2813–20, 1997; He et al., *Virology* 237: 249–60, 1997; Jin et al., *Virology* 251:206–14, 1998; Johnson et al., *J. Virol.* 71:5060–8, 1997; Kahn et al., *Virology* 254:81–91, 1999; Kretzschmar et al., *J. Virol.* 71:5982–9, 1997; Mebatsion et al., *Proc. Natl. Acad. Sci. USA* 93:7310–4, 1996; Moriya et al., *FEBS Lett.* 425: 105–11, 1998; Roberts et al., *J. Virol.* 73:3723–32, 1999; Roberts et al., *J. Virol.* 72:4704–11, 1998; Roberts et al., *Virology* 247:1–6, 1998; Sakai et al., *FEBS Letter* 456: 221–226, 1999; Schnell et al., *Proc. Natl. Acad. Sci. USA* 93:11359–65, 1996a; Schnell et al., *J. Virol.* 70:2318–23, 1996b; Schnell et al., *Cell* 90:849–57, 1997; Singh et al., *J. Gen. Virol.* 80:101–6, 1999; Singh et al., *J. Virol.* 73:4823–8, 1999; Spielhofer et al., *J. Virol.* 72, 2150–9, 1998; Yu et al., *Genes to Cells* 2:457–66 et al., 1999; U.S. Provisional Patent Application Ser. No. 60/143,425, filed on Jul. 13, 1999, each incorporated herein by reference). When inserted into the viral genome under the control of viral transcription gene-start and gene-end signals, the foreign gene may be transcribed as a separate mRNA and yield significant protein expression. Surprisingly, in some cases foreign sequence has been reported to be stable and capable of expressing functional protein during numerous passages in vitro.

However, to successfully develop vectors for vaccine use, it is insufficient to simply demonstrate a high, stable level of protein expression. For example, this has been possible since the early-to-mid 1980s with recombinant vaccinia viruses and adenoviruses, and yet these vectors have proven to be disappointments in the development of vaccines for human use. Similarly, most nonsegmented negative strand viruses which have been developed as vectors do not possess properties or immunization strategies amenable for human use. Examples in this context include vesicular stomatitis virus, an ungulate pathogen with no history of administration to humans except for a few laboratory accidents; Sendai virus, a mouse pathogen with no history of administration to humans; simian virus 5, a canine pathogen with no history of administration to humans; and an attenuated strain of measles virus which must be administered systemically and would be neutralized by measles-specific antibodies present in nearly all humans due to maternal antibodies and widespread use of a licensed vaccine. Furthermore, some of these prior vector candidates have adverse effects, such as immunosupression, which are directly inconsistent with their use as vectors. Thus, one must identify vectors whose growth characteristics, tropisms, and other biological properties make them appropriate as vectors for human use. It is further necessary to develop a viable vaccination strategy, including an immunogenic and efficacious route of administration.

Among a host of human pathogens for which a vector-based vaccine approach may be desirable is the measles virus. A live attenuated vaccine has been available for more than three decades and has been largely successful in eradicating measles disease in the United States. However, the World Health Organization estimates that more than 45 million cases of measles still occur annually, particularly in developing countries, and the virus contributes to approximately one million deaths per year Measles virus is a member of the Morbillivirus genus of the Paramyxoviridae family (Griffin et al., In "Fields Virology", B. N. Fields, D. M. Knipe, P. M. Howley, R. M. Chanock, J. L. Melnick, T. P. Monath, B. Roizman, and S. E. Straus, Eds., Vol. 1, pp. 1267–1312. Lippincott-Raven Publishers, Philadelphia, 1996). It is one of the most contagious infectious agents known to man and is transmitted from person to person via the respiratory route (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996). The measles virus has a complex pathogenesis, involving replication in both the respiratory tract and various systemic sites (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996).

Although both mucosal IgA and serum IgG measles virus-specific antibodies can participate in the control of measles virus, the absence of measles virus disease in very young infants possessing maternally-acquired measles virus-specific antibodies identifies serum antibodies as a major mediator of resistance to disease (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996). The two measles virus glycoproteins, the hemagglutinin (HA) and fusion (F) proteins, are the major neutralization and protective antigens (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996).

The currently available live attenuated measles vaccine is administered by a parenteral route (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996). Both the wild type measles virus and the vaccine virus are very readily neutralized by antibodies, and the measles virus vaccine is rendered non-infectious by even very low levels of maternally-acquired measles virus-specific neutralizing antibodies (Halsey et al., *N. Engl. J. Med.* 313:544–9, 1985; Osterhaus et al., *Vaccine* 16:1479–81, 1998). Thus, the vaccine virus is not given until the passively-acquired maternal antibodies have decreased to undetectable levels. In the United States, measles virus vaccine is not given until 12 to 15 months of age, a time when almost all children are readily infected with the measles virus vaccine. In the developing world, measles virus continues to have a high mortality rate, especially in children within the latter half of the first year of life (Gellin et al., *J. Infect. Dis.* 170, S3–14, 1994; Taylor et al., *Am. J. Epidemiol.* 127:788–94, 1988). This occurs because the measles virus, which is highly prevalent in these regions, is able to infect that subset of infants in whom maternally-acquired measles virus-specific antibody levels have decreased to a non-protective level. Therefore, there is a need for a measles virus vaccine that is able to induce a protective immune response even in the presence of measles virus neutralizing antibodies with the goal of eliminating measles virus disease occurring within the first year of life as well as that which occurs thereafter. Given this need, there have been numerous attempts to develop an immunization strategy to protect infants in the latter half of the first year of life against measles virus, but none of these strategies has been effective to date.

The first strategy for developing an early measles vaccine involved administration of the licensed live attenuated measles virus vaccine to infants about six months of age by one of the following two methods (Cutts et al., *Biologicals* 25, 323–38, 1997). In one general protocol, the live attenuated measles virus was administered intranasally by drops (Black et al., *New Eng. J. Med.* 263, 165–169; 1960; Kok et al., *Trans. R. Soc. Trop. Med. Hyg.* 77:171–6, 1983; Simasathien et al., *Vaccine* 15:329–34, 1997) or into the lower respiratory tract by aerosol (Sabin et al., *J. Infect. Dis.* 152:1231–7, 1985), to initiate an infection of the respiratory tract. In a second protocol, the measles virus was given parenterally but at a higher dose than that employed for the current vaccine. The administration of vaccines that can replicate on mucosal surfaces has been successfully achieved in early infancy for both live attenuated poliovirus and rotavirus vaccines (Melnick et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 655–712. 2 vols. Lippencott-Raven Publishers, Philadelphia, 1996; Perez-Schael et al., *N. Engl. J. Med.* 337, 1181–7, 1997), presumably because passively-acquired IgG antibodies have less access to mucosal surfaces than they do to systemic sites of viral replication. In this situation, the live attenuated poliovirus vaccine viruses are able to infect the mucosal surface of the gastrointestinal tract or the respiratory tract of young infants, including those with maternal antibodies, resulting in the induction of a protective immune response.

Therefore, a plausible method is to immunize via the respiratory tract of the young infant with the live attenuated measles virus vaccine, since this is the natural route of infection with the measles virus. However, the live attenuated measles virus that is infectious by the parenteral route was inconsistently infectious by the intranasal route (Black et al., *New Eng. J. Med.* 263:165–169, 1960; Cutts et al., *Biologicals* 25, 323–38, 1997; Kok et al., *Trans. R. Soc. Trop. Med. Hyg.* 77:171–6, 1983; Simasathien et al., *Vaccine* 15:329–34, 1997), and this decreased infectivity was especially apparent for the Schwartz stain of measles virus vaccine which is the current vaccine strain. Presumably, during the attenuation of this virus by passage in tissue culture cells of avian origin, the virus lost a significant amount of infectivity for the upper respiratory tract of humans. Indeed, a hallmark of measles virus biology is that the virus undergoes rapid changes in biological properties when grown in vitro. Since this relatively simple route of immunization was not successful, a second approach was tried involving administration of the live virus vaccine by aerosol into the lower respiratory tract (Cutts et al., *Biologicals* 25, 323–38, 1997; Sabin et al., *J. Infect. Dis.* 152: 1231–7, 1985).

Infection of young infants by aerosol administration of measles virus vaccine was accomplished in highly controlled experimental studies, but it has not been possible to reproducibly deliver a live attenuated measles virus vaccine in field settings by aerosol to the young uncooperative infant (Cutts et al., *Biologicals* 25, 323–38, 1997). In another attempt to immunize six-month old infants, the measles vaccine virus was administered parenterally at a 10- to 100-fold increased dose (Markowitz et al., *N. Engl. J. Med.* 322:580–7, 1990). Although high-titer live measles vaccination improved seroconversion in infants 4–6 months of age, there was an associated increase in mortality in the high-titer vaccine recipients later in infancy (Gellin et al., *J. Infect. Dis.* 170:S3–14, 1994; Holt et al., *J. Infect. Dis.* 168:1087–96, 1993; Markowitz et al., *N. Engl. J. Med.* 322:580–7, 1990) and this approach to immunization has been abandoned.

A second strategy previously explored for a measles virus vaccine was the use of an inactivated measles virus vaccine, specifically, a formalin inactivated whole measles virus or a subunit virus vaccine prepared from measles virus (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996). However, the clinical use of the vaccines in the 1960's revealed a very serious complication, namely, that the inactivated virus vaccines potentiated disease rather than prevented it (Fulginiti et al., *JAMA* 202:1075–80, 1967). This was first observed with formalin-inactivated measles virus vaccine (Fulginiti et al., *JAMA* 202:1075–80, 1967). Initially, this vaccine prevented measles, but after several years vaccines lost their resistance to infection. When subsequently infected with naturally circulating measles virus, the vaccines developed an atypical illness with accentuated systemic symptoms and pneumonia (Fulginiti et al., *JAMA* 202:1075–80, 1967; Nader et al., *J. Pediatr.* 72:22–8, 1968; Rauh et al., *Am. J. Dis. Child* 109:232–7, 1965). Retrospective analysis showed that formalin inactivation destroyed the ability of the measles fusion (F) protein to induce hemolysis-inhibiting antibodies, but it did not destroy the ability of the HA (hemagglutinin or attachment) protein to induce neutralizing antibodies (Norrby et al., *J. Infect. Dis.* 132:262–9, 1975; Norrby et al., *Infect. Immun.* 11:231–9, 1975). When the immunity induced by the HA protein had waned sufficiently to permit extensive infection with wild type measles virus, an altered and sometimes more severe disease was seen at the sites of measles virus replication (Bellanti, *Pediatrics* 48:715–29, 1971; Buser, *N. Engl. J. Med.* 277: 250–1, 1967). This atypical disease is believed to be mediated in part by an altered cell-mediated immune response in which Th-2 cells were preferentially induced leading to heightened disease manifestations at the sites of viral replication (Polack et al., *Nat. Med.* 5:629–34, 1999). Because of this experience with nonliving measles virus vaccines and also because the immunogenicity of such parenterally-administered vaccines can be decreased by passively-transferred antibodies, there has been considerable reluctance to evaluate such vaccines in human infants. It should be noted that disease potentiation appears to be associated only with killed vaccines.

Yet another strategy that has been explored for developing a vaccine against measles for use in young infants has been the use of viral vectors to express a protective antigen of the measles virus (Drillien et al., *Proc. Natl. Acad. Sci. USA* 85:1252–6, 1988; Fooks et al., *J. Gen. Virol.* 79:1027–31, 1998; Schnell et al., *Proc. Natl. Acad. Sci. USA* 93:11359–65, 1996a; Taylor et al., *Virology* 187:321–8, 1992; Wild et al., *Vaccine* 8:441–2, 1990; Wild et al., *J. Gen. Virol.* 73:359–67, 1992). A variety of vectors have been explored including poxviruses such as the replication-competent vaccinia virus or the replication-defective modified vaccinia virus Ankara (MVA) stain. Replication-competent vaccinia recombinants expressing the F or HA glycoprotein of measles virus were efficacious in immunologically naive vaccines. However, when they were administered parenterally in the presence of passive antibody against measles virus, their immunogenicity and protective efficacy was largely abrogated (Galletti et al., *Vaccine* 13, 197–201, 1995; Osterhaus et al., *Vaccine* 16:1479–81, 1998; Siegrist et al., *Vaccine* 16:1409–14, 1998; Siegrist et al., *Dev. Biol. Stand.* 95:133–9, 1998).

Replication-competent vaccinia recombinants expressing the protective antigens of RSV have also been shown to be ineffective in inducing a protective immune response when they are administered parenterally in the presence of passive antibody (Murphy et al., *J. Virol.* 62:3907–10, 1988a), but they readily protected such hosts when administered intranasally. Unfortunately, replication-competent vaccinia virus recombinants are not sufficiently attenuated for use in immunocompromised hosts such as persons with human immunodeficiency virus (HIV) infection (Fenner et al., World Health Organization, Geneva, 1988; Redfield et al., *N. Engl. J. Med.* 316, 673–676, 1987), and their administration by the intranasal route even to immunocompetent individuals would be problematic. Therefore they are not being pursued as vectors for use in human infants, some of whom could be infected with HIV.

The MVA vector, which was derived by more than 500 passages in chick embryo cells (Mayr et al., *Infection* 3:6–14, 1975; Meyer et al., *J. Gen. Virol.* 72:1031–1038, 1991), has also been evaluated as a potential vaccine vector for the protective antigens of several paramyxoviruses (Durbin et al., *J. Infect. Dis.* 179:1345–51, 1999a; Wyatt et al., *Vaccine* 14, 1451–1458, 1996). MVA is a highly attenuated host range mutant that replicates well in avian cells but not in most mammalian cells, including those obtained from monkeys and humans (Blanchard et al., *J. Gen. Virol.* 79:1159–1167, 1998; Carroll et al., *Virology* 238:198–211, 1997; Drexler et al., *J. Gen. Virol.* 79, 347–352, 1998; Sutter et al., *Proc. Natl. Acad. Sci. U.S.A.* 89:10847–10851, 1992). Avipox vaccine vectors, which have a host range restriction similar to that of MVA, also have been constructed that express measles virus protective antigens (Taylor et al., *Virology* 187, 321–8, 1992). MVA is non-pathogenic in immunocompromised hosts and has been administered to large numbers of humans without incident (Mayr et al., *Zentralbl Bakteriol* [B] 167, 375–90, 1978; Stickl et al., *Dtsch. Med. Wochenschr.* 99:2386–92, 1974; Werner et al., *Archives of Virology* 64, 247–256, 1980). Unfortunately, both the immunogenicity and efficacy of MVA expressing a paramyxovirus protective antigen were abrogated in passively-immunized rhesus monkeys whether delivered by a parenteral or a topical route (Durbin et al., *Virology* 235: 323–332, 1999). The immunogenicity of DNA vaccines expressing measles virus protective antigens delivered parenterally was also decreased in passively-immunized hosts (Siegrist et al., *Dev. Biol. Stand.* 95:133–9, 1998). Replication-defective vectors expressing measles virus protective antigens are presently being evaluated, including adenovirus-measles virus HA recombinants (Fooks et al., *J. Gen. Virol.* 79:1027–31, 1998). In this context, MVA recombinants expressing parainfluenza virus antigens, unlike replication-competent vaccinia virus recombinants, lacked protective efficacy when given by a mucosal route to animals with passively-acquired antibodies, and it is unlikely that they, or the similar avipox vectors, can be used in infants with maternally-acquired measles virus antibodies.

Based on the reports summarized above, it appears unlikely that a replication-competent or replication-defective poxvirus vector, or a DNA vaccine, expressing a measles virus protective antigen will be satisfactorily immunogenic or efficacious in infants possessing passively-acquired maternal measles virus-specific antibodies.

A recently developed replication-competent virus vector expressing measles virus HA that replicates in the respiratory tract of animal hosts has been developed, namely, vesicular stomatitis virus (VSV), a rhabdovirus which naturally infects cattle but not humans (Roberts et al., *J. Virol.* 73:3723–32, 1999; Schnell et al., *Proc. Natl. Acad. Sci. USA* 93:11359–65. 1996a). Since VSV is an animal virus that can cause disease in humans, development of this recombinant for use in humans will require that a VSV backbone that is satisfactorily attenuated in human infants be first identified (Roberts et al., *J. Virol.* 73:3723–32, 1999), but such clinical studies have not been initiated.

Although there have been numerous advances toward development of effective vaccine agents against PIV and other pathogens, including measles, there remains a clear need in the art for additional tools and methods to engineer safe and effective vaccines to alleviate the serious health problems attributable to these pathogens, particularly among young infants. Among the remaining challenges in this context is the need for additional tools to generate suitably attenuated, immunogenic and genetically stable vaccine candidates for use in diverse clinical settings against one or more pathogens. To facilitate these goals, existing methods for identifying and incorporating attenuating mutations into recombinant vaccine strains and for developing vector-based vaccines and immunization methods must be expanded. Surprisingly, the present invention fulfills these needs and provides additional advantages as described herein below.

SUMMARY OF THE INVENTION

The present invention provides chimeric parainfluenza viruses (PIVs) that are infectious in humans and other mammals and are useful in various compositions to generate desired immune responses against one or more PIVs, or against a PIV and one or more additional pathogens in a host susceptible to infection therefrom. In preferred aspects, the invention provides novel methods for designing and producing attenuated, chimeric PIVs that are useful as vaccine agents for preventing and/or treating infection and related disease symptoms attributable to PIV and one or more additional pathogens. Included within these aspects of the invention are novel, isolated polynucleotide molecules and vectors incorporating such molecules that comprise a chimeric PIV genome or antigenome including a partial or complete PIV vector genome or antigenome combined or integrated with one or more heterologous genes or genome segments that encode single or multiple antigenic determinants of a heterologous pathogen or of multiple heterologous pathogens. Also provided within the invention are methods and compositions incorporating a chimeric PIV for prophylaxis and treatment of infection by both a selected PIV and one or more heterologous pathogens, e.g., a heterologous PIV or a non-PIV pathogen such as a measles virus.

The invention thus involves methods and compositions for developing live vaccine candidates based on chimeras that employ a parainfluenza virus or subviral particle that is recombinantly modified to incorporate one or more antigenic determinants of a heterologous pathogen(s). Chimeric PIVs of the invention are constructed; through a cDNA-based virus recovery system. Recombinant chimeric PIVs made from cDNA replicate independently and are propagated in a similar manner as biologically-derived viruses. The recombinant viruses are engineered to incorporate nucleotide sequences from both a vector (i.e., a "recipient" or "background") PIV genome or antigenome, and one or more heterologous "donor" sequences encoding one or more antigenic determinants of a different PIV or heterologous pathoge—to produce an infectious, chimeric virus or subviral particle. In this manner, candidate vaccine viruses are recombinantly engineered to elicit an immune response against one or more PIVs or a polyspecific response against a selected PIV and a non-PIV pathogen in a mammalian host susceptible to infection therefrom. Preferably the PIV and/or non-PIV pathogen(s) from which the heterologous sequences encoding the antigenic determinant(s) are human pathogens and the host is a human host. Also preferably, the vector PIV is a human PIV, although non-human PIVs, for example a bovine PIV (BPIV), can be employed as a vector to incorporate antigenic determinants of human PIVs and other human pathogens. Chimeric PIVs according to the invention may elicit an immune response against a specific PIV, e.g., HPIV1, HPIV2, HPIV3, or a polyspecific immune response against multiple PIVs, e.g., HPIV1 and HPIV2. Alternatively, chimeric PIVs of the invention may elicit a polyspecific immune response against one or more PIVs and a non-PIV pathogen such as measles virus.

Exemplary chimeric PIV of the invention incorporate a chimeric PIV genome or antigenome as described above, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components.

Chimeric PIV of the invention include a partial or complete "vector" PIV genome or antigenome derived from or patterned after a human PIV or non-human PIV combined with one or more heterologous gene(s) or genome segment(s) of a different PIV or other pathogen to form the chimeric PIV genome or antigenome. In preferred aspects of the invention, chimeric PIV incorporate a partial or complete human PIV vector genome or antigenome combined with one or more heterologous gene(s) or genome segment(s) from a second human PIV or a non-PIV pathogen such as measles virus.

The PIV "vector" genome or antigenome typically acts as a recipient or, carrier to which are added or incorporated one or more "donor" genes or genome segments of a heterologous pathogen. Typically, polynucleotides encoding one or more antigenic determinants of the heterologous pathogen are added to or substituted within the vector genome or antigenome to yield a chimeric PIV that thus acquires the ability to elicit an immune response in a selected host against the heterologous pathogen. In addition, the chimeric virus may exhibit other novel phenotypic characteristics compared to one or both of the vector PIV and heterologous pathogens. For example, addition or substitution of heterologous genes or genome segments within a vector PIV strain may additionally, or independently, result in an increase in attenuation, growth changes, or other desired phenotypic changes as compared with a corresponding phenotype of the unmodified vector virus and/or donor. In one aspect of the invention, chimeric PIVs are attenuated for greater efficacy as a vaccine candidate by incorporation of large polynucleotide inserts which specify the level of attenuation in the resulting chimeric virus dependent upon the size of the insert.

Preferred chimeric PIV vaccine candidates of the invention bear one or more major antigenic determinants of a human PIV, e.g., of HPIV1, HPIV2 or HPIV3, and thus elicit an effective immune response against the selected PIV in human hosts. The antigenic determinant which is specific for a selected human PIV may be encoded by the vector genome or antigenome, or may be inserted within or joined to the PIV vector genome or antigenome as a heterologous polynucleotide sequence from a different PIV. The major protective antigens of human PIVs are their HN and F glycoproteins, although other proteins can also contribute to a protective or therapeutic immune response. In this context, both humoral and cell mediated immune responses are advantageously elicited by representative vaccine candidates within the invention. Thus, polynucleotides encoding antigenic determinants that may be present in the vector genome or antigenome, or integrated therewith as a heterologous gene or genome segment, may encode one or more PIV N, P, C, D, V, M, F, HN and/or L protein(s) or selected immunogenic fragment(s) or epitope(s) thereof from any human PIV.

In addition to having one or more major antigenic determinants of a selected human PIV, preferred chimeric PIV vaccine viruses of the invention bear one or more major antigenic determinants of a second human PIV or of a non-PIV pathogen. In exemplary aspects, the chimeric PIV includes a vector genome or antigenome that is a partial or complete human PIV (HPIV) genome or antigenome, for example of HPIV3, and further includes one or more heterologous gene(s) or genome segment(s) encoding antigenic determinant(s) of at least one heterologous PIV, for example HPIV1 and/or HPIV2. Preferably, the vector genome or antigenome is a partial or complete HPIV3 genome or antigenome and the heterologous gene(s) or genome segment(s) encoding the antigenic determinant(s) is/are of one or more heterologous HPIV(s). In alternative embodiments, one or more genes or genome segments encoding one or more antigenic determinants of HPIV1 may be added to or substituted within the partial or complete HPIV3 genome or antigenome. Preferably, the antigenic determinant(s) of HPIV1 is/are selected from HPIV1 HN and F glycoproteins or comprise one or more antigenic domains, fragments or epitopes of the HN and/or F glycoproteins. In various exemplary embodiments, both of the HPIV1 genes encoding the HN and F glycoproteins are substituted for counterpart HPIV3 HN and F genes in the HPIV3 vector genome or antigenome. These constructs yield chimeric PIVs that elicit a mono- or poly-specific immune response in humans to HPIV3 and/or HPIV1.

In additional exemplary embodiments, one or more genes or genome segments encoding one or more antigenic determinants of HPIV2 is/are added to, or incorporated within, a partial or complete HPIV3 genome or antigenome, yielding a new or additional immunospecificity of the resultant chimera against HPIV2 alone, or against HPIV3 and HPIV2. In more detailed aspects, one or more HPIV2 genes or genome segments encoding one or more HN and/or F glycoproteins or antigenic domains, fragments or epitopes thereof is/are added to or incorporated within the partial or complete HPIV3 vector genome or antigenome.

In yet additional aspects of the invention, multiple heterologous genes or genome segments encoding antigenic determinants of multiple heterologous PIVs are added to or incorporated within a partial or complete PIV vector genome or antigenome, preferably an HPIV vector genome or antigenome. In one preferred embodiment, heterologous genes or genome segments encoding antigenic determinants from both HPIV1 and HPIV2 are added to or incorporated within a partial or complete HPIV3 vector genome or antigenome. In more detailed aspects, one or more HPIV1 genes or genome segments encoding one or more HN and/or F glycoproteins (or antigenic domains, fragments or epitopes thereof) and one or more HPIV2 genes or genome segments encoding HN and/or F glycoproteins, antigenic domains, fragments or epitopes, is/are added to or incorporated within the partial or complete HPIV3 vector genome or antigenome. In one example, both HPIV1 genes encoding HN and F glycoproteins are substituted for counterpart HPIV3 HN and F genes to form a chimeric HPIV3-1 vector genome or antigenome, which is further modified by addition or incorporation of one or more genes or gene segments encoding single or multiple antigenic determinants of HPIV2. This is readily achieved within the invention, for example, by adding or substituting a transcription unit comprising an open reading frame (ORF) of an HPIV2 HN within the chimeric HPIV3-1 vector genome or antigenome. Following this method, specific constructs exemplifying the invention are provided which yield chimeric PIVs having antigenic determinants of both HPIV1 and HPIV2, as exemplified by the vaccine candidates rPIV3-1.2HN and rPIV3-1cp45.2HN described herein below.

In alternative aspects of the invention, chimeric PIVs of the invention are based on a human PIV vector genome or antigenome which is employed as a recipient for incorporation of major antigenic determinants from a non-PIV pathogen. Pathogens from which one or more antigenic determinants may be adopted into the chimeric PIV vaccine candidate include, but are not limited to, measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses. This assemblage of pathogens that may be thus targeted for vaccine development according to the methods of the invention is exemplary only, and those skilled in the art will understand that the use of PIV vectors for carrying antigenic determinants extends broadly to a large host of additional pathogens.

This, in various alternative aspects of the invention, a human PIV genome or antigenome can be employed as a vector for incorporation of one or more major antigenic determinants from a wide range of non-PIV pathogens. Representative major antigens that can be incorporated within chimeric PIVs of the invention include, but are not limited to the measles virus HA and F proteins; the F, G, SH and M2 proteins of subgroup A and subgroup B respiratory syncytial virus, mumps virus HN and F proteins, human papilloma virus L1 protein, type 1 or type 2 human immunodeficiency virus gp 160 protein, herpes simplex virus and cytomegalovirus gB, gC, gD, gE, gG, gH, gI, gJ, gK, gL, and gM proteins, rabies virus G Protein, Epstein Barr Virus gp350 protein; filovirus G protein, bunyavirus G protein, flavivirus E and NS1 proteins, and alphavirus E protein.

Various human PIV vectors can be employed to carry heterologous antigenic determinants of non-PIV pathogens to elicit one or more specific humoral or cell mediated immune responses against the antigenic determinant(s) carried by the chimeric vaccine virus and hence elicit an effective immune response against the wild-type "donor" pathogen in susceptible hosts. In preferred embodiments, one or more heterologous genes or genome segments from the donor pathogen is joined to or inserted within a partial or complete HPIV3 genome or antigenome. Alternatively, the heterologous gene or genome segment may be incorporated within a chimeric HPIV vector genome or antigenome, for example a partial or complete HPIV3 genome or antigenome bearing one or more genes or genome segments of a heterologous PIV. For example, the gene(s) or genome segment(s) encoding the antigenic determinant(s) of a non-PIV pathogen may be combined with a partial or complete chimeric HPIV3-1 vector genome or antigenome, e.g., as described above having one or both HPIV1 genes encoding HN and F glycoproteins substituted for counterpart HPIV3 HN and F genes. Alternatively, the gene(s) or genome segment(s) encoding the antigenic determinant(s) of a non-PIV pathogen may be combined with a partial or complete chimeric genome or antigenome that incorporates single or multiple antigenic determinants of HPIV2, e.g., an HPIV2

HN gene, within an HPIV1 or HPIV3 vector genome or antigenome, or a chimeric HPIV3-1 vector genome or antigemome as described above. The heterologous gene(s) or genome segment(s) encoding one or more measles antigenic determinant(s) may be combined with any of the PIV vectors or chimeric PIV vectors disclosed herein. In the examples provided herein, the vector genome or antigenome is a partial or complete HPIV3 genome or antigenome, or a chimeric HPIV genome or antigenome comprising a partial or complete HPIV3 genome or antigenome having one or more genes or genome segments encoding antigenic determinant(s) of a heterologous HPIV added or incorporated therein. In one such chimeric construct, a transcription unit comprising an open reading frame (ORF) of a measles virus HA gene is added to a HPIV3 vector genome or antigenome at various positions, yielding exemplary chimeric PIV/measles vaccine candidates rPIV3 (HA HN-L), rPIV3 (HA N-P), rcp45L(HA N-P), rPIV3(HA P-M), or rcp45L(HA P-M).

To construct chimeric PIV clones of the invention, a heterologous gene or genome segment of a donor PIV or non-PIV pathogen may be added or substituted at any operable position in the vector genome or antigenome. Often, the position of a gene or gene segment substitution will correspond to a wild-type gene order position of a counterpart gene or genome segment within the partial or complete PIV vector genome or antigenome. In other embodiments, the heterologous gene or genome segment is added or substituted at a position that is more promoter-proximal or promotor-distal compared to a wild-type gene order position of a counterpart gene or genome segment within the background genome or antigenome, to enhance or reduce expression, respectively, of the heterologous gene or genome segment.

In preferred detailed aspects of the invention, a heterologous genome segment, for example a genome segment encoding an immunogenic ectodomain of a heterologous PIV or non-PIV pathogen, can be substituted for a corresponding genome segment in a counterpart gene in the PIV vector genome or antigenome to yield constructs encoding chimeric proteins, e.g. fusion proteins having a cytoplasmic tail and/or transmembrane domain of one PIV fused to an ectodomain of another PIV or non-PIV pathogen. In alternate embodiments, a chimeric PIV genome or antigenome may be engineered to encode a polyspecific chimeric glycoprotein in the recombinant virus or subviral particle having immunogenic glycoprotein domains or epitopes from two different pathogens. In yet additional embodiments, heterologous genes or genome segments from one PIV or non-PIV pathogen can be added (i.e., without substitution) within a PIV vector genome or antigenome to create novel immunogenic properties within the resultant clone. In these cases, the heterologous gene or genome segment may be added as a supernumerary gene or genome segment, optionally for the additional purpose of attenuating the resultant chimeric virus, in combination with a complete PIV vector genome or antigenome. Alternatively, the heterologous gene or genome segment may be added in conjunction with deletion of a selected gene or genome segment in the vector genome or antigenome.

In preferred embodiments of the invention, the heterologous gene or genome segment is added at an intergenic position within the partial or complete PIV vector genome or antigenome. Alternatively, the gene or genome segment can be inserted within other noncoding regions of the genome, for example, within 5' or 3' noncoding regions or in other positions where noncoding nucleotides occur within the vector genome or antigenome. In some instances, it may be desired to insert the heterologous gene or genome segment at a non-coding site corresponding to or overlapping a cis-acting regulatory sequence within the vector genome or antigenome, e.g., within a sequence required for efficient replication, transcription, and/or translation. These regions of the vector genome or antigenome represent target sites for disruption or modification of regulatory functions associated with introduction of the heterologous gene or genome segment.

For the preferred purpose of constructing candidate vaccine viruses for clinical use, it is often desirable to adjust the attenuation phenotype of chimeric PIV of the invention by introducing additional mutations that increase or decrease the level of attenuation in the recombinant virus. Therefore, in additional aspects of the invention, attenuated, chimeric PIVs are produced in which the chimeric genome or antigenome is further modified by introducing one or more attenuating mutations that specify an attenuating phenotype in the resultant virus or subviral particle. These attenuating mutations may be generated de novo and tested for attenuating effects according to well known rational design mutagenesis strategies. Alternatively, the attenuating mutations may be identified in existing biologically derived mutant PIV or other viruses and thereafter incorporated into a chimeric PIV of the invention.

Preferred attenuating mutations in the latter context are readily identified and incorporated into a chimeric PIV, either by inserting the mutation within the vector genome or antigenome by cloning or mutagenizing the vector genome or antigenome to contain the attenuating mutation. Preferably, attenuating mutations are engineered within the vector genome or antigenome and are imported or copied from biologically derived, attenuated PIV mutants. These are recognized to include, for example, cold passaged (cp), cold adapted (ca), host range restricted (hr), small plaque (sp), and/or temperature sensitive (ts) PIV mutants. In exemplary embodiments, one or more attenuating mutations present in the well characterized JS HPIV3 cp45 mutant strain are incorporated within chimeric PIV of the invention, preferably including one or more mutations identified in the polymerase L protein, e.g., at a position corresponding to $Tyr_{942}$, $Leu_{992}$, or $Thr_{1558}$ of JS cp45. Alternatively or additionally, attenuating mutations present in the JS HPIV3 cp45 mutant strain are introduced in the N protein of chimeric PIV clones, for example which encode amino acid substitution(s) at a position corresponding to residues $Val_{96}$ or $Ser_{389}$ of JS cp45. Yet additional useful attenuating mutations encode amino acid substitution(s) in the C protein, e.g., at a position corresponding to $Ile_{96}$ of JS cp45. Other mutations identified in PIV3 JS cp45 that can be adopted to adjust attenuation of a chimeric PIV of the invention are found in the F protein, e.g., at a position corresponding to $Ile_{420}$ or $Ala_{450}$ of JS cp45, and in the HN protein, e.g., at a position corresponding to residue $Val_{384}$ of JS cp45.

Attenuating mutations from biologically derived PIV mutants for incorporation into chimeric PIV of the invention also include mutations in noncoding portions of the PIV genome or antigenome, for example in a 3' leader sequence. Exemplary mutations in this context may be engineered at a position in the 3' leader of a recombinant virus at a position corresponding to nucleotide 23, 24, 28, or 45 of JS cp45. Yet additional exemplary mutations may be engineered in the N gene start sequence, for example by changing one or more nucleotides in the N gene start sequence, e.g., at a position corresponding to nucleotide 62 of JS cp45.

From PIV3 JS cp45 and other biologically derived PIV mutants, a large "menu" of attenuating mutations is provided, each of which mutations can be combined with any other mutation(s) for finely adjusting the level of attenuation in chimeric PIV vaccine candidates of the invention. In exemplary embodiments, chimeric PIVs are constructed which include one or more, and preferably two or more, mutations of HPIV3 JS cp45. Thus, chimeric PIVs of the invention selected for vaccine use often have two and sometimes three or more attenuating mutations from biologically derived PIV mutants or like model sources to achieve a satisfactory level of attenuation for broad clinical use. Preferably, these attenuating mutations incorporated within recombinant chimeric PIVs of the invention are stabilized by multiple nucleotide substitutions in a codon specifying the mutation.

Additional attenuating mutations can be readily adopted or engineered within chimeric PIVs of the invention that are identified in other viruses, particularly other nonsegmented negative stranded RNA viruses. This is accomplished by mapping a mutation identified in a heterologous negative stranded RNA virus to a corresponding, homologous site in a PIV vector genome or antigenome (or heterologous insert in the PIV chimera) and mutating the existing sequence in the "recipient" to the mutant genotype (either by an identical or conservative mutation), as described in U.S. Provisional Patent Application Ser. No. 60/129,006, filed on Apr. 13, 1999, incorporated herein by reference.

In yet additional aspects of the invention, chimeric PIVs, with or without attenuating mutations modeled after biologically derived attenuated mutant viruses, are constructed to have additional nucleotide modification(s) to yield a desired phenotypic, structural, or functional change. Typically, the selected nucleotide modification will be made within the partial or complete PIV vector genome, but such modifications can be made as well within any heterologous gene or genome segment that contributes to the chimeric clone. These modifications preferably specify a desired phenotypic change, for example a change in growth characteristics, attenuation, temperature-sensitivity, cold-adaptation, plaque size, host range restriction, or immunogenicity. Structural changes in this context include introduction or ablation of restriction sites into PIV encoding cDNAs for ease of manipulation and identification.

In preferred embodiments, nucleotide changes within the genome or antigenome of a chimeric PIV include modification of a viral gene by partial or complete deletion of the gene or reduction or ablation (knock-out) of its expression. Target genes for mutation in this context include any of the PIV genes, including the nucleocapsid protein N, phosphoprotein P, large polymerase subunit L, matrix protein M, hemagglutinin-neuraminidase protein HN, fusion protein F, and the products of the C, D and V open reading frames (ORFs). To the extent that the recombinant virus remains viable and infectious, each of these proteins can be selectively deleted, substituted or rearranged, in whole or in part, alone or in combination with other desired modifications, to achieve novel deletion or knock out mutants. For example, one or more of the C, D, and/or V genes may be deleted in whole or in part, or its expression reduced or ablated (e.g., by introduction of a stop codon, by a mutation in an RNA editing site, by a mutation that alters the amino acid specified by an initiation codon, or by a frame shift mutation in the targeted ORF(s)). In one embodiment, a mutation can be made in the editing site that prevents editing and ablates expression of proteins whose mRNA is generated by RNA editing (Kato et al., *EMBO* 16:578–587, 1997 and Schneider et al., *Virology* 227:314–322, 1997, incorporated herein by reference). Alternatively, one or more of the C, D, and/or V ORF(s) can be deleted in whole or in part to alter the phenotype of the resultant recombinant clone to improve growth, attenuation, immunogenicity or other desired phenotypic characteristics (see, U.S. patent application Ser. No. 09/350,821, filed by Durbin et al. on Jul. 9, 1999, incorporated herein by reference).

Alternative nucleotide modifications in chimeric PIV of the invention include a deletion, insertion, addition or rearrangement of a cis-acting regulatory sequence for a selected gene in the recombinant genome or antigenome. In one example, a cis-acting regulatory sequence of one PIV gene is changed to correspond to a heterologous regulatory sequence, which may be a counterpart cis-acting regulatory sequence of the same gene in a different PIV, or a cis-acting regulatory sequence of a different PIV gene. For example, a gene end signal may be modified by conversion or substitution to a gene end signal of a different gene in the same PIV strain. In other embodiments, the nucleotide modification may comprise an insertion, deletion, substitution, or rearrangement of a translational start site within the recombinant genome or antigenome, e.g., to ablate an alternative translational start site for a selected form of a protein.

In addition, a variety of other genetic alterations can be produced in a chimeric PIV genome or antigenome, alone or together with one or more attenuating mutations adopted from a biologically derived mutant PIV. For example, genes or genome segments from non-PIV sources may be inserted in whole or in part. In one such aspect, the invention provides methods for attenuating chimeric PIV vaccine candidates based on host range effects due to the introduction of one or more gene(s) or genome segment(s) from, e.g., a non-human PIV into a human PIV vector-based chimeric virus. For example, host range attenuation can be conferred on a HPIV-vector based chimeric construct by introduction of nucleotide sequences from a bovine PIV (BPIV) (see, e.g., (e.g., as disclosed in U.S. Provisional Application Ser. No. 60/143,134 filed on Jul. 9, 1999, incorporated herein by reference). These effects are attributed to structural and functional divergence between the vector and donor viruses and provide a stable basis for attenuation. For example, between HPIV3 and BPIV3 the percent amino acid identity for each of the N proteins is 86%, for P is 65%, M 93%, F 83%, HN 77%, and L 91%. All of these proteins are therefore candidates for introduction into a HPIV vector to yield an attenuated chimeric virus which cannot readily be altered by reversion. In exemplary embodiments, the vector genome or antigenome is an HPIV3 genome or antigenome and the heterologous gene or genome segment is a N ORF derived from a selected BPIV3 strain.

In yet additional aspects of the invention, the order of genes can be changed to cause attenuation or reduce or enhance expression of a particular gene. Alternatively, a PIV genome promoter can be replaced with its antigenome counterpart to yield additional desired phenotypic changes. Different or additional modifications in the recombinant genome or antigenome can be made to facilitate manipulations, such as the insertion of unique restriction sites in various intergenic regions or elsewhere. Nontranslated gene sequences can be removed to increase capacity for inserting foreign sequences.

In yet additional aspects, polynucleotide molecules or vectors encoding the chimeric PIV genome or antigenome can be modified to encode non-PIV sequences, e.g., a cytokine, a T-helper epitope, a restriction site marker, or a protein or immunogenic epitope of a microbial pathogen (e.g., virus, bacterium or fungus) capable of eliciting a protective immune response in an intended host. In one such embodiment, chimeric PIVs are constructed that incorporate a gene encoding a cytokine to yield novel phenotypic and immunogenic effects in the resulting chimera.

In addition to providing chimeric PIV for vaccine use, the invention provides related cDNA clones and vectors which incorporate a PIV vector genome or antigenome and heterologous polynucleotide(s) encoding one or more heterologous antigenic determinants, wherein the clones and vectors optionally incorporate mutations and related modifications specifying one or more attenuating mutations or other phenotypic changes as described above. Heterologous sequences encoding antigenic determinants and/or specifying desired phenotypic changes are introduced in selected combinations, e.g., into an isolated polynucleotide which is a recombinant cDNA vector genome or antigenome, to produce a suitably attenuated, infectious virus or subviral particle in accordance with the methods described herein. These methods, coupled with routine phenotypic evaluation, provide a large assemblage of chimeric PIVs having such desired characteristics as attenuation, temperature sensitivity, altered immunogenicity, cold-adaptation, small plaque size, host range restriction, genetic stability, etc. Preferred vaccine viruses among these candidates are attenuated and yet sufficiently immunogenic to elicit a protective immune response in the vaccinated mammalian host.

In related aspects of the invention, compositions (e.g., isolated polynucleotides and vectors incorporating a chimeric PIV-encoding cDNA) and methods are provided for producing an isolated infectious chimeric PIV. Included within these aspects of the invention are novel, isolated polynucleotide molecules and vectors incorporating such molecules that comprise a chimeric PIV genome or antigenome. Also provided is the same or different expression vector comprising one or more isolated polynucleotide molecules encoding N, P, and L proteins. These proteins can alternatively be expressed directly from the genome or antigenome cDNA. The vector(s) is/are preferably expressed or coexpressed in a cell or cell-free lysate, thereby producing an infectious chimeric parainfluenza virus particle or subviral particle.

The above methods and compositions for producing chimeric PIV yield infectious viral or subviral particles, or derivatives thereof. An infectious virus is comparable to the authentic PIV particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, and L proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell-free lysate containing an expression vector which comprises an isolated polynucleotide molecule comprising a chimeric PIV genome or antigenome as described above, and an expression vector (the same or different vector) which comprises one or more isolated polynucleotide molecules encoding the N, P, and L proteins of PIV. One or more of these proteins also can be expressed from the genome or antigenome cDNA. Upon expression the genome or antigenome and N, P and L proteins combine to produce an infectious chimeric parainfluenza virus or subviral particle.

In other embodiments of the invention a cell or cell-free expression system (e.g., a cell-free lysate) is provided which incorporates an expression vector comprising an isolated polynucleotide molecule encoding a chimeric PIV, and an expression vector comprising one or more isolated polynucleotide molecules encoding N, P, and L proteins of a PIV. Upon expression, the genome or antigenome and N, P, and L proteins combine to produce an infectious PIV particle, such as a viral or subviral particle.

The chimeric PIVs of the invention are useful in various compositions to generate a desired immune response against one or more PIVs, or against PIV and a non-PIV pathogen, in a host susceptible to infection therefrom. Chimeric PIV recombinants are capable of eliciting a mono- or polyspecific protective immune response in an infected mammalian host, yet are sufficiently attenuated so as to not cause unacceptable symptoms of disease in the immunized host. The attenuated virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated chimeric parainfluenza virus or subviral particle as described above. In preferred embodiments, the vaccine is comprised of a chimeric PIV having at least one, and preferably two or more additional mutations or other nucleotide modifications that specify a suitable balance of attenuation and immunogenicity. The vaccine can be formulated in a dose of $10^3$ to $10^7$ PFU of attenuated virus. The vaccine may comprise attenuated chimeric PIV that elicits an immune response against a single PIV strain or against multiple PIV strains or groups. In this regard, chimeric PIV can be combined in vaccine formulations with other PIV vaccine strains, or with other viral vaccine viruses such as RSV.

In related aspects, the invention provides a method for stimulating the immune system of an individual to elicit an immune response against one or more PIVs, or against PIV and a non-PIV pathogen, in a mammalian subject. The method comprises administering a formulation of an immunologically sufficient amount a chimeric PIV in a physiologically acceptable carrier and/or adjuvant. In one embodiment; the immunogenic composition is a vaccine comprised of a chimeric PIV having at least one, and preferably two or more attenuating mutations or other nucleotide modifications specifying a desired phenotype and/or level of attenuation as described above. The vaccine can be formulated in a dose of $10^3$ to $10^7$ PFU of attenuated virus. The vaccine may comprise an attenuated chimeric PIV that elicits an immune response against a single PIV, against multiple PIVs, e.g., HPIV1 and HPIV3, or against one or more PIV(s) and a non-PIV pathogen such as measles or RSV. In this context, chimeric PIVs can elicit a monospecific immune response or a polyspecific immune response against multiple PIVs, or against one or more PIV(s) and a non-PIV pathogen. Alternatively, chimeric PIV having different immunogenic characteristics can be combined in a vaccine mixture or administered separately in a coordinated treatment protocol to elicit more effective protection against one PIV, against multiple PIVs, or against one or more PIV(s) and a non-PIV pathogen such as measles or RSV. Preferably the immunogenic compositions of the invention are administered to the upper respiratory tract, e.g., by spray, droplet or aerosol. Preferably the immunogenic composition is administered to the upper respiratory tract, e.g., by spray, droplet or aerosol.

RSV and PIV3 cause significant amount of illness within the first four months of life, whereas most of the illness caused by PIV1 and PIV2 occurs after six months of age (Collins et al., In *Fields Virology*, Vol. 1, pp. 1205–1243, Lippincott-Raven Publishers, Philadelphia, 1996; Reed et al., *J. Infect. Dis.* 175:807–13, 1997). A preferred immunization sequence employing live attenuated RSV and PIV vaccines is to administer RSV and PIV3 as early as one month of age (e.g., at one and two months of age) followed by a bivalent PIV1 and PIV2 vaccine at four and six months of age. It is thus desirable to employ the methods of the invention to administer multiple PIV vaccines, including one or more chimeric PIV vaccines, coordinately, e.g., simultaneously in a mixture or separately in a defined temporal sequence (e.g., in a daily or weekly sequence), wherein each vaccine virus preferably expresses a different heterologous protective antigen. Such a coordinate/sequential immunization strategy, which is able to induce secondary antibody responses to multiple viral respiratory pathogens, provides a highly powerful and extremely flexible immunization regimen that is driven by the need to immunize against each of the three PIV viruses and other pathogens in early infancy.

Importantly, the presence of multiple PIV serotypes and their unique epidemiology with PIV3 disease occurring at an earlier age than that of PIV1 and PIV2 makes it desirable to sequentially immunize an infant with different PIV vectors each expressing the same heterologous antigenic determinant such as the measles virus HA. This sequential immunization permits the induction of the high titer of antibody to the heterologous protein that is characteristic of the secondary antibody response. In one embodiment, early infants (e.g. 2–4 month old infants) can be immunized with an attenuated chimeric virus of the invention, for example a chimeric HPIV3 expressing the measles virus HA protein and also adapted to elicit an immune response against HPIV3, such as rcp45L(HA P-M). Subsequently, e.g., at four months of age the infant is again immunized but with a different, secondary vector construct, such as the rPIV3-1 cp45L virus expressing the measles virus HA gene and the HPIV1 antigenic determinants as the functional, obligate glycoproteins of the vector. Following the first vaccination, the vaccine will elicit a primary antibody response to both the PIV3 HN and F proteins and to the measles virus HA protein, but not to the PIV1 HN and F protein. Upon secondary immunization with the rPIV3-1 cp45L expressing the measles virus HA, the vaccine will be readily infected with the vaccine because of the absence of antibody to the PIV1 HN and F proteins and will develop both a primary antibody response to the PIV1 HN and F protective antigens and a high titered secondary antibody response to the heterologous measles virus HA protein. A similar sequential immunization schedule can be developed where immunity is sequentially elicited against HPIV3 and then HPIV2 by one or more of the chimeric vaccine viruses disclosed herein, simultaneous with stimulation of an initial and then secondary, high titer protective response against measles or another non-PIV pathogen. This sequential immunization strategy, preferably employing different serotypes of PIV as primary and secondary vectors, effectively circumvents immunity that is induced to the primary vector, a factor ultimately limiting the usefulness of vectors with only one serotype. The success of sequential immunization with rPIV3 and rPIV3-1 virus vaccine candidates as described above has been demonstrated. (Tao et al., *Vaccine* 17:1100–8, 1999).

BRIEF DESCRIPTION OF THE DRAWINGS

FIGS. 1A and 1B illustrate insertion of the HA gene of measles virus into the HPIV3 genome (Note: all of the figures presented herein and related descriptions refer to the positive-sense antigenome of HPIV3, 5' to 3').

FIG. 1A provides a diagram (top; not to scale) of the 1926 nt insert containing the complete open reading frame of the hemagglutinin (HA) gene of the Edmonston wildtype strain of measles virus engineered to express the measles virus HA from an extra transcriptional unit. The insert contains, in 5' to 3' order: an Af/II site; nts 3699–3731 from the HPIV3 antigenome which contains the P/M gene junction, including downstream noncoding sequence for the P gene, its gene-end signal, the intergenic region, and the M gene-start signal; three additional nts (GCG); the complete measles virus HA ORF; HPIV3 nt 3594–3623 from the downstream noncoding region of the P gene; and a second Af/II site. FIG. 1A, Panel 1 illustrates the complete antigenome of the JS wildtype strain of HPIV3 (rPIV3) with the introduced Af/II site in the 3'-noncoding region of the N gene before (top) and after (bottom) insertion of the measles HA ORF. FIG. 1A, Panel 2 illustrates the complete antigenome of the JS wildtype strain of HPIV3 (rPIV3) with the introduced Af/II site in the 3'-noncoding region of the P gene before (top) and after (bottom) insertion of the measles HA ORF. SEQ ID NO: 1 and SEQ ID NO: 2 are shown in FIG. 1A.

FIG. 1B provides a diagram (top; not to scale) of the 2028 nt insert containing the compete ORF of the HA gene of measles virus. The insert contains, in 5' to 3' order: a StuI site; nts 8602 to 8620 from the HPIV3 antigenome, which consist of downstream noncoding sequence from the HN gene and its gene-end signal; the conserved HPIV3 intergenic trinucleotide; nts 6733 to 6805 from the HPIV3 antigenome, which contains the HN gene-start and upstream noncoding region; the measles virus HA ORF; HPIV3 nts 8525–8597, which are downstream noncoding sequences from the HN gene; and a second StuI site. The construction is designed to, upon insertion, regenerate the HPIV3 HN gene containing the StuI site, and place the measles virus ORF directly after it flanked by the transcription signals and noncoding region of the HPIV3 HN gene. The complete antigenome of HPIV3 JS wildtype (rPIV3) with the introduced StuI site at nt position 8600 in the 3'-noncoding region of the HN gene is illustrated in the next (middle) diagram. Below is the antigenome of HPIV3 expressing the measles HA protein inserted into the StuI site. The HA cDNA used for this insertion came from an existing plasmid, rather than from the Edmonston wild type measles virus, which was used for the insertions in the N/P and P/M regions. This cDNA had two amino acid differences from the HA protein inserted in FIG. 1A, and their location in the HA gene of measles virus is indicated by the asterisks in FIG. 1B. SEQ ID NO: 3 and SEQ ID NO: 4 are shown in FIG. 1B.

DESCRIPTION OF THE SPECIFIC EMBODIMENTS

Figure 1A:
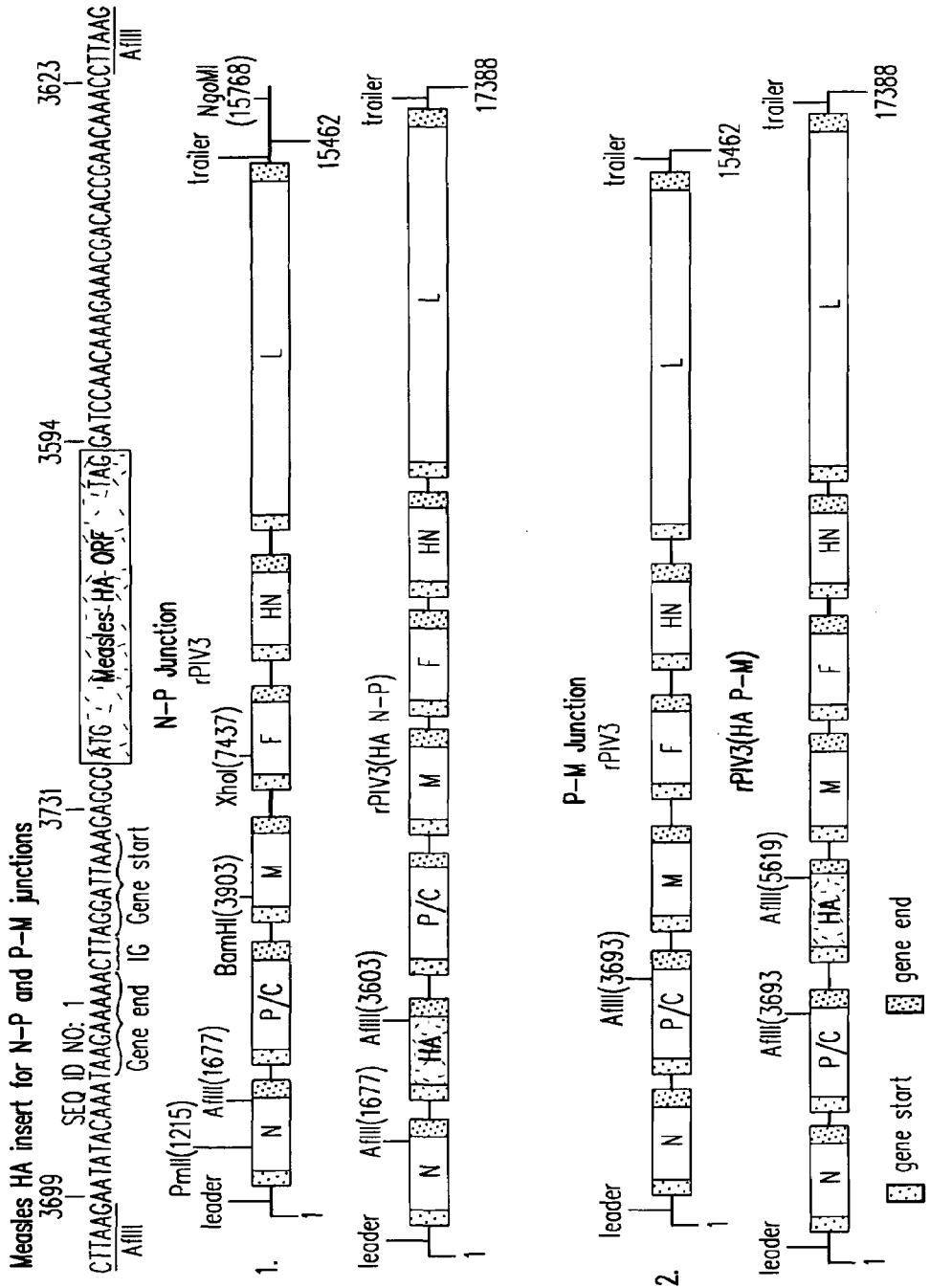

The instant invention provides methods and compositions for the production and use of novel, chimeric parainfluenza viruses (PIVs) and associated vaccines. The chimeric viruses of the invention are infectious and immunogenic in humans and other mammals and are useful for generating immune responses against one or more PIVs, for example against one or more human PIVs (HPIVs). Alternatively, chimeric PIVs are provided that elicit an immune response against a selected PIV and one or more additional pathogens, for example against both a HPIV and measles virus. The immune response elicited can involve either or both humoral and/or cell mediated responses. Preferably, chimeric PIVs of the invention are attenuated to yield a desired balance of attenuation and immunogenicity for vaccine use.

The invention thus provides novel methods for designing and producing attenuated, chimeric PIVs that are useful as vaccine agents for preventing and/or treating infection and related disease symptoms attributable to PIV and other pathogens. In accordance with the methods of the invention, chimeric parainfluenza viruses or subviral particles are constructed using a PIV "vector" genome or antigenome that is recombinantly modified to incorporate one or more antigenic determinants of a heterologous pathogen. The vector genome or antigenome is comprised of a partial or complete PIV genome or antigenome, which may itself incorporate nucleotide modifications such as attenuating mutations. The vector genome or antigenome is modified to form a chimeric structure through incorporation of a heterologous gene or genome segment. More specifically, chimeric PIVs of the invention are constructed through a cDNA-based virus recovery system that yields recombinant viruses that incorporate a partial or complete vector or "background" PIV genome or antigenome combined with one or more "donor" nucleotide sequences encoding the heterologous antigenic determinant(s). Preferably the PIV vector comprises a HPIV genome or antigenome, although non-human PIVs, for example a bovine PIV (BPIV), can be employed as a vector to incorporate antigenic determinants of human PIVs and other human pathogens. In exemplary embodiments described herein, a human PIV3 (HPIV3) vector genome or antigenome is modified to incorporate one or more genes or genome segments that encode antigenic determinant(s) of one or more heterologous PIVs (e.g., HPIV1 and/or HPIV2), and/or a non-PIV pathogen (e.g., measles virus). Thus constructed, chimeric PIVs of the invention may elicit an immune response against a specific PIV, e.g., HPIV1, HPIV2, and/or HPIV3, or against a non-PIV pathogen. Alternatively, compositions and methods are provided for eliciting a polyspecific immune response against multiple PIVs, e.g., HPIV1 and HPIV3, or against one or more HPIVs and a non-PIV pathogen such as measles virus.

Exemplary chimeric PIV of the invention incorporate a chimeric PIV genome or antigenome as described above, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components. Additional PIV proteins may be included in various combinations to provide a range of infectious subviral particles, up to a complete viral particle or a viral particle containing supernumerary proteins, antigenic determinants or other additional components.

In preferred aspects of the invention, chimeric PIV incorporate a partial or complete human PIV vector genome or antigenome combined with one or more heterologous gene(s) or genome segment(s) from a second human PIV or a non-PIV pathogen such as measles virus. The PIV "vector" genome or antigenome typically acts as a recipient or carrier to which are added or incorporated one or more "donor" genes or genome segments of a heterologous pathogen. Typically, polynucleotides encoding one or more antigenic determinants of the heterologous pathogen are added to or substituted within the vector genome or antigenome to yield a chimeric PIV that thus acquires the ability to elicit an immune response in a selected host against the heterologous pathogen. In addition, the chimeric virus may exhibit other novel phenotypic characteristics compared to one or both of the vector PIV and heterologous pathogens.

The partial or complete vector genome or antigenome generally acts as a backbone into which heterologous genes or genome segments of a different pathogen are incorporated. Often, the heterologous pathogen is a different PIV from which one or more gene(s) or genome segment(s) is/are of are combined with, or substituted within, the vector genome or antigenome. In addition to providing novel immunogenic characteristics, the addition or substitution of heterologous genes or genome segments within the vector PIV strain may confer an increase or decrease in attenuation, growth changes, or other desired phenotypic changes as compared with the corresponding phenotype(s) of the unmodified vector and donor viruses. Heterologous genes and genome segments from other PIVs that may be selected as inserts or additions within chimeric PIV of the invention include genes or genome segments encoding the PIV N, P, C, D, V, M, F, HN and/or L protein(s) or one or more antigenic determinant(s) thereof.

Heterologous genes or genome segments of one PIV may be added as a supernumerary genomic element to a partial or complete genome or antigenome of a different PIV. Alternatively, one or more heterologous gene(s) or genome segment(s) of one PIV may be substituted at a position corresponding to a wild-type gene order position of a counterpart gene(s) or genome segment(s) that is deleted within the PIV vector genome or antigenome. In yet additional embodiments, the heterologous gene or genome segment is added or substituted at a position that is more promoter-proximal or promotor-distal compared to a wild-type gene order position of the counterpart gene or genome segment within the vector genome or antigenome to enhance or reduce, respectively, expression of the heterologous gene or genome segment.

The introduction of heterologous immunogenic proteins, protein domains and immunogenic epitopes to produce chimeric PIV is particularly useful to generate novel immune responses in an immunized host. Addition or substitution of an immunogenic gene or genome segment from one, donor pathogen within a recipient PIV vector genome or antigenome can generate an immune response directed against the donor pathogen, the PIV vector, or against both the donor pathogen and vector.

To achieve this purpose, chimeric PIV may be constructed that express a chimeric protein, for example an immunogenic glycoprotein having a cytoplasmic tail and/or transmembrane domain specific to a vector fused to a heterologous ectodomain of a different PIV or non-PIV pathogen to provide a fusion protein that elicits an immune response against the heterologous pathogen. For example, a heterologous genome segment encoding a glycoprotein ectodomain from a human PIV1 HN or F glycoprotein may be joined with a genome segment encoding the corresponding HPIV3 HN or F glycoprotein cytoplasmic and transmembrane domains to form a HPIV3-1 chimeric glycoprotein that elicits an immune response against HPIV1.

Briefly, PIV of the invention expressing a chimeric glycoprotein comprise a major nucleocapsid (N) protein, a nucleocapsid phosphoprotein (P), a large polymerase protein (L), and a HPIV vector genome or antigenome that is modified to encode a chimeric glycoprotein. The chimeric glycoprotein incorporates one or more heterologous antigenic domains, fragments, or epitopes of a second, antigenically distinct HPIV: Preferably, this is achieved by substitution within the HPIV vector genome or antigenome of one or more heterologous genome segments of the second HPIV that encode one or more antigenic domains, fragments, or epitopes, whereby the genome or antigenome encodes the chimeric glycoprotein that is antigenically distinct from the parent, vector virus.

In more detailed aspects, the heterologous genome segment or segments preferably encode a glycoprotein ectodomain or immunogenic portion or epitope thereof, and optionally include other portions of the heterologous or "donor" glycoprotein, for example both an ectodomain and transmembrane region that are substituted for counterpart glycoprotein ecto- and transmembrane domains in the vector genome or antigenome. Preferred chimeric glycoproteins in this context may be selected from HPIV HN and/or F glycoproteins, and the vector genome or antigenome may be modified to encode multiple chimeric glycoproteins. In preferred embodiments, the HPIV vector genome or antigenome is a partial HPIV3 genome or antigenome and the second, antigenically distinct HPIV is either HPIV1 or HPIV2. In one exemplary embodiment described below, both glycoprotein ectodomain(s) of HPIV2 HN and F glycoproteins are substituted for corresponding HN and F glycoprotein ectodomains in the HPIV3 vector genome or antigenome. In another exemplary embodiment, PIV2 ectodomain and transmembrane regions of one or both HN and/or F glycoproteins are fused to one or more corresponding PIV3 cytoplasmic tail region(s) to form the chimeric glycoprotein.

To construct chimeric PIVs of the invention carrying a heterologous antigenic determinant of a non-PIV pathogen, a heterologous gene or genome segment of the donor pathogen may be added or substituted at any operable position in the vector genome or antigenome. In one embodiment, heterologous genes or genome segments from a non-PIV pathogen can be added (i.e., without substitution) within a PIV vector genome or antigenome to create novel immunogenic properties within the resultant clone. In these cases, the heterologous gene or genome segment may be added as a supernumerary gene or genome segment, optionally for the additional purpose of attenuating the resultant chimeric virus, in combination with a complete PIV vector genome or antigenome. Alternatively, the heterologous gene or genome segment may be added in conjunction with deletion of a selected gene or genome segment in the vector genome or antigenome.

In preferred embodiments of the invention, the heterologous gene or genome segment is added at an intergenic position within the partial or complete PIV vector genome or antigenome. Alternatively, the gene or genome segment can be inserted within other noncoding regions of the genome, for example, within 5' or 3' noncoding regions or in other positions where noncoding nucleotides occur within the vector genome or antigenome. In one aspect, the heterologous gene or genome segment is inserted at a non-coding site overlapping a cis-acting regulatory sequence within the vector genome or antigenome, e.g., within a sequence required for efficient replication, transcription, and/or translation. These regions of the vector genome or antigenome represent target sites for disruption or modification of regulatory functions associated with introduction of the heterologous gene or genome segment.

As used herein, the term "gene" generally refers to a portion of a subject genome, e.g., a PIV genome, encoding an mRNA and typically begins at the upstream end with a gene-start (GS) signal and ends at the downstream end with the gene-end (GE) signal. The term gene is also interchangeable with the term "translational open reading frame", or ORF, particularly in the case where a protein, such as the PIV C protein, is expressed from an additional ORF rather than from a unique mRNA. In the exemplary case of HPIV3, the genome is a single strand of negative-sense RNA 15462 nucleotides (nt) in length (Galinski et al., *Virology* 165: 499–510, (1988); Stokes et al., *Virus Res.* 25:91–103 (1992)). At least eight proteins are encoded by the HPIV3 genome: the nucleocapsid protein N, the phosphoprotein P, the C and D proteins of unknown functions, the matrix protein M, the fusion glycoprotein F, the hemagglutinin-neuraminidase glycoprotein HN, and the large polymerase protein L (Collins et al., 3rd ed. In "*Fields Virology*," B. N. Fields, D. M. Knipe, P. M. Howley, R. M. Chanock, J. L. Melnick, T. P. Monath, B. Roizman, and S. E. Straus, Eds., Vol. 1, pp. 1205–1243. Lippincott-Raven Publishers, Philadelphia, 1996). The viral genome of all PIVs also contains extragenic leader and trailer regions, possessing all or part of the promoters required for viral replication and transcription, as well as non-coding and intergenic regions. Thus, the PIV genetic map is represented as 3' leader-N-P/C/D/V-M-F-HN-L-5' trailer. Transcription initiates at the 3' end and proceeds by a sequential stop-start mechanism that is guided by short conserved motifs found at the gene boundaries. The upstream end of each gene contains a gene-start (GS) signal, which directs initiation of its respective mRNA. The downstream terminus of each gene contains a gene-end (GE) motif which directs polyadenylation and termination. Exemplary genome sequences have been described for the human PIV3 strains JS (GenBank accession number Z11575, incorporated herein by reference) and Washington (Galinski M. S. In Kingsbury, D. W. (Ed.), the Parayxoviruses, pp. 537–568, Plenum Press, New York, 1991, incorporated herein by reference), and for the bovine PIV3 strain 910N (GenBank accession number D80487, incorporated herein by reference).

To construct chimeric PIVs of the invention, one or more PIV gene(s) or genome segment(s) may be deleted, inserted or substituted in whole or in part. This means that partial or complete deletions, insertions and substitutions may include open reading frames and/or cis-acting regulatory sequences of any one or more of the PIV genes or genome segments. By "genome segment" is meant any length of continuous nucleotides from the PIV genome, which might be part of an ORF, a gene, or an extragenic region, or a combination thereof. When a subject genome segment encodes an antigenic determinant, the genome segment encodes at least one immunogenic epitope capable of eliciting a humoral or cell mediated immune response in a mammalian host. The genome segment may also encode an immunogenic fragment or protein domain. In other aspects, the donor genome segment may encode multiple immunogenic domains or epitopes, including recombinantly synthesized sequences that comprise multiple, repeating or different, immunogenic domains or epitopes.

Alternative chimeric PIV of the invention will contain protective antigenic determinants of HPIV1, HPIV2 and/or HPIV3. This is preferably achieved by expression of one or more HN and/or F genes or genome segments by the vector PIV, or as extra or substitute genes from the heterologous donor pathogen. In certain embodiments, a HPIV3-1 or HPIV3-2 chimeric virus may be constructed for use as a vaccine or vector strain, in which the HPIV1 or HPIV2 HN and/or F genes replace their PIV3 counterpart(s) (Skiadopoulos et al., *Vaccine* In press, 1999; Tao et al., *Vaccine* 17:1100–1108, 1999; U.S. patent application Ser. No.

09/083,793, filed May 22, 1998, each incorporated herein by reference). In this context, a chimeric PIV1 vaccine candidate has been generated using the PIV3 cDNA rescue system by replacing the PIV3 HN and F open reading frames (ORFs) with those of PIV1 in a PIV3 full-length cDNA that contains the three attenuating mutations in L. The recombinant chimeric virus derived from this cDNA is designated rPIV3-1.cp45L (Skiadopoulos et al., *J Virol* 72:1762–8, 1998; Tao et al., *J Virol* 72:2955–2961, 1998; Tao et al., *Vaccine* 17:1100–1108, 1999, incorporated herein by reference). rPIV3-1.cp45L is attenuated in hamsters and induced a high level of resistance to challenge with PIV1. A recombinant chimeric virus, designated rPIV3-1.cp45, has also been produced that contains 12 of the 15 cp45 mutations, i.e., excluding the mutations in HN and F, and is highly attenuated in the upper and lower respiratory tract of hamsters (Skiadopoulos et al., *Vaccine* 18:503–510, 1999, incorporated herein by reference).

In preferred embodiments of the invention, the chimeric PIV bear one or more major antigenic determinants of a human PIV, or against multiple human PIVs, including HPIV1, HPIV2 or HPIV3. These preferred vaccine candidates elicit an effective immune response in humans against one or more selected HPIVs. As noted above, the antigenic determinant(s) that elicit(s) an immune response against HPIV may be encoded by the vector genome or antigenome, or may be inserted within or joined to the PIV vector genome or antigenome as a heterologous gene or gene segment. The major protective antigens of human PIVs are their HN and F glycoproteins. However, all PIV genes are candidates for encoding antigenic determinants of interest, including internal protein genes which may encode such determinants as, for example, CTL epitopes.

Preferred chimeric PIV vaccine viruses of the invention bear one or more major antigenic determinants from each of a plurality of HPIVs or from a HPIV and a non-PIV pathoge. Chimeric PIV thus constructed include a partial or complete HPIV genome or antigenome, for example of HPIV3, and one or more heterologous gene(s) or genome segment(s) encoding antigenic determinant(s) of a heterologous PIV, for example HPIV1 or HPIV2. In alternative embodiments, one or more genes or genome segments encoding one or more antigenic determinants of HPIV1 or HPIV2 may be added to or substituted within a partial or complete HPIV3 genome or antigenome. In various exemplary embodiments described below, both HPIV1 genes encoding the HN and F glycoproteins are substituted for counterpart HPIV3 HN and F genes in a chimeric PIV vaccine candidate. These and other constructs yield chimeric PIVs that elicit either a mono- or poly-specific immune response in humans to one or more HPIVs. Further detailed aspects of the invention are provided in United States patent application entitled USE OF RECOMBINANT PARAINFLUENZA VIRUS (PIV) AS A VECTOR TO PROTECT AGAINST DISEASE CAUSED BY PIV AND RESPIRATORY SYNCYTIAL VIRUS (RSV), filed on Dec. 10, 1999 by Murphy et al. and identified by Ser. No. 09/458,813, and U.S. Provisional Patent Application entitled USE OF RECOMBINANT PARAINFLUENZA VIRUSES (PIVs) AS VECTORS TO PROTECT AGAINS INFECTION AND DISEASE CAUSED BY PIV AND OTHER HUMAN PATHOGENS, filed on Dec. 10, 1999 by Murphy et al. and identified by Ser. No. 60/170,195, each incorporated herein by reference.

In exemplary aspects of the invention, heterologous genes or genome segments encoding antigenic determinants from both HPIV1 and HPIV2 are added to or incorporated within a partial or complete HPIV3 vector genome or antigenome. For instance, one or more HPIV1 genes or genome segments encoding HN and/or F glycoproteins, or antigenic determinant(s) thereof, and one or more HPIV2 genes or genome segments encoding HN and/or F glycoproteins or antigenic determinants can be added to or incorporated within a partial or complete HPIV3 vector genome or antigenome. In one example described below, both HPIV1 genes encoding HN and F glycoproteins are substituted for counterpart HPIV3 HN and F genes to form a chimeric HPIV3-1 vector genome or antigenome. This vector construct can be further modified by addition or incorporation of one or more genes or gene segments encoding antigenic determinant(s) of HPIV2. Thus, specific constructs exemplifying the invention are provided which yield chimeric PIVs having antigenic determinants of both HPIV1 and HPIV2, as exemplified by the vaccine candidates rPIV3-1.2HN and rPIV3-1cp45.2HN described herein below.

In other preferred aspects of the invention, chimeric PIV incorporate a HPIV vector genome or antigenome modified to express one or more major antigenic determinants of non-PIV pathogen, for example measles virus. The methods of the invention are generally adaptable for incorporation of antigenic determinants from a wide range of additional pathogens within chimeric PIV vaccine candidates. In this regard the invention also provides for development of vaccine candidates against subgroup A and subgroup B respiratory syncytial viruses (RSV), mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses, among other pathogens. In this regard, pathogens that may be targeted for vaccine development according to the methods of the invention include viral and bacterial pathogens, as well as protozoans and multicellular pathogens. Useful antigenic determinants from many important human pathogens in this context are known or readily identified for incorporation within chimeric PIV of the invention. Thus, major antigens have been identified for the foregoing exemplary pathogens, including the measles virus HA and F proteins; the F, G, SH and M2 proteins of RSV, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, flavivirus E and NS1 proteins, and alphavirus E. These major antigens, as well as other antigens known in the art for the enumerated pathogens and others, are well characterized to the extent that many of their antigenic determinants, including the full length proteins and their constituent antigenic domains, fragments and epitopes, are identified, mapped and characterized for their respective immunogenic activities.

Among the numerous, exemplary mapping studies that identify and characterize major antigens of diverse pathogens for use within the invention are epitope mapping studies directed to the hemagglutinin-neuraminidase (HN) gene of HPIV3. van Wyke Coelingh et al., *J. Virol.* 61(5): 1473–1477, 1987, incorporated herein by reference. This report provides detailed antigenic structural analyses for 16 antigenic variants of HPIV3 variants selected by using monoclonal antibodies (MAbs) to the HN protein which inhibit neuraminidase, hemagglutination, or both activities. Each variant possessed a single-point mutation in the HN gene, coding for a single amino acid substitution in the HN protein. Operational and topographic maps of the HN protein correlated well with the relative positions of the substitutions. Computer-assisted analysis of the HN protein predicted a secondary structure composed primarily of hydrophobic β sheets interconnected by random hydrophilic coil structures. The HN epitopes were located in predicted coil regions. Epitopes recognized by MAbs which inhibit neuraminidase activity of the virus were located in a region which appears to be structurally conserved among several paramyxovirus HN proteins and which may represent the sialic acid-binding site of the HN molecule.

This exemplary work, employing conventional antigenic mapping methods, identified single amino acids which are important for the integrity of HN epitopes. Most of these epitopes are located in the C-terminal half of the molecule, as expected for a protein anchored at its N terminus (Elango et al., *J. Virol.* 57:481–489, 1986). Previously published operational and topographic maps of the PIV3 HN indicated that the MAbs employed recognized six distinct groups of epitopes (I to VI) organized into two topographically separate sites (A and B), which are partially bridged by a third site (C). These groups of epitopes represent useful candidates for antigenic determinants that may be incorporated, alone or in various combinations, within chimeric PIVs of the invention. (See, also, Coelingh et al., *Virology* 143: 569–582, 1985; Coelingh et al., *Virology* 162:137–143, 1988; Ray et al., *Virology* 148:232–236, 1986; Rydbeck et al., *J. Gen. Virol.* 67:1531–1542, 1986, each incorporated herein by reference), Additional studies by van Wyke Coelingh et al., *J. Virol.* 63(1):375–382, 1989, provide further information relating to selection of PIV antigenic determinants for use within the invention. In this study, twenty-six monoclonal antibodies (MAbs) (14 neutralizing and 12 normeutralizing) were used to examine the antigenic structure, biological properties, and natural variation of the fusion (F) glycoprotein of HPIV3. Analysis of laboratory-selected antigenic variants and of PIV3 clinical isolates indicated that the panel of MAbs recognizes at least 20 epitopes, 14 of which participate in neutralization. Competitive binding assays confirmed that the 14 neutralization epitopes are organized into three non-overlapping principal antigenic regions (A, B, and C) and one bridge site (AB), and that the 6 nonneutralization epitopes form four sites (D, E, F, and G). Most of the neutralizing MAbs were involved in nonreciprocal competitive binding reactions, suggesting that they induce conformational changes in other neutralization epitopes.

Other antigenic determinants for use within the invention have been identified and characterized for respiratory syncytial virus (RSV). For example, Beeler et al., *J. Virol.* 63(7):2941–2950, 1989, incorporated herein by reference, employed eighteen neutralizing monoclonal antibodies (MAbs) specific for the fusion glycoprotein of the A2 strain of RSV to construct a detailed topological and operational map of epitopes involved in RSV neutralization and fusion. Competitive binding assays identified three nonoverlapping antigenic regions (A, B, and C) and one bridge site (AB). Thirteen MAb-resistant mutants (MARMs) were selected, and the neutralization patterns of the MAbs with either MARMs or RSV clinical strains identified a minimum of 16 epitopes. MARMs selected with antibodies to six of the site A and AB epitopes displayed a small-plaque phenotype, which is consistent with an alteration in a biologically active region of the F molecule. Analysis of MARMs also indicated that these neutralization epitopes occupy topographically distinct but conformationally interdependent regions with unique biological and immunological properties. Antigenic variation in F epitopes was then examined by using 23 clinical isolates (18 subgroup A and 5 subgroup B) in cross-neutralization assays with the 18 anti-F MAbs. This analysis identified constant, variable, and hypervariable regions on the molecule and indicated that antigenic variation in the neutralization epitopes of the RSV F glycoprotein is the result of a noncumulative genetic heterogeneity. Of the 16 epitopes, 8 were conserved on all or all but 1 of 23 subgroup A or subgroup B clinical isolates. These antigenic determinants, including the full length proteins and their constituent antigenic domains, fragments and epitopes, all represent useful candidates for integration within chimeric PIV of the invention to elicit novel immune responses as described above. (See also, Anderson et al., *J. Infect. Dis.* 151:626–633, 1985; Coelingh et al., *J. Virol.* 63:375–382, 1989; Fenner et al., *Scand. J. Immunol.* 24:335–340, 1986; Fernie et al., *Proc. Soc. Exp. Biol. Med.* 171:266–271, 1982; Sato et al., *J. Gen. Virol.* 66:1397–1409, 1985; Walsh et al., *J. Gen. Virol.* 67:505–513, 1986, and Olmsted et al., *J. Virol.* 63(1):411–420, 1989, each incorporated herein by reference).

To express antigenic determinants of heterologous PIVs and non-PIV pathogens, the invention provides numerous human and non-human PIV vectors, including bovine PIV (BPIV) vectors. These vectors are readily modified according the recombinant methods described herein to carry heterologous antigenic determinants and elicit one or more specific humoral or cell mediated immune responses against the heterologous pathogen and vector PIV. In exemplary embodiments, one or more heterologous genes or genome segments from a donor pathogen is combined with a HPIV3 vector genome or antigenome. In other exemplary embodiments, the heterologous gene or genome segment is incorporated within a chimeric HPIV vector genome or antigenome, for example a chimeric HPIV3-1 vector genome or antigenome having one or both HPIV1 genes encoding the HN and F glycoproteins substituted for their counterpart HPIV3 HN and/or F gene(s). In more detailed embodiments, a transcription unit comprising an open reading frame (ORF) of the measles virus HA gene is added to a HPIV3 vector genome or antigenome at various positions, yielding exemplary chimeric PIV/measles vaccine candidates rPIV3(HA HN-L), rPIV3(HA N-P), rcp45L(HA N-P), rPIV3(HA P-M), or rcp45L(HA P-M). Alternatively, chimeric PIV for vaccine use may incorporate one or more antigenic determinants of HPIV2, for example an HPIV2 HN gene, within a chimeric HPIV3-1 vector genome or antigemome.

In other detailed embodiments of the invention, chimeric PIVs are engineered that incorporate heterologous nucleotide sequences encoding protective antigens from respiratory syncytial virus (RSV) to produce infectious, attenuated vaccine candidates. The cloning of RSV cDNA and other disclosure is provided in U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892, 403, filed Jul. 15, 1997 (corresponding to International Publication No. WO 98/02530); U.S. patent application Ser. No. 09/291,894, filed on Apr. 13, 1999; U.S. Provisional Patent Application Ser. No. 60/129,006, filed on Apr. 13, 1999; Collins, et al., *Proc Nat. Acad. Sci. USA* 92:11563–11567, 1995; Bukreyev, et al., *J Virol* 70:6634–41, 1996, Juhasz et al., *J. Virol.* 71(8):5814–5819, 1997; Durbin et al., *Virology* 235:323–332, 1997; He et al. *Virology* 237:249–260, 1997; Baron et al. *J. Virol.*

71:1265–1271, 1997; Whitehead et al., *Virology* 247(2): 232–9, 1998a; Whitehead et al., *J. Virol.* 72(5):4467–4471, 1998b; Jin et al. *Virology* 251:206–214, 1998; and Whitehead et al., *J. Virol.* 73:(4)3438–3442, 1999, and Bukreyev, et al., *Proc Nat Acad Sci USA* 96:2367–72, 1999, each incorporated herein by reference in its entirety for all purposes). Other reports and discussion incorporated or set forth herein identify and characterize RSV antigenic determinants that are useful within the invention.

PIV chimeras incorporating one or more RSV antigenic determinants, preferably comprise a human PIV (e.g., HPIV1, HPIV2, HPIV3) vector genome or antigenome with a heterologous gene or genome segment encoding an antigenic RSV glycoprotein, protein domain (e.g., a glycoprotein ectodomain) or one or more immunogenic epitopes. In one embodiment, one or more genes or genome segments from RSV F and/or G genes is/are combined with the vector genome or antigenome to form the chimeric PIV vaccine candidate. Certain of these constructs will express chimeric proteins, for example fusion proteins having a cytoplasmic tail and/or transmembrane domain of PIV fused to an ectodomain of RSV to yield a novel attenuated virus that elicits a multivalent immune response against both PIV and RSV As noted above, it is often desirable to adjust the phenotype of chimeric PIV for vaccine use by introducing additional mutations that increase or decrease attenuation or otherwise alter the phenotype of the chimeric virus. Detailed descriptions of the materials and methods for producing recombinant PIV from cDNA, and for making and testing various mutations and nucleotide modifications set forth herein as supplemental aspects of the present invention are provided in, e.g., Durbin et al., *Virology* 235:323–332, 1997; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference. In particular, these documents describe methods and procedures for mutagenizing, isolating and characterizing PIV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing documents detail procedures for determining replication, immunogenicity, genetic stability and protective efficacy of biologically derived and recombinantly produced attenuated human PIV in accepted model systems, including murine and non-human primate model systems. In addition, these documents describe general methods for developing and testing immunogenic compositions, including monovalent and bivalent vaccines, for prophylaxis and treatment of PIV infection. Methods for producing infectious recombinant PIV by construction and expression of cDNA encoding a PIV genome or antigenome coexpressed with essential PIV proteins are also described in the above-incorporated documents, which include description of the following exemplary plasmids that may be employed to produce infectious PIV clones: p3/7(131) (ATCC 97990); p3/7(131)2G (ATCC 97889); and p218(131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

Also disclosed in the above-incorporated references are methods for constructing and evaluating infectious recombinant PIV that are modified to incorporate phenotype-specific mutations identified in biologically-derived PIV mutants, e.g., cold passaged (cp), cold adapted (ca), host range restricted (hr), small plaque (sp), and/or temperature sensitive (ts) mutants, for example the JS HPIV3 cp 45 mutant strain. Mutations identified in these mutants can be readily incorporated into chimeric PIV of the instant invention. In exemplary embodiments, one or more attenuating mutations occur in the polymerase L protein, e.g., at a position corresponding to $Tyr_{942}$, $Leu_{992}$, or $Thr_{1558}$ of JS cp45. Preferably, these mutations are incorporated in chimeric PIV of the invention by an identical, or conservative, amino acid substitution as identified in the biological mutant. In more detailed aspects, chimeric PIV for vaccine use incorporate one or more mutation wherein $Tyr_{942}$ is replaced by His, $Leu_{992}$ is replaced by Phe, and/or $Thr_{1558}$ is replaced by Ile. Substitutions that are conservative to these replacement amino acids are also useful to achieve desired attenuation in chimeric vaccine candidates.

Other exemplary mutations that can be adopted in chimeric PIVs from biologically derived PIV mutants include one or more mutations in the N protein, including specific mutations at a position corresponding to residues $Val_{96}$ or $Ser_{389}$ of JS cp45. In more detailed aspects, these mutations are represented as $Val_{96}$ to Ala or $Ser_{389}$ to Ala or substitutions that are conservative thereto. Also useful within chimeric PIV of the invention are amino acid substitution in the C protein, e.g., a mutation at a position corresponding to $Ile_{96}$ of JS cp45, preferably represented by an identical or conservative substitution of $Ile_{96}$ to Thr. Further exemplary mutations that can be adopted from biologically derived PIV mutants include one or more mutations in the F protein, including mutations adopted from JS cp45 at a position corresponding to residues $Ile_{420}$ or $Ala_{450}$ of JS cp45, preferably represented by acid substitutions $Ile_{420}$ to Val or $Ala_{450}$ to Thr or substitutions conservative thereto. Alternatively or in addition, chimeric PIV of the invention can adopt one or more amino acid substitutions in the HN protein, as exemplified by a mutation at a position corresponding to residue $Val_{384}$ of JS cp45, preferably represented by the substitution $Val_{384}$ to Ala.

Yet additional embodiments of the invention include chimeric PIV which incorporate one or more mutations in noncoding portions of the PIV genome or antigenome, for example in a 3' leader sequence, that specify desired phenotypic changes such as attenuation. Exemplary mutations in this context may be engineered at a position in the 3' leader of the chimeric virus at a position corresponding to nucleotide 23, 24, 28, or 45 of JS cp45. Yet additional exemplary mutations may be engineered in the N gene start sequence, for example by changing one or more nucleotides in the N gene start sequence, e.g., at a position corresponding to nucleotide 62 of JS cp45. In more detailed aspects, chimeric PIV incorporate a T to C change at nucleotide 23, a C to T change at nucleotide 24, a G to T change at nucleotide 28, and/or a T to A change at nucleotide 45. Additional mutations in extragenic sequences are exemplified by a A to T change in the N gene start sequence at a position corresponding to nucleotide 62 of JS.

These foregoing exemplary mutations which can be engineered in a chimeric PIV of the invention have been successfully engineered and recovered in recombinant PIV—as represented by the recombinant PIV clones designated rcp45, rcp45 L, rcp45 F, rcp45 M, rcp45 HN, rcp45 C, rcp45 F, rcp45 3'N, rcp3'NL, and rcp45 3'NCMFHN (Durbin et al., *Virology* 235:323–332, 1997; Skiadopolos et al., *J. Virol.* 72:1762–1768 (1998); Skiadopolos et al., *J. Virol.* 73:1374–1381, 1999; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). In addition, the above-incorporated references describe construction of chimeric PIV recombinants, e.g., having the HN and F genes of HPIV1 substituted into a partial HPIV3 background genome or antigenome, which is further modified to bear one or more of the attenuating mutations identified in HPIV3 JS cp45. One such chimeric recombinant incorporates all of the attenuating mutations identified in the L gene of cp45. It has since been shown that all of the cp45 mutations outside of the heterologous (HPIV1) HN and F genes can be incorporated in a HPIV3-1 recombinant to yield an attenuated, chimeric vaccine candidate.

From JS cp45 and other biologically derived PIV mutants, a large "menu" of attenuating mutations is provided, each of which can be combined with any other mutation(s) for adjusting the level of attenuation, immunogenicity and genetic stability in chimeric PIV of the invention. In this context, many chimeric PIVs will include one or more, and preferably two or more, mutations from biologically derived PIV mutants, e.g., any one or combination of mutations identified in JS cp45. Preferred chimeric PIVs within the invention will incorporate a plurality and up to a full complement of the mutations present in JS cp45 or other biologically derived mutant PIV strains. Preferably, these mutations are stabilized against reversion in chimeric PIV by multiple nucleotide substitutions in a codon specifying each mutation.

Yet additional mutations that may be incorporated in chimeric PIV of the invention are mutations, e.g., attenuating mutations, identified in heterologous PIV or other nonsegmented negative stranded RNA viruses. In particular, attenuating and other desired mutations identified in one negative stranded RNA virus may be "transferred", e.g., copied, to a corresponding position within the genome or antigenome of a chimeric PIV. Briefly, desired mutations in one heterologous negative stranded RNA virus are transferred to the chimeric PIV recipient (either in the vector genome or antigenome or in the heterologous donor gene or genome segment). This involves mapping the mutation in the heterologous mutant virus, identifying by routine sequence alignment the corresponding site in the recipient PIV, and mutating the native sequence in the PIV recipient to the mutant genotype (either by an identical or conservative mutation), as described in U.S. Provisional Patent Application Ser. No. 60/129,006, filed on Apr. 13, 1999, incorporated herein by reference. As this disclosure teaches, it is preferable to modify the recipient chimeric PIV genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution can be engineered at the corresponding residue(s) in the recombinant virus. Preferably the substitution will specify an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue). Negative stranded RNA viruses from which exemplary mutations are identified and transferred into a recombinant PIV of the invention include other PIVs (e.g., HPIV1, HPIV2, HPIV3, BPIV and MPIV), RSV, Sendai virus (SeV), Newcastle disease virus (NDV), simian virus 5 (SV5), measles virus (MeV), rinderpest virus, canine distemper virus (CDV), rabies virus (RaV) and vesicular stomatitis virus (VSV), among others. A variety of exemplary mutations are disclosed, including but not limited to an amino acid substitution of phenylalanine at position 521 of the RSV L protein corresponding to and therefore transferable to a substitution of phenylalanine (or a conservatively related amino acid) at position 456 of the HPIV3 L protein. In the case of mutations marked by deletions or insertions, these can be introduced as corresponding deletions or insertions into the recombinant virus, however the particular size and amino acid sequence of the deleted or inserted protein fragment can vary.

Attenuating mutations in biologically derived PIV and other nonsegmented negative stranded RNA viruses for incorporation within chimeric PIV of the invention may occur naturally or may be introduced into wild-type PIV strains by well known mutagenesis procedures. For example, incompletely attenuated parental PIV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as described in the above incorporated references. By "biologically derived PIV" is meant any PIV not produced by recombinant means. Thus, biologically derived PIV include all naturally occurring PIV, including, e.g., naturally occurring PIV having a wild-type genomic sequence and PIV having allelic or mutant genomic variations from a reference wild-type PIV sequence, e.g., PIV having a mutation specifying an attenuated phenotype. Likewise, biologically derived PIV include PIV mutants derived from a parental PIV by, inter alia, artificial mutagenesis and selection procedures.

As noted above, production of a sufficiently attenuated biologically derived PIV mutant can be accomplished by several known methods. One such procedure involves subjecting a partially attenuated virus to passage in cell culture at progressively lower, attenuating temperatures. For example, partially attenuated mutants are produced by passage in cell cultures at suboptimal temperatures. Thus, a cp mutant or other partially attenuated PIV strain is adapted to efficient growth at a lower temperature by passage in culture. This selection of mutant PIV during cold-passage substantially reduces any residual virulence in the derivative strains as compared to the partially attenuated parent. Alternatively, specific mutations can be introduced into biologically derived PIV by subjecting a partially attenuated parent virus to chemical mutagenesis, e.g., to introduce ts mutations or, in the case of viruses which are already ts, additional ts mutations sufficient to confer increased attenuation and/or stability of the ts phenotype of the attenuated derivative. Means for the introduction of ts mutations into PIV include replication of the virus in the presence of a mutagen such as 5-fluorouridine according to generally known procedures. Other chemical mutagens can also be used. Attenuation can result from a ts mutation in almost any PIV gene, although a particularly amenable target for this purpose has been found to be the polymerase (L) gene. The level of temperature sensitivity of replication in exemplary attenuated PIV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of PIV correlate with the mutant's shutoff temperature.

The JS cp45 HPIV3 mutant has been found to be relatively stable genetically, highly immunogenic, and satisfactorily attenuated. Nucleotide sequence analysis of this biologically derived virus, and of recombinant viruses incorporating various individual and combined mutations found therein, indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious PIV clones. This process coupled with evaluation of phenotype characteristics of parental and derivative viruses identifies mutations responsible for such desired characteristics as attenuation, temperature sensitivity, cold-adaptation, small plaque size, host range restriction, etc.

Mutations thus identified are compiled into a "menu" and are then introduced as desired, singly or in combination, to adjust chimeric PIV of the invention to an appropriate level of attenuation, immunogenicity, genetic resistance to reversion from an attenuated phenotype, etc., as desired. In accordance with the foregoing description, the ability to produce infectious PIV from cDNA permits introduction of specific engineered changes within chimeric PIV. In particular, infectious, recombinant PIVs are employed for identification of specific mutation(s) in biologically derived, attenuated PIV strains, for example mutations which specify ts, ca, att and other phenotypes. Desired mutations are thus identified and introduced into chimeric PIV vaccine strains. The capability of producing virus from cDNA allows for routine incorporation of these mutations, individually or in various selected combinations, into a full-length cDNA clone, whereafter the phenotypes of rescued recombinant viruses containing the introduced mutations to be readily determined.

By identifying and incorporating specific mutations associated with desired phenotypes, e.g., a cp or ts phenotype, into infectious chimeric PIV clones, the invention provides for other, site-specific modifications at, or within close proximity to, the identified mutation. Whereas most attenuating mutations produced in biologically derived PIVs are single nucleotide changes, other "site specific" mutations can also be incorporated by recombinant techniques into a chimeric PIV. As used herein, site-specific mutations include insertions, substitutions, deletions or rearrangements of from 1 to 3, up to about 5–15 or more altered nucleotides (e.g., altered from a wild-type PIV sequence, from a sequence of a selected mutant PIV strain, or from a parent recombinant PIV clone subjected to mutagenesis). Such site-specific mutations may be incorporated at, or within the region of, a selected, biologically derived point mutation. Alternatively, the mutations can be introduced in various other contexts within a PIV clone, for example at or near a cis-acting regulatory sequence or nucleotide sequence encoding a protein active site, binding site, immunogenic epitope, etc. Site-specific PIV mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant PIV designed to incorporate additional, stabilizing nucleotide mutations in a codon specifying an attenuating point mutation. Where possible, two or more nucleotide substitutions are introduced at codons that specify attenuating amino acid changes in a parent mutant or recombinant PIV clone, yielding a PIV with greater genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5–10 and up to 15 nucleotides or more 5' or 3', relative to a targeted nucleotide position, e.g., to construct or ablate an existing cis-acting regulatory element.

In addition to single and multiple point mutations and site-specific mutations, changes to the chimeric PIV disclosed herein include deletions, insertions, substitutions or rearrangements of one or more gene(s) or genome segment(s). Particularly useful are deletions involving one or more gene(s) or genome segment(s), which deletions have been shown to yield additional desired phenotypic effects. Thus, U.S. patent application Ser. No. 09/350,821, filed by Durbin et al. on Jul. 9, 1999, incorporated herein by reference, describes methods and compositions whereby expression of one or more HPIV genes, for example one or more of the C, D, and/or V ORFs, is reduced or ablated by modifying the PIV genome or antigenome to incorporate a mutation that alters the coding assignment of an initiation codon or mutation(s) that introduce one or one or more stop codon(s). Alternatively, one or more of the C, D, and/or V ORFs can be deleted in whole or in part to render the corresponding protein(s) partially or entirely non-functional or to disrupt protein expression altogether. Chimeric PIV having such mutations in C, D, and/or V, or other non-essential gene(s), possess highly desirable phenotypic characteristics for vaccine development. For example, these modifications may specify one or more desired phenotypic changes including (i) altered growth properties in cell culture, (ii) attenuation in the upper and/or lower respiratory tract of mammals, (iii) a change in viral plaque size, (iv) a change in cytopathic effect, and (v) a change in immunogenicity. One exemplary "knock out" mutant PIV lacking C ORF expression, designated rC-KO, was able to induce a protective immune response against wild type HPIV3 challenge in a non-human primate model despite its beneficial attenuation phenotype.

Thus, in more detailed aspects of the instant invention, chimeric PIV incorporate deletion or knock out mutations in a C, D, and/or V ORF(s) or other non-essential gene which alters or ablates expression of the selected gene(s) or genome segment(s). This can be achieved, e.g., by introducing a frame shift mutation or termination codon within a selected coding sequence, altering translational start sites, changing the position of a gene or introducing an upstream start codon to alter its rate of expression, changing GS and/or GE transcription signals to alter phenotype, or modifying an RNA editing site (e.g., growth, temperature restrictions on transcription, etc.). In more detailed aspects of the invention, chimeric PIVs are provided in which expression of one or more gene(s), e.g., a C, D, and/or V ORF(s), is ablated at the translational or transcriptional level without deletion of the gene or of a segment thereof, by, e.g., introducing multiple translational termination codons into a translational open reading frame (ORF), altering an initiation codon, or modifying an editing site. These forms of knock-out virus will often exhibit reduced growth rates and small plaque sizes in tissue culture. Thus, these methods provide yet additional, novel types of attenuating mutations which ablate expression of a viral gene that is not one of the major viral protective antigens. In this context, knock-out virus phenotypes produced without deletion of a gene or genome segment can be alternatively produced by deletion mutagenesis, as described, to effectively preclude correcting mutations that may restore synthesis of a target protein. Several other gene knock-outs for the C, D, and/or V ORF(s) deletion and knock out mutants can be made using alternate designs and methods that are well known in the art (as described, for example, in (Kretschmer et al., *Virology* 216:309–316, 1996; Radecke et al., *Virology* 217:418–421, 1996; and Kato et al., *EMBO J.* 16:578–587, 1987; and Schneider et al., *Virology* 277:314–322, 1996, each incorporated herein by reference).

Nucleotide modifications that may be introduced into chimeric PIV constructs of the invention may alter small numbers of bases (e.g., from 15–30 bases, up to 35–50 bases or more), large blocks of nucleotides (e.g., 50–100, 100–300, 300–500, 500–1,000 bases), or nearly complete or complete genes (e.g., 1,000–1,500 nucleotides, 1,500–2,500 nucleotides, 2,500–5,000, nucleotides, 5,00–6,5000 nucleotides or more) in the vector genome or antigenome or heterologous, donor gene or genome segment, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In related aspects, the invention provides for supplementation of mutations adopted into a chimeric PIV clone from biologically derived PIV, e.g., cp and ts mutations, with additional types of mutations involving the same or different genes in a further modified PIV clone. Each of the PIV genes can be selectively altered in terms of expression levels, or can be added, deleted, substituted or rearranged, in whole or in part, alone or in combination with other desired modifications, to yield a chimeric PIV exhibiting novel vaccine characteristics. Thus, in addition to or in combination with attenuating mutations adopted from biologically derived PIV mutants, the present invention also provides a range of additional methods for attenuating or otherwise modifying the phenotype of a chimeric PIV based on recombinant engineering of infectious PIV clones. A variety of alterations can be produced in an isolated polynucleotide sequence encoding a targeted gene or genome segment, including a donor or recipient gene or genome segment in a chimeric PIV genome or antigenome for incorporation into infectious clones. More specifically, to achieve desired structural and phenotypic changes in recombinant PIV, the invention allows for introduction of modifications which delete, substitute, introduce, or rearrange a selected nucleotide or nucleotide sequence from a parent genome or antigenome, as well as mutations which delete, substitute, introduce or rearrange whole gene(s) or genome segment(s), within a chimeric PIV clone.

Thus provided are modifications in chimeric PIV of the invention which simply alter or ablate expression of a selected gene, e.g., by introducing a termination codon within a selected PIV coding sequence or altering its translational start site or RNA editing site, changing the position of a PIV gene relative to an operably linked promoter, introducing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected protein(s). In this context, any PIV gene or genome segment which is not essential for growth can be ablated or otherwise modified in a recombinant PIV to yield desired effects on virulence, pathogenesis, immunogenicity and other phenotypic characters. As for coding sequences, noncoding, leader, trailer and intergenic regions can be similarly deleted, substituted or modified and their phenotypic effects readily analyzed, e.g., by the use of minireplicons and recombinant PIV.

In addition, a variety of other genetic alterations can be produced in a PIV genome or antigenome for incorporation into a chimeric PIV, alone or together with one or more attenuating mutations adopted from a biologically derived mutant PIV, e.g., to adjust growth, attenuation, immunogenicity, genetic stability or provide other advantageous structural and/or phenotypic effects. These additional types of mutations are also disclosed in the foregoing incorporated references and can be readily engineered into chimeric PIV of the invention. For example, restriction site markers are routinely introduced within chimeric PIVs to facilitate cDNA construction and manipulation.

In addition to these changes, the order of genes in a chimeric PIV construct can be changed, a PIV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Other mutations for incorporation into chimeric PIV constructs of the invention include mutations directed toward cis-acting signals, which can be readily identified, e.g., by mutational analysis of PIV minigenomes. For example, insertional and deletional analysis of the leader and trailer and flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also has identified many mutations which affect RNA replication or transcription. Any of these mutations can be inserted into a chimeric PIV antigenome or genome as described herein. Evaluation and manipulation of trans-acting proteins and cis-acting RNA sequences using the complete antigenome cDNA is assisted by the use of PIV minigenomes as described in the above-incorporated references.

Additional mutations within chimeric PIVs of the invention may also include replacement of the 3' end of genome with its counterpart from antigenome, which is associated with changes in RNA replication and transcription. In one exemplary embodiment, the level of expression of specific PIV proteins, such as the protective HN and/or F antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315–324, 1996, incorporated herein by reference). Optimization by recombinant methods of the codon usage of the mRNAs encoding the HN and F proteins of PIV will provide improved expression for these genes.

In another exemplary embodiment, a sequence surrounding a translational start site (preferably including a nucleotide in the −3 position) of a selected PIV gene is modified, alone or in combination with introduction of an upstream start codon, to modulate PIV gene expression by specifying up- or down-regulation of translation. Alternatively, or in combination with other recombinant modifications disclosed herein, gene expression of a chimeric PIV can be modulated by altering a transcriptional GS or GE signal of any selected gene(s) of the virus. In alternative embodiments, levels of gene expression in a chimeric PIV vaccine candidate are modified at the level of transcription. In one aspect, the position of a selected gene in the PIV gene map can be changed to a more promoter-proximal or promotor-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. These and other transpositioning changes yield novel chimeric PIV vector virus having attenuated phenotypes, for example due to decreased expression of selected viral proteins involved in RNA replication, or having other desirable properties such as increased antigen expression.

In other embodiments, chimeric PIVs useful in vaccine formulations can be conveniently modified to accommodate antigenic drift in circulating virus. Typically the modification will be in the HN and/or F proteins. An entire HN or F gene, or a genome segment encoding a particular immunogenic region thereof, from one PIV strain or group is incorporated into a chimeric PIV genome or antigenome cDNA by replacement of a corresponding region in a recipient clone of a different PIV strain or group, or by adding one or more copies of the gene, such that multiple antigenic forms are represented. Progeny virus produced from the modified PIV clone can then be used in vaccination protocols against emerging PIV strains.

Replacement of a human PIV coding sequence or noncoding sequence (e.g., a promoter, gene-end, gene-start, intergenic or other cis-acting element) with a heterologous counterpart yields chimeric PIV having a variety of possible attenuating and other phenotypic effects. In particular, host range and other desired effects arise from substituting a bovine PIV (BPIV) or murine PIV (MPIV) protein, protein domain, gene or genome segment imported within a human PIV background, wherein the bovine or murine gene does not function efficiently in a human cell, e.g., from incompatibility of the heterologous sequence or protein with a biologically interactive human PIV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In exemplary embodiments, bovine PIV sequences are selected for introduction into human PIV based on known aspects of bovine and human PIV structure and function.

In more detailed aspects, the invention provides methods for attenuating chimeric PIV vaccine candidates based on the further construction of chimeras between HPIV and a non-human PIV, for example HPIV3 and BPIV3 (e.g., as disclosed in U.S. Provisional Application Ser. No. 60/143,134 filed on Jul. 9, 1999, incorporated herein by reference). This method of attenuation is based on host range effects due to the introduction of one or more gene(s) or genome segment(s) of the non-human PIV into a human PIV vector-based chimeric virus. For example, there are numerous nucleotide and amino acid sequence differences between BPIV and HPIVs, which are reflected in host range differences. Between HPIV3 and BPIV3 the percent amino acid identity for each of the following proteins is: N (86%), P (65%), M (93%), F (83%), HN (77%), and L (91%). The host range difference is exemplified by the highly permissive growth of HPIV3 in rhesus monkeys, compared to the restricted replication of two different strains of BPIV3 in the same animal (van Wyke Coelingh et al., *J. Infect. Dis.* 157:655–662, 1988, incorporated herein by reference). Although the basis of the host range differences between HPIV3 and BPIV3 remains to be determined, it is likely that they will involve more than one gene and multiple amino acid differences. The involvement of multiple genes and possibly cis-acting regulatory sequences, each involving multiple amino acid or nucleotide differences, gives a very broad basis for attenuation, one which cannot readily be altered by reversion. This is in contrast to the situation with other live attenuated HPIV3 viruses which are attenuated by one or several point mutations. In this case, reversion of any individual mutation may yield a significant reacquisition of virulence or, in a case where only a single residue specified attenuation, complete reacquisition of virulence.

In exemplary embodiments of the invention, the vector genome or antigenome is an HPIV3 genome or antigenome, and the heterologous gene or genome segment is a N ORF derived from, alternatively, a Ka or SF strain of BPIV3 (which are 99% related in amino acid sequence). The N ORF of the HPIV3 background antigenome is substituted by the counterpart BPIV3 N ORF—yielding a novel recombinant chimeric PIV clone. Replacement of the HPIV3 N ORF of HPIV3 with that of BPIV3 Ka or SF results in a protein with approximately 70 amino acid differences (depending on the strain involved) from that of HPIV3 N. N is one of the more conserved proteins, and substitution of other proteins such as P, singly or in combination, would result in many more amino acid differences. The involvement of multiple genes and genome segments each conferring multiple amino acid or nucleotide differences provides a broad basis for attenuation which is highly stable to reversion.

This mode of attenuation contrasts sharply to HPIV vaccine candidates that are attenuated by one or more point mutations, where reversion of an individual mutation may yield a significant or complete reacquisition of virulence. In addition, several known attenuating point mutations in HPIV typically yield a temperature sensitive phenotype. One problem with attenuation associated with temperature sensitivity is that the virus can be overly restricted for replication in the lower respiratory tract while being under attenuated in the upper respiratory tract. This is because there is a temperature gradient within the respiratory tract, with temperature being higher (and more restrictive) in the lower respiratory tract and lower (less restrictive) in the upper respiratory tract. The ability of an attenuated virus to replicate in the upper respiratory tract can result in complications including congestion, rhinitis, fever and otitis media. Thus, attenuation achieved solely by temperature sensitive mutations may not be ideal. In contrast, host range mutations present in chimeric PIV of the invention will not in most cases confer temperature sensitivity. Therefore, the novel method of PIV attenuation provided by these kinds of modifications will be more stable genetically and phenotypically and less likely to be associated with residual virulence in the upper respiratory tract compared to other known PIV vaccine candidates.

The above-incorporated reference discloses that both Ka and SF HPIV3/BPIV3 chimeric recombinants are viable and replicate as efficiently in cell culture as either HPIV3 or BPIV3 parent-indicating that the chimeric recombinants did not exhibit gene incompatibilities that restricted replication in vitro. This property of efficient replication in vitro is important since it permits efficient manufacture of this biological. Also, the Ka and the SF HPIV3/BPIV3 chimeric recombinants (termed cKa and cSF), bearing only one bovine gene, are nearly equivalent to their BPIV3 parents in the degree of host range restriction in the respiratory tract of the rhesus monkey. In particular, the cKa and cSF viruses exhibit approximately a 60-fold or 30-fold reduction, respectively, in replication in the upper respiratory tract of rhesus monkeys compared to replication of HPIV3. Based on this finding, it is expected that other BPIV3 genes will also confer desired levels of host range restriction within chimeric PIV of the invention. Thus, according to the methods herein, a list of attenuating determinants will be readily identified in heterologous genes and genome segments of BPIV and other non-human PIVs that will confer, in appropriate combination, a desired level of host range restriction and immunogenicity on chimeric PIV selected for vaccine use.

In preferred chimeric vaccine candidates of the invention, attenuation marked by replication in the lower and/or upper respiratory tract in an accepted animal model for PIV replication in humans, e.g., hamsters or rhesus monkeys, may be reduced by at least about two-fold, more often about 5-fold, 10-fold, or 20-fold, and preferably 50-100-fold and up to 1,000-fold or greater overall (e.g., as measured between 3–8 days following infection) compared to growth of the corresponding wild-type or mutant parental PIV strain.

Infectious chimeric PIV vector clones of the invention can also be engineered according to the methods and compositions disclosed herein to enhance immunogenicity and induce a level of protection greater than that provided by infection with a wild-type, parental (i.e., vector or heterologous donor) PIV or non-PIV pathogen. For example, one or more supplemental immunogenic epitope(s), protein domains, or proteins from a heterologous PIV strain or type, or from a non-PIV pathogen such as measles or RSV, can be added to a chimeric PIV by appropriate nucleotide changes in the chimeric genome or antigenome. Alternatively, chimeric PIVs of the invention can be engineered to add or ablate (e.g., by amino acid insertion, substitution or deletion) immunogenic proteins, protein domains, or forms of specific proteins associated with desirable or undesirable immunological reactions.

Within the methods of the invention, additional genes or genome segments may be inserted into or proximate to the chimeric PIV vector genome or antigenome. These genes may be under common control with recipient genes, or may be under the control of an independent set of transcription signals. In addition to genes and genome segments encoding antigenic determinants, genes of interest in this context include genes encoding cytokines, for example, an interleukin (e.g., interleukin 2 (IL-2), interleukin 4 (IL-4), interleukin 5 (IL-5), interleukin 6 (IL6), interleukin 18 (IL-18)), tumor necrosis factor alpha (TNFα), interferon gamma (IFNγ), or granulocyte-macrophage colony stimulating factor (GM-CSF), as well as IL-2 through IL-18, especially IL-2, IL-6 and IL-12, and IL-18, gamma-interferon (see, e.g., U.S. Provisional Application Ser. No. 60/143,425 filed Jul. 13, 1999, incorporated herein by reference). Coexpression of these additional proteins provides the ability to modify and improve immune responses against chimeric PIV of the invention both quantitatively and qualitatively.

Deletions, insertions, substitutions and other mutations involving changes of whole viral genes or genome segments within chimeric PIV of the invention yield highly stable vaccine candidates, which are particularly important in the case of immunosuppressed individuals. Many of these changes will result in attenuation of resultant vaccine strains, whereas others will specify different types of desired phenotypic changes. For example, accessory (i.e., not essential for in vitro growth) genes are excellent candidates to encode proteins that specifically interfere with host immunity (see, e.g., Kato et al., *EMBO. J.* 16:578–87, 1997, incorporated herein by reference). Ablation of such genes in vaccine viruses is expected to reduce virulence and pathogenesis and/or improve immunogenicity.

Introduction of the foregoing defined mutations into an infectious, chimeric PIV clone can be achieved by a variety of well known methods. By "infectious clone" with regard to DNA is meant cDNA or its product, synthetic or otherwise, which can be transcribed into genomic or antigenomic RNA capable of serving as template to produce the genome of an infectious virus or subviral particle. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the PIV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of a PIV genome or antigenome is cloned into the plasmid pTZ18U, and used to transform CJ236 cells (Life Technologies, Gaithersburg, Md.). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified and the mutated piece is then reintroduced into the full-length genome or antigenome clone.

The invention also provides methods for producing infectious chimeric PIV from one or more isolated polynucleotides, e.g., one or more cDNAs. According to the present invention cDNA encoding a PIV genome or antigenome is constructed for intracellular or in vitro coexpression with the necessary viral proteins to form infectious PIV. By "PIV antigenome" is meant an isolated positive-sense polynucleotide molecule which serves as the template for the synthesis of progeny PIV genome. Preferably a cDNA is constructed which is a positive-sense version of the PIV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, and L proteins.

For purposes of the present invention the genome or antigenome of the recombinant PIV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule, or can be expressed directly from the genome or antigenome cDNA.

By recombinant PIV is meant a PIV or PIV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious PIV from cDNA-expressed genome or antigenome, the genome or antigenome is coexpressed with those PIV proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Infectious PIV of the invention are produced by intracellular or cell-free coexpression of one or more isolated polynucleotide molecules that encode a PIV genome or antigenome RNA, together with one or more polynucleotides encoding viral proteins necessary to generate a transcribing, replicating nucleocapsid. Among the viral proteins useful for coexpression to yield infectious PIV are the major nucleocapsid protein (N) protein, nucleocapsid phosphoprotein (P), large (L) polymerase protein, fusion protein (F), hemagglutinin-neuraminidase glycoprotein (HN), and matrix (M) protein. Also useful in this context are products of the C, D and V ORFs of PIV.

cDNAs encoding a PIV genome or antigenome are constructed for intracellular or in vitro coexpression with the necessary viral proteins to form infectious PIV. By "PIV antigenome" is meant an isolated positive-sense polynucleotide molecule which serves as a template for synthesis of progeny PIV genome. Preferably a cDNA is constructed which is a positive-sense version of the PIV genome corresponding to the replicative intermediate RNA, or antigenome, so as to minimize the possibility of hybridizing with positive-sense transcripts of complementing sequences encoding proteins necessary to generate a transcribing, replicating nucleocapsid.

In some embodiments of the invention the genome or antigenome of a recombinant PIV (rPIV) need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule. In other embodiments, the PIV genome or antigenome encodes all functions necessary for viral growth, replication, and infection without the participation of a helper virus or viral function provided by a plasmid or helper cell line.

By "recombinant PIV" is meant a PIV or PIV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious PIV from a cDNA-expressed PIV genome or antigenome, the genome or antigenome is coexpressed with those PIV N, P and L proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Synthesis of PIV antigenome or genome together with the above-mentioned viral proteins can also be achieved in vitro (cell-free), e.g., using a combined transcription-translation reaction, followed by transfection into cells. Alternatively, antigenome or genome RNA can be synthesized in vitro and transfected into cells expressing PIV proteins.

In certain embodiments of the invention, complementing sequences encoding proteins necessary to generate a transcribing, replicating PIV nucleocapsid are provided by one or more helper viruses. Such helper viruses can be wild type or mutant. Preferably, the helper virus can be distinguished phenotypically from the virus encoded by the PIV cDNA. For example, it is desirable to provide monoclonal antibodies which react immunologically with the helper virus but not the virus encoded by the PIV cDNA. Such antibodies can be neutralizing antibodies. In some embodiments, the antibodies can be used in affinity chromatography to separate the helper virus from the recombinant virus. To aid the procurement of such antibodies, mutations can be introduced into the PIV cDNA to provide antigenic diversity from the helper virus, such as in the HN or F glycoprotein genes.

In alternate embodiments of the invention, the N, P, L and other desired PIV proteins are encoded by one or more non-viral expression vectors, which can be the same or separate from that which encodes the genome or antigenome. Additional proteins may be included as desired, each encoded by its own vector or by a vector encoding one or more of the N, P, L and other desired PIV proteins, or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology*, 210: 202–205 (1995), incorporated herein by reference in its entirety). The viral proteins, and/or T7 RNA polymerase, can also be provided by transformed mammalian cells or by transfection of preformed mRNA or protein.

A PIV antigenome may be constructed for use in the present invention by, e.g., assembling cloned cDNA segments, representing in aggregate the complete antigenome, by polymerase chain reaction or the like (PCR; described in, e.g., U.S. Pat. Nos. 4,683,195 and 4,683,202, and PCR Protocols: A Guide to Methods and Applications, Innis et al., eds., Academic Press, San Diego (1990), each incorporated herein by reference in its entirety) of reverse-transcribed copies of PIV mRNA or genome RNA. For example, a first construct is generated which comprises cDNAs containing the left hand end of the antigenome, spanning from an appropriate promoter (e.g., T7 RNA polymerase promoter) and assembled in an appropriate expression vector, such as a plasmid, cosmid, phage, or DNA virus vector. The vector may be modified by mutagenesis and/or insertion of synthetic polylinker containing unique restriction sites designed to facilitate assembly. For ease of preparation the N, P, L and other desired PIV proteins can be assembled in one or more separate vectors. The right hand end of the antigenome plasmid may contain additional sequences as desired, such as a flanking ribozyme and tandem T7 transcriptional terminators. The ribozyme can be hammerhead type (e.g., Grosfeld et al., (1995), supra), which would yield a 3' end containing a single nonviral nucleotide, or can be any of the other suitable ribozymes such as that of hepatitis delta virus (Perrotta et al., *Nature* 350:434–436, 1991), incorporated herein by reference in its entirety) which would yield a 3' end free of non-PIV nucleotides. The left- and right-hand ends are then joined via a common restriction site.

A variety of nucleotide insertions, deletions and rearrangements can be made in the PIV genome or antigenome during or after construction of the cDNA. For example, specific desired nucleotide sequences can be synthesized and inserted at appropriate regions in the cDNA using convenient restriction enzyme sites. Alternatively, such techniques as site-specific mutagenesis, alanine scanning, PCR mutagenesis, or other such techniques well known in the art can be used to introduce mutations into the cDNA.

Alternative means to construct cDNA encoding the genome or antigenome include reverse transcription-PCR using improved PCR conditions (e.g., as described in Cheng et al., *Proc. Natl. Acad. Sci. USA* 91:5695–5699 (1994)), incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the larger size genome or antigenome.

Isolated polynucleotides (e.g., cDNA) encoding the genome or antigenome may be inserted into appropriate host cells by transfection, electroporation, mechanical insertion, transduction or the like, into cells which are capable of supporting a productive PIV infection, e.g., HEp-2, FRhL-DBS2, LLC-MK2, MRC-5, and Vero cells. Transfection of isolated polynucleotide sequences may be introduced into cultured cells by, for example, calcium phosphate-mediated transfection (Wigler et al., *Cell* 14: 725 (1978); Corsaro and Pearson, *Somatic Cell Genetics* 7: 603 (1981); Graham and Van der Eb, *Virology* 52: 456 (1973)), electroporation (Neumann et al., *EMBO J.* 1: 841–845 (1982)), DEAE-dextran mediated transfection (Ausubel et al., (ed.) *Current Protocols in Molecular Biology*, John Wiley and Sons, Inc., NY (1987), cationic lipid-mediated transfection (Hawley-Nelson et al., *Focus* 15: 73–79 (1993)) or a commercially available transfection regent, e.g., LipofectACE® (Life Technologies) or the like (each of the foregoing references are incorporated herein by reference in its entirety).

As noted above, in some embodiments of the invention the N, P, L and other desired PIV proteins are encoded by one or more helper viruses which is phenotypically distinguishable from that which encodes the genome or antigenome. The N, P, L and other desired PIV proteins can also be encoded by one or more expression vectors which can be the same or separate from that which encodes the genome or antigenome, and various combinations thereof. Additional proteins may be included as desired, encoded by its own vector or by a vector encoding one or more of the N, P, L and other desired PIV proteins, or the complete genome or antigenome.

By providing infectious clones of PIV the invention permits a wide range of alterations to be recombinantly produced within the PIV genome (or antigenome), yielding defined mutations which specify desired phenotypic changes. By "infectious clone" is meant cDNA or its product, synthetic or otherwise, RNA capable of being directly incorporated into infectious virions which can be transcribed into genomic or antigenomic RNA capable of serving as a template to produce the genome of infectious viral or subviral particles. As noted above, defined mutations can be introduced by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA subjects provide for better ease of manipulation than large cDNA subjects, and then readily assembled into a complete cDNA. Thus, the complete antigenome or genome cDNA, or a selected subfragment thereof, can be used as a template for oligonucleotide-directed mutagenesis. This can be through the intermediate of a single-stranded phagemid form, such as using the MUTA-gen® kit of Bio-Rad Laboratories (Richmond, Calif.), or a method using the double-stranded plasmid directly as a template such as the Chameleon® a mutagenesis kit of Strategene (La Jolla, Calif.), or by the polymerase chain reaction employing either an oligonucleotide primer or a template which contains the mutation(s) of interest. A mutated subfragment can then be assembled into the complete antigenome or genome cDNA. A variety of other mutagenesis techniques are known and can be routinely adapted for use in producing the mutations of interest in a PIV antigenome or genome cDNA of the invention.

Thus, in one illustrative embodiment mutations are introduced by using the MUTA-gene® phagemid in vitro mutagenesis kit available from Bio-Rad Laboratories. In brief, cDNA encoding an PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

Mutations can vary from single nucleotide changes to the introduction, deletion or replacement of large cDNA segments containing one or more genes or genome segments. Genome segments can correspond to structural and/or functional domains, e.g., cytoplasmic, transmembrane or ectodomains of proteins, active sites such as sites that mediate binding or other biochemical interactions with different proteins, epitopic sites, e.g., sites that stimulate antibody binding and/or humoral or cell mediated immune responses, etc. Useful genome segments in this regard range from about 15–35 nucleotides in the case of genome segments encoding small functional domains of proteins, e.g., epitopic sites, to about 50, 75, 100, 200–500, and 500–1,500 or more nucleotides.

The ability to introduce defined mutations into infectious PIV has many applications, including the manipulation of PIV pathogenic and immunogenic mechanisms. For example, the functions of PIV proteins, including the N, P, M, F, HN, and L proteins and C, D and V ORF products, can be manipulated by introducing mutations which ablate or reduce the level of protein expression, or which yield mutant protein. Various genome RNA structural features, such as promoters, intergenic regions, and transcription signals, can also be routinely manipulated within the methods and compositions of the invention. The effects of trans-acting proteins and cis-acting RNA sequences can be readily determined, for example, using a complete antigenome cDNA in parallel assays employing PIV minigenomes (Dimock, et al., *J. Virol.* 67: 2772–8 (1993), incorporated herein by reference in its entirety), whose rescue-dependent status is useful in characterizing those mutants that may be too inhibitory to be recovered in replication-independent infectious virus.

Certain substitutions, insertions, deletions or rearrangements of genes or genome segments within recombinant PIV of the invention (e.g., substitutions of a genome segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or genome segment from the same or different PIV or other source. Such modifications yield novel recombinants having desired phenotypic changes compared to wild-type or parental PIV or other viral strains. For example, recombinants of this type may express a chimeric protein having a cytoplasmic tail and/or transmembrane domain of one PIV fused to an ectodomain of another PIV. Other exemplary recombinants of this type express duplicate protein regions, such as duplicate immunogenic regions.

As used herein, "counterpart" genes, genome segments, proteins or protein regions, are typically from heterologous sources (e.g., from different PIV genes, or representing the same (i.e., homologous or allelic) gene or genome segment in different PIV types or strains). Typical counterparts selected in this context share gross structural features, e.g., each counterpart may encode a comparable protein or protein structural domain, such as a cytoplasmic domain, transmembrane domain, ectodomain, binding site or region, epitopic site or region, etc. Counterpart domains and their encoding genome segments embrace an assemblage of species having a range of size and sequence variations defined by a common biological activity among the domain or genome segment variants.

Counterpart genes and genome segments, as well as other polynucleotides disclosed herein for producing recombinant PIV within the invention, often share substantial sequence identity with a selected polynucleotide "reference sequence," e.g., with another selected counterpart sequence. As used herein, a "reference sequence" is a defined sequence used as a basis for sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant PIV of the invention are also typically selected to have conservative relationships, i.e. to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (Immunology—A Synthesis (2nd ed., E. S. Golub & D. R. Gren, eds., Sinauer Associates, Sunderland, Mass., 1991), incorporated herein by reference) Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, E-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). Moreover, amino acids may be modified by glycosylation, phosphorylation and the like.

To select candidate vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccine sufficient to confer protection against serious disease caused by subsequent infection from wild-type virus. The recombinant PIV of the invention are not only viable and more appropriately attenuated than previous vaccine candidates, but are more stable genetically in vivo—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like.

Recombinant PIV of the invention can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant PIV) is tested, e.g., for temperature sensitivity of virus replication, i.e. ts phenotype, and for the small plaque or other desired phenotype. Modified viruses are further tested in animal models of PIV infection. A variety of animal models have been described and are summarized in various references incorporated herein. PIV model systems, including rodents and non-human primates, for evaluating attenuation and immunogenic activity of PIV vaccine candidates are widely accepted in the art, and the data obtained therefrom correlate well with PIV infection, attenuation and immunogenicity in humans.

In accordance with the foregoing description, the invention also provides isolated, infectious recombinant PIV compositions for vaccine use. The attenuated virus which is a component of a vaccine is in an isolated and typically purified form. By isolated is meant to refer to PIV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated PIV of the invention may be produced by an infected cell culture, separated from the cell culture and added to a stabilizer.

For vaccine use, recombinant PIV produced according to the present invention can be used directly in vaccine formulations, or lyophilized, as desired, using lyophilization protocols well known to the artisan. Lyophilized virus will typically be maintained at about 4° C. When ready for use the lyophilized virus is reconstituted in a stabilizing solution, e.g., saline or comprising SPG, $Mg^{++}$ and HEPES, with or without adjuvant, as further described below.

PIV vaccines of the invention contain as an active ingredient an immunogenically effective amount of PIV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPL™ (3-o-deacylated monophosphoryl lipid A; RIBI ImmunoChem Research, Inc., Hamilton, Mont.) and IL-12 (Genetics Institute, Cambridge Mass.), among many other suitable adjuvants well known in the art.

Upon immunization with a PIV composition as described herein, via aerosol, droplet, oral, topical or other route, the immune system of the host responds to the vaccine by producing antibodies specific for PIV proteins, e.g., F and HN glycoproteins. As a result of the vaccination with an immunogenically effective amount of PIV produced as described herein, the host becomes at least partially or completely immune to PIV infection, or resistant to developing moderate or severe PIV infection, particularly of the lower respiratory tract.

The host to which the vaccines are administered can be any mammal which is susceptible to infection by PIV or a closely related virus and which host is capable of generating a protective immune response to the antigens of the vaccinizing strain. Accordingly, the invention provides methods for creating vaccines for a variety of human and veterinary uses.

The vaccine compositions containing the PIV of the invention are administered to a host susceptible to or otherwise at risk for PIV infection to enhance the host's own immune response capabilities. Such an amount is defined to be a "immunogenically effective dose." In this use, the precise amount of PIV to be administered within an effective dose will depend on the host's state of health and weight, the mode of administration, the nature of the formulation, etc., but will generally range from about $10^3$ to about $10^7$ plaque forming units (PFU) or more of virus per host, more commonly from about $10^4$ to $10^6$ PFU virus per host. In any event, the vaccine formulations should provide a quantity of modified PIV of the invention sufficient to effectively protect the host patient against serious or life-threatening PIV infection.

The PIV produced in accordance with the present invention can be combined with viruses of other PIV serotypes or strains to achieve protection against multiple PIV serotypes or strains. Alternatively, protection against multiple PIV serotypes or strains can be achieved by combining protective epitopes of multiple serotypes or strains engineered into one virus, as described herein. Typically when different viruses are administered they will be in admixture and administered simultaneously, but they may also be administered separately. Immunization with one strain may protect against different strains of the same or different serotype.

In some instances it may be desirable to combine the PIV vaccines of the invention with vaccines which induce protective responses to other agents, particularly other childhood viruses. In another aspect of the invention the PIV can be employed as a vector for protective antigens of other pathogens, such as respiratory syncytial virus (RSV) or measles virus, by incorporating the sequences encoding those protective antigens into the PIV genome or antigenome which is used to produce infectious PIV, as described herein.

In all subjects, the precise amount of recombinant PIV vaccine administered, and the timing and repetition of administration, will be determined based on the patient's state of health and weight, the mode of administration, the nature of the formulation, etc. Dosages will generally range from about $10^3$ to about $10^7$ plaque forming units (PFU) or more of virus per patient, more commonly from about $10^4$ to $10^6$ PFU virus per patient. In any event, the vaccine formulations should provide a quantity of attenuated PIV sufficient to effectively stimulate or induce an anti-PIV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccines at levels approximately 10-fold or more lower than wild-type virus, or approximately 10-fold or more lower when compared to levels of incompletely attenuated PIV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) PIV infection. Similarly, adults who are particularly susceptible to repeated or serious PIV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered PIV strain expressing a cytokine or an additional protein rich in T cell epitopes may be particularly advantageous for adults rather than for infants.

PIV vaccines produced in accordance with the present invention can be combined with viruses expressing antigens of another subgroup or strain of PIV to achieve protection against multiple PIV subgroups or strains. Alternatively, the vaccine virus may incorporate protective epitopes of multiple PIV strains or subgroups engineered into one PIV clone, as described herein.

The PIV vaccines of the invention elicit production of an immune response that is protective against serious lower respiratory tract disease, such as pneumonia and bronchiolitis when the individual is subsequently infected with wild—type PIV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

Preferred PIV vaccine candidates of the invention exhibit a very substantial diminution of virulence when compared to wild-type virus that is circulating naturally in humans. The virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of PIV vaccine candidates may be determined by, for example, quantifying the amount of virus present in the respiratory tract of an immunized host and comparing the amount to that produced by wild-type PIV or other attenuated PIV which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of PIV in the nasopharynx of an infected host are well known in the literature.

Levels of induced immunity provided by the vaccines of the invention can also be monitored by measuring amounts of neutralizing secretory and serum antibodies. Based on these measurements, vaccine dosages can be adjusted or vaccinations repeated as necessary to maintain desired levels of protection. Further, different vaccine viruses may be advantageous for different recipient groups. For example, an engineered PIV strain expressing an additional protein rich in T cell epitopes may be particularly advantageous for adults rather than for infants.

In yet another aspect of the invention the PIV is employed as a vector for transient gene therapy of the respiratory tract. According to this embodiment the recombinant PIV genome or antigenome incorporates a sequence which is capable of encoding a gene product of interest. The gene product of interest is under control of the same or a different promoter from that which controls PIV expression. The infectious PIV produced by coexpressing the recombinant PIV genome or antigenome with the N, P, L and other desired PIV proteins, and containing a sequence encoding the gene product of interest, is administered to a patient. Administration is typically by aerosol, nebulizer, or other topical application to the respiratory tract of the patient being treated. Recombinant PIV is administered in an amount sufficient to result in the expression of therapeutic or prophylactic levels of the desired gene product. Representative gene products which may be administered within this method are preferably suitable for transient expression, including, for example, interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation. These examples document construction of representative chimeric PIVs bearing one or more heterologous antigenic determinant(s) according to the above described methods. In one example, the HA gene of the measles virus is inserted as an extra gene into one of three gene junctions of a JS wild type or attenuated strain of HPIV3, namely, the N/P, P/M, or HN/L junction, and recombinant chimeric viruses were recovered. Insertion of the measles HA gene at three different positions in the HPIV3 genome illustrates the range of useful constructs for transferring antigenic determinants from foreign pathogens into PIV vectors. Further, it is expected that inserted gene units that are more 3'-leader proximal will be transcribed and expressed at higher levels than the same gene units located more distally, which will allow for closer modulation of heterologous gene expression (Collins et al., 3rd ed. In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1205–1243. Lippincott-Raven Publishers, Philadelphia, 1996).

The chimeric rHPIV bearing the measles virus HA insertion in a wild type rHPIV3 background replicated efficiently in vitro but was restricted in replication in hamsters compared to that of the rHPIV3 virus from which it was derived. Similarly, the recombinant chimeric HPIV3 bearing the measles virus HA insertion in an attenuated rHPIV3 background replicated in vitro and in hamsters to a level that was also slightly less than that of the attenuated rHPIV3cp45L mutant virus from which it was derived. The amount of HA protein expressed by cells infected with the attenuated rHPIV3-measles virus HA recombinants with the HA gene in the N/P or P/M junction was very high and even exceeded that seen in cells infected with native measles virus. The level of replication of the rHPIV3cp45L with a measles-virus HA insert in the N/P or P/M junction was 10-fold lower in the upper respiratory tract of the hamster than that of the rHPIV3-cp45L parent virus indicating that gene insertions can unexpectedly contribute to the attenuation of an HPIV3 vector. These results which identify a unique host range phenotype are unexpected.

Importantly, infection of hamsters with each recombinant chimeric virus tested induced high levels of antibody to both HPIV3 and to measles virus. Animals immunized with the attenuated recombinant chimeric HPIV3 carrying the HA insertion were highly resistant to replication of HPIV3 challenge virus. While the wild type measles virus does not replicate efficiently in hamsters and thus cannot be used in challenge study, the protective efficacy of the attenuated recombinant chimeric vaccine is readily apparent from the high levels of neutralizing antibody induced. These levels are associated with a high level of resistance to measles in humans (Chen et al., *J. Infect. Dis.* 162:1036–42, 1990).

It is further demonstrated in the examples that attenuated chimeric recombinant HPIV vectors, combining a backbone of HPIV3 and one or more antigenic determinants of HPIV1, can also be used as vectors to express additional foreign antigens (e.g., of HPIV2 or a non-PIV virus). This aspect of the invention takes advantage of the efficient growth and excellent attenuation properties of the HPIV3 backbone to carry antigenic determinants of multiple heterologous pathogens, as exemplified by HPIV1 and HPIV2. The cDNA encoding rPIV3-1 (a non-attenuated recombinant bearing major antigens of HPIV1) or rPIV3-1cp45 (an attenuated recombinant bearing HPIV1 major antigens) was modified by the insertion of a gene unit containing the ORF of HPIV2 HN gene between the gene units containing the F and HN ORFs of HPIV1. The recombinant chimeric viruses, designated rPIV3-1.2HN and rPIV3-1cp45.2HN, were readily recovered and replicated efficiently in tissue culture. Each virus exhibited a level of temperature sensitivity of replication in vitro similar to that of its rPIV3-1 or rPIV3-1cp45 parent virus. The insertion of the PIV2 HN attenuated both the rPIV3-1 and rPIV3-cp45 viruses in hamsters, a finding similar to that observed with the insertion of the measles viruses HA into rJS and into rPIV3cp45. Infection of hamsters with these antigenic rPIV3-1 recombinants bearing the PIV2 HN gene insert induced serum antibody responses reactive against both HPIV1 and HPIV2.

Thus, it is possible to use an attenuated rHPIV3 or rHPIV3-1 vaccine candidate as a vector to infect the respiratory tract of susceptible hosts and thereby induce a vigorous antibody response to foreign protective antigens expressed from an extra gene unit, as well as against the HPIV vector itself. The presence of three antigenic serotypes of HPIV, which do not provide significant cross-protection, allows for more effective, sequential immunization of human infants with antigenically distinct variants of HPIV each bearing the same or different heterologous antigenic determinant(s), e.g., a protective antigen, antigenic domain or epitope of measles virus or of one or more different viral or microbial pathogens. Sequential immunization permits development of a primary immune response to the foreign protein, which is boosted during subsequent infections with a secondary, antigenically-distinct HPIV bearing one or more heterologous antigenic determinants, e.g., a protective antigen, antigenic domain or epitope of measles virus or of one or more different viral or microbial pathogens. In this way, the immunity induced to one HPIV vector can be circumvented by boosting with an antigenically distinct HPIV vector. In this context, successful immunization of animals that are immune to PIV3 has been achieved with attenuated PIV3-1 vaccine candidates, confirming the feasibility of sequential immunization with serotypically distinct PIV viruses even if these PIVs share proteins other than HN and F. (Tao et al., *Vaccine* 17:1100–8, 1999). In this study, the immunogenicity and efficacy of rPIV3-1.cp45L against PIV1 challenge was examined in hamsters with and without prior immunity to PIV3. rPIV3-1.cp45L efficiently infected hamsters previously infected with wild type or attenuated PIV3, but there was approximately a five-fold reduction in replication of rPIV3-1.cp45L virus in the PIV3-immune animals. However, rPIV3-1.cp45L immunization of PIV3-immune animals induced a vigorous serum antibody response to PIV1 and reduced replication of PIVL challenge virus 1000-fold in the lower respiratory tract and 200-fold in the upper respiratory tract. These results demonstrate that the recombinant chimeric rPIV3-1.cp45L candidate vaccine can induce immunity to PIV1 even in animals immune to PIV3. This establishes the feasibility of employing a sequential immunization schedule in which a recombinant chimeric rPIV3-1.cp45L or other PIV vaccine virus is given following a live attenuated PIV3 vaccine. since rPIV3-1.cp45L readily induced protective immunity against itself, it would also induce an effective immune response to any vectored protective antigen that it was carrying. Also, the PIVs and RSV have the unusual property of being able to reinfect the respiratory tract, although reinfections typically are not associated with serious disease. Thus, vector based vaccine constructs of the invention are useful to boost immune responses by a second, third or fourth administration of the same HPIV vector or by sequential use of different vectors.

In preferred sequential vaccination methods of the invention, it is desirable to sequentially immunize an infant with different PIV vectors each expressing the same heterologous antigenic determinant such as the measles virus HA. This sequential immunization permits the induction of the high titer of antibody to the heterologous protein that is characteristic of the secondary antibody response. In one embodiment, early infants (e.g. 2–4 month old infants) are immunized with an attenuated chimeric HPIV3 expressing a heterologous antigenic determinant, for example the measles virus HA protein, and also adapted to elicit an immune response against HPIV3. One exemplary vaccine candidate useful in this context is the rcp45L(HA P-M) recombinant. Subsequently, e.g., at four months of age the infant is again immunized but with a different, secondary PIV vector construct antigenically distinct from the first. An exemplary vaccine candidate in this context is the rPIV3-1 cp45L virus expressing the measles virus HA gene and HPIV1 antigenic determinants as functional, obligate glycoproteins of the vector. Following the first vaccination, the vaccine will elicit a primary antibody response to both the PIV3 HN and F proteins and to the measles virus HA protein, but not to the PIV1 HN and F protein. Upon secondary immunization with the rPIV3-1 cp45L expressing the measles virus HA, the vaccine will be readily infected with the vaccine because of the absence of antibody to the PIV1 HN and F proteins and will develop both a primary antibody response to the PIV1 HN and F protective antigens and a high titered secondary antibody response to the heterologous measles virus HA protein. A similar sequential immunization schedule can be developed where immunity is sequentially elicited against HPIV3 and then HPIV2 by one or more of the chimeric vaccine viruses disclosed herein, simultaneous with stimulation of an initial and then secondary, high titer protective response against measles or another non-PIV pathogen. This sequential immunization strategy, preferably employing different serotypes of PIV as primary and secondary vectors, effectively circumvents immunity that is induced to the primary vector, a factor ultimately limiting the usefulness of vectors with only one serotype.

Further in accordance with this aspect of the invention, exemplary coordinate vaccination protocols may incorporate two, three, four and up to six or more separate chimeric HPIV vaccine viruses administered simultaneously (e.g., in a polyspecific vaccine mixture) in a primary vaccination step, e.g., at one, two or four months of age. For example, two or more and up to a full panel of HPIV-based vaccine viruses can be adminstered that separately express one or more antigenic determinants (i.e., whole antigens, immunogenic domains, or epitopes) selected from the G protein of RSV subgroup A, the F protein of RSV subgroup A, the G protein of RSV subgroup B, the F protein of RSV subgroup B, the HA protein of measles virus, and/or the F protein of measles virus. Coordinate booster administration of these same PIV3-based vaccine constructs can be repeated at two months of age. Subsequently, e.g., at four months of age, a separate panel of 2–6 or more antigenically distinct (referring to vector antigenic specificity) live attenuated HPIV-based vaccine viruses can be adminstered in a secondary vaccination step. For example, secondary vaccination may involve concurrent administration of a mixture or multiple formulations that contain(s) multiple HPIV3-1 vaccine constructs that collectively express RSV G from subgroup A, RSV F from subgroup A, RSV F from subgroup B, RSV G from subgroup B, measles virus HA, and/or measles virus F, or antigenic determinants from any combination of these proteins. This secondary immunization provides a boost in immunity to each of the heterologous RSV and measles virus proteins or antigenic determinant(s) thereof. At six months of age, a tertiary vaccination step involving administration of one-six or more separate live attenuated PIV3-2 vector-based vaccine recombinants can be coordinately administered that separately or collectively express RSV G from subgroup A, RSV F from subgroup A, RSV G from subgroup B, RSV F from subgroup B, measles virus HA, and/or measles virus F, or antigenic determinant(s) thereof. Optionally at this step in the vaccination protocol, rPIV3 and rPIV3-1 vaccines may be adminstered in booster formulations. In this way, the strong immunity characteristic of secondary antibody to PIV1, PIV2, PIV3, RSV A, RSV B, and measles viruses are all induced within the first six months of infancy. Such a coordinate/sequential immunization strategy, which is able to induce secondary antibody responses to multiple viral respiratory pathogens, provides a highly powerful and extremely flexible immunization regimen that is driven by the need to immunize against each of the three PIV viruses and other pathogens in early infancy.

As described herein above and further detailed in the illustrative examples that follow, the present invention provides six major advantages over previous attempts to immunize the young infant against measles virus or other microbial pathogens. First, the PIV recombinant vector into which the protective antigen or antigens of measles virus or of other microbial pathogens is inserted is an attenuated rPIV bearing one or more attenuating genetic elements that are known to attenuate virus for the respiratory tract of the very young human infant (Karron et al., *Pediatr. Infect. Dis. J.* 15:650–654, 1996; Karron et al., *J. Infect. Dis.* 171:1107–1114, 1995a; Karron et al., *J. Infect. Dis.* 172: 1445–1450, 1995b). This extensive history of prior clinical evaluation and practice greatly facilitates evaluation of derivatives of these recombinants bearing foreign protective antigens in the very young human infant.

A second advantage satisfied by the invention is that the rPIV backbone carrying the HA or other protective antigen of a heterologous, non-PIV human pathogen will induce a dual protective immune response against (1) one or more PIVs, for which there are compelling independent needs for vaccines as indicated above, and (2) the measles virus or other microbial pathogen whose protective antigen is expressed by the vector. This contrasts with the VSV-measles virus HA recombinant described above which will induce immunity to only one human pathogen, i.e., the measles virus, and in which the immune response to the vector itself is at best irrelevant or is potentially disadvantageous. The coding sequences of the foreign genes inserted into various members of the *Mononegavirales* Order of viruses have remained intact in the genomes of the most of the recombinant viruses following multiple cycles of replication in tissue culture cells, indicating that members of this group of viruses are excellent candidates for use as vectors (Bukreyev et al., *J. Virol.* 70:6634–41, 1996; Schnell et al., *Proc. Natl. Acad. Sci. USA* 93:11359–65, 1996a; Singh et al., *J. Gen. Virol.* 80:101–6; Yu et al., *Genes Cells* 2:457–66, 1997).

Another advantage provided by the invention is that use of a human pathogen backbone, for which there is a need for a vaccine, will favor the introduction of such a live attenuated virus vector into an already crowded early childhood immunization schedule.

In addition, immunization via the mucosal surface of the respiratory tract offers various advantages. A live attenuated PIV3 was shown to replicate in the respiratory tract of rhesus monkeys and to induce a protective immune response against itself in the presence of high quantities of maternally-acquired PIV3-specific serum antibodies. The ability of two candidate PIV3 vaccines to infect and to replicate efficiently in the upper respiratory tract of the very young human infant who possess maternally-acquired antibodies has also been demonstrated (Karron et al., *Pediatr. Infect. Dis. J.* 15:650–654, 1996; Karron et al., *J. Infect. Dis.* 171:1107–1114, 1995a; Karron et al., *J. Infect. Dis.* 172: 1445–1450, 1995b). This is in contrast to the currently licensed measles virus vaccine which is poorly infectious when administered to the upper respiratory tract of humans and which is highly sensitive to neutralization when administered parenterally to young children (Black et al., *New Eng. J. Med.* 263:165–169, 1960; Kok et al., *Trans. R. Soc. Trop. Med. Hyg.* 77:171–6, 1983; Simasathien et al., *Vaccine* 15:329–34, 1997). The replication of the HPIV vector in the respiratory tract will stimulate the production of both mucosal IgA and systemic immunity to the HPIV vector and to the expressed foreign antigen. Upon subsequent natural exposure to wild type virus, e.g., measles virus, the existence of vaccine-induced local and systemic immunity should serve to restrict its replication at both its portal of entry, i.e., the respiratory tract, as well as at systemic sites of replication.

Also, the presence of three antigenic serotypes of HPIV, each of which causes significant disease in humans and hence can serve simultaneously as vector and vaccine, presents a unique opportunity to sequentially immunize the infant with antigenically distinct variants of HPIV each bearing the same foreign protein. In this manner the sequential immunization will permit the development of a primary immune response to the foreign protein which can be boosted during subsequent infections with the antigenically distinct HPIV also bearing the same or a different foreign protein or proteins, i.e., the protective antigen of measles virus or of another microbial pathogen. In this regard, several attenuated PIVs have been identified herein as exemplary vectors for use in this format of sequential immunization, e.g., PIV3cp45; PIV3-1cp45; PIV3-1cp45L, PIV3-2CT; and PIV3-2TM. It is also likely that readministration of homologous HPIV vectors will also boost the response to both HPIV and the foreign antigen since the ability to cause multiple reinfections in humans is an unusual but characteristic attribute of the HPIVs (Collins et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1205–1243. Lippincott-Raven Publishers, Philadelphia, 1996).

Yet another advantage is that the introduction of a gene unit into a PIV vector has several unexpected, but highly desirable effects, for the production of attenuated viruses. First, the insertion of gene units expressing the HA of measles virus or the HN of PIV2 each specify a host range phenotype on the PIV vector that has not been previously recognized, i.e., the resulting PIV vector replicates efficiently in vitro but is restricted in replication in vivo in both the upper and lower respiratory tracts. These findings identify the insertion of a gene unit expressing a viral protective antigen as an attenuating factor for the PIV vector, a desirable property in live attenuated virus vaccines of the invention.

The ability of chimeric HPIVs of the invention bearing heterologous sequences to replicate efficiently in vitro demonstrates the feasibility for large scale production of vaccine. This is in contrast to the replication of some single-stranded, negative-sense RNA viruses which can be inhibited in vitro by the insertion of a foreign gene (Bukreyev et al., *J. Virol.* 70:6634–41, 1996).

EXAMPLE I

Construction of cDNAs Encoding a Chimeric HPIV3/Measles Virus-HA Antigenome and Recovery of Infectious Virus Full-length cDNA clones, p3/7(131)2G+, encoding the complete 15462 nucleotide antigenome of the JS PIV3 wt virus, and pFLCcp45L, which encodes the antigenome of the derivative of JS wt containing three cp45-specific temperature-sensitive mutations in the L ORF of PIV3, have been previously described (Durbin et al., *Virology* 235: 323–332, 1997a; Skiadopoulos et al., *J. Virol.* 72:1762–8, 1998, each incorporated herein by reference). These clones were used as vectors for the insertion of the HA gene of measles virus to create both wildtype and attenuated HPIV3 chimeric constructs which express a heterologous antigenic determinant, exemplified by the HA protein, of measles virus. The size of each insert containing the HA gene of measles was a multiple of six such that the chimeric virus recovered from the cDNA would conform to the rule of six (Durbin et al., *Virology* 234:74–83, 1997b, incorporated herein by reference).

Construction of Full-Length Chimeric HPIV3 cDNAs Encoding the HA Protein of Measles Virus in the N/P or P/M Junctions.

The PmlI to BamHI fragment of p3/7(131)2G+ (nt 1215–3903 of the PIV3 antigenome) was subcloned into the plasmid pUC119 {pUC119(PmlI-BamHI)} which had been modified to include a PmlI site in the multiple cloning region. Two independent single-stranded mutagenesis reactions were performed on pUC119(PmlI-BamHI) using Kunkel's method (Kunkel et al., *Methods Enzymol.* 154: 367–382, 1987, incorporated herein by reference); the first reaction introduced an Af/II site in the 3' (downstream)-noncoding region of the N gene by mutating the CTAAAT sequence at nts 1677–1682 of the antigenome to CTTAAG (pAf/II N-P), and the second, separate, reaction introduced an Af/II site in the in the 3'-noncoding region of the P gene by mutating the TCAATC sequence at nts 3693–3698 of the antigenome to CTTAAG (pAf/II P-M).

The HA ORF of measles virus Edmonston strain was amplified from Edmonston wild type virus by reverse transcription polymerase chain reaction (RT-PCR). The nt sequence of the Edmonston wild type HA open reading frame (ORF) is in GenBank Accession # U03669, incorporated herein by reference (note that this sequence is the ORF only without the upstream 3 nts or the stop codon). Measles virus RNA was purified from clarified medium using TRIzol-LS (Life Technologies, Gaithersburg, Md.) following the manufacturer's recommended procedure. RT-PCR was performed with the Advantage RT-for-PCR and Advantage-HF PCR kits (Clontech, Palo Alto, Calif.) following the recommended protocols. Primers were used to generate a PCR fragment spanning the entire ORF of the measles virus HA gene flanked by PIV3 non-coding sequence and Af/II restriction sites. The forward primer 5'-TTAATCTTAA G AATATACAAATAAGAAAAACTTAGGATTAAAGAG-CGATGTCACCA CAACGAGACCGGATAAATGCCT-TCTAC-3' (SEQ ID NO. 5) encodes an Af/II site (italicized) upstream of PIV3 noncoding sequence derived from the N/P gene junction-nts 3699–3731(underlined), containing GE, IG and GS sequences (FIG. 1A) and the beginning of the measles HA ORF (bolded) preceded by three non-HPIV3, non-measles virus nts designated in the primer. The reverse primer 5'-ATTATTGCTTAA G GTTTGTTCGGTGTCGTTTCTTTGTTGGATCCTATCT-GCGATTGGT TCCATCTTC-3' (SEQ ID NO. 6) encodes an Af/II site (italicized) downstream (in the positive-sense complement) of PIV3 noncoding sequence derived from the P gene, nt 3594–3623 (underlined), and the end of the measles HA ORF (bolded). The resultant PCR fragment was then digested with Af/II and cloned into p(Af/II N-P) and p(Af/II P-M) to create pUC119(HA N-P) and pUC119(HA P-M) respectively. pUC119(HA N-P) and pUC119(HA P-M) were sequenced over the entire Af/II insert using the dRhodamine Terminator Cycle Sequencing Ready Reaction (ABI prism, PE Applied Biosystems, Foster city, Calif.), and the sequence was confirmed to be correct.

The PmlI to BamHI fragments of pUC119(HA N-P) and pUC119(HA P-M) were separately cloned into the full-length antigenome cDNA plasmid p3/7(131)2G+ as previously described (Durbin et al., *Virology* 235:323–332, 1997a, incorporated herein by reference) to create pFLC(HA N-P) and pFLC(HA P-M) (FIG. 1). The XhoI-NgoMI fragment (nt 7437–15929) of pFLCcp45L was then cloned into the XhoI-NgoMI window of both pFLC(HA N-P) and pFLC(HA P-M) to create pFLCcp45L(HA N-P) and pFLCcp45L(HA P-M). pFLCcp45L encodes the three amino acid changes in the L gene of PIV3 cp45 (aa position 942, 992, and 1558) which confer most of the temperature-sensitivity and attenuation of the cp45 vaccine candidate virus (Skiadopoulos et al., *J. Virol.* 72:1762–8, 1998, incorporated herein by reference), and the transfer of the XhoI-NgoMI fragment transferred those mutations.

Construction of Full-Length HPIV3 Chimeric cDNAs Encoding the HA Protein of Measles in the HN/L Junction A HPIV3 chimeric cDNA was constructed by PCR to include a heterologous polynucleotide sequence, exemplified by the measles virus HA gene, encoding a heterologous antigenic determinant of the measles virus, flanked by the transcription signals and the noncoding regions of the HPIV3 HN gene. This cDNA was designed to be combined with an rPIV3 vector as an extra gene following the HN gene. First, using Kunkel mutagenesis (Kunkel et al., *Methods Enzymol.* 154:367–382, 1987, incorporated herein by reference), a StuI site was introduced in the 3'-noncoding region of the HN gene by mutating the AGACAA sequence at nts 8598–8603 of the antigenome to AGGCCT yielding plasmid p3/7(131)2G-Stu (FIG. 1B). A cDNA containing the measles HA ORF flanked by HPIV3 sequences (see FIG. 1B) was then constructed in three pieces by PCR. The first PCR synthesized the left-hand, upstream piece of the gene. The forward primer 5'-GACAATAGGCCT AAAAGGGAAATATAAAAAACTTAGGAGTAAAGT-TACGCAATCC-3' (SEQ ID NO. 7) contains a StuI site (italicized) followed by HPIV3 sequence (underlined) which includes the downstream end of the HN gene (HPIV3 nts 8602–8620), an intergenic region, and the gene-start signal and sequence from the upstream end of the HN gene (HPIV3 nt 6733–6753). The reverse primer 5'-GTAGAA CGCGTT-TATCCGGTCTCGTTGTGGTGACAT CTCGAATTTGGATTTGTCTATTGGGTCCTTCC-3' (SEQ ID NO. 8) contains an MluI site (italicized) downstream of the start of the measles HA ORF (bolded) followed by the complement to HPIV3 nts 6744–6805 (underlined), which are part of the upstream HN noncoding region. The MluI site present in the introduced measles virus ORF was created by changing nt 27 from T (in the wild type Edmonston HA gene) to C and nt 30 from C to G. Both of these changes are noncoding in the measles virus ORF. The PCR was performed using p3/7(131)2G-Stu as template. The resulting product, termed PCR fragment 1, is flanked by a StuI site at the 5'-end and an MluI site at the 3'-end and contains the first 36 nt of the measles HA ORF downstream of noncoding sequence from the HPIV3 HN gene. The second PCR reaction synthesized the right-hand end of the HN gene. The forward primer 5'-CAGTCACCCGGGAA-GATGGAACCAATCGCAGATAG TCATAATTAACCATAATATGCATCAATCTATCTATAA-TACAA-3' (SEQ ID NO. 9) contains the XmaI (italics) and the end of the measles HA ORF (bold), followed by HPIV3 nts 8525–8566 (underlined) representing part of the downstream nontranslated region of the HN gene. The reverse primer 5'-CCATGTAATTGAATCCCCCAACACTAGC-3' (SEQ ID NO. 10), spans HPIV3 nts 11448–11475, located in the L gene. The template for the PCR was p3/7(131)2G-Stu. PCR fragment 2 which resulted from this reaction contains the last 35 nt of the measles HA ORF and approximately 2800 nt of the L ORF of PIV3 and is flanked by an XmaI site and an SphI site (which occurs naturally at HPIV3 position 11317). The third PCR reaction amplified the largest, central portion of the measles HA ORF from the template cDNA pTM-7, a plasmid which contains the HA ORF of the Edmonston strain of measles virus supplied by the ATCC. Sequence analysis of this plasmid showed that the measles virus HA ORF contained in PTM-7 contains 2 amino acid differences from pTM-7 ob the Edmonston wild type HA sequence used for insertion into the N-P and M-P junction, and these were at amino acid positions 46 (F to S) and at position 481 (Y to N). The forward primer 5'-CG-GATAAACGCGTTCTACAAAGATAACC-3' (SEQ ID NO.

11) (MluI site italicized) and reverse primer 5'-CCATCT-TCCCGGGTGACTGTGCAGC-3' (SEQ ID NO. 12) (XmaI site italicized) amplified PCR fragment 3 which contained nts 19–1838 of the measles HA ORF. To assemble the pieces, PCR fragment 1 was digested with StuI and MluI while PCR fragment 3 was digested with MluI and XmaI. These two digested fragments were then cloned by triple ligation into the StuI-XmaI window of pUC118 which had been modified to include a StuI site in its multiple cloning region. The resultant plasmid, pUC118(HA 1+3) was digested with StuI and XmaI while PCR fragment 2 was digested with XmaI and SphI. The two digested products were then cloned into the StuI-SphI window of p3/7(131) 2G-Stu, resulting in the plasmid pFLC(HA HN-L). The StuI-SphI fragment, including the entire measles HA ORF, was then sequenced using the dRhodamine Terminator Cycle Sequencing Ready Reaction (ABI prism, PE Applied Biosystems, Foster city, Calif.). The chimeric construct sequence was confirmed. In this way, the measles virus HA ORF flanked by HPIV3 transcription signals was inserted as an extra gene into the N/P, P/M, or HN/L junction of an antigenomic cDNA vector comprising a wild type HPIV3 or into the N/P or P/M junction of an antigenomic cDNA vector comprising an attenuated HPIV3.

Recovery of Chimeric rPIV3 Wild Type and rcp45L Expressing the HA Protein of Measles Virus The five full-length vector cDNAs bearing the measles HA ORF as a separate gene were transfected separately into HEp-2 cells on six-well plates (Costar, Cambridge, Mass.) together with the support plasmids {pTM(N), pTM(P no C), and pTM(L)}, and LipofectACE (Life Technologies), and the cells were simultaneously infected with MVA-T7, a replication-defective vaccinia virus recombinant encoding the bacteriophage T7 polymerase protein as previously described (Durbin et al., Virology 235:323–332, 1997; Durbin et al., Virology 234:74–83, 1997, each incorporated herein by reference). pTM(P no C) is a derivative of pTM(P) (Durbin et al., Virology 261:319–330, 1999) in which the C ORF expression has been silenced by mutation of the C start codon. After incubation at 32° C. for three days, the transfection harvest was passaged onto a fresh monolayer of Vero cells in a T25 flask and incubated for 5 days at 32° C. (referred to as passage 1). The presence of HPIV3 in the passage 1 harvest was determined by plaque titration on LLC-MK2 monolayer cultures with plaques visualized by immunoperoxidase staining with HPIV3 HN-specific and measles HA-specific monoclonal antibodies as previously described (Durbin et al., Virology 235:323–332, 1997, incorporated herein by reference).

The rPIV3(HA HN-L) virus present in the supernatant of the appropriate passage 1 harvest was biologically-cloned by plaque purification three times on LLC-MK2 cells as previously described (Hall et al., Virus Res. 22:173–184, 1992, incorporated herein by reference). rPIV3 (HA N-P), rcp45L (HA N-P), rPIV3 (HA P-M), and rcp45L(HA P-M) were biologically-cloned from their respective passage 1 harvests by terminal dilution using serial 2-fold dilutions on 96-well plates (12 wells per dilution) of Vero cell monolayers. The biologically-cloned recombinant viruses from the third round of plaque purification or from the second or third round of terminal dilution were then amplified twice in LLC-MK2 cells {rPIV3(HA HN-L)} or Vero cells {rPIV3 (HA N-P), rcp45L(HA N-P), rPIV3(HA P-M), rcp45L (HA P-M)} at 32° C. to produce virus for further characterization. As a first step in confirming and characterizing the recombinant chimeric PIV3s expressing the HA glycoprotein of measles virus, each passage 1 harvest was analyzed by RT-PCR using three different primer pairs; one pair for each location of the HA ORF insert. The first primer pair amplified a fragment of PIV3 spanning nucleotides 1596–1968 of the full-length HPIV3 genome, which includes the N/P insertion site. This fragment size increased to 2298 nucleotides with the measles HA ORF inserted between the N and P genes. The second primer pair amplified a fragment of PIV3 spanning nucleotides 3438–3866 of the full-length HPIV3 genome, which includes the P/M insertion site. With the measles HA ORF inserted between the P and M genes, this fragment size increased to 2352 nucleotides. The third primer pair amplified a fragment of PIV3 spanning nucleotides 8466–8649 of the full-length antigenome. With the measles HA ORF inserted between the HN and L genes, this fragment size increased to 2211 nucleotides, which includes the HN/L insertion site. All five recovered viruses contained an insert of the appropriate size at the appropriate location. The generation of each PCR product was dependent upon the inclusion of reverse transcriptase, indicating that each was derived from RNA and not from contaminating cDNA.

Figure 2:
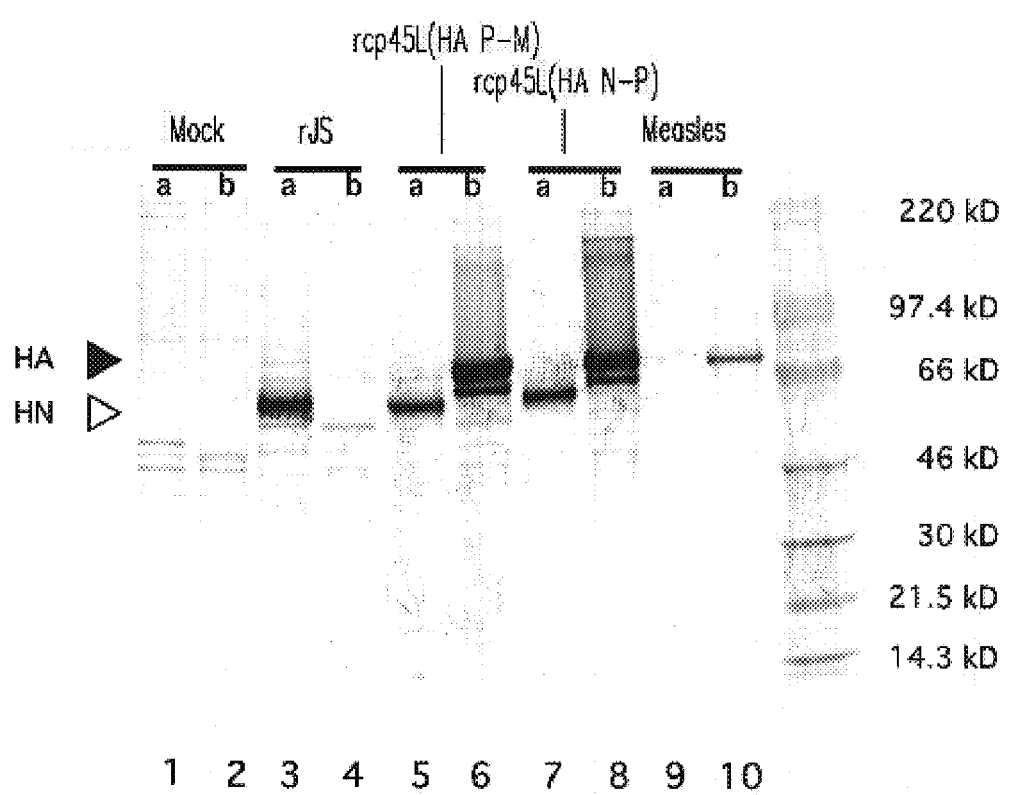
FIG. 2 illustrates expression of the HA protein of measles virus by rHPIV3-measles virus-HA chimeric viruses in LLC-MK2 cells. The figure presents a radioimmunoprecipitation assay (RIPA) demonstrating that the measles HA protein is expressed by the recombinant chimeric viruses rcp45L(HA P-M) and rcp45L(HA N-P), and by the Edmonston wild type strain of measles virus (Measles), but not by the rJS wild type HPIV3 (rJS). Lanes A—$^{35}$S-labeled infected cell lysates were immunoprecipitated by a mixture of three monoclonal antibodies specific to the HPIV3 HN protein). The 64 kD band corresponding to the HN protein (open arrow) is present in each of the three HPIV3 infected cell lysates (lanes 3, 5, and 7), but not in the measles virus infected cell lysates (lane 9), confirming that the rcp45L(HA P-M) and rcp45L(HA N-P) chimeras are indeed HPIV3 and express similar levels of HN proteins. Lanes (b)—$^{35}$S-labeled infected cell lysates were immunoprecipitated by a mixture of monoclonal antibodies which recognizes the HA glycoprotein of measles virus (79-XV-V17, 80-III-B2, 81-1-366) (Hummel et al., *J. Virol.* 69:1913–6, 1995; Sheshberadaran et al., *Arch. Virol.* 83:251–68, 1985, each incorporated herein by reference). The 76 kD band corresponding to the HA protein (closed arrow) is present in lysates from cells infected with the rcp45L(HA) chimeric viruses (lanes 6, 8) and the measles virus (lane 10), but not in the lysates from rJS infected cells (lane 4), a HPIV3 wild type virus which does not encode a measles virus HA gene.

Monolayers of LLC-MK2 cells in T25 flasks were infected at a multiplicity of infection (MOI) of 5 with either rcp45L(HA N-P), rcp45L(HA P-M), rJS or were mock infected. Monolayers of Vero cells in T25 flasks were infected with the Edmonston wild type strain of measles virus at an MOI of 5. Vero cell monolayers were chosen for the measles Edmonston virus infection because measles virus does not grow well in LLC-MK2 cells. At 24 hours post-infection, the monolayer was washed with methionine-minus DMEM (Life Technologies). $^{35}$S methionine was added to DMEM-minus media at a concentration of 10 uCi/ml and 1 ml was added to each flask which was then incubated at 32° C. for 6 hours. The cells were harvested and washed 3 times in PBS. The cell pellets were resuspended in 1 ml RIPA buffer {1% (w/v) sodium deoxycholate, 1% (v/v) Triton X-100 (Sigma), 0.2% (w/v) SDS, 150 mM NaCl, 50 mM Tris-HCl, pH 7.4}, freeze-thawed and clarified by centrifugation at 6500×G for 5 minutes. The cell extract was transferred to a fresh eppendorf tube and a mixture of monoclonal antibodies which recognizes the HA glycoprotein of measles virus (79-XV-V17, 80-III-B2, 81-1-366) (Hummel et al., J. Virol. 69:1913–6, 1995; Sheshberadaran et al., Arch. Virol. 83:251–68, 1985, each incorporated herein by reference) or which recognizes the HN protein (101/1, 403/7, 166/11) of PIV3 (van Wyke Coelingh et al., Virology 160:465–72, 1987, incorporated herein by reference) was added to each sample and incubated with constant mixing for 2 hours at 4° C. Immune complexes were precipitated by adding 200 μl of a 10% suspension of protein A Sepharose beads (Sigma, St. Louis, Mo.) to each sample followed by constant mixing at 4° C. overnight. Each sample was suspended in 90 μl of 1× loading buffer and 10 μl of reducing agent was added. After heating at 70° C. for 10 minutes, 20 μl of each sample was loaded onto a 4–12% polyacrylamide gel (NuPAGE, Novex, San Diego, Calif.) per the manufacturer's recommendations. The gel was dried and autoradiographed (FIG. 2). rcp45L(HA P-M) and rcp45L(HA N-P) encoded a protein precipitated by the anti-measles HA monoclonal antibodies which was the same size as the authentic measles HA protein. rcp45L(HA P-M) and rcp45L(HA N-P) expressed the measles virus HA protein to a greater extent than did the Edmonston wild type strain of measles virus indicating that these constructs efficiently expressed the measles virus HA from the N/P and P/M junctions of the attenuated strain rcp45L. rcp45L(HA N-P) and rcp45L(HA P-M) were confirmed to be HPIV3-based by their reactivity with the PIV3 anti-HN monoclonal antibodies.

The Temperature Sensitivity of Replication of rPIV3 Parent and rPIV3(HA) Chimeric Viruses In Vitro The level of temperature sensitivity of replication of the chimeric rPIV3s bearing the measles virus HA insertion was evaluated to assess whether acquisition of the HA insert modified the level of replication in the chimeric virus compared to the parental, vector virus at various temperatures (Table 1). Serial 10-fold dilutions of rcp45L, rcp45L (N-P), rcp45L(HA P-M), rPIV3(HA HN-L), rPIV3(HA P-M), or rJS were carried out in L-15 supplemented with 5% FBS, 4 mM glutamine, and 50 µg/ml gentamicin on LLC-MK2 cell monolayers in 96 well plates and incubated at 32, 36, 37, 38, 39, or 40° C. for 6 days. Virus was detected by hemadsorption and reported as $\log_{10}$ $TCID_{50}$/ml. Interestingly, chimeric derivatives of both wild type vector viruses bearing the measles virus HA gene, rPIV3 (HA HN-L) and rPIV3(HA P-M), were slightly restricted in replication at 40° C. (Table 1). The two attenuated rPIV3s bearing the measles virus HA gene, rcp45L(N-P) and rcp45L(HA P-M), possessed a level of temperature sensitivity similar to that of the rcp45L parental, vector virus with rcp45L(HA P-M) being slightly more ts than its parent. Thus, the viruses bearing the inserts replicated in tissue culture similarly to the parental vector rPIV3 from which they were derived, with only a slight increase in temperature sensitivity. These results indicate that rPIV3 can readily serve as a vector to accommodate the HA insert at different sites without major alteration in replication in vitro, and that rPIV3(HA) chimeric viruses can readily accommodate the further addition of one or more attenuating mutations.

TABLE 1

Replication at permissive and elevated temperatures of recombinant HPIV3s expressing the HA protein of measles virus as an extra gene in the N-P, P-M, or HN-L junctions.

| Virus | Virus titer ($\log_{10} TCID_{50}$/ml) at indicated temperature | | | | | |
|---|---|---|---|---|---|---|
| | 32° C.[1] | 36° C. | 37° C. | 38° C. | 39° C. | 40° C. |
| rcp45L[2] | 8.2 | 8.2 | 7.2 | <u>5.2</u>[6] | 3.4 | 3.0 |
| rcp45L(HA P-M)[3] | 7.4 | 6.7 | <u>5.2</u> | 4.2 | 1.4 | 1.4 |
| rcp45L(HA N-P)[3] | 7.4 | 7.2 | 5.7 | <u>4.2</u> | 2.2 | ≦1.2 |
| rPIV3(HA HN-L)[4] | 7.7 | 8.2 | 7.0 | 7.7 | 6.7 | <u>5.2</u> |
| rPIV3(HA P-M)[4] | 7.7 | 7.4 | 6.7 | 6.2 | 6.2 | <u>4.7</u> |
| PIV3-rJS[5] | 8.7 | 9.0 | 9.0 | 8.4 | 8.2 | 9.0 |

[1]Permissive temperature.
[2]Recombinant ts derivative of the JS wild type strain of HPIV3, bearing 3 attenuating amino acid substitutions derived from cp45.
[3]Recombinant attenuated ts derivative of JS wild type HPIV3 expressing the HA protein of measles virus.
[4]Recombinant wild type HPIV3 expressing the HA protein of measles virus.
[5]Recombinant wild type HPIV3, strain JS.
[6]Underlined titer represents the lowest restrictive temperature at which a 100-fold or greater reduction in titer from that at 32° C. is seen and defines that shut-off temperature of the virus.

EXAMPLE II

Chimeric rPIV3s Bearing an Antigenic Determinant of Measles Virus Replicate Efficiently in Hamsters and Induce High Titers of Antibodies Against Both HPIV3 and Measles Determination of the Level of Replication and Immunogenicity of the rPIV3(HA) Viruses in Hamsters The levels of replication of chimeric rPIV3s bearing an antigenic determinant of the measles virus was compared with that of their parent rPIV3s to determine if the acquisition of the determinant, exemplified by an HA insert, significantly modified their ability to replicate and to induce an immune response in vivo. In two different experiments, groups of 6 or 7 4–6 week-old Golden Syrian hamsters were inoculated intranasally with 0.1 ml of EMEM (Life Technologies) containing $10^{6.0}$ PFU of rJS, rcp45L, rcp45L(HA P-M), rcp45L(HA N-P), rPIV3(HA HN-L), or rPIV3(HA P-M) (Tables 2 and 3). On day 4 post-inoculation the hamsters were sacrificed and the lungs and nasal turbinates were harvested. The nasal turbinates and lungs were homogenized in 10% or 20% w/v suspension of L-15 (Quality Biologicals, Gaithersburg, Md.) respectively, and the samples were rapidly frozen. Virus present in the samples was titered on 96 well plates of LLC-MK2 cell monolayers and incubated at 32° C. for 7 days. Virus was detected by hemadsorption, and the mean $\log_{10}$ $TCID_{50}$/g was calculated for each group of hamsters. Insertion of the HA gene into wild type rJS (Table 2) restricted its replication 4 to 20-fold in the upper respiratory tract and up to five-fold in the lower respiratory tract indicating only a slight effect of the acquisition of the HA gene on replication of wild type rJS virus in hamsters. The replication of each of the two rcp45(HA) antigenic chimeras was 10-fold less in the upper respiratory tract of hamsters (Table 3)-than that of rcp45L, the recombinant parent virus bearing the three attenuating ts mutations in the L protein, but was the same as the rcp45L parent in the lower respiratory tract. Thus, for each of the two rcp45(HA) antigenic chimeras there was a slight, but statistically significant, reduction in replication in the upper respiratory tract of hamsters indicating that the acquisition of the HA gene by rcp45L increased its attenuation for the upper, but not the lower, respiratory tract. Thus, the effect of the insertion of the HA gene on the replication of wild type or attenuated PIV3 was comparable in the upper respiratory tract.

TABLE 2

Replication of wildtype rPIV3(HA) chimeric viruses in the upper and lower respiratory tract of hamsters

| | | Virus Titer ($\log_{10} TCID_{50}$/gm ± S.E.[2]) [Tukey-Kramer Grouping][3] | |
|---|---|---|---|
| Virus[1] | # Animals | Nasal Turbinates | Lungs |
| rcp45L | 8 | 4.0 ± 0.1[A] | 1.5 ± 0.1[A] |
| rPIV3(HA N-P) | 8 | 5.1 ± 0.1[B] | 5.9 ± 0.1[B] |
| rPIV3(HA P-M) | 8 | 5.9 ± 0.1[C] | 6.7 ± 0.2[C] |
| rPIV3(HA HN-L) | 8 | 5.9 ± 0.2[C] | 5.8 ± 0.1[B] |
| rJS | 8 | 6.5 ± 0.1[D] | 6.6 ± 0.2[C] |

[1]Animals received $10^6 TCID^{50}$ of the indicated virus given intranasally in a 0.1 ml inoculum and the lungs and nasal turbinates were harvested 4 days later.
[2]Standard Error.
[3]Mean virus titers were assigned to statistically similar groups (A–D) by the Tukey-Kramer test. Therefore, means in each column with different letters are significantly different (α = 0.05) and those with the same letter are not significantly different.

TABLE 3

Replication of the rPIV3cp45L(HA) antigenic chimeric viruses in the upper and lower respiratory tract of hamsters

| Virus[1] | # Animals | Virus Titer ($\log_{10}TCID_{50}$/gm ± S.E.[2]) [Tukey-Kramer Grouping][3] | |
|---|---|---|---|
| | | Nasal Turbinates | Lungs |
| rcp45L | 6 | 4.7 ± 0.2[A] | 2.9 ± 0.1[A] |
| rcp45L(HA N-P) | 6 | 3.7 ± 0.2[B] | 2.9 ± 0.1[A] |
| rcp45L(HA P-M) | 7 | 3.7 ± 0.1[B] | 2.9 ± 0.2[A] |
| rJS | 7 | 6.5 ± 0.1[C] | 5.6 ± 0.2[B] |

[1]Animals received $10^6$ pfu of the indicated virus given intranasally in a 0.1 ml inoculum and the lungs and nasal turbinates were harvested 4 days later.
[2]Standard Error.
[3]Mean virus titers were assigned to statistically similar groups (A–D) by the Tukey-Kramer test. Therefore, means in each column with different letters are significantly different ($\alpha = 0.05$) and those with the same letter are not significantly different.

The ability of the chimeric rHPIV3(HA) viruses to induce an immune response to HPIV3 and to measles virus was studied next. Groups of 6–24 Golden Syrian hamsters (age 4–6 weeks) were infected as described above with either $10^{6.0}$ PFU rJS, rPIV3(HA P-M), rcp45L, rcp45L(HA P-M), or rcp45L(HA N-P) (Table 4) on day 0. Serum was collected from each hamster on day −1 and on day 25 post-inoculation. The serum antibody response to HPIV3 was evaluated by hemagglutination-inhibition (HAI) assay as previously described (van Wyke Coelingh et al., *Virology* 143:569–582, 1985, incorporated herein by reference), and the serum antibody response to measles virus was evaluated by 60% plaque-reduction assay as previously described (Coates et al., *Am. J. Epidemiol.* 83:299–313, 1966, incorporated herein by reference). These results were compared with that from an additional control group of cotton rats that received $10^{5.0}$ of the live-attenuated measles virus (Moraten strain) administered intramuscularly on day 0. Cotton rats, rather than hamsters, were used in this group because measles virus is only weakly infectious for hamsters. As can be seen in Table 4, each of the PIV3(HA) chimeric viruses was able to elicit a robust serum neutralizing antibody response against measles virus. There was no significant difference between the amount of serum neutralizing antibody elicited by the attenuated derivative rcp45L(HA P-M) as compared to its counterpart in the wild type background, rPIV3(HA P-M). Furthermore, the level of measles virus-neutralizing serum antibodies induced by the rPIV3(HA) recombinants were on average 5-fold greater than that achieved by the intramuscular immunization with the live attenuated measles virus vaccine. In addition, the serum antibody response to HPIV3 produced by all the chimeric viruses was also robust and comparable to that produced by infection with wild type rJS.

TABLE 4 rPIV3(HA) antigenic chimeric viruses elicit an excellent serum antibody response to both measles virus and PIV3

| Virus[1] | # Animals | Serum antibody titer to measles virus (60% plaque reduction neutralization titer, mean reciprocal $\log_2$ ± S.E.[2]) | | Serum antibody response to HPIV3 (HAI titer; mean reciprocal $\log_2$ ± S.E.) | |
|---|---|---|---|---|---|
| | | Day 0 | Day 25 | Day 0 | Day 25 |
| rcp45L[3] | 18 | ≤3.3 ± 0 | ≤3.3 ± 0 | ≤2.0 ± 0 | 10.7 ± 0.2 |
| rcp45L(HA P-M)[4] | 24 | ≤3.3 ± 0 | 12.8 ± 0.1 | ≤2.0 ± 0 | 9.2 ± 0.2 |
| rcp45L(HA N-P)[5] | 6 | ≤3.3 ± 0 | 13.4 ± 0.4 | ≤2.0 ± 0 | 10.8 ± 0.3 |
| rPIV3(HA P-M)[6] | 6 | ≤3.3 ± 0 | 13.3 ± 0.3 | ≤2.0 ± 0 | 10.3 ± 0.2 |
| Measles virus (Moraten)[7] | 4 | ≤3.3 ± 0 | 10.8 ± 0.2 | ≤2.0 ± 0 | ≤2.0 ± 0 |
| rJS[8] | 6 | ≤3.3 ± 0 | ≤3.3 ± 0 | ≤2.0 ± 0 | 10.7 ± 0.2 |

[1]Virus was administered at a dose of $10^{6.0}$PFU in a 0.1 ml inoculum intranasally on day 0 to all animals with the exception of those in the measles virus group which received virus by intramuscular injection.
[2]Standard Error.
[3]Recombinant attenuated HPIV3 with three temperature sensitive (ts) mutations in the L protein, derived from cp45.
[4]Recombinant attenuated HPIV3 in the cp45L background with the HA ORF of measles virus in the P/M noncoding region of rPIV3.
[5]Recombinant attenuated HPIV3 in the cp45L background with the HA ORF of measles virus in the N/P noncoding region of rPIV3.
[6]Recombinant HPIV3 with the HA ORF of measles virus in the P/M noncoding region of wild type rPIV3.
[7]The live attenuated measles vaccine virus, Moraten strain, was administered at a dose of $10^5$ pfu in a 0.1 inoculum by IM injection to 4 cotton rats in a separate study. All other animals were hamsters.
[8]Recombinant wildtype HPIV3.

Six hamsters from each group and from a control group similarly infected with RSV were challenged on day 25 with $10^{6.0}$ pfu of biologically-derived HPIV3 wildtype virus given intranasally in a 0.1 ml inoculum. The lungs and nasal turbinates were harvested on day 4 and processed as described above. Virus present in the samples was titered on 96 well plates of LLC-MK2 cell monolayers and incubated at 32° C. for 7 days. Virus was detected by hemadsorption and the mean $\log_{10}$ TCID$_{50}$/g was calculated for each group of hamsters. As shown in Table 5, those hamsters which had received the chimeric viruses, whether in the attenuated or wild type backbone, were highly protected against replication of challenge wild type HPIV3 in both the upper and the lower respiratory tract. Thus, despite the slight attenuating effect of the acquisition of the measles virus HA gene on replication of the rcp45(HA) chimeric viruses, infection with either rcp45L(HA P-M) or rcp45L(HA N-P) induced a high level of protection against HPIV3 as indicated by approximately a 1000-fold reduction of its replication in the upper and lower respiratory tract of hamsters. Since wild type measles virus does not replicate efficiently in hamsters, it cannot be used to challenge this host. However, it is expected that the attenuated chimeric rcp45L(HA) vaccine candidates will be highly efficacious against measles virus since high levels of neutralizing antibody, ie., mean titer of greater than 1:5000, were induced. Comparable levels of measles virus antibodies are associated with strong resistance to measles virus disease in humans (Chen et al., *J. Infect. Dis.* 162:1036–42, 1990, incorporated herein by reference).

TABLE 5

Attenuated and wildtype HPIV3-measles HA chimeric viruses are highly protective against replication of challenge wildtype PIV3 in the upper and lower respiratory tracts of hamsters.

| Animals Immunized with[1] | # Animals | Virus titer ($\log_{10}TCID_{50}/g$) [Tukey-Kramer Grouping[3]] | | Reduction in Titer ($\log_{10}$) | |
|---|---|---|---|---|---|
| | | Nasal Turbinates | Lungs | Nasal Turbinates | Lungs |
| RSV | 6 | 7.0 ± 0.3[A] | 5.7 ± 0.4[A] | NA[2] | NA |
| rcp45L(HA P-M) | 6 | 3.4 ± 0.3[B] | 2.9 ± 0.0[B] | 3.6 | 2.8 |
| rcp45L(HA N-P) | 6 | 2.6 ± 0.3[B] | 3.4 ± 0.2[B] | 4.4 | 2.3 |
| rPIV3(HA P-M) | 6 | 2.0 ± 0.3[B] | 3.2 ± 0.1[B] | 5.0 | 2.5 |
| rcp45L | 6 | 1.9 ± 0.2[B,C] | 3.6 ± 0.1[B] | 5.1 | 2.1 |
| rJS | 6 | <1.4 ± 0.0[C] | 2.9 ± 0.2[B] | >5.7 | 2.8 |

[1]All groups were challenged with $10^6$ pfu biologically-derived JS wildtype PIV3 in a 0.1 ml inoculum given intranasally.
[2]Not applicable.
[3]Mean virus titers were assigned to statistically similar groups (A–C) by the Tukey-Kramer test. Therefore, means in each column with different letters are significantly different ($\alpha$ = 0.05) and means with the same letter are not significantly different.

EXAMPLE III

Figure 3:
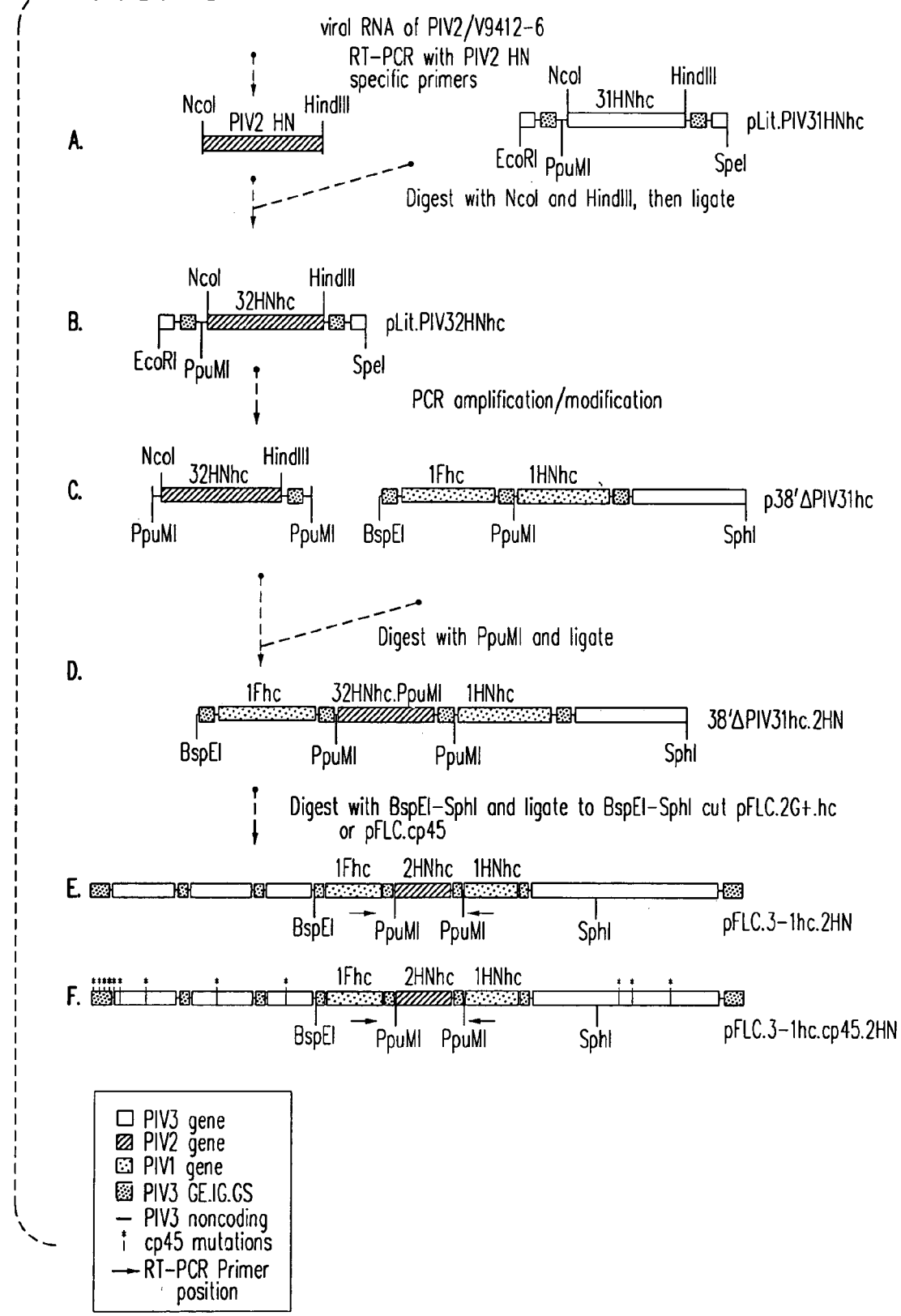
FIG. 3 ill pLit.PIV32hc was further digested with BspEI and SpeI and introduced into the BspEI-SpeI window of p38'ΔPIV31hc (F) to generate p38'ΔPIC32hc (G). the chimeric PIV3-PIV2 construct was introduced into the BspEI-SphI window of pFLC.2G+hc to generate pFLC.PIC32hc (H).

Construction of Antigenomic cDNAs Encoding a Chimeric HPIV3-1 Vector Bearing a HPIV2 HN Gene as an Extra Transcription/Translation Unit Inserted Between the F and HN Genes, and Recovery of Infectious Viruses rPIV3-1 is a recombinant chimeric HPIV3 in which the HN and F genes have been replaced by those of HPIV1 (see, e.g., Skiadopoulos et al., *Vaccine* 18:503–510, 1999; Tao et al., *Vaccine* 17:1100–1108, 1999; U.S. patent application Ser. No. 09/083,793, filed May 22, 1998, each incorporated herein by reference). In the present example, the HN gene of HPIV2 was inserted into the rPIV3-1 chimeric virus that served as a vector to produce a chimeric derivative virus, bearing an introduced heterologous antigenic determinant from HPIV2, able to protect against both HPIV1 and HPIV2. The HPIV2 HN gene also was inserted into an attenuated derivative of rPIV3-1, designated rPIV3-1cp45, which contains 12 of the 15 cp45 mutations, i.e., those mutations on genes other than HN and F, inserted into the rPIV3 backbone (Skiadopoulos et al., *Vaccine* 18:503–510, 1999). The source of the HPIV2 wild type virus was the wild type strain V9412-6 (designated PIV2/V94) (Tao et al., *Vaccine* 17:1100–1108, 1999), which was isolated in Vero cells from a nasal wash that was obtained in 1994 from a child with a natural HPIV2 infection. PIV2/V94 was plaque purified 3 times on Vero cells before being amplified twice on Vero cells using OptiMEM tissue culture medium without FBS. A cDNA clone of the HN gene of PIV2/V94 was generated from virion RNA by reverse transcription (RT) using random hexamers and Superscript Preamplification System (Life Technologies) followed by PCR using Advantage cDNA Synthesis kit (Clontech, Palo Alto, Calif.) and synthetic primers which introduced NcoI-HindIII sites flanking the HN cDNA (FIG. 3A). The sequences of these primers were: (with HPIV specific sequences in upper case, restriction sites underlined, nts which are non-HPIV or which are altered from wt in lower case, and start and stop codons in bold), upstream HPIV2 HN 5'-ggg ccATGGAAGATTACAGCAAT-3' (SEQ ID NO. 13); downstream HPIV2 HN 5'-caat aagcTTAAAGCATTAGTTCCC-3' (SEQ ID NO. 14). The HN PCR fragment was digested with NcoI-HindIII and cloned into pLit.PIV31HNhc to generate pLit.32HNhc (FIG. 3 B). The HPIV2 HN heterologous gene insert in pLit.32HNhc was completely sequenced using the ThermoSequenase Kit and $^{33}$P-labeled terminators (Pharmacia Amersham, Piscataway, N.J.) and was confirmed to contain the authentic sequence of the PIV2/94 HN coding region.

The HPIV2 HN gene in pLit.32HNhc was further modified by PCR and Deep Vent thermostable DNA polymerase (New England Biolab, Beverly, Mass.) to introduce PpuMI sites for cloning into the unique PpuMI site in p38'ΔPIV31hc, FIG. 3C (Skiadopoulos et al., *Vaccine* 18:503–510, 1999). The sequences of these primers were (with HPIV specific sequences in upper case, relevant restriction sites underlined, non-HPIV nt or nt altered from wt in lower case): upstream HPIV2 HN 5'-gcgatgggc-ccGAGGAAGGACCCAATAGACA-3' (SEQ ID NO. 15); downstream HPIV2 HN 5'-ccc gggtcctgATTTCCCGAGCACGCTTTG-3' (SEQ ID NO. 16). The modified cDNA bearing the HPIV2 HN ORF consists of (from left to right) a partial 5'-untranslated region (5'-UTR) of HPIV3 HN including the PpuMI site at the 5'-end, the HPIV2 HN ORF, the 3'-UTR of HPIV3 HN, a complete set of HPIV3 transcription signals (i.e. gene stop, intergenic region and gene start sequences) whose sequences match those at the HPIV3 HN and L gene junction, a partial 5'-UTR of HPIV3 L, and an added PpuMI site at its 3'-end (FIG. 3C). This fragment was digested with PpuMI and inserted into p38'ΔPIV31hc digested with PpuMI to generate p38'ΔPIV31hc.2HN (FIG. 3D). The inserted PpuMI cassette was sequenced in full and found to be as designed. The insert from p38'ΔPIV31hc.2HN was isolated as a 8.5 kb BspEI-SphI fragment and introduced into the BspEI-SphI window of pFLC.2G+.hc or pFLCcp45 to generate pFLC.31hc.2HN or pFLC.31hc.cp45.2HN, respectively (FIG. 3, E and F). pFLC.2G+.hc and pFLCcp45 are full-length antigenomic clones encoding wt rPIV3-1 and rPIV3cp45, respectively, as described previously (Skiadopoulos et al., *J. Virol.* 73:1374–81, 1999; Tao et al., *J. Virol.* 72:2955–2961, 1998, each incorporated herein by reference).

Confluent HEp-2 cells were transfected with pFLC.31hc.2HN or pFLC.3-1hc.cp45.2HN plus the pTM (N), pTM(P no C), and pTM(L) support plasmids in the presence of MVA-T7 as previously described (Durbin et al., *Virology* 235:323–332, 1997, incorporated herein by reference). The recombinant chimeric viruses recovered from transfection were activated by addition of TPCK trypsin (Catalog No. 3741, Worthington Biochemical Corp., Freehold, N.J.) as were all passages and titrations of viruses bearing the HPIV1 HN and F glycoproteins as described previously (Tao et al., *J. Virol.* 72:2955–2961, 1998, incorporated herein by reference). Recovered chimeric recombinant viruses rPIV3-1.2HN and rPIV3-1cp45.2HN were purified by plaque-to-plaque-to-plaque passage on LLC-MK2 monolayer in agarose overlay as previously described (Tao et al., *Vaccine* 17:1100–1108, 1999, incorporated herein by reference).

Figure 4:
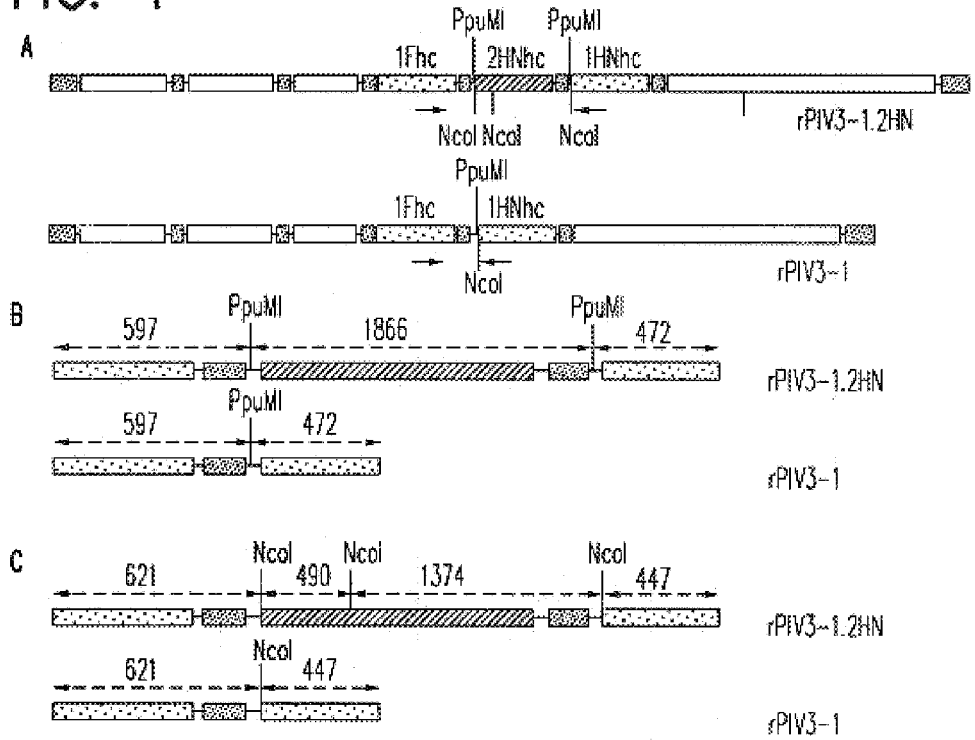
Figure 4:
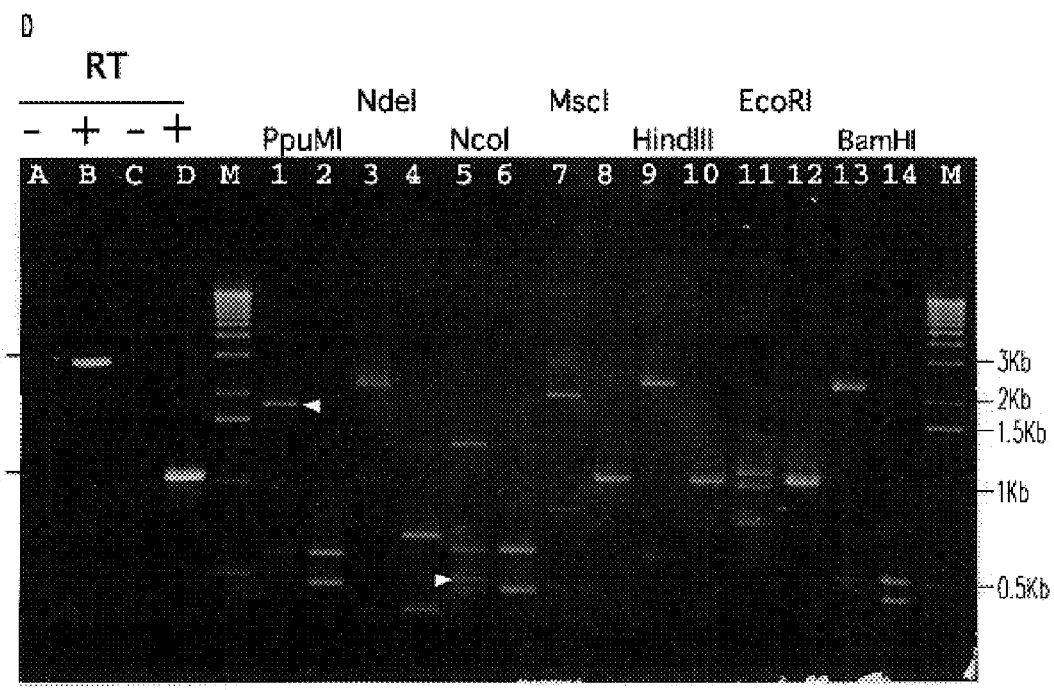

To determine if the rPIV3-1.2HN and rPIV3-1cp45.2HN recombinants contain the heterologous HPIV2 HN gene, viral RNA from each recovered recombinant chimeric virus was amplified on LLC-MK2 cells and concentrated by polyethylene glycol (PEG) precipitation (Mbiguino et al., *J. Virol. Methods* 31:161–170, 1991, incorporated herein by reference). Virion RNA (vRNA) was extracted with Trizol (Life Technologies) and used as template to synthesize first strand cDNA using Superscript Preamplification system (Life Technologies, Gaithersburg, Md.) and random hexamer primers as described above. The synthesized cDNA was amplified by PCR with the Advantage cDNA Synthesis kit (Clontech, Palo Alto, Calif.) with primers specific for HPIV1 F and HPIV1 HN coding region (for HPIV1 F 5'-AGTGGCTAATTGCATTGCATCCACAT-3' (SEQ ID NO. 17) and for HPIV1 HN 5'-GCCGTCTGCATGGT-GAATAGCAAT-3' (SEQ ID NO. 18). The relative locations of the PIV1 F and HN primers are indicated by arrows in FIGS. 3 and 4. Amplified DNA fragments were digested and analyzed on agarose gels (FIG. 4). Data for rPIV3-1cp45.2HN is not shown, but was comparable and confirmed in structure. rPIV3-1.2HN and rPIV3-1cp45.2HN each contained the insert of the expected size, and the digestion patterns with a number of restriction enzymes confirmed the identity and authenticity of the inserts. The presence of the cp45 mutations in rPIV3-1cp45.2HN was also confirmed.

Figure 5:
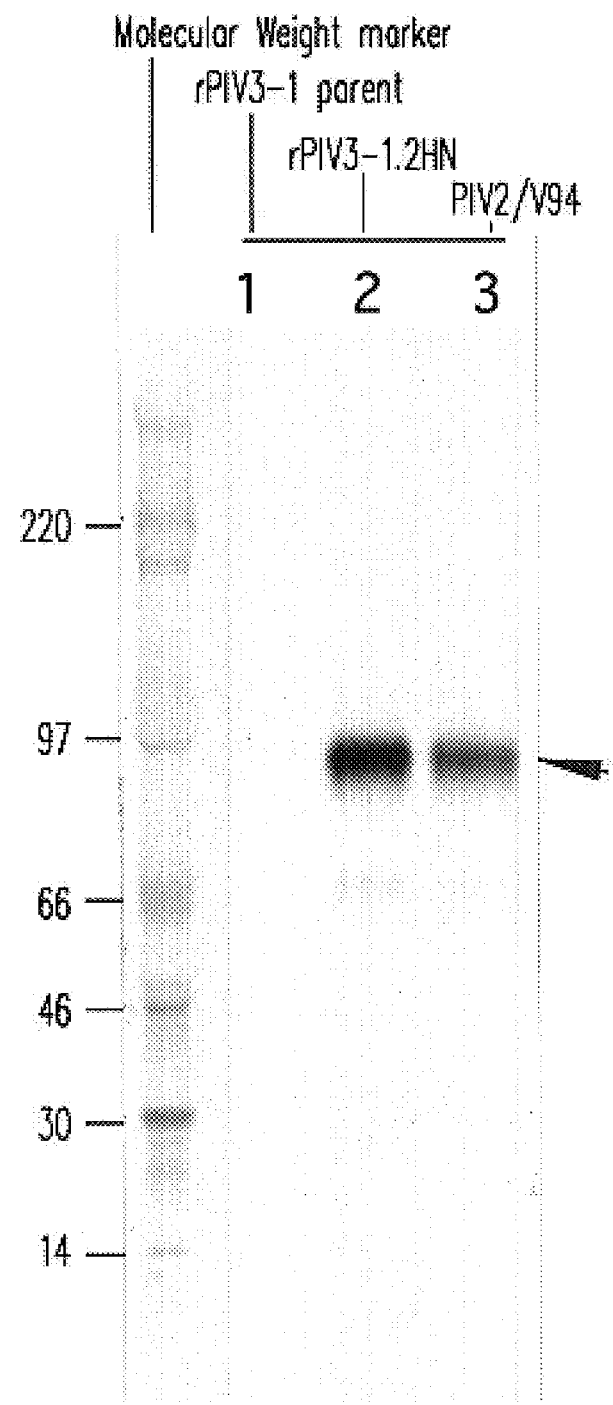

To confirm the expression of HPIV2 HN by the rPIV3-1.2HN chimeric virus, LLC-MK2 monolayers in T25 flasks were infected with PIV2/V94, rPIV3-1, or rPIV3-1.2HN at a MOI of 5 in 5 ml of serum-free OptiMEM containing 0.5 µg/ml TPCK trypsin. After incubation for 18 hours at 32° C., the flasks were washed three times with 5 ml of methionine and cysteine deficient DMEM (BioWhittacker, Walkersville, Md.). Cells were then fed with 1 ml of methionine and cysteine deficient DMEM supplemented with 120 µCi of ProMix 35S-methionine and 35S-cysteine mixture (Pharmacia Amersham, Piscataway, N.J.) and incubated for 18 hours at 32° C. Cells were scraped into medium, pelleted by brief centrifugation in a microfuge, and washed three times with cold PBS. Each cell pellet was resuspended in 1 ml RIPA buffer (1% sodium deoxycholate, 1% Triton X-100, 0.2% SDS, 150 mM NaCl, and 50 mM Tris-HCl, pH7.4) containing 250 units/ml of Benzonase (Sigma), freeze/thawed once, and clarified by centrifugation at 12,000×g for 5 min in a microfuge. Clarified supernatants were transferred to a clean microfuge tube, mixed with 50 µl of anti-HPIV2 HN monoclonal antibody (mAb) 150S1 (Tsurudome et al., *Virology* 171:38–48, 1989, incorporated herein by reference), and incubated with mixing at 4° C. for 3 hours. The monoclonal antibody was precipitated by the addition to each tube of 0.2 ml of 10% Protein A sepharose suspension (in RIPA buffer) and incubation with mixing at 4° for 18 hours. The beads were washed three times with RIPA buffer and pelleted by brief centrifugation in a microfuge. Each sample was suspended in 90 µl of 1× loading buffer, and 10 µl was resolved on a 4–12% SDS polyacrylamide gel (PAGE; NOVEX, San Diego, Calif.). The gel was dried and autoradiographed (FIG. 5). The mAb, specific to PIV2 HN, precipitated a protein from both rPIV3-1.2HN and PIV2/V94 infected LLC-MK2 cells, but not from rPIV3-1-infected cells, with a size expected for the 86 kD Kd HN protein of HPIV2 (Rydbeck et al., *J. Gen. Virol.* 69:931–5, 1988, incorporated herein by reference).

EXAMPLE IV

The rPIV3-1 Viruses Carrying an HPIV2 Antigenic Determinant Exhibit Temperature Sensitive Phenotypes Similar to Those of Their Parental Vector Viruses The level of temperature sensitivity of replication of rPIV3-1.2HN and rPIV3-1.cp45.2HN in LLC-MK2 cells was evaluated to determine if the acquisition of the HN ORF of HPIV2 by rPIV3-1 wild type or attenuated viruses employed as vectors altered the level of temperature sensitivity of replication in the resultant chimeric derivatives bearing the heterologous antigenic determinant of HPIV2 compared to the parental, vector viruses (Table 6). rPIV3-1.2HN and rPIV3-1cp45.2HN, along with control viruses, were serially diluted 1:10 in 1×L15 supplemented with 0.5 µg/ml TPCK trypsin and used to infect LLC-MK2 monolayers in 96 well plates in quadruplicate. Infected plates were placed at various temperatures for 7 days before the virus titers were determined by hemadsorption using 0.2% guinea pig erythrocytes (in 1×PBS) The virus titers are presented as $\log_{10}$ TCID$_{50}$±standard error (S.E.). As shown in Table 6, rPIV3-1.2HN and rPIV3-1cp45.2HN exhibited a level of temperature sensitivity similar to that of their parental, vector viruses, i.e. rPIV3-1 and rPIV3-1cp45, respectively, each of which lacks the HPIV2 HN insert. This indicated that the introduction of one extra transcription/translation unit in rPIV3-1.2HN and rPIV3-1cp45.2HN, does not significantly alter their level of temperature sensitivity of replication in vitro.

TABLE 6

The rPIV3-1 viruses carrying the PIV2 HN insertion have a temperature sensitive phenotype similar to that of their parental virus.

| Virus | Titer at 32° C.[a] ($\log_{10}$TCID$_{50}$) | Titer reduction ($\log_{10}$TCID$_{50}$) at various temperatures (° C.)[a] | | | | | |
|---|---|---|---|---|---|---|---|
| | | 35°[b] | 36° | 37° | 38° | 39° | 40° |
| PIV2/V9412 | 7.8 | 0.3 | (0.1)[c] | 0.0 | (0.4) | (0.4) | 0.0 |
| PIV1/Wash64 | 8.5 | 1.5 | 1.1 | 1.4 | 0.6 | 0.5 | 0.9 |
| rPIV3/JS | 7.9 | 0.3 | 0.1 | 0.1 | (0.3) | (0.4) | 0.4 |
| PIV3 cp45 | 7.8 | 0.5 | 0.3 | 1.3 | <u>3.4</u>[d] | 6.8 | 6.9 |
| rPIV3-1 | 8.0 | 0.8 | 0.5 | 0.6 | 0.9 | 1.1 | <u>2.6</u> |
| rPIV3-1.2HN | 8.3 | 0.5 | (0.3) | 0.3 | 0.6 | 1.5 | <u>2.6</u> |
| rPIV3-1cp45 | 8.0 | 0.5 | 0.4 | <u>3.4</u> | 4.8 | 6.6 | 7.5 |
| rPIV3-1 cp45.2HN | 8.0 | 0.3 | 1.4 | <u>2.9</u> | 5.3 | 7.6 | 7.6 |

[a]Data presented are means of two experiments.
[b]Data at 35° C. were from single experiment.
[c]Numbers in parentheses represent titer increase.
[d]Underlined value indicates shut-off temperature at which the virus titer showed a reduction of 100-fold or more in comparison to the titer at 32° C.

EXAMPLE V

Replication and immunogenicity of rHPIV3-1.2HN Chimeric Viruses in Animals

To determine the level of replication of the chimeric viruses in vivo, Golden Syrian hamsters in groups of six were inoculated intranasally with 0.1 ml of 1×L-15 medium containing $10^{5.3}$TCID$_{50}$ (or $10^6$ pfu) of virus (Table 7). Four days after infection, hamsters were sacrificed and their lungs and nasal turbinates harvested. Virus titers, expressed as mean $\log_{10}$ TCID$_{50}$ gram of tissue (Table 7), were determined. rPIV3-1 expressing the PIV2 HN gene, termed rPIV2-1.2HN, is more restricted in replication than its rPIV3-1 parent as indicated by a 30-fold reduction in virus titer in both the upper and lower respiratory tracts of hamsters. Thus, the insertion of a transcription/translation unit expressing the PIV2 HN protein into rPIV3-1 attenuates the virus for hamsters. The attenuating effect of insertion of a transcription/translation unit containing PIV2 HN ORF into rPIV3-1 was slightly more than that observed for the insertion of a similar unit containing the measles HA ORF into the recombinant JS strain of wild type PIV3. The rPIV3-1cp45.2HN virus was 1,000-fold more restricted in replication than the rPIV3-1cp45 parent indicating that the attenuating effect of the PIV2 HN insertion and the cp45 mutations are additive. It should be possible to adjust the level of attenuation as needed by adding fewer cp45 mutations than the 12 that are present in rPIV3-1.cp45.2HN.

TABLE 7

The chimeric rPIV3-1 expressing the HN glycoprotein of PIV2 (rPIV3-1.2HN) is attenuated in the respiratory tract of hamsters

| | | Virus titer in indicated tissue $\log_{10}TCID_{50}/g \pm S.E.)^c$ | |
|---|---|---|---|
| Experiment No. | Virus | NT | Lungs |
| 1[a] | rPIV3-1 | 6.9 ± 0.1[A][d] | 6.0 ± 0.3[A] |
| | rPIV3-1.2HN | 5.4 ± 0.2[B] | 4.4 ± 0.4[C] |
| 2[b] | rPIV3-1 | 6.7 ± 0.1[A] | 6.6 ± 0.2[A] |
| | rPIV3-1.2HN | 5.1 ± 0.1[B,C] | 5.2 ± 0.2[B] |
| | rPIV3-1cp45 | 4.6 ± 0.3[C] | 1.8 ± 0.4[D] |
| | rPIV3-1cp45.2HN | 1.5 ± 0.1[D] | ≦1.2[D] |
| | rPIV3/JS | 6.5 ± 0.2[A] | 6.7 ± 0.1[A] |
| | rcp45 | 4.9 ± 0.2[B,C] | 1.2 ± 0.04[D] |

[a]Groups of six animals were inoculated intranasally with $10^6$ pfu of indicated virus in 0.1 ml medium on day 0.
[b]Groups of 6 hamsters were inoculated intranasally as in Experiment 1 with $10^{5.3}$ TCID$_{50}$ of indicated virus on day 0.
[c]Lungs and nasal turbinates of the hamsters were harvested on day 4. Virus titers in tissue were determined and the titer expressed as $\log_{10}TCID_{50}$ /gram ± standard error (S.E.). NT = nasal turbinates.
[d]Means in each column with a different letter are significantly different (a = 0.05) by Duncan's Multiple Range test whereas those with the same letter are not significantly different.

Since the single rPIV3-1.2HN virus expresses protective antigens of PIV1 (the F and HN glycoprotein) and PIV2 (the HN glycoprotein only), infection with this virus will induce resistance against challenge with either PIV1 or PIV2 wild type viruses. To verify this, Golden Syrian hamsters in groups of 12 were immunized intranasally with $10^{5.3}$ TCID$_{50}$ of virus as described above. Half of the hamsters were challenged with PIV2 on day 29, the remaining half with PIV1 on day 32. Hamster lung and nasal turbinate tissues were harvested 4 days after challenge, and titer of challenge virus were determined as described above (Table 8). Sera were obtained before and 28 days after immunization and tested for their neutralizing antibody titer against PIV1 and PIV2.

As expected PIV3 provided no resistance against either PIV1 or PIV2, while previous infection with PIV2 wild type virus and rPIV3-1 induced complete resistance to replication of PIV2 and PIV1 challenge viruses, respectively. In contrast to these viruses that provided protection against only one virus, rPIV3-1.2HN induced antibody to both PIV1 and PIV2 and included strong resistance to both PIV1 and PIV2 as indicated by the 1,000- to 10,000-fold reduction in replication of each virus in the upper and lower respiratory tract of rPIV3-1.2HN immunized hamsters. This indicated that a single recombinant chimeric PIV can induce resistance against two human viral pathogens. However, the derivative of rPIV3-1.2HN carrying the cp45 mutations failed to induce significant resistance to replication of wild type PIV1 or PIV2 challenge virus indicating that this particular recombinant chimeric virus is over-attenuated in hamsters. Introduction of one or several selected cp45 mutations, rather than the complete set of 12 mutations, into rPIV3-1.2HN can be done to adjust the level of attenuation of rPIV3-1.2HN if necessary.

EXAMPLE VI

Construction and Characterization of Chimeric HPIV3-2 Vaccine Recombinants Expressing Chimeric Glycoproteins The present example details development of a live attenuated PIV2 candidate vaccine virus for use in infants and young children using reverse genetic techniques. Preliminary efforts to recover recombinant chimeric PIV3-PIV2 virus carrying full-length PIV2 glycoproteins in a wild type PIV3 backbone, as described above for HPIV3-1 chimeric constructs, did not yield infectious virus. However, viable PIV2-PIV3 chimeric viruses were recovered when chimeric HN and F ORFs rather than full-length PIV2 ORFs were used to construct the full-length cDNA. The recovered viruses, designated rPIV3-2CT in which the PIV2 ectodomain and transmembrane domain was fused to the PIV3 cytoplasmic domain and rPIV3-2TM in which the PIV2 ectodomain was fused to the PIV3 transmembrane and cytoplasmic tail domain, possessed similar, although not identical, in vitro and in vivo phenotypes. Thus, it appears

TABLE 8

The chimeric rPIV3-1 virus expressing the HN glycoprotein of PIV2 (rPIV3-1.2HN) protects hamsters against challenge with both PIV1 and PIV2

| | Serum neutralizing antibody titer against indicated virus (reciprocal mean $\log_2$ ± SE)[b] | | | | Titer of challenge virus in indicated tissues $(\log_{10}TCID_{50}/g \pm SE)^c$ | | | |
|---|---|---|---|---|---|---|---|---|
| | PIV1 | | PIV2 | | PIV1 | | PIV2 | |
| Immunizing virus[a] | pre | post | pre | post | NT | Lung | NT | Lung |
| rPIV3/JS | ≦4.0 ± 0.0 | ≦4.0 ± 0.0 | 4.5 ± 0.1 | 4.6 ± 0.2 | 5.4 ± 0.2 | 5.1 ± 0.1 | 6.8 ± 0.2 | 6.0 ± 0.3 |
| PIV2 | ≦4.0 ± 0.0 | ≦4.0 ± 0.0 | 4.3 ± 0.2 | 9.6 ± 0.2 | 5.7 ± 0.2 | 5.7 ± 0.2 | ≦1.2 | ≦1.2 |
| rPIV3-1 | 4.2 ± 0.1 | 8.5 ± 0.3 | 4.0 ± 0.0 | 4.2 ± 0.1 | ≦1.2 | ≦1.2 | 6.3 ± 0.1 | 6.5 ± 0.2 |
| rPIV3-1.2HN | ≦4.0 ± 0.0 | 6.2 ± 0.2 | 4.1 ± 0.1 | 8.3 ± 0.2 | 2.3 ± 0.5 | ≦1.2 | ≦1.2 | ≦1.2 |
| rPIV3-1cp45 | ≦4.0 ± 0.0 | 6.2 ± 0.4 | ≦4.0 ± 0.0 | 4.0 ± 0.0 | 3.6 ± 0.3 | 2.7 ± 0.5 | 6.0 ± 0.1 | 5.7 ± 0.4 |
| rPIV3-1cp45.2HN | 4.0 ± 0.9 | 4.1 ± 0.1 | 4.0 ± 0.0 | 4.2 ± 0.1 | 5.1 ± 0.2 | 4.8 ± 0.2 | 6.8 ± 0.1 | 6.6 ± 0.2 |

[a]Hamsters in groups of 12 were immunized with $10^{5.3}$ TCID$_{50}$ of indicated virus intranasally on day 0.
[b]Serum was diluted 1:10 with OptiMEM and heat-inactivated by incubation at 56° for 30 min. The serum neutralizing antibody titer was determined on LLC-MK2, and the titers are expressed as reciprocal mean $\log_2$ ± standard error (SE).
[c]Half of the hamsters from each immunized group were challenged with $10^6$ TCID$_{50}$ PIV2 on day 29, and the remaining half were challenged with $10^6$ TCID$_{50}$ PIV1 on day 32. Tissue samples were harvested 4 days after challenge, and challenge virus titers are expressed as $\log_{10}TCID_{50}$/gram of tissue ± SE. NT = nasal turbinates.

that only the cytoplasmic tail of the HN or F glycoprotein of PIV3 is required for successful recovery of PIV2-PIV3 chimeric viruses.

The rPIV3-2 recombinant chimeric viruses exhibit a strong host range phenotype, i.e. they replicate efficiently in vitro but are strongly restricted in replication in vivo. This attenuation in vivo occurs in the absence of any added mutations from cp45. Although rPIV3-2CT and rPIV3-2TM replicated efficiently in vitro, they were highly attenuated in both the upper and the lower respiratory tract of hamsters and African green monkeys (AGMs), indicating that chimerization of the HN and F proteins of PIV2 and PIV3 itself specified an attenuation phenotype in vivo. A phenotype including efficient replication in vitro and highly restricted growth in vivo is greatly desired for vaccine candidates. Despite this attenuation, they were highly immunogenic and protective against challenge with PIV2 wild type virus in both species. rPIV3-2CT and rPIV3-2TM were further modified by the introduction of the 12 PIV3 cp45 mutations located outside of the HN and F coding sequences to derive rPIV3-2CTcp45 and rPIV3-2TMcp45. These derivatives replicated efficiently in vitro but were even further attenuated in hamsters and AGMs indicating that the attenuation specified by the glycoprotein chimerization and by the cp45 mutations was additive. These findings identify the rPIV3-2CT and rPIV3-2TM recombinants as preferred candidates for use in live attenuated PIV2 vaccines.

Viruses and Cells

The wild type PIV1 strain used in this study, PIV1/Washington/20993/1964. (PIV1/Wash64) (Murphy et al., *Infect. Immun.* 12:62–68, 1975, incorporated herein by reference), was propagated in LLC-MK2 cells (ATCC CCL 7.1) as previously described (Tao et al., *J. Virol.* 72:2955–2961, 1998, incorporated herein by reference). The PIV wild type virus, strain V9412-6, designated PIV2/V94, was isolated in qualified Vero cells from a nasal wash of a sick child in 1994. PIV2/V94 was plaque purified three times on Vero cells before being amplified twice on Vero cells using OptiMEM without FBS. The wild type cDNA-derived recombinant PIV3/JS strain (rPIV3/JS) was propagated as previously described (Durbin et al., *Virology* 235:323–332, 1997, incorporated herein by reference). The modified vaccinia Ankara virus (MVA) recombinant that expresses the bacteriophage T7 RNA polymerase was generously provided by Drs. L. Wyatt and B. Moss (Wyatt et al., *Virology* 210:202–205, 1995, incorporated herein by reference).

HEp-2 cells (ATCC CCL 23) were maintained in MEM (Life Technologies, Gaithersburg, Md.) with 10% fetal bovine serum, 50 μg/ml gentamicin sulfate, and 2 mM glutamine. Vero cells below passage 150 were maintained in serum-free medium VP-SFM (Formula No. 96-0353SA, Life Technologies) with 50 μg/ml gentamicin sulfate and 2 mM glutamine.

Virion RNA Isolation, Reverse Transcription and PCR Amplification of Viral Genes, and Automated Sequencing To clone viral genes of or to verify genetic markers of recombinant chimeric viruses, viruses were amplified on cultured cells and concentrated by polyethylene glycol precipitation as previously described (Mbiguino et al., *J. Virol.* *Methods* 31:161–170, 1.991, incorporated herein by reference). Virion RNA was extracted from the virus pellet using Trizol reagent (Life Technologies) and used as template for reverse transcription (RT) with the Superscript Preamplification system (Life Technologies). The cDNA was further PCR amplified using the Advantage cDNA kit (Clontech, Palo Alto, Calif.). For cloning or sequencing purposes, the RT-PCR amplified DNA was purified from agarose gels using NA45 DEAE membrane as suggested by the manufacturer (Schleicher & Schuell, Keene, N. H.). Sequencing was performed with the dRhodamine dye terminator cycling sequencing kit (Perkin Elmer, Forster City, Calif.) and an ABI 310 Gene Analyzer (Perkin Elmer, Forster City, Calif.).

Figure 6:
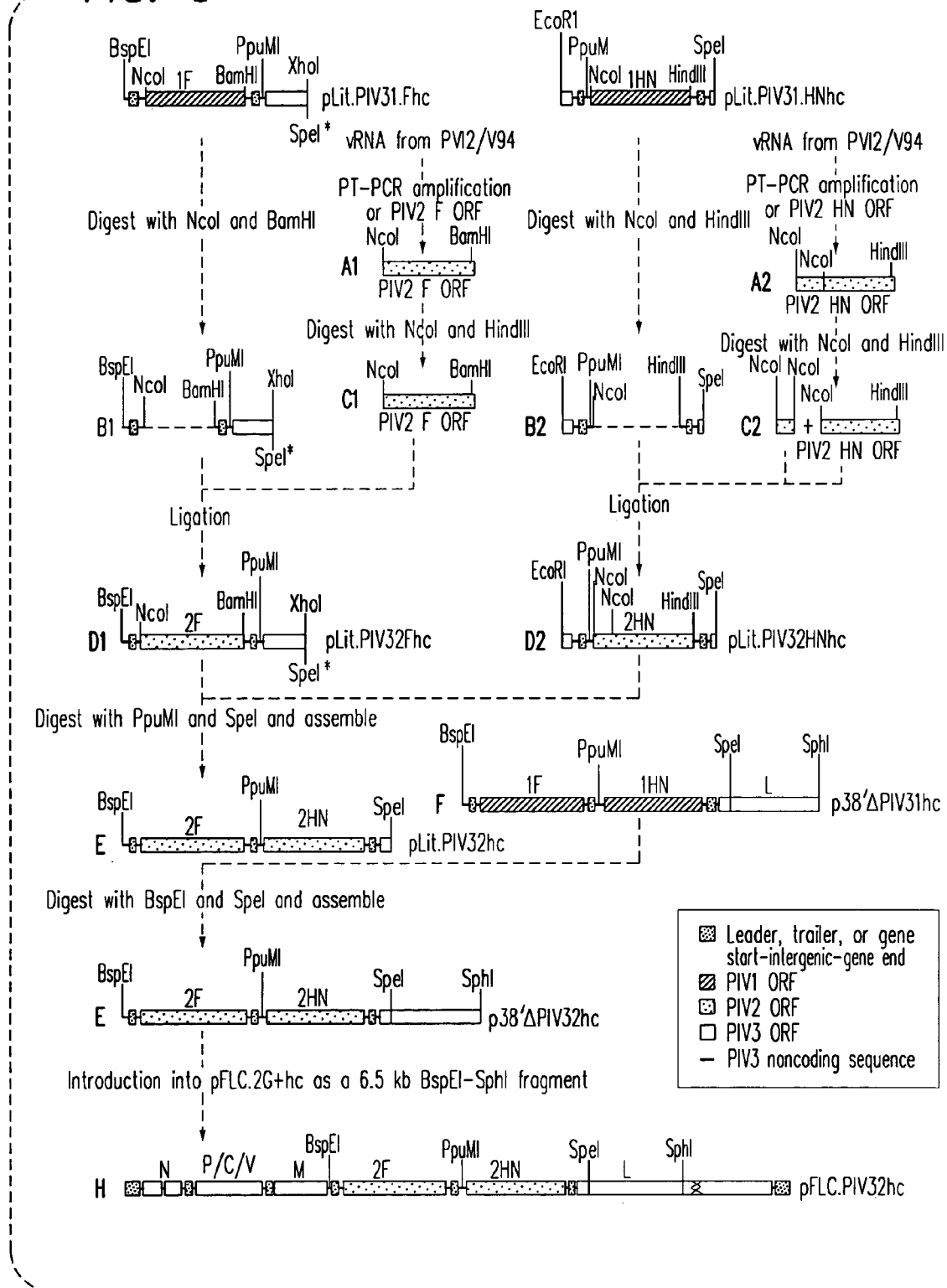
Figure 7:
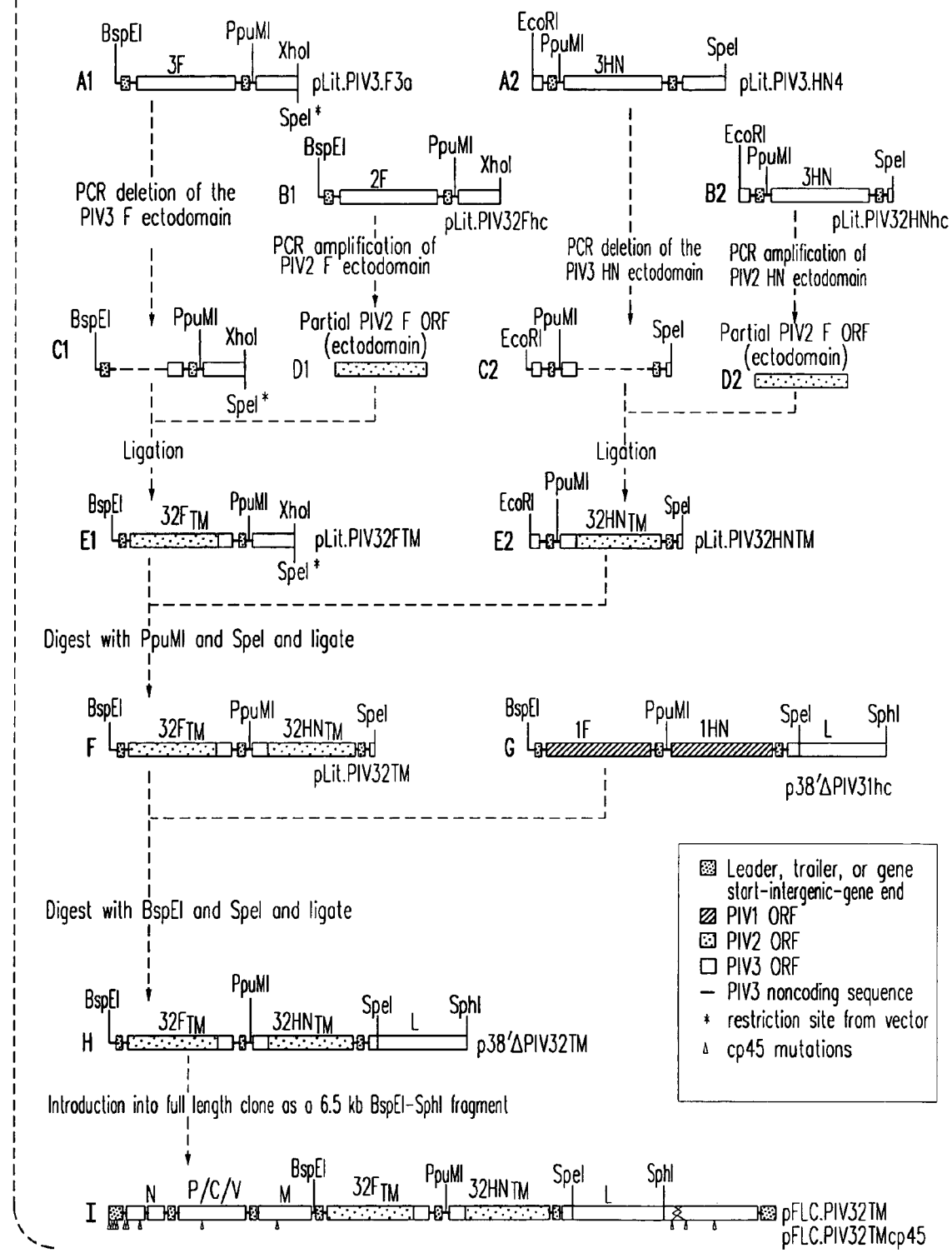
FIG. 7 depicts construction of full-length PIV3-PIV2 chimeric antigenomic cDNA pFLC.PIV32TM and pFLC.PIV32TMcp45, which encode F and HN proteins containing PIV2-derived ectodomains and PIV3-derived transmembrane and cytoplasmic domains. The region of the PIV3 F ORF, in pLit.PIV3.F3a (A1), encoding the ectodomain was deleted (C1) by PCR using a PIV3 F specific primer pair (9, 10 in Table 9). The region of the PIV2 F ORF encoding the ectodomain was amplified from pLit.PIV32Fhc (B1) using PCR and PIV2 F specific primer pair (5, 6 in Table 9). The two resulting fragments (C1 and D1) were ligated to generate pLit.PIV32FTM (E1). In parallel, the region of the PIV3 HN ORF, in pLit.PIV3.HN4 (A2), encoding the ectodomain was deleted (C2) by PCR using a PIV3 HN specific primer pair (11, 12 in Table 9). The region of the PIV2 HN ORF encoding the ectodomain was amplified from pLit.PIV32HNhc (B2) by PCR and a PIV2 HN specific primer pair (8, 9 in Table 9). Those two DNA fragments (C2 and D2) were ligated together to generate pLit.PIV32HNTM (E2). pLit.PIV32FTM and pLit.PIV32HNTM were digested with PpuMI and SpeI and assembled to generate pLit.PIV32TM (F). The BspEI-SpeI fragment from pLit.PIV32TM was ligated to the BspEI-SpeI window of p38'_PIV31hc (G) to generate p38'_PIV32TM (H). The insert containing chimeric PIV3-PIV2 F and HN was introduced as a 6.5 kb BspEI-SphI fragment into the BspEI-SphI window of pFLC.2G+.hc and pFLCcp45 to generate pFLC.PIV32TM and pFLC.PIV32TMcp45 (I), respectively.
Figure 8:
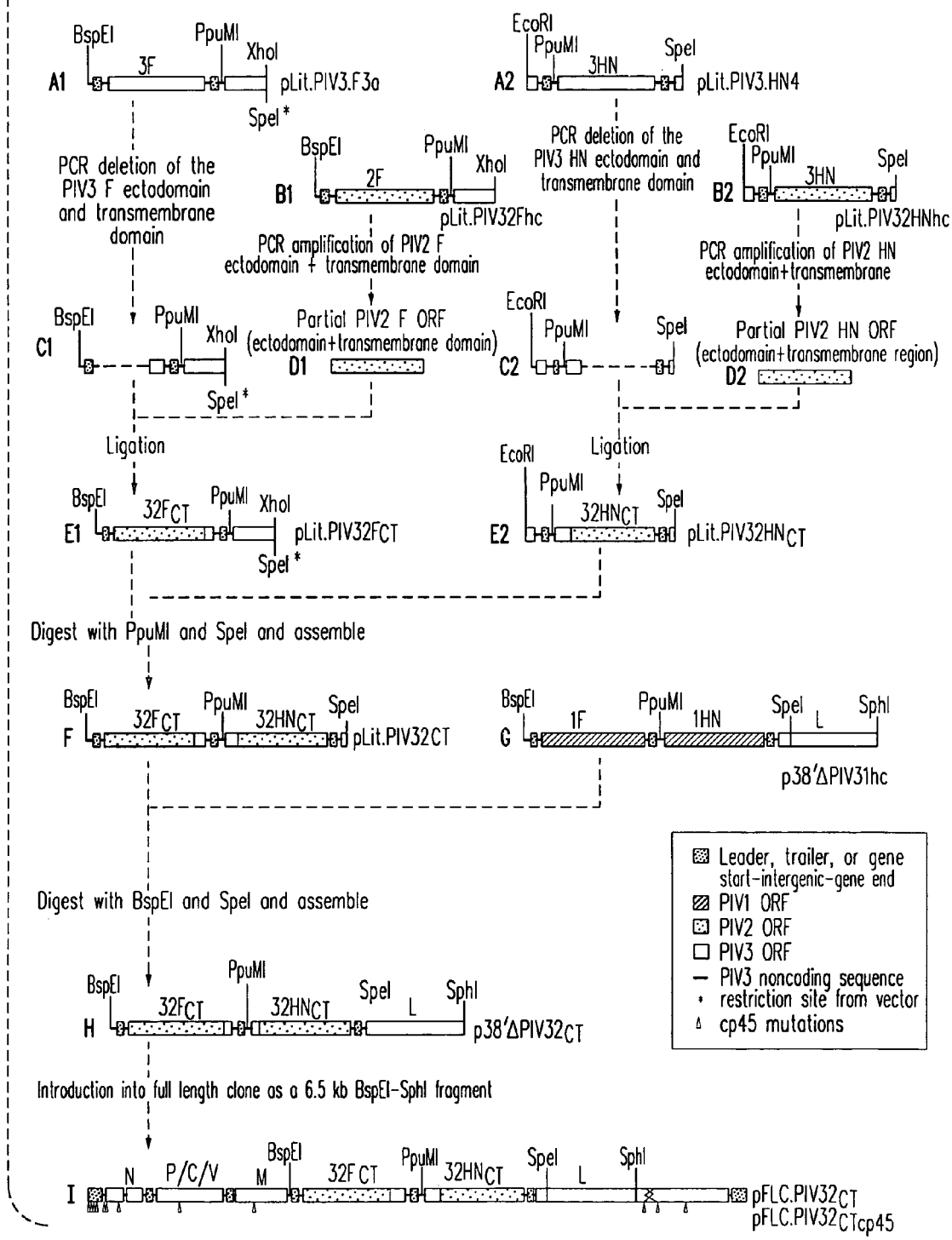
FIG. 8 shows construction of full-length PIV3-PIV2 chimeric antigenomic cDNA pFLC.PIV32CT and pFLC.PIV32Ctcp45 which encode F and HN proteins containing a PIV2-derived ectodomain, a PIV2-derived transmembrane domain, and a PIV3-derived cytoplasmic domain. The region of the PIV3 F ORF in pLit.PIV3.F3a (A1) encoding the ectodomain and the transmembrane domain was deleted (C1) by PCR using a PIV3 F specific primer pair (17, 18 in Table 9). The region of the PIV2 F ORF encoding the ectodomain plus the transmembrane domain was amplified from pLit.PIV32Fhc (B1) using PCR and a PIV2 F specific primer pair (13, 14 in Table 9). The two resulting fragments (C1 and D1) were ligated to generate pLit.PIV32FCT (E1). In parallel, the region of the PIV3 HN ORF in pLit.PIV3.HN4 (A2), encoding the ectodomain and transmembrane domain was deleted (C2) by PCR using a PIV3 HN specific primer pair (19, 20 in Table 9). The region of the PIV2 HN ORF encoding the ectodomain plus the transmembrane domain was amplified from pLit.PIV32HNhc (B2) by PCR using a PIV2 HN specific primer pair (15, 16 in Table 9). Those two DNA fragments (C2 and D2) were ligated to generate pLit.PIV32HNCT (E2). pLit.PIV32FCT and pLit.PIV32HNCT were digested with PpuMI and SpeI and assembled to generate pLit.PIV32CT (F). The BspEI-SpeI fragment from pLit.PIV32CT was ligated to the BspEI-SpeI window of p38'_PIV31hc (G) to generate p38'_PIV32CT (H). The insert containing chimeric PIV3-PIV2 F and HN was introduced as a 6.5 kb BspEI-SphI fragment into the BspEI-SphI window of pFLC.2G+.hc and pFLC.cp45 to generate pFLC.PIV32CT and pFLC.PIV32CTcp45 (I), respectively.

Construction of the Chimeric PIV3-PIV2 Antigenomic cDNAs Encoding the Complete PIV2 F and HN Proteins or Chimeric F and HN Proteins Containing a PIV2-Derived Ectodomain and PIV3-Derived Cytoplasmic Tail Domain A DNA encoding a full-length PIV3 antigenomic RNA was constructed in which the PIV3 F and HN ORFs were replaced by their PIV2 counterparts following the strategy described previously (Tao et al., *J. Virol.* 72:2955–2961, 1998) for PIV3-PIV1. Details of this construction are presented in FIG. 6. PIV2/V94 propagated in Vero cells was concentrated and virion RNA (vRNA) was extracted from the virus pellet using Trizol reagent. The F and HN ORFs of PIV2/V94 were reverse transcribed from vRNA using random hexamer primers and the SuperScript Preamplification System before being amplified by PCR using the cDNA Advantage kit and primer pairs specific to PIV2 F and HN genes, respectively (1, 2 and 3, 4; Table 9). The amplified cDNA fragment of PIV2 F ORF was digested with NcoI plus BamHI and ligated into the NcoI-BamHI window of pLit.PIV31.Fhc (Tao et al., *J. Virol.* 72:2955–2961, 1998, incorporated herein by reference) to generate pLit.PIV32Fhc. The BspEI site in the PIV3 full-length cDNA is unique and we planned to use it to exchange segments between cDNAs (see FIGS. 6–8). Therefore, a BspEI site that was found in the PIV2 F ORF was removed by site-directed mutagenesis without affecting the amino acid sequence. The cDNA fragment of PIV2 HN ORF was digested with NcoI plus HindIII and ligated into the NcoI-HindIII window of pLit.PIV31.HNhc (Tao et al., *J. Virol.* 72:2955–2961, 1998) to generate pLit.PIV32HNhc. The PIV2 ORFs in pLit.PIV32Fhc and pLit.PIV32HNhc were sequenced, and the sequence was found to be as designed. The nucleotide sequences for the PIV2 F and HN ORFs are submitted in the GenBank (Accession No. pending). pLit.PIV32Fhc and pLit.PIV32HNhc were each digested with PpuMI plus SpeI and assembled to generate pLit.PIV32hc. The 4 kb BspEI-SpeI fragment of pLit.PIV32hc was introduced into the BspEI-SpeI window of p38'ΔPIV31hc (Skiadopoulos et al., *Vaccine* 18:503–510, 1999, incorporated herein by reference) to generate p38'ΔPIV32hc. The 6.5 kb fragment, generated by BspEI and SphI digestion of p38'ΔPIV32hc, containing the PIV2 full-length F and HN ORFs was introduced into the BspEI-SphI window of pFLC.2G+.hc (Tao et al., *J. Virol.* 72:2955–2961, 1998) to generate pFLC.PIV32hc (FIG. 6; Table 10=SEQ ID NO: 19).

TABLE 9

Primers used in construction of PIV3-2 full-length chimeric antigenomic cDNAs

| Primer no. | Gene | Direction | Position Beginning | Position End | Used in the construction or characterization of: | Sequence[a] |
|---|---|---|---|---|---|---|
| 1 | PIV2 F | sense | PIV2 F start codon 5070[b] | 20 bp down stream 5091 | pFLC.PIV32hc | gtaccATGgATCACCTGCATCCAAT (SEQ ID NO. 20) |
| 2 | PIV2 F | antisense | PIV2 F stop codon 6732[b] | 20 bp upstream 6705[b] | pFLC.PIV32hc | tgtggatccTAAGATATCCCATATATGTTTC (SEQ ID NO. 21) |
| 3 | PIV2 HN | sense | PIV2 HN start codon 6837[b] | 18 bp down stream 6856[b] | pFLC.PIV32hc | gggccATGGAAGATTACAGCAAT (SEQ ID NO. 13) |
| 4 | PIV2 HN | antisense | PIV2 HN stop codon 8558[b] | 17 bp upstream 8538[b] | pFLC.PIV32hc | caataagcTTAAAGCATTAGTTCCC (SEQ ID NO. 14) |
| 5 | PIV2 F | sense | 5069[c] | 5088[c] | pFLC.PIV32TM | ATGCATCACCTGCATCCAAT (SEQ ID NO. 22) |
| 6 | PIV2 F | antisense | 6538[c] | 6517[c] | pFLC.PIV32TM | TAGTGAATAAAGTGTCTTGGCT (SEQ ID NO. 23) |
| 7 | PIV2 HN | sense | 6962[c] | 6985[c] | pFLC.PIV32TM | CATGAGATAATTCATCTTGATGTT (SEQ ID NO. 24) |
| 8 | PIV2 HN | antisense | 8560[c] | 8537[c] | pFLC.PIV32TM | agcTTAAAGCATTAGTTCCCTTAA (SEQ ID NO. 25) |
| 9 | PIV3 F | sense | 6539[c] | 6566[c] | pFLC.PIV32TM | ATCATAATTATTTTGATAATGATCATTA (SEQ ID NO. 26) |
| 10 | PIV3 F | antisense | 5068[c] | 5050[c] | pFLC.PIV32TM | GTTCAGTGCTTGTTGTGTT (SEQ ID NO. 27) |
| 11 | PIV3 HN | sense | 8561[c] | 8587[c] | pFLC.PIV32TM | TCATAATTAACCATAATATGCATCAAT (SEQ ID NO. 28) |
| 12 | PIV3 HN | antisense | 6961[c] | 6938[c] | pFLC.PIV32TM | GATGGAATTAATTAGCACTATGAT (SEQ ID NO. 29) |
| 13 | PIV2 F | sense | 5069[d] | 5088[d] | pFLC.PIV32CT | ATGCATCACCTGCATCCAAT (SEQ ID NO. 30) |
| 14 | PIV2 F | antisense | 6607[d] | 6589[d] | pFLC.PIV32CT | GATGATGTAGGCAATCAGC (SEQ ID NO. 31) |
| 15 | PIV2 HN | sense | 6887[d] | 6904[d] | pFLC.PIV32CT | ACTGCCACAATTCTTGGC (SEQ ID NO. 32) |
| 16 | PIV2 HN | antisense | 8536[d] | 8511[d] | pFLC.PIV32CT | TTAAAGCATTAGTTCCCTTAAAAATG (SEQ ID NO. 33) |
| 17 | PIV3 F | sense | 6620[d] | 6642[d] | pFLC.PIV32GT | AAGTATTACAGAATTCAAAAGAG (SEQ ID NO. 34) |
| 18 | PIV3 F | antisense | 5068[d] | 5050[d] | pFLC.PIV32CT | GTTCAGTGCTTGTTGTGTT (SEQ ID NO. 27) |
| 19 | PIV3 HN | sense | 8525[d] | 8551[d] | pFLC.PIV32CT | TCATAATTAACCATAATATGCATCAAT (SEQ ID NO. 28) |
| 20 | PIV3 HN | antisense | 6898[d] | 6879[d] | pFLC.PIV32CT | CTTATTAGTGAGCTTGTTGC (SEQ ID NO. 35) |
| 21 | PIV2 F | Sense | 6608[c,d] | 6630[c,d] | Chimera confirmation | ACCGCAGCTGTAGCAATAGT (SEQ ID NO. 36) |
| 22 | PIV2 HN | antisense | 7522[c] 7501[d] | 7502[c] 7481[d] | Chimera confirmation | GATTCCATCACTTAGGTAAAT (SEQ ID NO. 37) |
| 23 | PIV3 M | sense | 4759[c,d] | 4780[c,d] | Chimera confirmation | GATACTATCCTAATATTATTGC (SEQ ID NO. 38) |
| 24 | PIV3 L | antisense | 9100[c] 9076[d] | 9081[c] 9057[d] | Chimera confirmation | GCTAATTTTGATAGCACATT (SEQ ID NO. 39) |

[a]All the primers are anotated in that the PIV specific sequences are in uppercase, non-PIV sequences in lowercase, start and stop codons in bold, and restriction sites underlined.
[b]The numbers are the nt positions in the full-length antigenomic cDNA construct pFLC.PIV32hc.
[c]The numbers are the nt positions in the full-length antigenomic cDNA construct pFLC.PIV32TM and pFLC.PIV32TMcp45.
[d]The numbers are the nt positions in the full-length antigenomic cDNA construct pFLC.PIV32CT and pFLC.PIV32CTcp45.

TABLE 10

(SEQ ID NO: 19)
Sequence of pFLC.PIV32, 15492 bp in sense orientation
(only the insert is shown)

```
  1 ACCAAACAAG AGAAGAAACT TGTCTGGGAA TATAAATTTA ACTTTAAATT AACTTAGGAT

61 TAAAGACATT GACTAGAAGG TCAAGAAAAG GGAACTCTAT AATTTCAAAA ATGTTGAGCC

121 TATTTGATAC ATTTAATGCA CGTAGGCAAG AAAACATAAC AAAATCAGCC GGTGGAGCTA

181 TCATTCCTGG ACAGAAAAAT ACTGTCTCTA TATTCGCCCT TGGACCGACA ATAACTGATG

241 ATAATGAGAA AATGACATTA GCTCTTCTAT TTCTATCTCA TTCACTAGAT AATGAGAAAC
```

TABLE 10-continued (SEQ ID NO: 19)
Sequence of pFLC.PIV32, 15492 bp in sense orientation
(only the insert is shown)

```
 301 AACATGCACA AAGGGCAGGG TTCTTGGTGT CTTTATTGTC AATGGCTTAT GCCAATCCAG
 361 AGCTCTACCT AACAACAAAT GGAAGTAATG CAGATGTCAA GTATGTCATA TACATGATTG
 421 AGAAAGATCT AAAACGGCAA AAGTATGGAG GATTTGTGGT TAAGACGAGA GAGATGATAT
 481 ATGAAAAGAC AACTGATTGG ATATTTGGAA GTGACCTGGA TTATGATCAG GAAACTATGT
 541 TGCAGAACGG CAGGAACAAT TCAACAATTG AAGACCTTGT CCACACATTT GGGTATCCAT
 601 CATGTTTAGG AGCTCTTATA ATACAGATCT GGATAGTTCT GGTCAAAGCT ATCACTAGTA
 661 TCTCAGGGTT AAGAAAAGGC TTTTTCACCC GATTGGAAGC TTTCAGACAA GATGGAACAG
 721 TGCAGGCAGG GCTGGTATTG AGCGGTGACA CAGTGGATCA GATTGGGTCA ATCATGCGGT
 781 CTCAACAGAG CTTGGTAACT CTTATGGTTG AAACATTAAT AACAATGAAT ACCAGCAGAA
 841 ATGACCTCAC AACCATAGAA AAGAATATAC AAATTGTTGG CAACTACATA AGAGATGCAG
 901 GTCTCGCTTC ATTCTTCAAT ACAATCAGAT ATGGAATTGA GACCAGAATG GCAGCTTTGA
 961 CTCTATCCAC TCTCAGACCA GATATCAATA GATTAAAAGC TTTGATGGAA CTGTATTTAT
1021 CAAAGGGACC ACGCGCTCCT TTCATCTGTA TCCTCAGAGA TCCTATACAT GGTGAGTTCG
1081 CACCAGGCAA CTATCCTGCC ATATGGAGCT ATGCAATGGG GGTGGCAGTT GTACAAAATA
1141 GAGCCATGCA ACAGTATGTG ACGGGAAGAT CATATCTAGA CATTGATATG TTCCAGCTAG
1201 GACAAGCAGT AGCACGTGAT GCCGAAGCTC AAATGAGCTC AACACTGGAA GATGAACTTG
1261 GAGTGACACA CGAATCTAAA GAAAGCTTGA AGAGACATAT AAGGAACATA AACAGTTCAG
1321 AGACATCTTT CCACAAACCG ACAGGTGGAT CAGCCATAGA GATGGCAATA GATGAAGAGC
1381 CAGAACAATT CGAACATAGA GCAGATCAAG AACAAAATGG AGAACCTCAA TCATCCATAA
1441 TTCAATATGC CTGGGCAGAA GGAAATAGAA GCGATGATCA GACTGAGCAA GCTACAGAAT
1501 CTGACAATAT CAAGACCGAA CAACAAAACA TCAGAGACAG ACTAAACAAG AGACTCAACG
1561 ACAAGAAGAA ACAAAGCAGT CAACCACCCA CTAATCCCAC AAACAGAACA AACCAGGACG
1621 AAATAGATGA TCTGTTTAAC GCATTTGGAA GCAACTAATC GAATCAACAT TTTAATCTAA
1681 ATCAATAATA AATAAGAAAA ACTTAGGATT AAAGAATCCT ATCATACCGG AATATAGGGT
1741 GGTAAATTTA GAGTCTGCTT GAAACTCAAT CAATAGAGAG TTGATGGAAA GCGATGCTAA
1801 AAACTATCAA ATCATGGATT CTTGGGAAGA GGAATCAAGA GATAAATCAA CTAATATCTC
1861 CTCGGCCCTC AACATCATTG AATTCATACT CAGCACCGAC CCCCAAGAAG ACTTATCGGA
1921 AAACGACACA ATCAACACAA GAACCCAGCA ACTCAGTGCC ACCATCTGTC AACCAGAAAT
1981 CAAACCAACA GAAACAAGTG AGAAAGATAG TGGATCAACT GACAAAAATA GACAGTCCGG
2041 GTCATCACAC GAATGTACAA CAGAAGCAAA AGATAGAAAT ATTGATCAGG AAACTGTACA
2101 GAGAGGACCT GGGAGAAGAA GCAGCTCAGA TAGTAGAGCT GAGACTGTGG TCTCTGGAGG
2161 AATCCCCAGA AGCATCACAG ATTCTAAAAA TGGAACCCAA AACACGGAGG ATATTGATCT
2221 CAATGAAATT AGAAAGATGG ATAAGGACTC TATTGAGGGG AAAATGCGAC AATCTGCAAA
2281 TGTTCCAAGC GAGATATCAG GAAGTGATGA CATATTTACA ACAGAACAAA GTAGAAACAG
2341 TGATCATGGA AGAAGCCTGG AATCTATCAG TACACCTGAT ACAAGATCAA TAAGTGTTGT
2401 TACTGCTGCA ACACCAGATG ATGAAGAAGA AATACTAATG AAAAATAGTA GGACAAAGAA
2461 AAGTTCTTCA ACACATCAAG AAGATGACAA AAGAATTAAA AAGGGGGAA AAGGGAAAGA
2521 CTGGTTTAAG AAATCAAAAG ATACCGACAA CCAGATACCA ACATCAGACT ACAGATCCAC
```

TABLE 10-continued (SEQ ID NO: 19)
Sequence of pFLC.PIV32, 15492 bp in sense orientation
(only the insert is shown)

```
2581 ATCAAAAGGG CAGAAGAAAA TCTCAAAGAC AACAACCACC AACACCGACA CAAAGGGGCA

2641 AACAGAAATA CAGACAGAAT CATCAGAAAC ACAATCCTCA TCATGGAATC TCATCATCGA

2701 CAACAACACC GACCGGAACG AACAGACAAG CACAACTCCT CCAACAACAA CTTCCAGATC

2761 AACTTATACA AAAGAATCGA TCCGAACAAA CTCTGAATCC AAACCCAAGA CACAAAAGAC

2821 AAATGGAAAG GAAAGGAAGG ATACAGAAGA GAGCAATCGA TTTACAGAGA GGGCAATTAC

2881 TCTATTGCAG AATCTTGGTG TAATTCAATC CACATCAAAA CTAGATTTAT ATCAAGACAA

2941 ACGAGTTGTA TGTGTAGCAA ATGTACTAAA CAATGTAGAT ACTGCATCAA AGATAGATTT

3001 CCTGGCAGGA TTAGTCATAG GGGTTTCAAT GGACAACGAC ACAAAATTAA CACAGATACA

3061 AAATGAAATG CTAAACCTCA AAGCAGATCT AAAGAAAATG GACGAATCAC ATAGAAGATT

3121 GATAGAAAAT CAAAGAGAAC AACTGTCATT GATCACGTCA CTAATTTCAA ATCTCAAAAT

3181 TATGACTGAG AGAGGAGGAA AGAAAGACCA AAATGAATCC AATGAGAGAG TATCCATGAT

3241 CAAAACAAAA TTGAAAGAAG AAAAGATCAA GAAGACCAGG TTTGACCCAC TTATGGAGGC

3301 ACAAGGCATT GACAAGAATA TACCCGATCT ATATCGACAT GCAGGAGATA CACTAGAGAA

3361 CGATGTACAA GTTAAATCAG AGATATTAAG TTCATACAAT GAGTCAAATG CAACAAGACT

3421 AATACCCAAA AAAGTGAGCA GTACAATGAG ATCACTAGTT GCAGTCATCA ACAACAGCAA

3481 TCTCTCACAA AGCACAAAAC AATCATACAT AAACGAACTC AAACGTTGCA AAAATGATGA

3541 AGAAGTATCT GAATTAATGG ACATGTTCAA TGAAGATGTC AACAATTGCC AATGATCCAA

3601 CAAAGAAACG ACACCGAACA AACAGACAAG AAACAACAGT AGATCAAAAC CTGTCAACAC

3661 ACACAAAATC AAGCAGAATG AAACAACAGA TATCAATCAA TATACAAATA AGAAAAACTT

3721 AGGATTAAAG AATAAATTAA TCCTTGTCCA AAATGAGTAT AACTAACTCT GCAATATACA

3781 CATTCCCAGA ATCATCATTC TCTGAAAATG GTCATATAGA ACCATTACCA CTCAAAGTCA

3841 ATGAACAGAG GAAAGCAGTA CCCCACATTA GAGTTGCCAA GATCGGAAAT CCACCAAAAC

3901 ACGGATCCCG GTATTTAGAT GTCTTCTTAC TCGGCTTCTT CGAGATGGAA CGAATCAAAG

3961 ACAAATACGG GAGTGTGAAT GATCTCGACA GTGACCCGAG TTACAAAGTT TGTGGCTCTG

4021 GATCATTACC AATCGGATTG CTAAGTACA CTGGGAATGA CCAGGAATTG TTACAAGCCG

4081 CAACCAAACT GGATATAGAA GTGAGAAGAA CAGTCAAAGC GAAAGAGATG GTTGTTTACA

4141 CGGTACAAAA TATAAAACCA GAACTGTACC CATGGTCCAA TAGACTAAGA AAAGGAATGC

4201 TGTTCGATGC CAACAAAGTT GCTCTTGCTC CTCAATGTCT TCCACTAGAT AGGAGCATAA

4261 AATTTAGAGT AATCTTCGTG AATTGTACGG CAATTGGATC AATAACCTTG TTCAAAATTC

4321 CTAAGTCAAT GGCATCACTA TCTCTACCCA ACACAATATC AATCAATCTG CAGGTACACA

4381 TAAAAACAGG GGTTCAGACT GATTCTAAAG GGATAGTTCA AATTTTGGAT GAGAAAGGCG

4441 AAAAATCACT GAATTTCATG GTCCATCTCG GATTGATCAA AGAAAAGTA GGCAGAATGT

4501 ACTCTGTTGA ATACTGTAAA CAGAAAATCG AGAAATGAG ATTGATATTT TCTTTAGGAC

4561 TAGTTGGAGG AATCAGTCTT CATGTCAATG CAACTGGGTC CATATCAAAA ACACTAGCAA

4621 GTCAGCTGGT ATTCAAAAGA GAGATTTGTT ATCCTTTAAT GGATCTAAAT CCGCATCTCA

4681 ATCTAGTTAT CTGGGCTTCA TCAGTAGAGA TTACAAGAGT GGATGCAATT TTCCAACCTT

4741 CTTTACCTGG CGAGTTCAGA TACTATCCTA ATATTATTGC AAAAGGAGTT GGGAAAATCA
```

TABLE 10-continued (SEQ ID NO: 19)
Sequence of pFLC.PIV32, 15492 bp in sense orientation
(only the insert is shown)

```
4801 AACAATGGAA CTAGTAATCT CTATTTTAGT CCGGACGTAT CTATTAAGCC GAAGCAAATA
4861 AAGGATAATC AAAAACTTAG GACAAAAGAG GTCAATACCA ACAACTATTA GCAGTCACAC
4921 TCGCAAGAAT AAGAGAGAAG GGACCAAAAA AGTCAAATAG GAGAAATCAA AACAAAAGGT
4981 ACAGAACACC AGAACAACAA AATCAAAACA TCCAACTCAC TCAAAACAAA AATTCCAAAA
5041 GAGACCGGCA ACACAACAAG CACTGAACAC CATGGATCAC CTGCATCCAA TGATAGTATG
5101 CATTTTTGTT ATGTACACTG GAATTGTAGG TTCAGATGCC ATTGCTGGAG ATCAACTCCT
5161 CAATGTAGGG GTCATTCAAT CAAAGATAAG ATCACTCATG TACTACACTG ATGGTGGCGC
5221 TAGCTTTATT GTTGTAAAAT TACTACCCAA TCTTCCCCCA AGCAATGAA CATGCAACAT
5281 CACCAGTCTA GATGCATATA ATGTTACCCT ATTTAAGTTG CTAACACCCC TGATTGAGAA
5341 CCTGAGCAAA ATTTCTGCTG TTACAGATAC CAAACCCCGC CGAGAACGAT TTGCAGGAGT
5401 CGTTATTGGG CTTGCTGCAC TAGGAGTAGC TACAGCTGCA CAAATAACCG CAGCTGTAGC
5461 AATAGTAAAA GCCAATGCAA ATGCTGCTGC GATAAACAAT CTTGCATCTT CAATTCAATC
5521 CACCAACAAG GCAGTATCCG ATGTGATAAC TGCATCAAGA ACAATTGCAA CCGCAGTTCA
5581 AGCGATTCAG GATCACATCA ATGGAGCCAT TGTCAACGGG ATAACATCTG CATCATGCCG
5641 TGCCCATGAT GCACTAATTG GGTCAATATT AAATTTGTAT CTCACTGAGC TTACTACAAT
5701 ATTTCATAAT CAAATAACAA ACCCTGCGCT GACACCACTT TCCATCCAAG CTTTAAGAAT
5761 CCTCCTCGGT AGCACCTTGC CAATTGTCAT TGAATCCAAA CTCAACACAA AACTCAACAC
5821 AGCAGAGCTG CTCAGTAGCG GACTGTTAAC TGGTCAAATA ATTTCCATTT CCCCAATGTA
5881 CATGCAAATG CTAATTCAAA TCAATGTTCC GACATTTATA ATGCAACCCG GTGCGAAGGT
5941 AATTGATCTA ATTGCTATCT CTGCAAACCA TAAATTACAA GAAGTAGTTG TACAAGTTCC
6001 TAATAGAATT CTAGAATATG CAAATGAACT ACAAAACTAC CCAGCCAATG ATTGTTTCGT
6061 GACACCAAAC TCTGTATTTT GTAGATACAA TGAGGGTTCC CCGATCCCTG AATCACAATA
6121 TCAATGCTTA AGGGGGAATC TTAATTCTTG CACTTTTACC CCTATTATCG GAACTTTCT
6181 CAAGCGATTC GCATTTGCCA ATGGTGTGCT CTATGCCAAC TGCAAATCTT TGCTATGTAA
6241 GTGTGCCGAC CCTCCCCATG TTGTGTCTCA AGATGACAAC CAAGGCATCA GCATAATTGA
6301 TATTAAGAGG TGCTCTGAGA TGATGCTTGA CACTTTTTCA TTTAGGATCA CATCTACATT
6361 CAATGCTACA TACGTGACAG ACTTCTCAAT GATTAATGCA AATATTGTAC ATCAAGTCC
6421 TCTAGACTTG TCAAATCAAA TCAATTCAAT AAACAAATCT CTTAAAAGTG CTGAGGATTG
6481 GATTGCAGAT AGCAACTTCT TCGCTAATCA AGCCAGAACA GCCAAGACAC TTTATTCACT
6541 AAGTGCAATC GCATTAATAC TATCAGTGAT TACTTTGGTT GTTGTGGGAT TGCTGATTGC
6601 CTACATCATC AAGCTGGTTT CTCAAATCCA TCAATTCAGA GCACTAGCTG CTACAACAAT
6661 GTTCCACAGG GAGAATCCTG CCGTCTTTTC CAAGAACAAT CATGGAAACA TATATGGGAT
6721 ATCTTAGGAT CCCTACAGAT CATTAGATAT TAAAATTATA AAAACTTAG GAGTAAAGTT
6781 ACGCAATCCA ACTCTACTCA TATAATTGAG GAAGGACCCA ATAGACAAAT CCAAATCCAT
6841 GGAAGATTAC AGCAATCTAT CTCTTAAATC AATTCCTAAA AGGACATGTA GAATCATTTT
6901 CCGAACTGCC ACAATTCTTG GCATATGCAC ATTAATTGTG CTATGTTCAA GTATTCTTCA
6961 TGAGATAATT CATCTTGATG TTTCCTCTGG TCTTATGAAT TCTGATGAGT CACAGCAAGG
7021 CATTATTCAG CCTATCATAG AATCATTAAA ATCATTGATT GCTTTGGCCA ACCAGATTCT
```

TABLE 10-continued (SEQ ID NO: 19)
Sequence of pFLC.PIV32, 15492 bp in sense orientation
(only the insert is shown)

```
7081 ATATAATGTT GCAATAGTAA TTCCTCTTAA AATTGACAGT ATCGAAACTG TAATACTCTC

7141 TGCTTTAAAA GATATGCACA CCGGGAGTAT GTCCAATGCC AACTGCACGC CAGGAAATCT

7201 GCTTCTGCAT GATGCAGCAT ACATCAATGG AATAAACAAA TTCCTTGTAC TTGAATCATA

7261 CAATGGGACG CCTAAATATG GACCTCTCCT AAATATACCC AGCTTTATCC CCTCAGCAAC

7321 ATCTCCCCAT GGGTGTACTA GAATACCATC ATTTTCACTC ATCAAGACCC ATTGGTGTTA

7381 CACTCACAAT GTAATGCTTG GAGATTGTCT TGATTTCACG GCATCTAACC AGTATTTATC

7441 AATGGGGATA ATACAACAAT CTGCTGCAGG GTTTCCAATT TTCAGGACTA TGAAAACCAT

7501 TTACCTAAGT GATGGAATCA ATCGCAAAAG CTGTTCAGTC ACTGCTATAC CAGGAGGTTG

7561 TGTCTTGTAT TGCTATGTAG CTACAAGGTC TGAAAAAGAA GATTATGCCA CGACTGATCT

7621 AGCTGAACTG AGACTTGCTT TCTATTATTA TAATGATACC TTTATTGAAA GAGTCATATC

7681 TCTTCCAAAT ACAACAGGGC AGTGGGCCAC AATCAACCCT GCAGTCGGAA GCGGGATCTA

7741 TCATCTAGGC TTTATCTTAT TTCCTGTATA TGGTGGTCTC ATAAATGGGA CTACTTCTTA

7801 CAATGAGCAG TCCTCACGCT ATTTTATCCC AAAACATCCC AACATAACTT GTGCCGGTAA

7861 CTCCAGCAAA CAGGCTGCAA TAGCACGGAG TTCCTATGTC ATCCGTTATC ACTCAAACAG

7921 GTTAATTCAG AGTGCTGTTC TTATTTGTCC ATTGTCTGAC ATGCATACAG AAGAGTGTAA

7981 TCTAGTTATG TTTAACAATT CCCAAGTCAT GATGGGTGCA GAAGGTAGGC TCTATGTTAT

8041 TGGTAATAAT TTGTATTATT ATCAACGCAG TTCCTCTTGG TGGTCTGCAT CGCTCTTTTA

8101 CAGGATCAAT ACAGATTTTT CTAAAGGAAT TCCTCCGATC ATTGAGGCTC AATGGGTACC

8161 GTCCTATCAA GTTCCTCGTC CTGGAGTCAT GCCATGCAAT GCAACAAGTT TTTGCCCTGC

8221 TAATTGCATC ACAGGGGTGT ACGCAGATGT GTGGCCGCTT AATGATCCAG AACTCATGTC

8281 ACGTAATGCT CTGAACCCCA ACTATCGATT TGCTGGAGCC TTTCTCAAAA ATGAGTCCAA

8341 CCGAACTAAT CCCACATTCT ACACTGCATC GGCTAACTCC CTCTTAAATA CTACCGGATT

8401 CAACAACACC AATCACAAAG CAGCATATAC ATCTTCAACC TGCTTTAAAA ACACTGGAAC

8461 CCAAAAAATT TATTGTTTAA TAATAATTGA AATGGGCTCA TCTCTTTTAG GGGAGTTCCA

8521 AATAATACCA TTTTTAAGGG AACTAATGCT TTAAGCTTAA TTAACCATAA TATGCATCAA

8581 TCTATCTATA ATACAAGTAT ATGATAAGTA ATCTGCAATC AGACAATAGA CAAAAGGGAA

8641 ATATAAAAAA CTTAGGAGCA AAGCGTGCTC GGGAAATGGA CACTGAATCT AACAATGGCA

8701 CTGTATCTGA CATACTCTAT CCTGAGTGTC ACCTTAACTC TCCTATCGTT AAAGGTAAAA

8761 TAGCACAATT ACACACTATT ATGAGTCTAC CTCAGCCTTA TGATATGGAT GACGACTCAA

8821 TACTAGTTAT CACTAGACAG AAAATAAAAC TTAATAAATT GGATAAAAGA CAACGATCTA

8881 TTAGAAGATT AAAATTAATA TTAACTGAAA AAGTGAATGA CTTAGGAAAA TACACATTTA

8941 TCAGATATCC AGAAATGTCA AAAGAAATGT TCAAATTATA TATACCTGGT ATTAACAGTA

9001 AAGTGACTGA ATTATTACTT AAAGCAGATA GAACATATAG TCAAATGACT GATGGATTAA

9061 GAGATCTATG GATTAATGTG CTATCAAAAT TAGCCTCAAA AAATGATGGA AGCAATTATG

9121 ATCTTAATGA AGAAATTAAT AATATATCGA AGTTCACAC AACCTATAAA TCAGATAAAT

9181 GGTATAATCC ATTCAAAACA TGGTTTACTA TCAAGTATGA TATGAGAAGA TTACAAAAAG

9241 CTCGAAATGA GATCACTTTT AATGTTGGGA AGGATTATAA CTTGTTAGAA GACCAGAAGA
```

TABLE 10-continued (SEQ ID NO: 19)
Sequence of pFLC.PIV32, 15492 bp in sense orientation
(only the insert is shown)

```
 9301 ATTTCTTATT GATACATCCA GAATTGGTTT TGATATTAGA TAAACAAAAC TATAATGGTT
 9361 ATCTAATTAC TCCTGAATTA GTATTGATGT ATTGTGACGT AGTCGAAGCC CGATGGAATA
 9421 TAAGTGCATG TGCTAAGTTA GATCCAAAAT TACAATCTAT GTATCAGAAA GGTAATAACC
 9481 TGTGGGAAGT GATAGATAAA TTGTTTCCAA TTATGGGAGA AAAGACATTT GATGTGATAT
 9541 CGTTATTAGA ACCACTTGCA TTATCCTTAA TTCAAACTCA TGATCCTGTT AAACAACTAA
 9601 GAGGAGCTTT TTTAAATCAT GTGTTATCCG AGATGGAATT AATATTTGAA TCTAGAGAAT
 9661 CGATTAAGGA ATTTCTGAGT GTAGATTACA TTGATAAAAT TTTAGATATA TTTAATAAGT
 9721 CTACAATAGA TGAAATAGCA GAGATTTTCT CTTTTTTTAG AACATTTGGG CATCCTCCAT
 9781 TAGAAGCTAG TATTGCAGCA GAAAAGGTTA GAAAATATAT GTATATTGGA AAACAATTAA
 9841 AATTTGACAC TATTAATAAA TGTCATGCTA TCTTCTGTAC AATAATAATT AACGGATATA
 9901 GAGAGAGGCA TGGTGGACAG TGGCCTCCTG TGACATTACC TGATCATGCA CACGAATTCA
 9961 TCATAAATGC TTACGGTTCA AACTCTGCGA TATCATATGA AAATGCTGTT GATTATTACC
10021 AGAGCTTTAT AGGAATAAAA TTCAATAAAT TCATAGAGCC TCAGTTAGAT GAGGATTTGA
10081 CAATTTATAT GAAAGATAAA GCATTATCTC CAAAAAAATC AAATTGGGAC ACAGTTTATC
10141 CTGCATCTAA TTTACTGTAC CGTACTAACG CATCCAACGA ATCACGAAGA TTAGTTGAAG
10201 TATTTATAGC AGATAGTAAA TTTGATCCTC ATCAGATATT GGATTATGTA GAATCTGGGG
10261 ACTGGTTAGA TGATCCAGAA TTTAATATTT CTTATAGTCT TAAAGAAAAA GAGATCAAAC
10321 AGGAAGGTAG ACTCTTTGCA AAAATGACAT ACAAAATGAG AGCTACACAA GTTTTATCAG
10381 AGACCCTACT TGCAAATAAC ATAGGAAAAT TCTTTCAAGA AAATGGGATG GTGAAGGGAG
10441 AGATTGAATT ACTTAAGAGA TTAACAACCA TATCAATATC AGGAGTTCCA CGGTATAATG
10501 AAGTGTACAA TAATTCTAAA AGCCATACAG ATGACCTTAA AACCTACAAT AAAATAAGTA
10561 ATCTTAATTT GTCTTCTAAT CAGAAATCAA AGAAATTTGA ATTCAAGTCA ACGGATATCT
10621 ACAATGATGG ATACGAGACT GTGAGCTGTT TCCTAACAAC AGATCTCAAA AAATACTGTC
10681 TTAATTGGAG ATATGAATCA ACAGCTCTAT TTGGAGAAAC TTGCAACCAA ATATTTGGAT
10741 TAAATAAATT GTTTAATTGG TTACACCCTC GTCTTGAAGG AAGTACAATC TATGTAGGTG
10801 ATCCTTACTG TCCTCCATCA GATAAAGAAC ATATATCATT AGAGGATCAC CCTGATTCTG
10861 GTTTTTACGT TCATAACCCA AGAGGGGGTA TAGAAGGATT TTGTCAAAAA TTATGGACAC
10921 TCATATCTAT AAGTGCAATA CATCTAGCAG CTGTTAGAAT AGGCGTGAGG GTGACTGCAA
10981 TGGTTCAAGG AGACAATCAA GCTATAGCTG TAACCACAAG AGTACCCAAC AATTATGACT
11041 ACAGAGTTAA GAAGGAGATA GTTTATAAAG ATGTAGTGAG ATTTTTTGAT TCATTAAGAG
11101 AAGTGATGGA TGATCTAGGT CATGAACTTA AATTAAATGA AACGATTATA AGTAGCAAGA
11161 TGTTCATATA TAGCAAAAGA ATCTATTATG ATGGGAGAAT TCTTCCTCAA GCTCTAAAAG
11221 CATTATCTAG ATGTGTCTTC TGGTCAGAGA CAGTAATAGA CGAAACAAGA TCAGCATCTT
11281 CAAATTTGGC AACATCATTT GCAAAGCAA TTGAGAATGG TTATTCACCT GTTCTAGGAT
11341 ATGCATGCTC AATTTTTAAG AATATTCAAC AACTATATAT TGCCCTTGGG ATGAATATCA
11401 ATCCAACTAT AACACAGAAT ATCAGAGATC AGTATTTTAG GAATCCAAAT TGGATGCAAT
11461 ATGCCTCTTT AATACCTGCT AGTGTTGGGG GATTCAATTA CATGGCCATG TCAAGATGTT
11521 TTGTAAGGAA TATTGGTGAT CCATCAGTTG CCGCATTGGC TGATATTAAA AGATTTATTA
```

TABLE 10-continued (SEQ ID NO: 19)
Sequence of pFLC.PIV32, 15492 bp in sense orientation
(only the insert is shown)

```
11581 AGGCGAATCT ATTAGACCGA AGTGTTCTTT ATAGGATTAT GAATCAAGAA CCAGGTGAGT

11641 CATCTTTTTT GGACTGGGCT TCAGATCCAT ATTCATGCAA TTTACCACAA TCTCAAAATA

11701 TAACCACCAT GATAAAAAAT ATAACAGCAA GGAATGTATT ACAAGATTCA CCAAATCCAT

11761 TATTATCTGG ATTATTCACA AATACAATGA TAGAAGAAGA TGAAGAATTA GCTGAGTTCC

11821 TGATGGACAG GAAGGTAATT CTCCCTAGAG TTGCACATGA TATTCTAGAT AATTCTCTCA

11881 CAGGAATTAG AAATGCCATA GCTGGAATGT TAGATACGAC AAAATCACTA ATTCGGGTTG

11941 GCATAAATAG AGGAGGACTG ACATATAGTT TGTTGAGGAA AATCAGTAAT TACGATCTAG

12001 TACAATATGA AACACTAAGT AGGACTTTGC GACTAATTGT AAGTGATAAA ATCAAGTATG

12061 AAGATATGTG TTCGGTAGAC CTTGCCATAG CATTGCGACA AAAGATGTGG ATTCATTTAT

12121 CAGGAGGAAG GATGATAAGT GGACTTGAAA CGCCTGACCC ATTAGAATTA CTATCTGGGG

12181 TAGTAATAAC AGGATCAGAA CATTGTAAAA TATGTTATTC TTCAGATGGC ACAAACCCAT

12241 ATACTTGGAT GTATTTACCC GGTAATATCA AAATAGGATC AGCAGAAACA GGTATATCGT

12301 CATTAAGAGT TCCTTATTTT GGATCAGTCA CTGATGAAAG ATCTGAAGCA CAATTAGGAT

12361 ATATCAAGAA TCTTAGTAAA CCTGCAAAAG CCGCAATAAG AATAGCAATG ATATATACAT

12421 GGGCATTTGG TAATGATGAG ATATCTTGGA TGGAAGCCTC ACAGATAGCA CAAACACGTG

12481 CAAATTTTAC ACTAGATAGT CTCAAAATTT AACACCGGT AGCTACATCA ACAAATTTAT

12541 CACACAGATT AAAGGATACT GCAACTCAGA TGAAATTCTC CAGTACATCA TTGATCAGAG

12601 TCAGCAGATT CATAACAATG TCCAATGATA ACATGTCTAT CAAAGAAGCT AATGAAACCA

12661 AAGATACTAA TCTTATTTAT CAACAAATAA TGTTAACAGG ATTAAGTGTT TTCGAATATT

12721 TATTTAGATT AAAAGAAACC ACAGGACACA ACCCTATAGT TATGCATCTG CACATAGAAG

12781 ATGAGTGTTG TATTAAAGAA AGTTTTAATG ATGAACATAT TAATCCAGAG TCTACATTAG

12841 AATTAATTCG ATATCCTGAA AGTAATGAAT TTATTTATGA TAAAGACCCA CTCAAAGATG

12901 TGGACTTATC AAAACTTATG GTTATTAAAG ACCATTCTTA CACAATTGAT ATGAATTATT

12961 GGGATGATAC TGACATCATA CATGCAATTT CAATATGTAC TGCAATTACA ATAGCAGATA

13021 CTATGTCACA ATTAGATCGA GATAATTTAA AAGAGATAAT AGTTATTGCA AATGATGATG

13081 ATATTAATAG CTTAATCACT GAATTTTTGA CTCTTGACAT ACTTGTATTT CTCAAGACAT

13141 TTGGTGGATT ATTAGTAAAT CAATTTGCAT ACACTCTTTA TAGTCTAAAA ATAGAAGGTA

13201 GGGATCTCAT TTGGGATTAT ATAATGAGAA CACTGAGAGA TACTTCCCAT TCAATATTAA

13261 AAGTATTATC TAATGCATTA TCTCATCCTA AAGTATTCAA GAGGTTCTGG GATTGTGGAG

13321 TTTTAAACCC TATTTATGGT CCTAATACTG CTAGTCAAGA CCAGATAAAA CTTGCCCTAT

13381 CTATATGTGA ATATTCACTA GATCTATTTA TGAGAGAATG GTTGAATGGT GTATCACTTG

13441 AAATATACAT TTGTGACAGC GATATGGAAG TTGCAAATGA TAGGAAACAA GCCTTTATTT

13501 CTAGACACCT TTCATTTGTT TGTTGTTTAG CAGAAATTGC ATCTTTCGGA CCTAACCTGT

13561 TAAACTTAAC ATACTTGGAG AGACTTGATC TATTGAAACA ATATCTTGAA TTAAATATTA

13621 AAGAAGACCC TACTCTTAAA TATGTACAAA TATCTGGATT ATTAATTAAA TCGTTCCCAT

13681 CAACTGTAAC ATACGTAAGA AAGACTGCAA TCAAATATCT AAGGATTCGC GGTATTAGTC

13741 CACCTGAGGT AATTGATGAT TGGGATCCGG TAGAAGATGA AAATATGCTG GATAACATTG
```

TABLE 10-continued (SEQ ID NO: 19)
Sequence of pFLC.PIV32, 15492 bp in sense orientation
(only the insert is shown)

```
13801 TCAAAACTAT AAATGATAAC TGTAATAAAG ATAATAAAGG GAATAAAATT AACAATTTCT

13861 GGGGACTAGC ACTTAAGAAC TATCAAGTCC TTAAAATCAG ATCTATAACA AGTGATTCTG

13921 ATGATAATGA TAGACTAGAT GCTAATACAA GTGGTTTGAC ACTTCCTCAA GGAGGGAATT

13981 ATCTATCGCA TCAATTGAGA TTATTCGGAA TCAACAGCAC TAGTTGTCTG AAAGCTCTTG

14041 AGTTATCACA AATTTTAATG AAGGAAGTCA ATAAAGACAA GGACAGGCTC TTCCTGGGAG

14101 AAGGAGCAGG AGCTATGCTA GCATGTTATG ATGCCACATT AGGACCTGCA GTTAATTATT

14161 ATAATTCAGG TTTGAATATA ACAGATGTAA TTGGTCAACG AGAATTGAAA ATATTTCCTT

14221 CAGAGGTATC ATTAGTAGGT AAAAAATTAG GAAATGTGAC ACAGATTCTT AACAGGGTAA

14281 AAGTACTGTT CAATGGGAAT CCTAATTCAA CATGGATAGG AAATATGGAA TGTGAGAGCT

14341 TAATATGGAG TGAATTAAAT GATAAGTCCA TTGGATTAGT ACATTGTGAT ATGGAAGGAG

14401 CTATCGGTAA ATCAGAAGAA ACTGTTCTAC ATGAACATTA TAGTGTTATA AGAATTACAT

14461 ACTTGATTGG GGATGATGAT GTTGTTTTAG TTTCCAAAAT TATACCTACA ATCACTCCGA

14521 ATTGGTCTAG AATACTTTAT CTATATAAAT TATATTGGAA AGATGTAAGT ATAATATCAC

14581 TCAAAACTTC TAATCCTGCA TCAACAGAAT TATATCTAAT TTCGAAAGAT GCATATTGTA

14641 CTATAATGGA ACCTAGTGAA ATTGTTTTAT CAAAACTTAA AAGATTGTCA CTCTTGGAAG

14701 AAAATAATCT ATTAAAATGG ATCATTTTAT CAAAGAAGAG GAATAATGAA TGGTTACATC

14761 ATGAAATCAA AGAAGGAGAA AGAGATTATG GAATCATGAG ACCATATCAT ATGGCACTAC

14821 AAATCTTTGG ATTTCAAATC AATTTAAATC ATCTGGCGAA AGAATTTTTA TCAACCCCAG

14881 ATCTGACTAA TATCAACAAT ATAATCCAAA GTTTTCAGCG AACAATAAAG GATGTTTTAT

14941 TTGAATGGAT TAATATAACT CATGATGATA AGAGACATAA ATTAGGCGGA AGATATAACA

15001 TATTCCCACT GAAAAATAAG GGAAAGTTAA GACTGCTATC GAGAAGACTA GTATTAAGTT

15061 GGATTTCATT ATCATTATCG ACTCGATTAC TTACAGGTCG CTTTCCTGAT GAAAAATTTG

15121 AACATAGAGC ACAGACTGGA TATGTATCAT TAGCTGATAC TGATTTAGAA TCATTAAAGT

15181 TATTGTCGAA AAACATCATT AAGAATTACA GAGAGTGTAT AGGATCAATA TCATATTGGT

15241 TTCTAACCAA AGAAGTTAAA ATACTTATGA AATTGATCGG TGGTGCTAAA TTATTAGGAA

15301 TTCCCAGACA ATATAAAGAA CCCGAAGACC AGTTATTAGA AAACTACAAT CAACATGATG

15361 AATTTGATAT CGATTAAAAC ATAAATACAA TGAAGATATA TCCTAACCTT TATCTTTAAG

15421 CCTAGGAATA GACAAAAAGT AAGAAAAACA TGTAATATAT ATATACCAAA CAGAGTTCTT

15481 CTCTTGTTTG GT
```

In a second strategy (FIG. 7), chimeric PIV3-PIV2 F and HN ORFs rather than the complete ORF exchange were constructed in which regions of the PIV2 F and HN ORFs encoding the ectodomains were amplified from pLit.PIV32Fhc and pLit.PIV32HNhc, respectively, using PCR, Vent DNA polymerase (NEB, Beverly, Mass.), and primer pairs specific to PIV2 F (5, 6 in Table 9) and HN (7, 8 in Table 9). In parallel, the regions of PIV3 F and HN ORFs encoding the ectodomains were deleted from their cDNA subclones pLit.PIV3.F3a and pLit.PIV3.HN4 (Tao et al., *J. Virol.* 72:2955–2961, 1998, incorporated herein by reference), respectively, using PCR, Vent DNA polymerase, and primer pairs specific to PIV3 F (9, 10 in Table 9) and HN (11, 12 in Table 9). The amplified F and HN cDNA fragments of PIV2 and PIV3 were purified from agarose gels and ligated to generate pLit.PIV32FTM and pLit.PIV32HNTM, respectively. The chimeric F and HN constructs were digested with PpuMI plus SpeI and assembled together to generate pLit.PIV32TM, which was subsequently sequenced with the dRhodamine dye terminator sequencing kit across its PIV specific region in its entirety and found to be as designed. The 4 kb BspEI-SpeI fragment from pLit.PIV32TM was then introduced into the BspEI-SpeI window of p38'ΔPIV31hc to generate p38'ΔPIV32TM. The 6.5 kb BspEI-SphI fragment from p38'ΔPIV32TM, containing the PIV3-PIV2 chimeric F and HN genes, was introduced into the BspEI-SphI window of pFLC.2G+.hc and pFLCcp45 (Skiadopoulos et al., *J. Virol.* 73:1374–81, 1999, incorporated herein by reference) to generate pFLC.PIV32TM (Table 11; SEQ ID NO: 40) and pFLC.PIV32TMcp45, respectively. The nucleotide sequence of the BspEI-SpeI fragment, containing the chimeric PIV3-PIV2 F and HN genes, is submitted in the GenBank (Accession No. pending).

TABLE 11

(SEQ ID NO. 40)
Sequence of pFLC.PIV32TM, 15498 bp in sense orientation
(only the antigenome is shown)

| | | | | | | |
|---|---|---|---|---|---|---|
| 1 | ACCAAACAAG | AGAAGAAACT | TGTCTGGGAA | TATAAATTTA | ACTTTAAATT | AACTTAGGAT |
| 61 | TAAAGACATT | GACTAGAAGG | TCAAGAAAAG | GGAACTCTAT | AATTTCAAAA | ATGTTGAGCC |
| 121 | TATTTGATAC | ATTTAATGCA | CGTAGGCAAG | AAAACATAAC | AAAATCAGCC | GGTGGAGCTA |
| 181 | TCATTCCTGG | ACAGAAAAAT | ACTGTCTCTA | TATTCGCCCT | TGGACCGACA | ATAACTGATG |
| 241 | ATAATGAGAA | AATGACATTA | GCTCTTCTAT | TTCTATCTCA | TTCACTAGAT | AATGAGAAAC |
| 301 | AACATGCACA | AAGGGCAGGG | TTCTTGGTGT | CTTTATTGTC | AATGGCTTAT | GCCAATCCAG |
| 361 | AGCTCTACCT | AACAACAAAT | GGAAGTAATG | CAGATGTCAA | GTATGTCATA | TACATGATTG |
| 421 | AGAAAGATCT | AAAACGGCAA | AAGTATGGAG | GATTTGTGGT | TAAGACGAGA | GAGATGATAT |
| 481 | ATGAAAAGAC | AACTGATTGG | ATATTTGGAA | GTGACCTGGA | TTATGATCAG | GAAACTATGT |
| 541 | TGCAGAACGG | CAGGAACAAT | TCAACAATTG | AAGACCTTGT | CCACACATTT | GGGTATCCAT |
| 601 | CATGTTTAGG | AGCTCTTATA | ATACAGATCT | GGATAGTTCT | GGTCAAAGCT | ATCACTAGTA |
| 661 | TCTCAGGGTT | AAGAAAAGGC | TTTTTCACCC | GATTGGAAGC | TTTCAGACAA | GATGGAACAG |
| 721 | TGCAGGCAGG | GCTGGTATTG | AGCGGTGACA | CAGTGGATCA | GATTGGGTCA | ATCATGCGGT |
| 781 | CTCAACAGAG | CTTGGTAACT | CTTATGGTTG | AAACATTAAT | AACAATGAAT | ACCAGCAGAA |
| 841 | ATGACCTCAC | AACCATAGAA | AAGAATATAC | AAATTGTTGG | CAACTACATA | AGAGATGCAG |
| 901 | GTCTCGCTTC | ATTCTTCAAT | ACAATCAGAT | ATGGAATTGA | GACCAGAATG | GCAGCTTTGA |
| 961 | CTCTATCCAC | TCTCAGACCA | GATATCAATA | GATTAAAAGC | TTTGATGGAA | CTGTATTTAT |
| 1021 | CAAAGGGACC | ACGCGCTCCT | TTCATCTGTA | TCCTCAGAGA | TCCTATACAT | GGTGAGTTCG |
| 1081 | CACCAGGCAA | CTATCCTGCC | ATATGGAGCT | ATGCAATGGG | GGTGGCAGTT | GTACAAAATA |
| 1141 | GAGCCATGCA | ACAGTATGTG | ACGGGAAGAT | CATATCTAGA | CATTGATATG | TTCCAGCTAG |
| 1201 | GACAAGCAGT | AGCACGTGAT | GCCGAAGCTC | AAATGAGCTC | AACACTGGAA | GATGAACTTG |
| 1261 | GAGTGACACA | CGAATCTAAA | GAAAGCTTGA | AGAGACATAT | AAGGAACATA | AACAGTTCAG |
| 1321 | AGACATCTTT | CCACAAACCG | ACAGGTGGAT | CAGCCATAGA | GATGGCAATA | GATGAAGAGC |
| 1381 | CAGAACAATT | CGAACATAGA | GCAGATCAAG | AACAAAATGG | AGAACCTCAA | TCATCCATAA |
| 1441 | TTCAATATGC | CTGGGCAGAA | GGAAATAGAA | GCGATGATCA | GACTGAGCAA | GCTACAGAAT |
| 1501 | CTGACAATAT | CAAGACCGAA | CAACAAAACA | TCAGAGACAG | ACTAAACAAG | AGACTCAACG |
| 1561 | ACAAGAAGAA | ACAAAGCAGT | CAACCACCCA | CTAATCCCAC | AAACAGAACA | AACCAGGACG |
| 1621 | AAATAGATGA | TCTGTTTAAC | GCATTTGGAA | GCAACTAATC | GAATCAACAT | TTTAATCTAA |
| 1681 | ATCAATAATA | AATAAGAAAA | ACTTAGGATT | AAAGAATCCT | ATCATACCGG | AATATAGGGT |
| 1741 | GGTAAATTTA | GAGTCTGCTT | GAAACTCAAT | CAATAGAGAG | TTGATGGAAA | GCGATGCTAA |
| 1801 | AAACTATCAA | ATCATGGATT | CTTGGGAAGA | GGAATCAAGA | GATAAATCAA | CTAATATCTC |
| 1861 | CTCGGCCCTC | AACATCATTG | AATTCATACT | CAGCACCGAC | CCCCAAGAAG | ACTTATCGGA |
| 1921 | AAACGACACA | ATCAACACAA | GAACCCAGCA | ACTCAGTGCC | ACCATCTGTC | AACCAGAAAT |
| 1981 | CAAACCAACA | GAAACAAGTG | AGAAAGATAG | TGGATCAACT | GACAAAAATA | GACAGTCCGG |
| 2041 | GTCATCACAC | GAATGTACAA | CAGAAGCAAA | AGATAGAAAT | ATTGATCAGG | AAACTGTACA |

TABLE 11-continued (SEQ ID NO. 40)
Sequence of pFLC.PIV32TM, 15498 bp in sense orientation
(only the antigenome is shown)

```
2101 GAGAGGACCT GGGAGAAGAA GCAGCTCAGA TAGTAGAGCT GAGACTGTGG TCTCTGGAGG

2161 AATCCCCAGA AGCATCACAG ATTCTAAAAA TGGAACCCAA AACACGGAGG ATATTGATCT

2221 CAATGAAATT AGAAAGATGG ATAAGGACTC TATTGAGGGG AAAATGCGAC AATCTGCAAA

2281 TGTTCCAAGC GAGATATCAG GAAGTGATGA CATATTTACA ACAGAACAAA GTAGAAACAG

2341 TGATCATGGA AGAAGCCTGG AATCTATCAG TACACCTGAT ACAAGATCAA TAAGTGTTGT

2401 TACTGCTGCA ACACCAGATG ATGAAGAAGA AATACTAATG AAAAATAGTA GGACAAAGAA

2461 AAGTTCTTCA ACACATCAAG AAGATGACAA AGAATTAAA AAAGGGGGAA AAGGGAAAGA

2521 CTGGTTTAAG AAATCAAAAG ATACCGACAA CCAGATACCA ACATCAGACT ACAGATCCAC

2581 ATCAAAAGGG CAGAAGAAAA TCTCAAAGAC AACAACCACC AACACCGACA CAAAGGGGCA

2641 AACAGAAATA CATACAGAAT CATCAGAAAC ACAATCCTCA TCATGGAATC TCATCATCGA

2701 CAACAACACC GACCGGAACG AACAGACAAG CACAACTCCT CCAACAACAA CTTCCAGATC

2761 AACTTATACA AAAGAATCGA TCCGAACAAA CTCTGAATCC AAACCCAAGA CACAAAAGAC

2821 AAATGGAAAG GAAAGGAAGG ATACAGAAGA GAGCAATCGA TTTACAGAGA GGGCAATTAC

2881 TCTATTGCAG AATCTTGGTG TAATTCAATC CACATCAAAA CTAGATTTAT ATCAAGACAA

3721 AGGATTAAAG AATAAATTAA TCCTTGTCCA AAATGAGTAT AACTAACTCT GCAATATACA

3781 CATTCCCAGA ATCATCATTC TCTGAAAATG GTCATATAGA ACCATTACCA CTCAAAGTCA

3841 ATGAACAGAG GAAAGCAGTA CCCCACATTA GAGTTGCCAA GATCGGAAAT CCACCAAAAC

3901 ACGGATCCCG GTATTTAGAT GTCTTCTTAC TCGGCTTCTT CGAGATGGAA CGAATCAAAG

3961 ACAAATACGG GAGTGTGAAT GATCTCGACA GTGACCCGAG TTACAAAGTT TGTGGCTCTG

4021 GATCATTACC AATCGGATTG CTAAGTACA CTGGGAATGA CCAGGAATTG TTACAAGCCG

4081 CAACCAAACT GGATATAGAA GTGAGAAGAA CAGTCAAAGC GAAAGAGATG GTTGTTTACA

4141 CGGTACAAAA TATAAAACCA GAACTGTACC CATGGTCCAA TAGACTAAGA AAAGGAATGC

4201 TGTTCGATGC CAACAAAGTT GCTCTTGCTC CTCAATGTCT TCCACTAGAT AGGAGCATAA

4261 AATTTAGAGT AATCTTCGTG AATTGTACGG CAATTGGATC AATAACCTTG TTCAAAATTC

4321 CTAAGTCAAT GGCATCACTA TCTCTACCCA ACACAATATC AATCAATCTG CAGGTACACA

4381 TAAAAACAGG GGTTCAGACT GATTCTAAAG GGATAGTTCA AATTTTGGAT GAGAAAGGCG

4441 AAAAATCACT GAATTTCATG GTCCATCTCG GATTGATCAA AACAAAGTA GGCAGAATGT

4501 ACTCTGTTGA ATACTGTAAA CAGAAAATCG AGAAATGAG ATTGATATTT TCTTTAGGAC

4561 TAGTTGGAGG AATCAGTCTT CATGTCAATG CAACTGGGTC CATATCAAAA ACACTAGCAA

4621 GTCAGCTGGT ATTCAAAAGA GAGATTTGTT ATCCTTTAAT GGATCTAAAT CCGCATCTCA

4681 ATCTAGTTAT CTGGGCTTCA TCAGTAGAGA TTACAAGAGT GGATGCAATT TTCCAACCTT

4741 CTTTACCTGG CGAGTTCAGA TACTATCCTA ATATTATTGC AAAAGGAGTT GGGAAAATCA

4801 AACAATGGAA CTAGTAATCT CTATTTTAGT CCGGACGTAT CTATTAAGCC GAAGCAAATA

4861 AAGGATAATC AAAAACTTAG GACAAAAGAG GTCAATACCA ACAACTATTA GCAGTCACAC

4921 TCGCAAGAAT AAGAGAGAAG GGACCAAAAA AGTCAAATAG GAGAAATCAA AACAAAAGGT

4981 ACAGAACACC AGAACAACAA AATCAAAACA TCCAACTCAC TCAAAACAAA AATTCCAAAA

5041 GAGACCGGCA ACACAACAAG CACTGAACAT GCATCACCTG CATCCAATGA TAGTATGCAT
```

TABLE 11-continued (SEQ ID NO. 40)
Sequence of pFLC.PIV32TM, 15498 bp in sense orientation
(only the antigenome is shown)

```
5101 TTTTGTTATG TACACTGGAA TTGTAGGTTC AGATGCCATT GCTGGAGATC AACTCCTCAA

5161 TGTAGGGGTC ATTCAATCAA AGATAAGATC ACTCATGTAC TACACTGATG GTGGCGCTAG

5221 CTTTATTGTT GTAAAATTAC TACCCAATCT TCCCCCAAGC AATGGAACAT GCAACATCAC

5281 CAGTCTAGAT GCATATAATG TTACCCTATT TAAGTTGCTA ACACCCCTGA TTGAGAACCT

5341 GAGCAAAATT TCTGCTGTTA CAGATACCAA ACCCCGCCGA GAACGATTTG CAGGAGTCGT

5401 TATTGGGCTT GCTGCACTAG GAGTAGCTAC AGCTGCACAA ATAACCGCAG CTGTAGCAAT

5461 AGTAAAAGCC AATGCAAATG CTGCTGCGAT AAACAATCTT GCATCTTCAA TTCAATCCAC

5521 CAACAAGGCA GTATCCGATG TGATAACTGC ATCAAGAACA ATTGCAACCG CAGTTCAAGC

5581 GATTCAGGAT CACATCAATG GAGCCATTGT CAACGGGATA ACATCTGCAT CATGCCGTGC

5641 CCATGATGCA CTAATTGGGT CAATATTAAA TTTGTATCTC ACTGAGCTTA CTACAATATT

5701 TCATAATCAA ATAACAAACC CTGCGCTGAC ACCACTTTCC ATCCAAGCTT TAAGAATCCT

5761 CCTCGGTAGC ACCTTGCCAA TTGTCATTGA ATCCAAACTC AACACAAAAC TCAACACAGC

5821 AGAGCTGCTC AGTAGCGGAC TGTTAACTGG TCAAATAATT CCATTTCCC CAATGTACAT

5881 GCAAATGCTA ATTCAAATCA ATGTTCCGAC ATTTATAATG CAACCCGGTG CGAAGGTAAT

5941 TGATCTAATT GCTATCTCTG CAAACCATAA ATTACAAGAA GTAGTTGTAC AAGTTCCTAA

6001 TAGAATTCTA GAATATGCAA ATGAACTACA AAACTACCCA GCCAATGATT GTTTCGTGAC

6061 ACCAAACTCT GTATTTTGTA GATACAATGA GGGTTCCCCG ATCCCTGAAT CACAATATCA

6121 ATGCTTAAGG GGGAATCTTA ATTCTTGCAC TTTTACCCCT ATTATCGGGA ACTTTCTCAA

6181 GCGATTCGCA TTTGCCAATG GTGTGCTCTA TGCCAACTGC AAATCTTTGC TATGTAAGTG

6241 TGCCGACCCT CCCCATGTTG TGTCTCAAGA TGACAACCAA GGCATCAGCA TAATTGATAT

6301 TAAGAGGTGC TCTGAGATGA TGCTTGACAC TTTTTCATTT AGGATCACAT CTACATTCAA

6361 TGCTACATAC GTGACAGACT TCTCAATGAT TAATGCAAAT ATTGTACATC TAAGTCCTCT

6421 AGACTTGTCA AATCAAATCA ATTCAATAAA CAAATCTCTT AAAAGTGCTG AGGATTGGAT

6481 TGCAGATAGC AACTTCTTCG CTAATCAAGC CAGAACAGCC AAGACACTTT ATTCACTAAT

6541 CATAATTATT TTGATAATGA TCATTATATT GTTTATAATT AATATAACGA TAATTACAAT

6601 TGCAATTAAG TATTACAGAA TTCAAAAGAG AAATCGAGTG GATCAAAATG ACAAGCCATA

6661 TGTACTAACA AACAAATAAC ATATCTACAG ATCATTAGAT ATTAAAATTA TAAAAACTT

6721 AGGAGTAAAG TTACGCAATC CAACTCTACT CATATAATTG AGGAAGGACC CAATAGACAA

6781 ATCCAAATTC GAGATGGAAT ACTGGAAGCA TACCAATCAC GGAAAGGATG CTGGTAATGA

7621 TCTAGCTGAA CTGAGACTTG CTTTCTATTA TTATAATGAT ACCTTTATTG AAAGAGTCAT

7681 ATCTCTTCCA AATACAACAG GGCAGTGGGC CACAATCAAC CCTGCAGTCG GAAGCGGGAT

7741 CTATCATCTA GGCTTTATCT TATTTCCTGT ATATGGTGGT CTCATAAATG GGACTACTTC

7801 TTACAATGAG CAGTCCTCAC GCTATTTTAT CCCAAAACAT CCCAACATAA CTTGTGCCGG

7861 TAACTCCAGC AAACAGGCTG CAATAGCACG GAGTTCCTAT GTCATCCGTT ATCACTCAAA

7921 CAGGTTAATT CAGAGTGCTG TTCTTATTTG TCCATTGTCT GACATGCATA CAGAAGAGTG

7981 TAATCTAGTT ATGTTTAACA ATTCCCAAGT CATGATGGGT GCAGAAGGTA GGCTCTATGT

8041 TATTGGTAAT AATTTGTATT ATTATCAACG CAGTTCCTCT TGGTGGTCTG CATCGCTCTT

8101 TTACAGGATC AATACAGATT TTTCTAAAGG AATTCCTCCG ATCATTGAGG CTCAATGGGT
```

TABLE 11-continued (SEQ ID NO. 40)
Sequence of pFLC.PIV32TM, 15498 bp in sense orientation
(only the antigenome is shown)

```
8161 ACCGTCCTAT CAAGTTCCTC GTCCTGGAGT CATGCCATGC AATGCAACAA GTTTTTGCCC

8221 TGCTAATTGC ATCACAGGGG TGTACGCAGA TGTGTGGCCG CTTAATGATC CAGAACTCAT

8281 GTCACGTAAT GCTCTGAACC CCAACTATCG ATTTGCTGGA GCCTTTCTCA AAAATGAGTC

8341 CAACCGAACT AATCCCACAT TCTACACTGC ATCGGCTAAC TCCCTCTTAA ATACTACCGG

8401 ATTCAACAAC ACCAATCACA AAGCAGCATA TACATCTTCA ACCTGCTTTA AAAACACTGG

8461 AACCCAAAAA ATTTATTGTT AATAATAAT TGAAATGGGC TCATCTCTTT TAGGGGAGTT

8521 CCAAATAATA CCATTTTTAA GGGAACTAAT GCTTTAAGCT TCATAATTAA CCATAATATG

8581 CATCAATCTA TCTATAATAC AAGTATATGA TAAGTAATCA GCAATCAGAC AATAGACAAA

8641 AGGGAAATAT AAAAAACTTA GGAGCAAAGC GTGCTCGGGA AATGGACACT GAATCTAACA

8701 ATGGCACTGT ATCTGACATA CTCTATCCTG AGTGTCACCT TAACTCTCCT ATCGTTAAAG

8761 GTAAAATAGC ACAATTACAC ACTATTATGA GTCTACCTCA GCCTTATGAT ATGGATGACG

8821 ACTCAATACT AGTTATCACT AGACAGAAAA TAAAACTTAA TAAATTGGAT AAAAGACAAC

8881 GATCTATTAG AAGATTAAAA TTAATATTAA CTGAAAAAGT GAATGACTTA GGAAAATACA

8941 CATTTATCAG ATATCCAGAA ATGTCAAAAG AAATGTTCAA ATTATATATA CCTGGTATTA

9001 ACAGTAAAGT GACTGAATTA TTACTTAAAG CAGATAGAAC ATATAGTCAA ATGACTGATG

9061 GATTAAGAGA TCTATGGATT AATGTGCTAT CAAAATTAGC CTCAAAAAAT GATGGAAGCA

9121 ATTATGATCT TAATGAAGAA ATTAATAATA TATCGAAAGT TCACACAACC TATAAATCAG

9181 ATAAATGGTA TAATCCATTC AAAACATGGT TTACTATCAA GTATGATATG AGAAGATTAC

9241 AAAAGCTCG AAATGAGATC ACTTTTAATG TTGGGAAGGA TTATAACTTG TTAGAAGACC

9301 AGAAGAATTT CTTATTGATA CATCCAGAAT TGGTTTTGAT ATTAGATAAA CAAAACTATA

9361 ATGGTTATCT AATTACTCCT GAATTAGTAT TGATGTATTG TGACGTAGTC GAAGGCCGAT

9421 GGAATATAAG TGCATGTGCT AAGTTAGATC CAAAATTACA ATCTATGTAT CAGAAAGGTA

9481 ATAACCTGTG GGAAGTGATA GATAAATTGT TTCCAATTAT GGGAGAAAAG ACATTTGATG

9541 TGATATCGTT ATTAGAACCA CTTGCATTAT CCTTAATTCA AACTCATGAT CCTGTTAAAC

9601 AACTAAGAGG AGCTTTTTTA AATCATGTGT TATCCGAGAT GGAATTAATA TTTGAATCTA

9661 GAGAATCGAT TAAGGAATTT CTGAGTGTAG ATTACATTGA TAAAATTTTA GATATATTTA

9721 ATAAGTCTAC AATAGATGAA ATAGCAGAGA TTTTCTCTTT TTTTAGAACA TTTGGGCATC

9781 CTCCATTAGA AGCTAGTATT GCAGCAGAAA AGGTTAGAAA ATATATGTAT ATTGGAAAAC

9841 AATTAAAATT TGACACTATT AATAAATGTC ATGCTATCTT CTGTACAATA ATAATTAACG

9901 GATATAGAGA GAGGCATGGT GGACAGTGGC CTCCTGTGAC ATTACCTGAT CATGCACACG

9961 AATTCATCAT AAATGCTTAC GGTTCAAACT CTGCGATATC ATATGAAAAT GCTGTTGATT

10021 ATTACCAGAG CTTTATAGGA ATAAAATTCA ATAAATTCAT AGAGCCTCAG TTAGATGAGG

10081 ATTTGACAAT TTATATGAAA GATAAAGCAT TATCTCCAAA AAAATCAAAT TGGGACACAG

10141 TTTATCCTGC ATCTAATTTA CTGTACCGTA CTAACGCATC CAACGAATCA CGAAGATTAG

10201 TTGAAGTATT TATAGCAGAT AGTAAATTTG ATCCTCATCA GATATTGGAT TATGTAGAAT

10261 CTGGGGACTG GTTAGATGAT CCAGAATTTA ATATTTCTTA GTCTTAAA GAAAAAGAGA

10321 TCAAACAGGA AGGTAGACTC TTTGCAAAAA TGACATACAA AATGAGAGCT ACACAAGTTT
```

TABLE 11-continued

| (SEQ ID NO. 40) Sequence of pFLC.PIV32TM, 15498 bp in sense orientation (only the antigenome is shown) |
|---|
| 10381 TATCAGAGAC CCTACTTGCA AATAACATAG GAAAATTCTT TCAAGAAAAT GGGATGGTGA |
| 10441 AGGGAGAGAT TGAATTACTT AAGAGATTAA CAACCATATC AATATCAGGA GTTCCACGGT |
| 10501 ATAATGAAGT GTACAATAAT TCTAAAAGCC ATACAGATGA CCTTAAAACC TACAATAAAA |
| 10561 TAAGTAATCT TAATTTGTCT TCTAATCAGA AATCAAAGAA ATTTGAATTC AAGTCAACGG |
| 10621 ATATCTACAA TGATGGATAC GAGACTGTGA GCTGTTTCTT AACAACAGAT CTCAAAAAAT |
| 10681 ACTGTCTTAA TTGGAGATAT GAATCAACAG CTCTATTTGG AGAAACTTGC AACCAAATAT |
| 11521 GATGTTTTGT AAGGAATATT GGTGATCCAT CAGTTGCCGC ATTGGCTGAT ATTAAAAGAT |
| 11581 TTATTAAGGC GAATCTATTA GACCGAAGTG TTCTTTATAG GATTATGAAT CAAGAACCAG |
| 11641 GTGAGTCATC TTTTTTGGAC TGGGCTTCAG ATCCATATTC ATGCAATTTA CCACAATCTC |
| 11701 AAAATATAAC CACCATGATA AAAAATATAA CAGCAAGGAA TGTATTACAA GATTCACCAA |
| 11761 ATCCATTATT ATCTGGATTA TTCACAAATA CAATGATAGA AGAAGATGAA GAATTAGCTG |
| 11821 AGTTCCTGAT GGACAGGAAG GTAATTCTCC CTAGAGTTGC ACATGATATT CTAGATAATT |
| 11881 CTCTCACAGG AATTAGAAAT GCCATAGCTG GAATGTTAGA TACGACAAAA TCACTAATTC |
| 11941 GGGTTGGCAT AAATAGAGGA GGACTGACAT ATAGTTTGTT GAGGAAAATC AGTAATTACG |
| 12001 ATCTAGTACA ATATGAAACA CTAAGTAGGA CTTTGCGACT AATTGTAAGT GATAAAATCA |
| 12061 AGTATGAAGA TATGTGTTCG GTAGACCTTG CCATAGCATT GCGACAAAAG ATGTGGATTC |
| 12121 ATTTATCAGG AGGAAGGATG ATAAGTGGAC TTGAAACGCC TGACCCATTA GAATTACTAT |
| 12181 CTGGGGTAGT AATAACAGGA TCAGAACATT GTAAAATATG TTATTCTTCA GATGGCACAA |
| 12241 ACCCATATAC TTGGATGTAT TTACCCGGTA ATATCAAAAT AGGATCAGCA GAAACAGGTA |
| 12301 TATCGTCATT AAGAGTTCCT TATTTTGGAT CAGTCACTGA TGAAAGATCT GAAGCACAAT |
| 12361 TAGGATATAT CAAGAATCTT AGTAAACCTG CAAAAGCCGC AATAAGAATA GCAATGATAT |
| 12421 ATACATGGGC ATTTGGTAAT GATGAGATAT CTTGGATGGA AGCCTCACAG ATAGCACAAA |
| 12481 CACGTGCAAA TTTTACACTA GATAGTCTCA AAATTTTAAC ACCGGTAGCT ACATCAACAA |
| 12541 ATTTATCACA CAGATTAAAG GATACTGCAA CTCAGATGAA ATTCTCCAGT ACATCATTGA |
| 12601 TCAGAGTCAG CAGATTCATA ACAATGTCCA ATGATAACAT GTCTATCAAA GAAGCTAATG |
| 12661 AAACCAAAGA TACTAATCTT ATTTATCAAC AAATAATGTT AACAGGATTA AGTGTTTTCG |
| 12721 AATATTTATT TAGATTAAAA GAAACCACAG GACACAACCC TATAGTTATG CATCTGCACA |
| 12781 TAGAAGATGA GTGTTGTATT AAAGAAAGTT TTAATGATGA ACATATTAAT CCAGAGTCTA |
| 12841 CATTAGAATT AATTCGATAT CCTGAAAGTA ATGAATTTAT TTATGATAAA GACCCACTCA |
| 12901 AAGATGTGGA CTTATCAAAA CTTATGGTTA TTAAAGACCA TTCTTACACA ATTGATATGA |
| 12961 ATTATTGGGA TGATACTGAC ATCATACATG CAATTTCAAT ATGTACTGCA ATTACAATAG |
| 13021 CAGATACTAT GTCACAATTA GATCGAGATA ATTTAAAAGA GATAATAGTT ATTGCAAATG |
| 13081 ATGATGATAT TAATAGCTTA ATCACTGAAT TTTTGACTCT TGACATACTT GTATTTCTCA |
| 13141 AGACATTTGG TGGATTATTA GTAAATCAAT TTGCATACAC TCTTTATAGT CTAAAAATAG |
| 13201 AAGGTAGGGA TCTCATTTGG GATTATATAA TGAGAACACT GAGAGATACT TCCCATTCAA |
| 13261 TATTAAAAGT ATTATCTAAT GCATTATCTC ATCCTAAAGT ATTCAAGAGG TTCTGGGATT |
| 13321 GTGGAGTTTT AAACCCTATT TATGGTCCTA ATACTGCTAG TCAAGACCAG ATAAAACTTG |
| 13381 CCCTATCTAT ATGTGAATAT TCACTAGATC TATTTATGAG AGAATGGTTG AATGGTGTAT |

TABLE 11-continued (SEQ ID NO. 40)
Sequence of pFLC.PIV32TM, 15498 bp in sense orientation
(only the antigenome is shown)

```
13441 CACTTGAAAT ATACATTTGT GACAGCGATA TGGAAGTTGC AAATGATAGG AAACAAGCCT

13501 TTATTTCTAG ACACCTTTCA TTTGTTTGTT GTTTAGCAGA AATTGCATCT TTCGGACCTA

13561 ACCTGTTAAA CTTAACATAC TTGGAGAGAC TTGATCTATT GAAACAATAT CTTGAATTAA

13621 ATATTAAAGA AGACCCTACT CTTAAATATG TACAAATATC TGGATTATTA ATTAAATCGT

13681 TCCCATCAAC TGTAACATAC GTAAGAAAGA CTGCAATCAA ATATCTAAGG ATTCGCGGTA

13741 TTAGTCCACC TGAGGTAATT GATGATTGGG ATCCGGTAGA AGATGAAAAT ATGCTGGATA

13801 ACATTGTCAA AACTATAAAT GATAACTGTA ATAAAGATAA TAAAGGGAAT AAAATTAACA

13861 ATTTCTGGGG ACTAGCACTT AAGAACTATC AAGTCCTTAA AATCAGATCT ATAACAAGTG

13921 ATTCTGATGA TAATGATAGA CTAGATGCTA ATACAAGTGG TTTGACACTT CCTCAAGGAG

13981 GGAATTATCT ATCGCATCAA TTGAGATTAT TCGGAATCAA CAGCACTAGT TGTCTGAAAG

14041 CTCTTGAGTT ATCACAAATT TTAATGAAGG AAGTCAATAA AGACAAGGAC AGGCTCTTCC

14101 TGGGAGAAGG AGCAGGAGCT ATGCTAGCAT GTTATGATGC CACATTAGGA CCTGCAGTTA

14161 ATTATTATAA TTCAGGTTTG AATATAACAG ATGTAATTGG TCAACGAGAA TTGAAAATAT

14221 TTCCTTCAGA GGTATCATTA GTAGGTAAAA AATTAGGAAA TGTGACACAG ATTCTTAACA

14281 GGGTAAAAGT ACTGTTCAAT GGGAATCCTA ATTCAACATG GATAGGAAAT ATGGAATGTG

14341 AGAGCTTAAT ATGGAGTGAA TTAAATGATA AGTCCATTGG ATTAGTACAT TGTGATATGG

14401 AAGGAGCTAT CGGTAAATCA GAAGAAACTG TTCTACATGA ACATTATAGT GTTATAAGAA

14461 TTACATACTT GATTGGGGAT GATGATGTTG TTTTAGTTTC CAAAATTATA CCTACAATCA

14521 CTCCGAATTG GTCTAGAATA CTTTATCTAT ATAAATTATA TTGGAAAGAT GTAAGTATAA

14581 TATCACTCAA AACTTCTAAT CCTGCATCAA CAGAATTATA TCTAATTTCG AAAGATGCAT

15421 TTTAAGCCTA GGAATAGACA AAAAGTAAGA AAAACATGTA ATATATATAT ACCAAACAGA

15481 GTTCTTCTCT TGTTTGGT
```

In a third strategy (FIG. 8), chimeric PIV3-PIV2 F and HN genes were constructed in which regions of the PIV2 F and HN ORFs encoding the ectodomains and the transmembrane domains were amplified from pLit.PIV32Fhc and pLit.PIV32HNhc, respectively, using PCR, Vent DNA polymerase, and primer pairs specific to PIV2 F (13, 14 in Table 9) and PIV2 HN (15, 16 in Table 9). In parallel, the partial ORFs of PIV3 F and HN genes encoding the ectodomains plus transmembrane domains were deleted from their cDNA subclones pLit.PIV3.F3a and pLit.PIV3.HN4 (Tao et al., *J. Virol.* 72:2955–2961, 1998, incorporated herein by reference), respectively, using PCR, Vent DNA polymerase, and primer pairs specific to PIV3 F (17, 18 in Table 1) and PIV3 HN (19, 20 in Table 9). The F and HN cDNA fragments of PIV2 and PIV3 were gel purified and ligated to generate pLit.PIV32FCT and pLit.PIV32HNCT, respectively. The chimeric F and HN constructs were digested with PpuMI plus SpeI and assembled together to generate pLit.PIV32CT, which was sequenced across the PIV specific region in its entirety and found to be as designed. The 4 kb BspEI-SpeI fragment from pLit.PIV32CT was introduced into the BspEI-SpeI window of p38'ΔPIV31hc to generate p38'ΔPIV32CT. The 6.5 kb BspEI-SphI fragment from p38'ΔPIV32CT, containing the PIV3-PIV2 F and HN chimeric genes, was introduced into the BspEI-SphI window of pFLC.2G+.hc and pFLCcp45, to generate pFLC.PIV32CT (Table 12, SEQ ID NO: 41) and pFLC.PIV32CTcp45, respectively. The nucleotide sequence of this BspEI-SpeI fragment is submitted in the GenBank (Accession No. pending).

TABLE 12

(SEQ ID NO. 41)
Sequence of pFLC.PIV32CT, 15474 bp in sense orientation
(only the insert is shown)

```
   1 ACCAAACAAG AGAAGAAACT TGTCTGGGAA TATAAATTTA ACTTTAAATT AACTTAGGAT
  61 TAAAGACATT GACTAGAAGG TCAAGAAAAG GGAACTCTAT AATTTCAAAA ATGTTGAGCC
 121 TATTTGATAC ATTTAATGCA CGTAGGCAAG AAAACATAAC AAAATCAGCC GGTGGAGCTA
 181 TCATTCCTGG ACAGAAAAAT ACTGTCTCTA TATTCGCCCT TGGACCGACA ATAACTGATG
 241 ATAATGAGAA AATGACATTA GCTCTTCTAT TTCTATCTCA TTCACTAGAT AATGAGAAAC
 301 AACATGCACA AAGGGCAGGG TTCTTGGTGT CTTTATTGTC AATGGCTTAT GCCAATCCAG
 361 AGCTCTACCT AACAACAAAT GGAAGTAATG CAGATGTCAA GTATGTCATA TACATGATTG
 421 AGAAAGATCT AAAACGGCAA AAGTATGGAG GATTTGTGGT TAAGACGAGA GAGATGATAT
 481 ATGAAAAGAC AACTGATTGG ATATTTGGAA GTGACCTGGA TTATGATCAG GAAACTATGT
 541 TGCAGAACGG CAGGAACAAT TCAACAATTG AAGACCTTGT CCACACATTT GGGTATCCAT
 601 CATGTTTAGG AGCTCTTATA ATACAGATCT GGATAGTTCT GGTCAAAGCT ATCACTAGTA
 661 TCTCAGGGTT AAGAAAAGGC TTTTTCACCC GATTGGAAGC TTTCAGACAA GATGGAACAG
 721 TGCAGGCAGG GCTGGTATTG AGCGGTGACA CAGTGGATCA GATTGGGTCA ATCATGCGGT
 781 CTCAACAGAG CTTGGTAACT CTTATGGTTG AAACATTAAT AACAATGAAT ACCAGCAGAA
 841 ATGACCTCAC AACCATAGAA AAGAATATAC AAATTGTTGG CAACTACATA AGAGATGCAG
 901 GTCTCGCTTC ATTCTTCAAT ACAATCAGAT ATGGAATTGA GACCAGAATG GCAGCTTTGA
 961 CTCTATCCAC TCTCAGACCA GATATCAATA GATTAAAAGC TTTGATGGAA CTGTATTTAT
1021 CAAAGGGACC ACGCGCTCCT TTCATCTGTA TCCTCAGAGA TCCTATACAT GGTGAGTTCG
1081 CACCAGGCAA CTATCCTGCC ATATGGAGCT ATGCAATGGG GGTGGCAGTT GTACAAAATA
1141 GAGCCATGCA ACAGTATGTG ACGGGAAGAT CATATCTAGA CATTGATATG TTCCAGCTAG
1201 GACAAGCAGT AGCACGTGAT GCCGAAGCTC AAATGAGCTC AACACTGGAA GATGAACTTG
1261 GAGTGACACA CGAATCTAAA GAAAGCTTGA AGAGACATAT AAGGAACATA AACAGTTCAG
1321 AGACATCTTT CCACAAACCG ACAGGTGGAT CAGCCATAGA GATGGCAATA GATGAAGAGC
1381 CAGAACAATT CGAACATAGA GCAGATCAAG AACAAAATGG AGAACCTCAA TCATCCATAA
1441 TTCAATATGC CTGGGCAGAA GGAAATAGAA GCGATGATCA GACTGAGCAA GCTACAGAAT
1501 CTGACAATAT CAAGACCGAA CAACAAACA TCAGACACAG ACTAAACAAG AGACTCAACG
1561 ACAAGAAGAA ACAAAGCAGT CAACCACCCA CTAATCCCAC AAACAGAACA AACCAGGACG
1621 AAATAGATGA TCTGTTTAAC GCATTTGGAA GCAACTAATC GAATCAACAT TTTAATCTAA
1681 ATCAATAATA AATAAGAAAA ACTTAGGATT AAAGAATCCT ATCATACCGG AATATAGGGT
1741 GGTAAATTTA GAGTCTGCTT GAAACTCAAT CAATAGAGAG TTGATGGAAA GCGATGCTAA
1801 AAACTATCAA ATCATGGATT CTTGGGAAGA GGAATCAAGA GATAAATCAA CTAATATCTC
1861 CTCGGCCCTC AACATCATTG AATTCATACT CAGCACCGAC CCCCAAGAAG ACTTATCGGA
1921 AAACGACACA ATCAACACAA GAACCCAGCA ACTCAGTGCC ACCATCTGTC AACCAGAAAT
1981 CAAACCAACA GAAACAAGTG AGAAAGATAG TGGATCAACT GACAAAAATA GACAGTCCGG
2041 GTCATCACAC GAATGTACAA CAGAAGCAAA AGATAGAAAT ATTGATCAGG AAACTGTACA
2101 GAGAGGACCT GGGAGAAGAA GCAGCTCAGA TAGTAGAGCT GAGACTGTGG TCTCTGGAGG
2161 AATCCCCAGA AGCATCACAG ATTCTAAAAA TGGAACCCAA AACACGGAGG ATATTGATCT
2221 CAATGAAATT AGAAAGATGG ATAAGGACTC TATTGAGGGG AAAATGCGAC AATCTGCAAA
```

TABLE 12-continued (SEQ ID NO. 41)
Sequence of pFLC.PIV32CT, 15474 bp in sense orientation
(only the insert is shown)

```
2281 TGTTCCAAGC GAGATATCAG GAAGTGATGA CATATTTACA ACAGAACAAA GTAGAAACAG
2341 TGATCATGGA AGAAGCCTGG AATCTATCAG TACACCTGAT ACAAGATCAA TAAGTGTTGT
2401 TACTGCTGCA ACACCAGATG ATGAAGAAGA AATACTAATG AAAAATAGTA GGACAAAGAA
2461 AAGTTCTTCA ACACATCAAG AAGATGACAA AGAATTAAA AAAGGGGAA AAGGGAAAGA
2521 CTGGTTTAAG AAATCAAAAG ATACCGACAA CCAGATACCA ACATCAGACT ACAGATCCAC
2581 ATCAAAAGGG CAGAAGAAAA TCTCAAAGAC AACAACCACC AACACCGACA CAAAGGGGCA
2641 AACAGAAATA CAGACAGAAT CATCAGAAAC ACAATCCTCA TCATGGAATC TCATCATCGA
2701 CAACAACACC GACCGGAACG AACAGACAAG CACAACTCCT CCAACAACAA CTTCCAGATC
2761 AACTTATACA AAAGAATCGA TCCGAACAAA CTCTGAATCC AAACCCAAGA CACAAAAGAC
2821 AAATGGAAAG GAAAGGAAGG ATACAGAAGA GAGCAATCGA TTTACAGAGA GGGCAATTAC
2881 TCTATTGCAG AATCTTGGTG TAATTCAATC CACATCAAAA CTAGATTTAT ATCAAGACAA
2941 ACGAGTTGTA TGTGTAGCAA ATGTACTAAA CAATGTAGAT ACTGCATCAA AGATAGATTT
3001 CCTGGCAGGA TTAGTCATAG GGGTTTCAAT GGACAACGAC ACAAAATTAA CACAGATACA
3061 AAATGAAATG CTAAACCTCA AGCAGATCT AAAGAAAATG GACGAATCAC ATAGAAGATT
3121 GATAGAAAAT CAAAGAGAAC AACTGTCATT GATCACGTCA CTAATTTCAA ATCTCAAAAT
3181 TATGACTGAG AGAGGAGGAA AGAAAGACCA AAATGAATCC AATGAGAGAG TATCCATGAT
3241 CAAAACAAAA TTGAAAGAAG AAAAGATCAA GAAGACCAGG TTTGACCCAC TTATGGAGGC
3301 ACAAGGCATT GACAAGAATA TACCCGATCT ATATCGACAT GCAGGAGATA CACTAGAGAA
3361 CGATGTACAA GTTAAATCAG AGATATTAAG TTCATACAAT GAGTCAAATG CAACAAGACT
3421 AATACCCAAA AAAGTGAGCA GTACAATGGA ATCACTAGTT GCAGTCATCA ACAACAGCAA
3481 TCTCTCACAA AGCACAAAAC AATCATACAT AAACGAACTC AAACGTTGCA AAAATGATGA
3541 AGAAGTATCT GAATTAATGG ACATGTTCAA TGAAGATGTC AACAATTGCC AATGATCCAA
3601 CAAAGAAACG ACACCGAACA AACAGACAAG AAACAACAGT AGATCAAAAC CTGTCAACAC
3661 ACACAAAATC AAGCAGAATG AAACAACAGA TATCAATCAA TATACAAATA AGAAAAACTT
3721 AGGATTAAAG AATAAATTAA TCCTTGTCCA AAATGAGTAT AACTAACTCT GCAATATACA
3781 CATTCCCAGA ATCATCATTC TCTGAAAATG GTCATATAGA ACCATTACCA CTCAAAGTCA
3841 ATGAACAGAG GAAAGCAGTA CCCCACATTA GAGTTGCCAA GATCGGAAAT CCACCAAAAC
3901 ACGGATCCCG GTATTTAGAT GTCTTCTTAC TCGGCTTCTT CGAGATGGAA CGAATCAAAG
3961 ACAAATACGG GAGTGTGAAT GATCTCGACA GTGACCCGAG TTACAAAGTT TGTGGCTCTG
4021 GATCATTACC AATCGGATTG GCTAAGTACA CTGGGAATGA CCAGGAATTG TTACAAGCCG
4081 CAACCAAACT GGATATAGAA GTGAGAAGAA CAGTCAAAGC GAAAGAGATG GTTGTTTACA
4141 CGGTACAAAA TATAAAACCA GAACTGTACC CATGGTCCAA TAGACTAAGA AAAGGAATGC
4201 TGTTCGATGC CAACAAAGTT GCTCTTGCTC CTCAATGTCT TCCACTAGAT AGGAGCATAA
4261 AATTTAGAGT AATCTTCGTG AATTGTACGG CAATTGGATC AATAACCTTG TTCAAAATTC
4321 CTAAGTCAAT GGCATCACTA TCTCTACCCA ACACAATATC AATCAATCTG CAGGTACACA
4381 TAAAAACAGG GGTTCAGACT GATTCTAAAG GGATAGTTCA ATTTTGGAT GAGAAAGGCG
4441 AAAAATCACT GAATTTCATG GTCCATCTCG GATTGATCAA AGAAAAGTA GGCAGAATGT
```

TABLE 12-continued (SEQ ID NO. 41)
Sequence of pFLC.PIV32CT, 15474 bp in sense orientation
(only the insert is shown)

```
4501 ACTCTGTTGA ATACTGTAAA CAGAAAATCG AGAAAATGAG ATTGATATTT TCTTTAGGAC

4561 TAGTTGGAGG AATCAGTCTT CATGTCAATG CAACTGGGTC CATATCAAAA ACACTAGCAA

4621 GTCAGCTGGT ATTCAAAAGA GAGATTTGTT ATCCTTTAAT GGATCTAAAT CCGCATCTCA

4681 ATCTAGTTAT CTGGGCTTCA TCAGTAGAGA TTACAAGAGT GGATGCAATT TTCCAACCTT

4741 CTTTACCTGG CGAGTTCAGA TACTATCCTA ATATTATTGC AAAAGGAGTT GGGAAAATCA

4801 AACAATGGAA CTAGTAATCT CTATTTTAGT CCGGACGTAT CTATTAAGCC GAAGCAAATA

4861 AAGGATAATC AAAAACTTAG GACAAAAGAG GTCAATACCA ACAACTATTA GCAGTCACAC

4921 TCGCAAGAAT AAGAGAGAAG GGACCAAAAA AGTCAAATAG GAGAAATCAA AACAAAAGGT

4981 ACAGAACACC AGAACAACAA AATCAAAACA TCCAACTCAC TCAAAACAAA AATTCCAAAA

5041 GAGACCGGCA ACACAACAAG CACTGAACAT GCATCACCTG CATCCAATGA TAGTATGCAT

5101 TTTTGTTATG TACACTGGAA TTGTAGGTTC AGATGCCATT GCTGGAGATC AACTCCTCAA

5161 TGTAGGGGTC ATTCAATCAA AGATAAGATC ACTCATGTAC TACACTGATG GTGGCGCTAG

5221 CTTTATTGTT GTAAAATTAC TACCCAATCT TCCCCCAAGC AATGGAACAT GCAACATCAC

5281 CAGTCTAGAT GCATATAATG TTACCCTATT TAAGTTGCTA ACACCCCTGA TTGAGAACCT

5341 GAGCAAAATT TCTGCTGTTA CAGATACCAA ACCCCGCCGA GAACGATTTG CAGGAGTCGT

5401 TATTGGGCTT GCTGCACTAG GAGTAGCTAC AGCTGCACAA ATAACCGCAG CTGTAGCAAT

5461 AGTAAAAGCC AATGCAAATG CTGCTGCGAT AAACAATCTT GCATCTTCAA TTCAATCCAC

5521 CAACAAGGCA GTATCCGATG TGATAACTGC ATCAAGAACA ATTGCAACCG CAGTTCAAGC

5581 GATTCAGGAT CACATCAATG GAGCCATTGT CAACGGGATA ACATCTGCAT CATGCCGTGC

5641 CCATGATGCA CTAATTGGGT CAATATTAAA TTTGTATCTC ACTGAGCTTA CTACAATATT

5701 TCATAATCAA ATAACAAACC CTGCGCTGAC ACCACTTTCC ATCCAAGCTT TAAGAATCCT

5761 CCTCGGTAGC ACCTTGCCAA TTGTCATTGA ATCCAAACTC AACACAAAAC TCAACACAGC

5821 AGAGCTGCTC AGTAGCGGAC TGTTAACTGG TCAAATAATT TCCATTTCCC CAATGTACAT

5881 GCAAATGCTA ATTCAAATCA ATGTTCCGAC ATTTATAATG CAACCCGGTG CGAAGGTAAT

5941 TGATCTAATT GCTATCTCTG CAAACCATAA ATTACAAGAA GTAGTTGTAC AAGTTCCTAA

6001 TAGAATTCTA GAATATGCAA ATGAACTACA AAACTACCCA GCCAATGATT GTTTCGTGAC

6061 ACCAAACTCT GTATTTTGTA GATACAATGA GGGTTCCCCG ATCCCTGAAT CACAATATCA

6121 ATGCTTAAGG GGGAATCTTA ATTCTTGCAC TTTTACCCCT ATTATCGGGA ACTTTCTCAA

6181 GCGATTCGCA TTTGCCAATG GTGTGCTCTA TGCCAACTGC AAATCTTTGC TATGTAAGTG

6241 TGCCGACCCT CCCCATGTTG TGTCTCAAGA TGACAACCAA GGCATCAGCA TAATTGATAT

6301 TAAGAGGTGC TCTGAGATGA TGCTTGACAC TTTTTCATTT AGGATCACAT CTACATTCAA

6361 TGCTACATAC GTGACAGACT TCTCAATGAT TAATGCAAAT ATTGTACATC TAAGTCCTCT

6421 AGACTTGTCA AATCAAATCA ATTCAATAAA CAAATCTCTT AAAAGTGCTG AGGATTGGAT

6481 TGCAGATAGC AACTTCTTCG CTAATCAAGC CAGAACAGCC AAGACACTTT ATTCACTAAG

6541 TGCAATCGCA TTAATACTAT CAGTGATTAC TTTGGTTGTT GTGGGATTGC TGATTGCCTA

6601 CATCATCAAG TATTACAGAA TTCAAAAGAG AAATCGAGTG GATCAAAATG ACAAGCCATA

6661 TGTACTAACA AACAAATAAC ATATCTACAG ATCATTAGAT ATTAAAATTA TAAAAACTTA

6721 AGGAGTAAAG TTACGCAATC CAACTCTACT CATATAATTG AGGAAGGACC CAATAGACAA
```

TABLE 12-continued (SEQ ID NO. 41)
Sequence of pFLC.PIV32CT, 15474 bp in sense orientation
(only the insert is shown)

```
6781 ATCCAAATTC GAGATGGAAT ACTGGAAGCA TACCAATCAC GGAAAGGATG CTGGTAATGA

6841 GCTGGAGACG TCTATGGCTA CTCATGGCAA CAAGCTCACT AATAAGACTG CCACAATTCT

6901 TGGCATATGC ACATTAATTG TGCTATGTTC AAGTATTCTT CATGAGATAA TTCATCTTGA

6961 TGTTTCCTCT GGTCTTATGA ATTCTGATGA GTCACAGCAA GGCATTATTC AGCCTATCAT

7021 AGAATCATTA AAATCATTGA TTGCTTTGGC CAACCAGATT CTATATAATG TTGCAATAGT

7081 AATTCCTCTT AAAATTGACA GTATCGAAAC TGTAATACTC TCTGCTTTAA AAGATATGCA

7141 CACCGGGAGT ATGTCCAATG CCAACTGCAC GCCAGGAAAT CTGCTTCTGC ATGATGCAGC

7201 ATACATCAAT GGAATAAACA AATTCCTTGT ACTTGAATCA TACAATGGGA CGCCTAAATA

7261 TGGACCTCTC CTAAATATAC CCAGCTTTAT CCCCTCAGCA ACATCTCCCC ATGGGTGTAC

7321 TAGAATACCA TCATTTTCAC TCATCAAGAC CCATTGGTGT ACACTCACA ATGTAATGCT

7381 TGGAGATTGT CTTGATTTCA CGGCATCTAA CCAGTATTTA TCAATGGGGA TAATACAACA

7441 ATCTGCTGCA GGGTTTCCAA TTTTCAGGAC TATGAAAACC ATTTACCTAA GTGATGGAAT

7501 CAATCGCAAA AGCTGTTCAG TCACTGCTAT ACCAGGAGGT TGTGTCTTGT ATTGCTATGT

7561 AGCTACAAGG TCTGAAAAAG AAGATTATGC CACGACTGAT CTAGCTGAAC TGAGACTTGC

7621 TTTCTATTAT TATAATGATA CCTTTATTGA AGAGTCATA TCTCTTCCAA ATACAACAGG

7681 GCAGTGGGCC ACAATCAACC CTGCAGTCGG AAGCGGGATC TATCATCTAG GCTTTATCTT

7741 ATTTCCTGTA TATGGTGGTC TCATAAATGG GACTACTTCT TACAATGAGC AGTCCTCACG

7801 CTATTTTATC CCAAAACATC CCAACATAAC TTGTGCCGGT AACTCCAGCA AACAGGCTGC

7861 AATAGCACGG AGTTCCTATG TCATCCGTTA TCACTCAAAC AGGTTAATTC AGAGTGCTGT

7921 TCTTATTTGT CCATTGTCTG ACATGCATAC AGAAGAGTGT AATCTAGTTA TGTTTAACAA

7981 TTCCCAAGTC ATGATGGGTG CAGAAGGTAG GCTCTATGTT ATTGGTAATA ATTTGTATTA

8041 TTATCAACGC AGTTCCTCTT GGTGGTCTGC ATCGCTCTTT ACAGGATCA ATACAGATTT

8101 TTCTAAAGGA ATTCCTCCGA TCATTGAGGC TCAATGGGTA CCGTCCTATC AAGTTCCTCG

8161 TCCTGGAGTC ATGCCATGCA ATGCAACAAG TTTTTGCCCT GCTAATTGCA TCACAGGGGT

8221 GTACGCAGAT GTGTGGCCGC TTAATGATCC AGAACTCATG TCACGTAATG CTCTGAACCC

8281 CAACTATCGA TTTGCTGGAG CCTTTCTCAA AAATGAGTCC AACCGAACTA ATCCCACATT

8341 CTACACTGCA TCGGCTAACT CCCTCTTAAA TACTACCGGA TTCAACAACA CCAATCACAA

8401 AGCAGCATAT ACATCTTCAA CCTGCTTTAA AAACACTGGA ACCCAAAAAA TTTATTGTTT

8461 AATAATAATT GAAATGGGCT CATCTCTTTT AGGGGAGTTC CAAATAATAC CATTTTTAAG

8521 GGAACTAATG CTTTAATCAT AATTAACCAT AATATGCATC AATCTATCTA TAATACAAGT

8581 ATATGATAAG TAATCAGCAA TCAGACAATA GACAAAAGGG AAATATAAAA AACTTAGGAG

8641 CAAAGCGTGC TCGGGAAATG GACACTGAAT CTAACAATGG CACTGTATCT GACATACTCT

8701 ATCCTGAGTG TCACCTTAAC TCTCCTATCG TTAAAGGTAA AATAGCACAA TTACACACTA

8761 TTATGAGTCT ACCTCAGCCT TATGATATGG ATGACGACTC AATACTAGTT ATCACTAGAC

8821 AGAAAATAAA ACTTAATAAA TTGGATAAAA GACAACGATC TATTAGAAGA TTAAAATTAA

8881 TATTAACTGA AAAAGTGAAT GACTTAGGAA ATACACATT TATCAGATAT CCAGAAATGT

8941 CAAAGAAAAT GTTCAAATTA TATATACCTG GTATTAACAG TAAAGTGACT GAATTATTAC
```

TABLE 12-continued (SEQ ID NO. 41)
Sequence of pFLC.PIV32CT, 15474 bp in sense orientation
(only the insert is shown)

```
9001  TTAAAGCAGA TAGAACATAT AGTCAAATGA CTGATGGATT AAGAGATCTA TGGATTAATG
9061  TGCTATCAAA ATTAGCCTCA AAAAATGATG GAAGCAATTA TGATCTTAAT GAAGAAATTA
9121  ATAATATATC GAAAGTTCAC ACAACCTATA AATCAGATAA ATGGTATAAT CCATTCAAAA
9181  CATGGTTTAC TATCAAGTAT GATATGAGAA GATTACAAAA AGCTCGAAAT GAGATCACTT
9241  TTAATGTTGG GAAGGATTAT AACTTGTTAG AAGACCAGAA GAATTTCTTA TTGATACATC
9301  CAGAATTGGT TTTGATATTA GATAAACAAA ACTATAATGG TTATCTAATT ACTCCTGAAT
9361  TAGTATTGAT GTATTGTGAC GTAGTCGAAG GCCGATGGAA TATAAGTGCA TGTGCTAAGT
9421  TAGATCCAAA ATTACAATCT ATGTATCAGA AAGGTAATAA CCTGTGGGAA GTGATAGATA
9481  AATTGTTTCC AATTATGGGA GAAAAGACAT TTGATGTGAT ATCGTTATTA GAACCACTTG
9541  CATTATCCTT AATTCAAACT CATGATCCTG TTAAACAACT AAGAGGAGCT TTTTTAAATC
9601  ATGTGTTATC CGAGATGGAA TTAATATTTG AATCTAGAGA ATCGATTAAG GAATTTCTGA
9661  GTGTAGATTA CATTGATAAA ATTTTAGATA TATTTAATAA GTCTACAATA GATGAAATAG
9721  CAGAGATTTT CTCTTTTTTT AGAACATTTG GGCATCCTCC ATTAGAAGCT AGTATTGCAG
9781  CAGAAAAGGT TAGAAAATAT ATGTATATTG GAAAACAATT AAAATTTGAC ACTATTAATA
9841  AATGTCATGC TATCTTCTGT ACAATAATAA TTAACGGATA TAGAGAGAGG CATGGTGGAC
9901  AGTGGCCTCC TGTGACATTA CCTGATCATG CACACGAATT CATCATAAAT GCTTACGTT
9961  CAAACTCTGC GATATCATAT GAAAATGCTG TTGATTATTA CCAGAGCTTT ATAGGAATAA
10021 AATTCAATAA ATTCATAGAG CCTCAGTTAG ATGAGGATTT GACAATTTAT ATGAAAGATA
10081 AAGCATTATC TCCAAAAAAA TCAAATTGGG ACACAGTTTA TCCTGCATCT AATTTACTGT
10141 ACCGTACTAA CGCATCCAAC GAATCACGAA GATTAGTTGA AGTATTTATA GCAGATAGTA
10201 AATTTGATCC TCATCAGATA TTGGATTATG TAGAATCTGG GGACTGGTTA GATGATCCAG
10261 AATTTAATAT TTCTTATAGT CTTAAAGAAA AAGAGATCAA ACAGGAAGGT AGACTCTTTG
10321 CAAAAATGAC ATACAAAATG AGAGCTACAC AAGTTTTATC AGAGACACTA CTTGCAAATA
10381 ACATAGGAAA ATTCTTTCAA GAAAATGGGA TGGTGAAGGG AGAGATTGAA TTACTTAAGA
10441 GATTAACAAC CATATCAATA TCAGGAGTTC CACGGTATAA TGAAGTGTAC AATAATTCTA
10501 AAAGCCATAC AGATGACCTT AAAACCTACA ATAAAATAAG TAATCTTAAT TTGTCTTCTA
10561 ATCAGAAATC AAAGAAATTT GAATTCAAGT CAACGGATAT CTACAATGAT GGATACGAGA
10621 CTGTGAGCTG TTTCCTAACA ACAGATCTCA AAAATACTG TCTTAATTGG AGATATGAAT
10681 CAACAGCTCT ATTTGGAGAA ACTTGCAACC AAATATTTGG ATTAAATAAA TTGTTTAATT
10741 GGTTACACCC TCGTCTTGAA GGAAGTACAA TCTATGTAGG TGATCCTTAC TGTCCTCCAT
10801 CAGATAAAGA ACATATATCA TTAGAGGATC ACCCTGATTC TGGTTTTTAC GTTCATAACC
10861 CAAGAGGGGG TATAGAAGGA TTTTGTCAAA AATTATGGAC ACTCATATCT ATAAGTGCAA
10921 TACATCTAGC AGCTGTTAGA ATAGGCGTGA GGGTGACTGC AATGGTTCAA GGAGACAATC
10981 AAGCTATAGC TGTAACCACA AGAGTACCCA ACAATTATGA CTACAGAGTT AAGAAGGAGA
11041 TAGTTTATAA AGATGTAGTG AGATTTTTTG ATTCATTAAG AGAAGTGATG GATGATCTAG
11101 GTCATGAACT TAAATTAAAT GAAACGATTA TAAGTAGCAA GATGTTCATA TATAGCAAAA
11161 GAATCTATTA TGATGGGAGA ATTCTTCCTC AAGCTCTAAA AGCATTATCT AGATGTGTCT
11221 TCTGGTCAGA GACAGTAATA GACGAAACAA GATCAGCATC TTCAAATTTG GCAACATCAT
```

TABLE 12-continued (SEQ ID NO. 41)
Sequence of pFLC.PIV32CT, 15474 bp in sense orientation
(only the insert is shown)

```
11281 TTGCAAAAGC AATTGAGAAT GGTTATTCAC CTGTTCTAGG ATATGCATGC TCAATTTTTA
11341 AGAATATTCA ACAACTATAT ATTGCCCTTG GGATGAATAT CAATCCAACT ATAACACAGA
11401 ATATCAGAGA TCAGTATTTT AGGAATCCAA ATTGGATGCA ATATGCCTCT TTAATACCTG
11461 CTAGTGTTGG GGGATTCAAT TACATGGCCA TGTCAAGATG TTTTGTAAGG AATATTGGTG
11521 ATCCATCAGT TGCCGCATTG GCTGATATTA AAAGATTTAT TAAGGCGAAT CTATTAGACC
11581 GAAGTGTTCT TTATAGGATT ATGAATCAAG AACCAGGTGA GTCATCTTTT TTGGACTGGG
11641 CTTCAGATCC ATATTCATGC AATTTACCAC AATCTCAAAA TATAACCACC ATGATAAAAA
11701 ATATAACAGC AAGGAATGTA TTACAAGATT CACCAAATCC ATTATTATCT GGATTATTCA
11761 CAAATACAAT GATAGAAGAA GATGAAGAAT TAGCTGAGTT CCTGATGGAC AGGAAGGTAA
11821 TTCTCCCTAG AGTTGCACAT GATATTCTAG ATAATTCTCT CACAGGAATT AGAAATGCCA
11881 TAGCTGGAAT GTTAGATACG ACAAAATCAC TAATTCGGGT TGCATAAAT AGAGGAGGAC
11941 TGACATATAG TTTGTTGAGG AAAATCAGTA ATTACGATCT AGTACAATAT GAAACACTAA
12001 GTAGGACTTT GCGACTAATT GTAAGTGATA AAATCAAGTA TGAAGATATG TGTTCGGTAG
12061 ACCTTGCCAT AGCATTGCGA CAAAAGATGT GGATTCATTT ATCAGGAGGA AGGATGATAA
12121 GTGGACTTGA AACGCCTGAC CCATTAGAAT TACTATCTGG GGTAGTAATA ACAGGATCAG
12181 AACATTGTAA AATATGTTAT TCTTCAGATG GCACAAACCC ATATACTTGG ATGTATTTAC
12241 CCGGTAATAT CAAAATAGGA TCAGCAGAAA CAGGTATATC GTCATTAAGA GTTCCTTATT
12301 TTGGATCAGT CACTGATGAA AGATCTGAAG CACAATTAGG ATATATCAAG AATCTTAGTA
12361 AACCTGCAAA AGCCGCAATA AGAATAGCAA TGATATATAC ATGGGCATTT GGTAATGATG
12421 AGATATCTTG GATGGAAGCC TCACAGATAG CACAAACACG TGCAAATTTT ACACTAGATA
12481 GTCTCAAAAT TTTAACACCG GTAGCTACAT CAACAAATTT ATCACACAGA TTAAAGGATA
12541 CTGCAACTCA GATGAAATTC TCCAGTACAT CATTGATCAG AGTCAGCAGA TTCATAACAA
12601 TGTCCAATGA TAACATGTCT ATCAAAGAAG CTAATGAAAC CAAAGATACT AATCTTATTT
12661 ATCAACAAAT AATGTTAACA GGATTAAGTG TTTTCGAATA TTTATTTAGA TTAAAAGAAA
12721 CCACAGGACA CAACCCTATA GTTATGCATC TGCACATAGA AGATGAGTGT TGTATTAAAG
12781 AAAGTTTTAA TGATGAACAT ATTAATCCAG AGTCTACATT AGAATTAATT CGATATCCTG
12841 AAAGTAATGA ATTTATTTAT GATAAAGACC CACTCAAAGA TGTGGACTTA TCAAAACTTA
12901 TGGTTATTAA AGACCATTCT TACACAATTG ATATGAATTA TTGGGATGAT ACTGACATCA
12961 TACATGCAAT TTCAATATGT ACTGCAATTA CAATAGCAGA TACTATGTCA CAATTAGATC
13021 GAGATAATTT AAAAGAGATA ATAGTTATTG CAAATGATGA TGATATTAAT AGCTTAATCA
13081 CTGAATTTTT GACTCTTGAC ATACTTGTAT TTCTCAAGAC ATTTGGTGGA TTATTAGTAA
13141 ATCAATTTGC ATACACTCTT TATAGTCTAA AAATAGAAGG TAGGGATCTC ATTTGGGATT
13201 ATATAATGAG AACACTGAGA GATACTTCCC ATTCAATATT AAAAGTATTA TCTAATGCAT
13261 TATCTCATCC TAAAGTATTC AAGAGGTTCT GGGATTGTGG AGTTTTAAAC CCTATTTATG
13321 GTCCTAATAC TGCTAGTCAA GACCAGATAA AACTTGCCCT ATCTATATGT GAATATTCAC
13381 TAGATCTATT TATGAGAGAA TGGTTGAATG GTGTATCACT TGAAATATAC ATTTGTGACA
13441 GCGATATGGA AGTTGCAAAT GATAGGAAAC AAGCCTTTAT TTCTAGACAC CTTTCATTTG
```

TABLE 12-continued (SEQ ID NO. 41)
Sequence of pFLC.PIV32CT, 15474 bp in sense orientation
(only the insert is shown)

```
13501 TTTGTTGTTT AGCAGAAATT GCATCTTTCG GACCTAACCT GTTAAACTTA ACATACTTGG

13561 AGAGACTTGA TCTATTGAAA CAATATCTTG AATTAAATAT TAAAGAAGAC CCTACTCTTA

13621 AATATGTACA AATATCTGGA TTATTAATTA AATCGTTCCC ATCAACTGTA ACATACGTAA

13681 GAAAGACTGC AATCAAATAT CTAAGGATTC GCGGTATTAG TCCACCTGAG GTAATTGATG

13741 ATTGGGATCC GGTAGAAGAT GAAAATATGC TGGATAACAT TGTCAAAACT ATAAATGATA

13801 ACTGTAATAA AGATAATAAA GGGAATAAAA TTAACAATTT CTGGGGACTA GCACTTAAGA

13861 ACTATCAAGT CCTTAAAATC AGATCTATAA CAAGTGATTC TGATGATAAT GATAGACTAG

13921 ATGCTAATAC AAGTGGTTTG ACACTTCCTC AAGGAGGGAA TTATCTATCG CATCAATTGA

13981 GATTATTCGG AATCAACAGC ACTAGTTGTC TGAAAGCTCT TGAGTTATCA CAAATTTTAA

14041 TGAAGGAAGT CAATAAAGAC AAGGACAGGC TCTTCCTGGG AGAAGGAGCA GGAGCTATGC

14101 TAGCATGTTA TGATGCCACA TTAGGACCTG CAGTTAATTA TTATAATTCA GGTTTGAATA

14161 TAACGATGT AATTGGTCAA CGAGAATTGA AAATATTTCC TTCAGAGGTA TCATTAGTAG

14221 GTAAAAAATT AGGAAATGTG ACACAGATTC TTAACAGGGT AAAAGTACTG TTCAATGGGA

14281 ATCCTAATTC AACATGGATA GGAAATATGG AATGTGAGAG CTTAATATGG AGTGAATTAA

14341 ATGATAAGTC CATTGGATTA GTACATTGTG ATATGGAAGG AGCTATCGGT AAATCAGAAG

14401 AAACTGTTCT ACATGAACAT TATAGTGTTA TAAGAATTAC ATACTTGATT GGGGATGATG

14461 ATGTTGTTTT AGTTTCCAAA ATTATACCTA CAATCACTCC GAATTGGTCT AGAATACTTT

14521 ATCTATATAA ATTATATTGG AAAGATGTAA GTATAATATC ACTCAAAACT TCTAATCCTG

14581 CATCAACAGA ATTATATCTA ATTTCGAAAG ATGCATATTG TACTATAATG GAACCTAGTG

14641 AAATTGTTTT ATCAAAACTT AAAAGATTGT CACTCTTGGA AGAAAATAAT CTATTAAAAT

14701 GGATCATTTT ATCAAAGAAG AGGAATAATG AATGGTTACA TCATGAAATC AAAGAAGGAG

14761 AAAGAGATTA TGGAATCATG AGACCATATC ATATGGCACT ACAAATCTTT GGATTTCAAA

14821 TCAATTTAAA TCATCTGGCG AAAGAATTTT TATCAACCCC AGATCTGACT AATATCAACA

14881 ATATAATCCA AAGTTTTCAG CGAACAATAA AGGATGTTTT ATTTGAATGG ATTAATATAA

14941 CTCATGATGA TAAGAGACAT AAATTAGGCG GAAGATATAA CATATTCCCA CTGAAAAATA

15001 AGGGAAAGTT AAGACTGCTA TCGAGAAGAC TAGTATTAAG TTGGATTTCA TTATCATTAT

15061 CGACTCGATT ACTTACAGGT CGCTTTCCTG ATGAAAAATT TGAACATAGA GCACAGACTG

15121 GATATGTATC ATTAGCTGAT ACTGATTTAG AATCATTAAA GTTATTGTCG AAAAACATCA

15181 TTAAGAATTA CAGAGAGTGT ATAGGATCAA TATCATATTG GTTTCTAACC AAAGAAGTTA

15241 AAATACTTAT GAAATTGATC GGTGGTGCTA AATTATTAGG AATTCCCAGA CAATATAAAG

15301 AACCCGAAGA CCAGTTATTA GAAAACTACA ATCAACATGA TGAATTTGAT ATCGATTAAA

15361 ACATAAATAC AATGAAGATA TATCCTAACC TTTATCTTTA AGCCTAGGAA TAGACAAAAA

15421 GTAAGAAAAA CATGTAATAT ATATATACCA AACAGAGTTC TTCTCTTGTT TGGT
```

The cDNA engineering was designed so that the final PIV3-2 antigenomes conformed to the rule of six (Calain et al., *J. Virol.* 67:4822–30, 1993; Durbin et al., *Virology* 234:74–83, 1997, each incorporated herein by reference). The PIV3-2 insert in pFLC.PIV32TM is 15498 nt in length, and that in pFLC.PIV32CT is 15474 nt in length. These total lengths do not include two 5'-terminal G residues contributed by the T7 promoter, because it is assumed that they are removed during recovery.

Transfection and Recovery of Recombinant Chimeric PIV3-PIV2 Viruses

HEp-2 cell monolayers were grown to confluence in six-well plates, and transfections were performed essentially as described (Tao et al., 72:2955–2961, 1998, incorporated herein by reference). The HEp-2 monolayer in one well was transfected with 5 μg PIV3-PIV2 antigenomic cDNA and three support plasmids, 0.2 μg pTM(N), 0.2 μg pTM(PnoC), 0.1 μg pTM(L) in 0.2 ml of MEM containing 12 μl LipofectACE (Life Technologies). The cells were infected simultaneously with MVA-T7 at a multiplicity of infection (MOI) of 3 in 0.8 ml of serum-free MEM containing 50 μg/ml gentamicin and 2 mM glutamine. The chimeric antigenomic cDNA pFLC.2G+.hc (Tao et al., *J. Virol.* 72:2955–2961, 1998), was transfected in parallel as a positive control. After incubation at 32° C. for 12 hours, the transfection medium was replaced with 1.5 ml of fresh serum-free MEM supplemented with 50 μg/ml gentamicin and 2 mM glutamine. Transfected cells were incubated at 32° C. for two additional days. Gamma-irradiated porcine trypsin (p-trypsin; T1311, Sigma, St Louis, Mo.) was added to a final concentration of 0.5 μg/ml on day 3 post transfection. Cell culture supernatants were harvested and passaged (referred to as passage 1) onto fresh Vero cell monolayers in T25 flasks. After overnight adsorption, the transfection harvest was replaced with fresh VP-SFM supplemented with 0.5 μg/ml p-trypsin. Cultures from passage 1 were incubated at 32° C. for 4 days, and the amplified virus was harvested and further passaged on Vero cells (referred to as passage 2) for another 4 days at 32° C. in the presence of 0.5 μg/ml p-trypsin. The presence of viruses in the passage 2 cultures was determined by hemadsorption with 0.2% guinea pig red blood cells (RBCs). Viruses were further purified by three consecutive terminal dilutions performed using Vero cells maintained in VP-SFM supplemented with 2 mM glutamine, 50 μg/ml gentamicin, and 0.5 μg/ml p-trypsin. Following the third terminal dilution, virus was further amplified three times on Vero cells, and this virus suspension was used for further characterization in vitro and in vivo.

Confirmation of the Chimeric Nature of vRNA Using Sequencing and Restriction Analysis of PCR Products For analysis of the genetic structure of vRNAs, the recombinant PIVs were amplified on LLC-MK2 cells and concentrated. vRNA was extracted from the viral pellets and reverse transcribed using the Superscript Preamplification System. RT-PCR was performed using the Advantage cDNA synthesis kit and primer pairs specific to PIV2 or PIV3 (21, 22 or 23, 24 in Table 9). RT-PCR products were either analyzed by restriction digestion or gel purified and analyzed by sequencing.

Replication of PIVs in LLC-MK2 Cells

Growth of the PIV viruses in tissue culture was evaluated by infecting confluent LLC-MK2 cell monolayers on six-well plates in triplicate at an MOI of 0.01. The inoculum was removed after absorption for 1 hour at 32° C. Cells were washed 3 times with serum-free OptiMEM I, fed with 2 ml/well of OptiMEM I supplemented with 50 μg/ml gentamicin and 0.5 μg/ml p-trypsin, and incubated at 32° C. At each 24 hour interval, a 0.5 ml aliquot of medium was removed from each well and flash-frozen, and 0.5 ml fresh medium with p-trypsin was added to the cultures. The virus in the aliquots was titrated at 32° C. on LLC-MK2 cell monolayers using fluid overlay as previously described (Tao et al., *J. Virol.* 72:2955–2961, 1998, incorporated herein by reference), and the endpoint of the titration was determined by hemadsorption, and the titers are expressed as $\log_{10} TCID_{50}$/ml.

Replication of Recombinant Chimeric PIV3-PIV2 Viruses at Various Temperatures

Viruses were serially diluted in 1×L15 supplemented with 2 mM glutamine and 0.5 μg/ml p-trypsin. Diluted viruses were used to infect LLC-MK2 monolayers in 96 well plates. Infected plates were incubated at various temperatures for 7 days as described (Skiadopoulos et al., *Vaccine* 18:503–510, 1999, incorporated herein by reference). Virus titers were determined as above.

Replication, Immunogenicity, and Protective Efficacy of Recombinant Chimeric PIV3-PIV2 Viruses in the Respiratory Tract of Hamsters Golden Syrian hamsters in groups of six were inoculated intranasally with $10^{5.3}$ $TCID_{50}$ of recombinant or biologically-derived viruses. Four days after inoculation, hamsters were sacrificed and their lungs and nasal turbinates were harvested and prepared for quantitation of virus as described (Skiadopoulos et al., *Vaccine* 18:503–510, 1999). The titers are expressed as mean $\log_{10} TCID_{50}$/gram of tissue for each group of six hamsters.

Hamsters in groups of 12 were infected intranasally with $10^{5.3}$ $TCID_{50}$ of viruses on day 0, and six hamsters from each group were challenged four weeks later with $10^6$ $TCID_{50}$ of PIV1 or $10^6$ $TCID_{50}$ of PIV2. Hamsters were sacrificed 4 days after challenge and their lungs and nasal turbinates were harvested. Challenge virus titers in the harvested tissue was determined as previously described (Tao et al., *J. Virol.* 72:2955–2961, 1998). The virus titers are expressed as mean $\log_{10} TCID_{50}$/gram of tissue for each group of six hamsters. Serum samples were collected three days prior to inoculation and on day 28, and hemagglutination-inhibition antibody (HAI) titers against PIV1, PIV2, and PIV3 were determined as previously described (van Wyke Coelingh et al., *Virology* 143:569–582, 1985). The titers are expressed as reciprocal mean $\log_2$.

Replication, Immunogenicity, and Protective Efficacy of Recombinant Chimeric PIV3-PIV2 Viruses in African Green Monkeys (AGMs)

AGMs in groups of 4 were infected intranasally and intratracheally with $10^5$ $TCID_{50}$ of virus at each site on day 0. Nasal/throat (NT) swab specimens and tracheal lavages were collected for 12 and 5 days, respectively, as previously described (van Wyke Coelingh et al., *Virology* 143:569–582, 1985). On day 29, immunized AGMs were challenged intranasally and intratracheally with $10^5$ $TCID_{50}$ of PIV2/V94 at each site. NT swab specimens and tracheal lavages were collected for 10 and 5 days, respectively. Pre-immunization, post-immunization, and post challenge serum samples were collected on days –3, 28, and 60, respectively. Virus titers in the NT swab specimens and in tracheal lavages were determined as previously described (Tao et al., *J. Virol.* 72:2955–2961, 1998). Titers are expressed as $\log_{10} TCID_{50}$/ml. Serum neutralizing antibody titers against PIV1 and PIV2 were determined as previously described (van Wyke Coelingh et al., *Virology* 143:569–582, 1985), and the titers are expressed as reciprocal mean $\log_2$.

Replication and Immunogenicity of Recombinant Chimeric PIV3-PIV2 Viruses in Chimpanzees Chimpanzees in groups of 4 were infected intranasally and intratracheally with $10^5$ $TCID_{50}$ of PIV2/V94 or rPIV3-

2TM on day 0 as previously described (Whitehead et al., *J. Virol.* 72:4467–4471, 1998). NT swab specimens were collected daily for 12 days and tracheal lavages were obtained on days 2, 4, 6, 8, and 10. Virus titers in the specimens were determined as previously described (Tao et al., *J. Virol.* 72:2955–2961, 1998). The peak virus titers are expressed as mean $\log_{10}$ TCID$_{50}$/ml. Pre-immunization and post-immunization serum samples were collected on days −3 and 28, respectively. Serum neutralizing antibody titers against PIV1 and PIV2 were determined as previously described (van Wyke Coelingh et al., *Virology* 143:569–582, 1985), and the titers are expressed as reciprocal mean $\log_2$.

Viable Recombinant Chimeric Virus was not Recovered from PIV3-PIV2 Chimeric cDNA Encoding the Complete PIV2 F and HN Proteins The construction of the PIV3-PIV2 chimeric cDNA, in which the F and HN ORFs of the JS wild type PIV3 were replaced by those of PIV2/V94, is described above and summarized in FIG. 6. The final plasmid construct, pFLC.PIV32hc (FIG. 6), encodes a PIV3-PIV2 chimeric antigenomic RNA of 15492 nt, which conforms to the rule of six.

HEp-2 cell monolayers were transfected with pFLC.PIV32hc along with the three support plasmids pTM(N), pTM(PnoC), and pTM(L) using LipofectACE, and the cells were simultaneously infected with MVA-T7 as previously described (Tao et al., *J. Virol.* 72:2955–2961, 1998, incorporated herein by reference). Virus was not recovered from several initial transfections using pFLC.PIV32hc, while chimeric viruses were recovered from all the transfections using control plasmid pFLC.2G+.hc.

Consistent with these results is the possibility that a mutation occurred outside of the 4 kb BspEI-SpeI segment of pFLC.PIV32hc that prevented the recovery of rPIV3-2 virus from cells transfected with this cDNA clone. To examine this possibility, the BspEI-SpeI fragments of p38'ΔPIV31hc and p38'ΔPIV32hc were exchanged. The regenerated p38'ΔPIV31hc and p38'ΔPIV32hc were identical to those in FIG. 6 except that the SpeI-SphI fragments containing PIV3 L gene sequences were exchanged. The BspEI-SphI fragments of these two regenerated cDNAs were introduced into the BspEI-SphI window of a PIV3 full-length clone, p3/7-(131)2G+, in five separate independent legations to give 10 pFLC.2G+.hc and pFLC.PIV32hc clones (2 clones selected from each ligation), respectively. (Note that the PIV3 sequences outside of the BspEI-SphI window of p3/7-(131)2G+, pFLC.2G+.hc, and pFLC.PIV32hc are identical). Thus, this would have replaced any PIV3 backbone sequence which might have acquired a spurious mutation with sequence known to be functional. Furthermore, the functionality of the backbone was reevalualuated in parallel. None of the 10 pFLC.PIV32hc cDNA clones yielded viable virus, but each of the 10 pFLC.2G+.hc cDNA clones yielded viable virus. Virus was not recovered from pFLC.PIV32hc despite passaging the transfection harvest in a fashion similar to that used successfully to recover the highly defective PIV3 C-knock out recombinant (Durbin et al., *Virology* 261:319–30, 1999, incorporated herein by reference). Since each of the unique components used to generate the pFLC.PIV32hc was used to successfully generate other recombinant viruses except the cytoplasmic tail domains of F and HN, it is highly unlikely that errors in the cDNA account for the failure to yield recombinant virus in this case. Rather, the favored interpretation is that the full-length PIV2 F and HN glycoproteins are not compatible with one or more of the PIV3 proteins needed for virus growth.

Figure 9A:
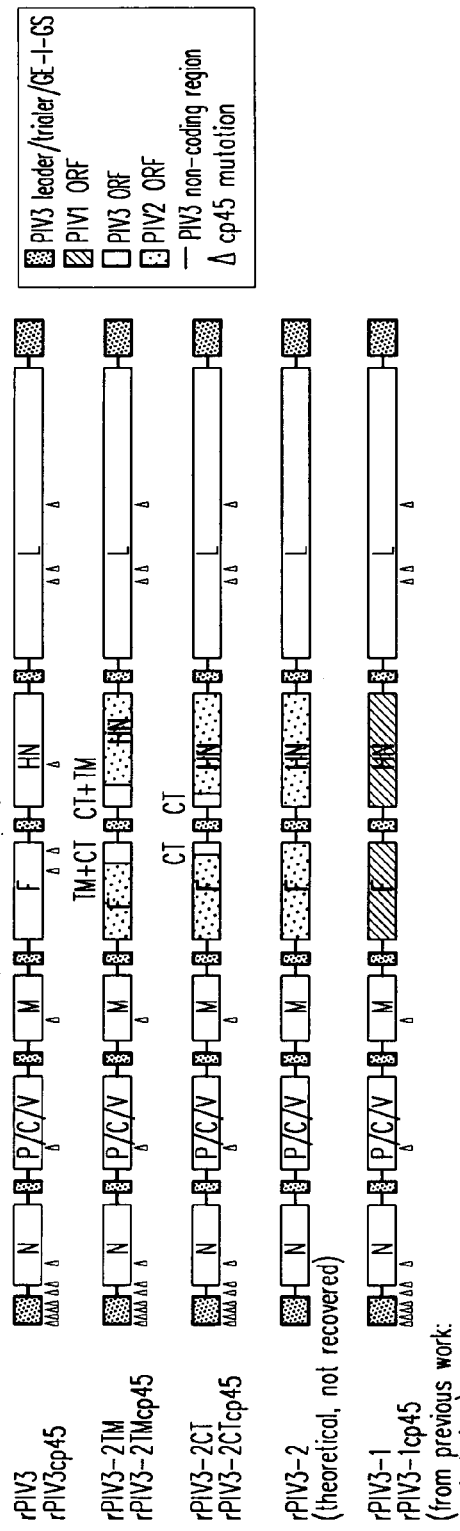
FIG. 9 details genetic structures of the PIV3-PIV2 chimeric viruses and the gene junction sequences for rPIV3-2CT and rPIV3-2TM. Panel A illustrates the genetic structures of rPIV3-2 chimeric viruses (middle three diagrams) are compared with that of rPIV3 (top diagram) and rPIV3-1 (bottom diagram) viruses. The cp45 derivatives are shown marked with arrows depicting the relative positions of cp45 mutations. For the cp45 derivatives, only the F and HN genes are different while the remaining genes remained identical, all from PIV3. From top to bottom, the three chimeric PIV3-PIV2 viruses carry decreasing amount of PIV3 glycoprotein genes. Note that rPIV3-2, carrying the complete PIV2 HN and F ORF, was not recoverable. Panel B provides the nucleotide sequences of the junctions of the chimeric F and HN glycoprotein genes for rPIV3-2TM are given along with the protein translation. The shaded portions represent sequences from PIV2. The amino acids are numbered with respect to their positions in the corresponding wild type glycoproteins. Three extra nucleotides were inserted in PIV3-PIV2 HN TM as indicated to make the construct conform to rule of six. Panel C shows the nucleotide sequences of the junctions of the chimeric F and HN glycoprotein genes for rPIV3-2CT, given along with the protein translation. The shaded portions represent sequences from PIV2. The amino acids are numbered with respect to their positions in the corresponding wild type glycoproteins. GE=gene end; I=intergenic; GS=gene start; ORF=open reading frame; TM=transmembrane domain; CT=clytoplasmic domain; *=stop codon. The Figure includes SEQ ID NOs: 42–51.
Figure 9A:
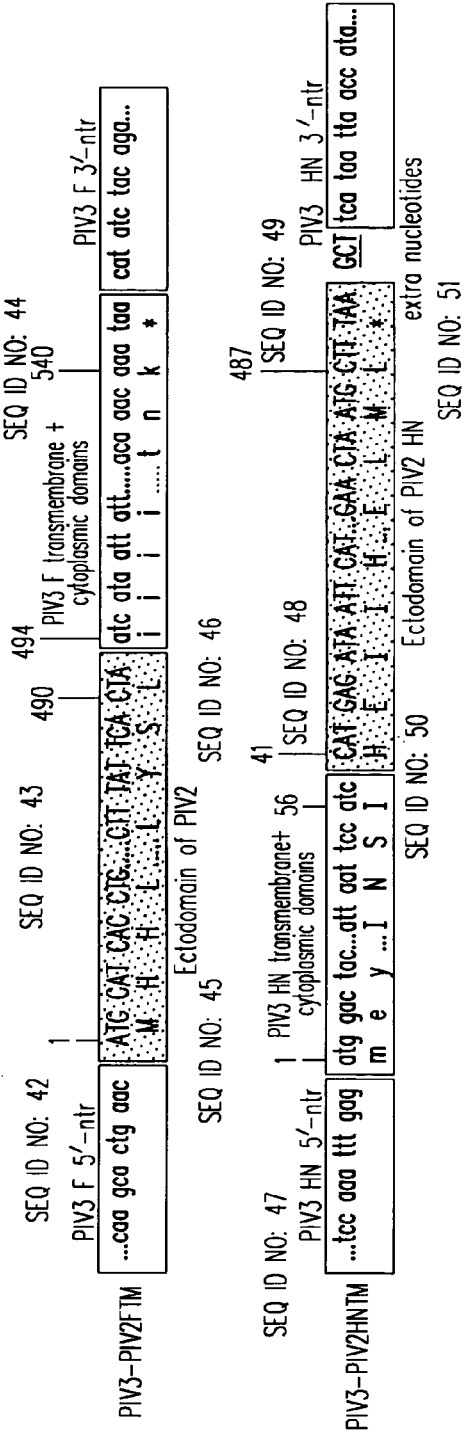
Figure 9B:
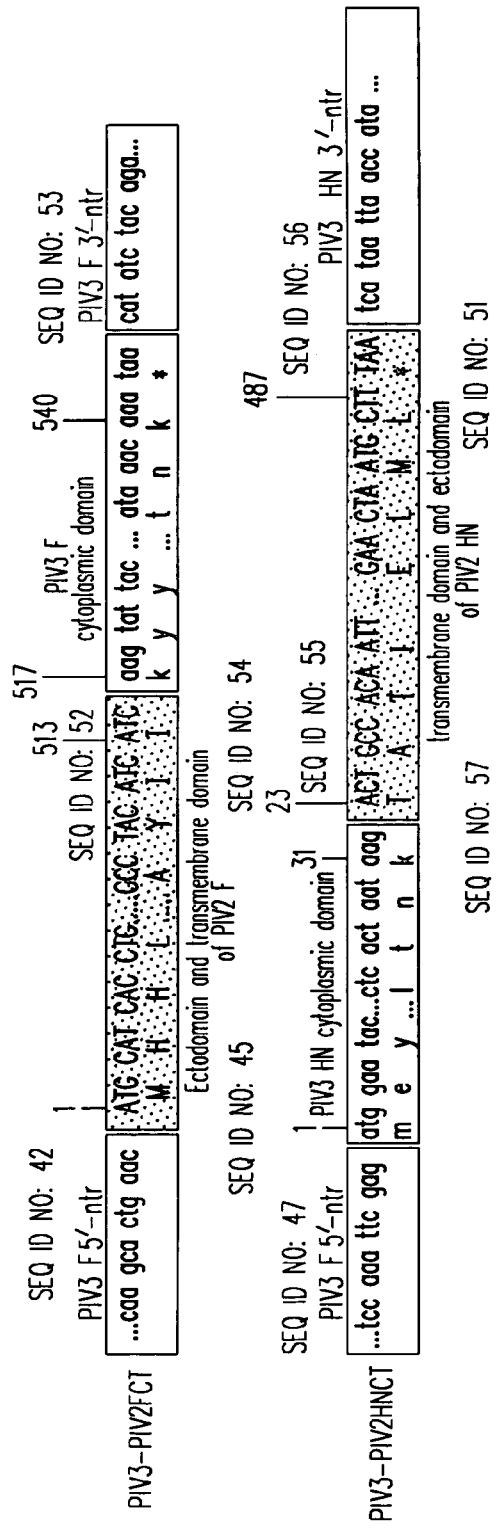

Recovery of Chimeric Viruses from PIV3-PIV2 Chimeric cDNAs Encoding the Chimeric PIV3-PIV2 F and HN Proteins Using two other strategies, new chimeric PIV3-PIV2 antigenomic cDNAs were constructed, in which the ectodomain or the ectodomain and the transmembrane domain of PIV3 F and HN glycoproteins were replaced by their PIV2 counterparts. The construction of the four full-length cDNAs, namely pFLC.PIV32TM, pFLC.PIV32TMcp45, pFLC.PIV32CT, and pFLC.PIV32CTcp45, is described above and summarized in FIGS. 7, 8, and 9. The PIV3-2 inserts in the final plasmids pFLC.PIV32TM and pFLC.PIV32CT, in which the F and HN genes encoded chimeric glycoproteins, were 15498 nt and 15474 nt in length, respectively, and conformed to the rule of six (Calain et al., *J. Virol.* 67:4822–30, 1993; Durbin et al., *Virology* 234:74–83, 1997, each incorporated herein by reference). The authenticity of those four constructs was confirmed by sequencing of the BspEI-SphI region and by restriction analysis.

Recombinant chimeric viruses were recovered from full-length clones pFLC.PIV32TM, pFLC.PIV32CT, pFLC.PIV32TMcp45, or pFLC.PIV32CTcp45 and were designated rPIV3-2TM, rPIV3-2CT, rPIV3-2TMcp45, and rPIV3-2CTcp45, respectively. These viruses were biologically cloned by 3 consecutive terminal dilutions on Vero cells and then amplified three times in Vero cells.

Genetic Characterization of Recombinant Chimeric PIV3-PIV2 Viruses

The biologically-cloned chimeric PIV3-PIV2 viruses, rPIV3-2TM, rPIV3-2CT, rPIV3-2TMcp45, and rPIV3-2CTcp45, were propagated on LLC-MK2 cells and then concentrated. Viral RNAs extracted from pelleted viruses were used in RT-PCR amplification of specific gene segments using primer pairs specific to PIV2 or PIV3 (21, 22 or 23, 24 in Table 9). The restriction enzyme digestion patterns of the RT-PCR products amplified with PIV2 specific primer pairs from rPIV3-2TM, rPIV3-2CT, rPIV3-2TMcp45, and rPIV3-2CTcp45, were each distinct from that derived from PIV2N94, and their patterns, using EcoRI, MfeI, NcoI, or PpuMI, were those expected from the designed cDNA. Nucleotide sequences for the 8 different PIV3-PIV2 junctions in F and HN genes of rPIV3-2TM and rPIV3-2CT are given in FIG. 9. Also, the cp45 markers present in rPIV3-2TMcp45 and rPIV3-2CTcp45, except those in the 3'-leader region and the gene start of NP, were verified with RT-PCR and restriction enzyme digestion as previously described (Skiadopoulos et al., *J. Virol.* 73:1374–81, 1999, incorporated herein by reference). These results confirmed the chimeric nature of the recovered PIV3-PIV2 viruses as well as the presence of the introduced cp45 mutations.

Figure 10:
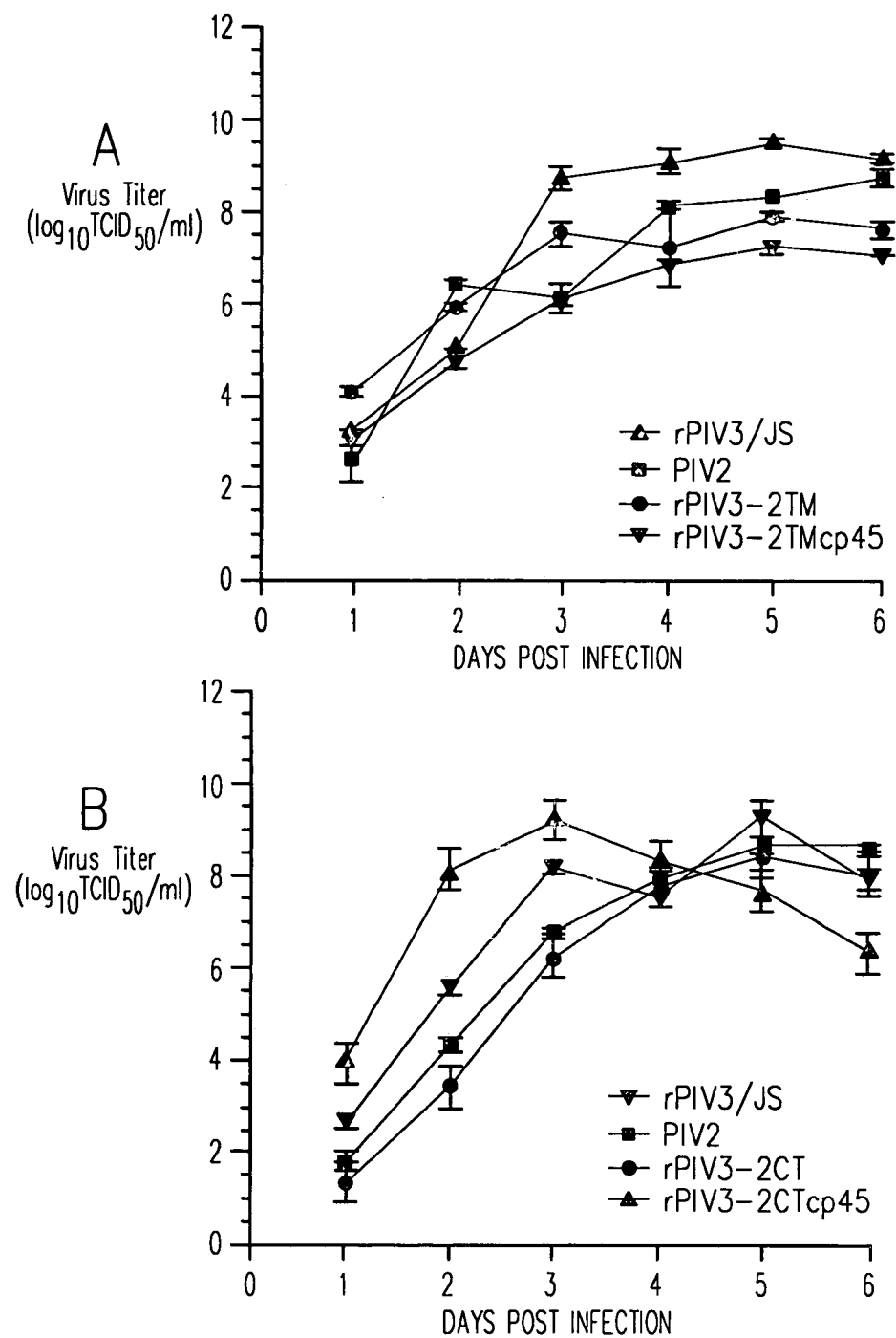
FIG. 10 documents multicycle replication of rPIV3-2 chimeric viruses compared with that of rPIV3/JS and PIV2/V94 wild type parent viruses. Panel A—the rPIV3-2TM and rPIV3-2TMcp45 viruses, along with the rPIV3/JS and PIV2/V94 wt parent viruses, were used to infect LLC-MK2 cells in 6 well plates, each in triplicate, at an MOI of 0.01. All cultures were incubated at 32° C. After a 1 hour adsorption period, the inocula were removed, and the cells were washed three times with serum-free OptiMEM. The cultures were overlayed with 2 ml per well of the same medium. For rPIV3-2TM and rPIV3-2TMcp45 infected plates, 0.5 mg/ml of p-trypsin was added to each well. Aliquots of 0.5 ml were taken from each well at 24 hour intervals for 6 days, flash frozen on dry ice, and stored at −80° C. Each aliquot was replaced with 0.5 ml of fresh medium with or without p-trypsin as indicated above. The virus present in the aliquots was titered on LLC-MK2 plates with liquid overlay at 32° C. for 7 days, and the endpoints were identified with hemadsorption. Panel B—The rPIV3-2CT and rPIV3-2CTcp45, along with the rPIV3/JS and PIV2/V94 wt parent viruses, were used to infect LLC-MK2 in 6 well plates, each in triplicate, as described in Panel A. Aliquots were taken and processed in the same manner as described in Panel A. Virus titers are expressed as log 10TCID50/ml±standard errors for both experiments-presented in Panel A and B.

PIV3-PIV2 Recombinant Chimeric Viruses Replicate Efficiently in LLC-MK2 Cells In Vitro The kinetics and magnitude of replication in vitro of the PIV3-PIV2 recombinant chimeric viruses were assessed by multicycle replication in LLC-MK2 cells (FIG. 10). LLC-MK2 cell monolayer cultures in six-well plates were infected in triplicate with rPIV3-2TM, rPIV3-2CT, rPIV3-2TMcp45, or rPIV3-2CTcp45 at an MOI of 0.01 in the presence of p-trypsin (0.5 μg/ml). Samples were removed from culture supernate at 24 hour intervals for 6 days. Each of the recombinant chimeric viruses, except rPIV3-2CTcp45 (clone 2A1), replicated at the same rate and to a similar level as their PIV2/V94 parent virus indicating that PIV3-PIV2 chimerization of F and HN proteins did not alter the rates of growth of the recombinant chimeric viruses, and all reached a titer of $10^7$ TCID$_{50}$/ml or higher. Only the rPIV3-2CTcp45 grew slightly faster in each of two experiments and reached its peak titer earlier than PIV2/V94. This accelerated growth pattern was likely a result of an unidentified mutation in this clone since a sister clone failed to exhibit this growth pattern. rPIV3-2CTcp45 clone 2A1 was used in the studies described below.

The Level of Temperature Sensitivity of rPIV3-2 Chimeric Viruses and their cp45 Derivatives The level of temperature sensitivity of replication of PIV3-PIV2 recombinant chimeric viruses was tested to determine if rPIV3-2TM and rPIV3-2CT viruses exhibit a ts phenotype and to determine if the acquisition of the 12 cp45 mutations by these viruses specified a level of temperature sensitivity characteristic of cp45 derivatives bearing these 12 PIV3 cp45 mutations (Skiadopoulos et al., J. Virol. 73:1374–81, 1999, incorporated herein by reference). The level of temperature sensitivity of the virus was determined in LLC-MK2 cell monolayers as previously described (Skiadopoulos et al., Vaccine 18:503–510, 1999) (Table 13). The titer of rPIV3-2TM and rPIV3-2CT was fairly constant at permissive temperature (32° C.) and the various restrictive temperatures tested indicating these recombinants were ts+. In contrast, their cp45 derivatives, rPIV3-2TMcp45 and rPIV3-2CTcp45, were ts and the level of temperature sensitivity was similar to that of rPIV3-1cp45, the chimeric PIV3-PIV1 virus carrying the complete PIV1 F and HN glycoproteins and the same set of 12 cp45 mutations. Thus the in vitro properties of rPIV3-2TM and rPIV3-2CT viruses and their cp45 derivative are similar to those of rPIV3-1 and rPIV3-1 cp45, respectively, suggesting that the in vivo properties of the rPIV3-2 and rPIV3-1 viruses would also be similar, but surprisingly this was not the case.

TABLE 13

The replication of rPIV3-2CT and rPIV3-2TM are not temperature sensitive in LLC-MK2 cells, whereas the inclusion of the cp45 mutations confers the cp45 temperature sensitive phenotype

| Virus | Titer at 32° C.[a] ($\log_{10}$ TCID$_{50}$) | Change in titer ($\log_{10}$) at various temperatures compared to that at 32°[a,b] | | | | |
|---|---|---|---|---|---|---|
| | | 35°[c] | 36° | 37° | 38° | 39° | 40° |
| rPIV3/JS | 7.9 | 0.3[b] | 0.1 | 0.1 | (0.3)[b] | (0.4) | 0.4 |
| PIV3cp45[e] | 7.8 | 0.5 | 0.3 | 1.3 | 3.4[d] | 6.8 | 6.9 |
| PIV1/Wash64[e] | 8.5 | 1.5 | 1.1 | 1.4 | 0.6 | 0.5 | 0.9 |
| rPIV3-1 | 8.0 | 0.8 | 0.5 | 0.6 | 0.9 | 1.1 | 2.6 |
| rPIV3-1cp45 | 8.0 | 0.5 | 0.4 | 3.4[d] | 4.8 | 6.6 | 7.5 |
| PIV2/V9412[e] | 7.8 | 0.3 | (0.1) | 0.0 | (0.4) | (0.4) | 0.0 |
| rPIV3-2CT | 6.9 | 0.3 | 0.3 | 0.6 | (0.1) | 0.6 | 0.4 |
| rPIV3-2TM | 8.3 | 0.3 | (0.1) | 0.3 | 0.6 | 1.0 | 2.1[d] |
| rPIV3-2CTcp45 | 8.0 | 0.8 | (0.4) | 2.0[d] | 4.3 | 7.5 | ≥7.6 |
| rPIV3-2TMcp45 | 8.0 | 0.3 | 0.6 | 2.4[d] | 5.4 | 7.5 | ≥7.6 |

[a]Data presented are means of two experiments.
[b]Numbers not in parentheses represent titer decrease; numbers in parentheses represent titer increase.
[c]Data at 35° were from one experiment only.
[d]Values which are underlined represent the lowest temperature at which there was a 100-fold reduction of virus titer compared to the titer at permissive temperature (32° C.). This restrictive temperature is referred to as the shut-off temperature.
[e]Biologically-derived viruses.

rPIV3-2TM and rPIV3-2CT are Attenuated, Immunogenic, and Highly Protective in Hamsters, and Introduction of cp45 Mutations Results in Highly Attenuated and Less Protective Viruses Hamsters in groups of six were inoculated intranasally with $10^{5.3}$ TCID$_{50}$ of rPIV3-2TM, rPIV3-2CT, rPIV3-2TMcp45, rPIV3-2CTcp45, or control viruses. It was previously seen that rPIV3-1 virus replicated in the upper and lower respiratory tract of hamsters like that of its PIV3 and PIV1 parents (Skiadopoulos et al., Vaccine 18:503–510, 1999; Tao et al., J. Virol. 72:2955–2961, 1998, each incorporated herein by reference). PIV2 virus replicates efficiently in hamsters, but rPIV3-2TM and rPIV3-2CT viruses each replicated to a 50- to 100-fold lower titer than their PIV2 and PIV3 parents in the upper respiratory tract and to a 320- to 2000-fold lower titer in the lower respiratory tract (Table 14). This indicates that the chimeric PIV3-PIV2 F and HN glycoproteins specify an unexpected attenuation phenotype in hamsters. rPIV3-2TMcp45 and rPIV3-2CTcp45, the derivatives carrying the cp45 mutations, were 50- to 100-fold more attenuated than their respective rPIV3-2 parents, with only barely detectable replication in the nasal turbinates, and none in the lungs. These rPIV3-2cp45 viruses were clearly more attenuated than rPIV3-1cp45, exhibiting an additional 50-fold reduction of replication in the nasal turbinates. Thus, the attenuating effects of the chimerization of F and HN glycoproteins and that specified by cp45 mutations were additive.

TABLE 14

The rPIV3-2TM and rPIV3-2CT viruses, in contrast to rPIV3-1, are attenuated in the respiratory tract of hamsters and importation of the cp45 mutations resulted in further attenuation.

| | Virus titers in the indicated tissue ($\log_{10}$ TCID$_{50}$/g ± S.E.)[b] [Duncan Group][c] | | | |
|---|---|---|---|---|
| Virus[a] | NT | $\log_{10}$ titer reduction | Lung | $\log_{10}$ titer reduction |
| rPIV3/JS | 5.9 ± 0.1[AB] | 0 | 6.5 ± 0.1[A] | 0 |
| rPIV3cp45 | 4.5 ± 0.2[C] | 1.4[c] | 1.8 ± 0.2[E] | 4.7[c] |
| PIV1/Wash64[d] | 5.7 ± 0.1[B] | — | 5.5 ± 0.1[B] | — |
| rPIV3-1 | 6.4 ± 0.2[A] | 0 | 6.6 ± 0.2[A] | 0 |
| rPIV3-1cp45 | 3.1 ± 0.1[D] | 3.3[c] | 1.2 ± 0.0[F] | 5.4[c] |
| PIV2/V94[d] | 6.2 ± 0.2[A] | 0 | 6.4 ± 0.2[A] | 0 |
| rPIV3-2CT | 4.5 ± 0.4[C] | 1.7[c] | 3.1 ± 0.1[D] | 3.3[c] |
| rPIV3-2TM | 3.9 ± 0.3[C] | 2.3[c] | 3.9 ± 0.4[C] | 2.5[c] |
| rPIV3-2CTcp45 | 1.4 ± 0.1[E] | 4.8[c] | 1.5 ± 0.2[E] | 4.9[c] |
| rPLV3-2TMcp45 | 1.6 ± 0.2[E] | 4.6[c] | 1.4 ± 0.1[E] | 5.0[c] |

[a]Hamsters in group of six were inoculated intranasally with $10^{5.3}$ TCID$_{50}$ of indicated virus on day 0.
[b]Hamsters were sacrificed and their tissue samples harvested on day 4. The virus titer in hamster tissues was determined and the results are expressed as $\log_{10}$ TCID$_{50}$/g ± standard error (SE). NT = nasal turbinates.
[c]The $\log_{10}$ titer reduction values are derived by comparing: rPIV3cp45 against rPIV3/JS; rPIV3-1cp45 against rPIV3-1; each of the PIV3-PIV2 chimeras against PIV2/V94.
[d]Biologically-derived viruses.
[e]Grouping as analyzed by Duncan mult:range test.

To determine the immunogenicity and protective efficacy of the PIV3-PIV2 chimeric viruses, hamsters in groups of twelve were immunized with $10^{5.3}$ TCID$_{50}$ of rPIV3-2TM, rPIV3-2CT, rPIV3-2TMcp45, rPIV3-2CTcp45, or control viruses on day 0. Six of the hamsters from each group were challenged with $10^6$ TCID$_{50}$ of PIV1 on day 29, and the remaining half were challenged with PIV2 on day 32. Hamsters were sacrificed 4 days after challenge and the lungs and nasal turbinates harvested. Serum samples were collected on day −3 and day 28, and their HAI antibody titer against PIV1, PIV2, and PIV3 was determined. As shown in Table 15, despite their attenuated growth in hamsters, immunization with rPIV3-2TM or rPIV3-2CT each elicited a level of serum HAI antibody against PIV2 that was comparable to that induced by infection with wild type PIV2/V94. Immunization of hamsters with rPIV3-2TM and rPIV3-2CT resulted in complete restriction of the replication of PIV2 challenge virus. rPIV3-2TMcp45 and rPIV3-2CTcp45 failed to elicit a detectable serum antibody response, and immunization of hamsters with either of these two viruses resulted in only a 10- to 100-fold reduction of replication of the PIV2 challenge virus in the lower respiratory tract (Table 15).

TABLE 15

The rPIV3-2CT and rPIV3-2TM viruses are highly protective in hamsters against challenge with wild type PIV2, but not against PIV1

| | HAI antibody titer[b] against indicated virus | | | Challenge virus titer[c] in indicated tissue ($\log_{10}TCID_{50}/g \pm SE$) | | | |
|---|---|---|---|---|---|---|---|
| | (reciprocal mean $\log_2 \pm$ SE) | | | PIV1 | | PIV2 | |
| Immunizing virus[a] | PIV1 | PIV2 | PIV3 | NT | Lung | NT | Lung |
| rPIV3/JS | ≤1 | ≤1 | 10.2 ± 0.1 | 6.2 ± 0.2 | 5.8 ± 0.1 | 5.9 ± 0.2 | 5.7 ± 0.2 |
| rPIV3cp45 | ≤1 | ≤1 | 8.6 ± 0.2 | 5.9 ± 0.3 | 5.1 ± 0.3 | 5.6 ± 0.2 | 4.5 ± 0.7 |
| PIV1 | 6.7 ± 0.2 | ≤1 | ≤1 | 1.3 ± 0.1 | ≤1.2 ± 0.0 | 6.1 ± 0.2 | 6.2 ± 0.3 |
| rPIV3-1 | 6.4 ± 0.2 | ≤1 | ≤1 | ≤1.2 ± 0.0 | ≤1.2 ± 0.0 | 6.5 ± 0.2 | 5.0 ± 0.6 |
| rPIV3-1cp45 | 1.8 ± 0.6 | ≤1 | ≤1 | 3.9 ± 0.4 | 1.6 ± 0.3 | 6.2 ± 0.2 | 4.5 ± 0.6 |
| PIV2 | ≤1 | 4.0 ± 0.0 | ≤1 | 5.9 ± 0.2 | 5.5 ± 0.1 | ≤1.2 ± 0.0 | ≤1.2 ± 0.0 |
| rPIV3-2CT | ≤1 | 3.6 ± 0.8 | ≤1 | 5.3 ± 0.1 | 5.2 ± 0.3 | ≤1.2 ± 0.0 | ≤1.2 ± 0.0 |
| rPIV3-2TM | ≤1 | 4.5 ± 0.2 | ≤1 | 5.9 ± 0.2 | 4.4 ± 0.3 | ≤1.2 ± 0.0 | ≤1.2 ± 0.0 |
| rPIV3-2CT.cp45 | ≤1 | ≤1 | ≤1 | 6.2 ± 0.2 | 5.7 ± 0.1 | 5.3 ± 0.2 | 3.3 ± 0.8 |
| rPIV3-2TM.cp45 | ≤1 | ≤1 | ≤1 | 5.8 ± 0.3 | 4.4 ± 0.3 | 5.5 ± 0.2 | 3.7 ± 0.7 |

[a]Hamsters in groups of 12 were immunized intranasally with $10^{5.3}$ TCID$_{50}$ of the indicated virus on day 0.
[b]Serum samples were collected two days before immunization and 28 days after immunization. They were tested for HAI antibody titer against the three PIVs, and the antibody titers are presented as reciprocal mean $\log_2 \pm$ standard error (SE).
[c]Six hamsters from each group were challenged intranasally with $10^6$ TCID$_{50}$ of PIV1 (on day 29) or PIV2 (on day 32). Hamster tissues were harvested 4 days after challenge, and the virus titer in indicated tissues are expressed as $\log_{10}TCID_{50}/g \pm SE$.

rPIV3-2TM and rPIV3-2CT are Attenuated, Immunogenic, and Highly Protective in AGMs, whereas Introduction of cp45 Mutations Results in Highly Attenuated and Poorly Protective Viruses Certain recombinant PIV3 and RSV viruses may exhibit different levels of attenuation in rodents and primates (Skiadopoulos et al., *Virology* In press, 1999; Whitehead et al., *J. Virol.* 73:9773–9780, 1999, each incorporated herein by reference), indicating that attenuation can be somewhat species specific. Therefore, the rPIV3-2 viruses were evaluated for their level of replication and immunogenicity in AGMs. AGMs in groups of four were intranasally and intratracheally administered $10^5$ TCID$_{50}$ per site of rPIV3-2TM, rPIV3-2CT, rPIV3-2TMcp45, rpiv3-2CTcp45, PIV2/V94, or rPIV3-1 on day 0. Virus in the NT swab specimens (collected day 1 to 12) and tracheal lavages (collected on day 2, 4, 5, 8, and 10) were titered as previously described (van Wyke Coelingh et al., *Virology* 143:569–582, 1985, incorporated herein by reference). As shown in Table 16, rPIV3-2TM and rPIV3-2CT were clearly attenuated in the respiratory tract of AGMs as indicated by a peak titer of virus shedding lower in both the upper and lower respiratory tract than their PIV2/V94 parent virus.

rPIV3-2TMcp45 and rPIV3-2CTcp45, the derivatives carrying cp45 mutations, were detected at very low levels, if at all, in the NT swab and tracheal lavage specimens suggesting that the attenuating effects of chimerization of the F and HN glycoproteins and that specified by the cp45 mutations were additive for AGMs as well as for hamsters.

To determine whether immunization of AGMs with the PIV3-PIV2 chimeric viruses is protective against PIV2 challenge, AGMs previously infected with a rPIV3-2 virus were challenged with $10^5$ TCID$_{50}$ of PIV2 on day 28 (Table 16). Virus present in the NT swab specimens (collected day 29 to 38) and tracheal lavages fluids (collected on day 30, 32, 34, 36, and 38) was titered as previously described (Durbin et al., *Virology* 261:319–30, 1999, incorporated herein by reference). As shown in Table 16, immunization with rPIV3-2TM and rPIV3-2CT induced a high level of restriction of the replication of PIV2/V94 challenge virus. In contrast, immunization of AGMs with rPIV3-2TMcp45 and rPIV3-2CTcp45 failed to restrict the replication of PIV2/V94 challenge virus and these animals developed very low levels of pre-challenge serum neutralizing antibody to PIV2. The complete restriction of replication of PIV2/V94 challenge virus in rPIV3-2CT immunized AGMs was associated with a 2.5-fold greater level of pre-challenge serum antibody to PIV2 than that of rPIV3-2TM immunized AGMs which provided incomplete protection.

TABLE 16

The rPIV3-2CT or rPIV3-2TM viruses are attenuated for replication in the respiratory tract of African green monkeys, yet still induce resistance to challenge with wild type PIV2

| Immunizing[a] virus | Mean peak titer[b] of immunizing virus in indicated site ($\log_{10}TCID_{50}$/ml ± SE) | | Serum neutralization antibody titer[c] against indicated virus (mean reciprocal $\log_2$ ± SE) | | Mean peak titer[d] of PIV2/V94 challenge virus in indicated site ($\log_{10}TCID_{50}$/ml ± SE) | |
|---|---|---|---|---|---|---|
| | NT | TL | PIV1 | PIV2 | NT | TL |
| rPIV3-1 | 2.6 ± 0.5 | 3.2 ± 0.1 | 6.3 ± 0.4 | 3.1 ± 0.3 | 3.6 ± 0.2 | 3.3 ± 0.7 |
| P1V2/V94 | 2.8 ± 0.7 | 5.0 ± 0.3 | 3.8 ± 0.0 | 7.1 ± 0.7 | ≦0.2 | ≦0.2 |
| rPIV3-2CT | 1.5 ± 0.4 | 0.5 ± 0.2 | 2.9 ± 0.1 | 7.2 ± 0.1 | ≦0.2 | ≦0.2 |
| rPIV3-2TM | 1.4 ± 0.1 | 1.6 ± 0.7 | 4.1 ± 0.1 | 5.9 ± 0.2 | 1.6 ± 0.6 | 1.3 ± 0.9 |
| rPIV3-2CTcp45 | 1.0 ± 0.2 | ≦0.2 | 4.1 ± 0.1 | 5.3 ± 0.0 | 3.3 ± 0.4 | 3.5 ± 0.3 |
| rPIV3-2TMcp45 | 0.6 ± 0.3 | ≦0.2 | 3.4 ± 0.2 | 4.6 ± 0.6 | 3.0 ± 0.5 | 4.1 ± 0.2 |

[a]African green monkeys in group of 4 were inoculated with $10^5$ $TCID_{50}$ of indicated virus intranasally and intratracheally on day 0.
[b]Combined nasal wash and throat swab (NT) samples were collected on days 1 to 12. Tracheal lavage (TL) samples were collected on days 2, 4, 6, 8, and 10. The virus titers were determined on LLC-MK2 monolayers and expressed as $\log_{10}TCID_{50}$/ml ± standard error (SE).
[c]Serum samples collected on day 28 were assayed for their neutralizing antibody titers against PIV1 and PIV2. The titers were expressed as reciprocal mean $\log_2$ ± SE.
[d]NT specimens were collected on days 29 to 38. TL specimens were collected on days 30, 32, 34, 36, and 38.

rPIV3-2TM is Attenuated in its Replication in the Respiratory Tract of Chimpanzees Chimpanzees in groups of 4 were inoculated intranasally and intratracheally with $10^5$ $TCID_{50}$ of rPIV3-2TM or PIV2/V94 on day 0. NT swab specimens (day 1 to 12) and tracheal lavage (days 2, 4, 6, 8, and 10) samples were collected. Virus titer was determined as previously described (Durbin et al., *Virology* 261:319–30, 1999, incorporated herein by reference), and results are expressed as $\log_{10}$ $TCID_{50}$/ml. As shown in Table 17, rPIV3-2TM had a lower peak titer than it wild type parent PIV2/V94 and was shed for a significantly shorter duration than PIV2/94, indicating that rPIV3-2TM is attenuated in chimpanzees. PIV2/94 wt virus replicates to low levels in chimpanzees compared to hamsters and AFGs, whereas rPIV3-2TM virus was attenuated in each of these model hosts.

TABLE 17 rPIV3-2TM is attenuated in the respiratory tract of chimpanzees and yet still elicits a strong serum immune response to PIV2

| Inoculated virus[a] | Mean peak titer[b] of virus shed in indicated site ($\log_{10}TCID_{50}$/ml ± SE) | | Mean days of virus shedding in the upper respiratory tract (days ± SE) | Serum neutralizing antibody titer[c] against indicated virus (reciprocal mean $\log_2$ ± SE) | |
|---|---|---|---|---|---|
| | NT | TL | | PRE | POST |
| PIV2/V94 | 2.9 ± 0.6 | 1.2 ± 0.5 | 8.8 ± 1.1[d] | ≦2.8 ± 0.0 | 6.2 ± 0.5 |
| rPIV3-2TM | 2.0 ± 0.3 | ≦0.5 ± 0.0 | 2.5 ± 0.7[d] | 3.3 ± 0.2 | 4.3 ± 0.4 |

[a]Chimpanzees in group of four were inoculated intranasally and intratracheally with $10^5$ TCID50 of indicated virus.
[b]Nose/throat (NT) swab specimens and tracheal lavages (TL) were collected for 12 and 10 days, respectively, and virus titer were determined. The peak titers are expressed as $\log_{10}TCID_{50}$/ml ± standard error (SE).
[c]Serum samples collected 3 days prior and 28 days after virus inoculation were assayed for their neutralizing antibody titer against indicated virus. The titers are expressed as reciprocal mean $\log_2$ ± SE.
[d]Significant difference in duration of shedding, p ≦ 0.005, Student T test.

Briefly summarizing the foregoing description and Examples, recombinant chimeric PIVs bearing heterologous viral genes or genome segments have been constructed in accordance with the description herein using a cDNA-based virus recovery system. Recombinant viruses made from cDNA replicate independently and can be propagated in the same manner as if they were biologically-derived viruses. In preferred embodiments, recombinant chimeric human PIV (HPIV) vaccine candidates bear one or more major antigenic determinant(s) of a HPIV, preferably in a background that is attenuated by one or more nucleotide modifications. Preferably, chimeric PIVs of the invention also express one or more protective antigens of another pathogen, for example a microbial pathogen. In these cases, the HPIV acts as an attenuated virus vector and is used with the dual purpose of inducing a protective immune response against one or more HPIVs as well as against the pathogen(s) from which the foreign protective antigen(s) was/were derived.

As mentioned above, the major protective antigens of PIVs are their HN and F glycoproteins. Thus, in exemplary embodiments, live attenuated PIV candidate vaccine viruses for use in infants and young children include chimeric HPIV3-1 and HPIV3-2 viruses carrying full-length PIV1 and partial PIV2 glycoproteins, respectively in a PIV3 background genome or antigenome. In the latter case, chimeric HN and F ORFs rather than full-length PIV2 ORFs are used to construct the full-length cDNA. The recovered viruses, designated rPIV3-2CT in which the PIV2 ectodomain and transmembrane domain is fused to the PIV3 cytoplasmic domain and rPIV3-2TM in which the PIV2 ectodomain was fused to the PIV3 transmembrane and cytoplasmic tail domain, possessed similar in vitro and in vivo phenotypes. In particular, the rPIV3-2 recombinant chimeric viruses exhibit a host range phenotype, i.e. they replicate efficiently in vitro but are restricted in replication in vivo. This attenuation in vivo occurs in the absence of any added mutations from cp45. This is an unexpected host range effect which is highly desirable for vaccine purposes, in part because the phenotype is not specified by point mutations which may refert to wt. At the same time, the unrestricted growth in vitro is highly advantageous for efficient vaccine production.

Although rPIV3-2CT and rPIV3-2TM replicate efficiently in vitro, they are highly attenuated in both the upper and the lower respiratory tract of hamsters and African green monkeys (AGMs), indicating that chimerization of the HN and F proteins of PIV2 and PIV3 itself specified an attenuation phenotype in vivo. Despite this attenuation, they are highly immunogenic and protective against challenge with PIV2 wild virus in both species. rPIV3-2CT and rPIV3-2TM were further modified by the introduction of the 12 PIV3 cp45 mutations located outside of the HN and F coding sequences to derive rPIV3-2CTcp45 and rPIV3-2TMcp45 which replicated efficiently in vitro but were even further attenuated in hamsters and AGMs indicating that the attenuation specified by the glycoprotein chimerization and by the cp45 mutations was additive.

The development of antigenic chimeric viruses possessing protective antigens of one virus and attenuating mutations from another virus has been reported by others for influenza viruses (Belshe et al., *N. Engl. J. Med.* 338: 1405–1, 1998; Murphy et al., *Infectious Diseases in Clinical Practice* 2:174–181, 1993) and for rotaviruses (Perez-Schael et al., *N. Engl. J. Med.* 337:1181–7, 1997). Attenuated antigenic chimeric vaccines are more readily generated for these viruses which have segmented genomes, since genome segment reassortment occurs with high frequency during coinfection. Live attenuated influenza virus vaccine candidates are antigenically updated annually by replacement of the HA and NA genes of the attenuated donor virus with those of a new epidemic or pandemic virus. Recombinant DNA technology is also actively being used to construct live attenuated antigenic chimeric virus vaccines for flaviviruses and for paramyxoviruses. For flaviviruses, a live attenuated virus vaccine candidate for Japanese encephalitis virus (JEV) has been made by the replacement of the premembrane (prM) and envelope (E) regions of the attenuated yellow fever virus (YFV) with those from an attenuated strain of JEV (Guirakhoo et al., *Virology* 257:363–72, 1999). The JEV-YFV antigenic chimeric recombinant vaccine candidate was attenuated and immunogenic in vivo (Guirakhoo et al., *Virology* 257:363–72, 1999). Both the structural and the non-structural proteins of this chimeric virus came from a live attenuated vaccine virus. Antigenic chimeric vaccines have also been made between a naturally attenuated tick-borne flavivirus (Langat virus) and a wild type mosquito-borne dengue 4 virus, and the resulting recombinant was found to be significantly more attenuated for mice than its tick-borne parent virus (Pletnev et al., *Proc. Natl. Acad. Sci. USA.* 95:1746–51, 1998), but this chimeric virus was highly restricted in replication in Vero cells in vitro. This is an example of an attenuating effect that stems from partial incompatibility between the evolutionarily divergent structural proteins specified by the Langat virus and the non-structural proteins of the dengue virus. A third strategy is being pursued for the production of a quadrivalent dengue virus vaccine in which a dengue 4 backbone containing an attenuating deletion mutation in the 3' non-coding region is used to construct antigenic chimeric viruses containing the protective antigens of dengue 1, 2 or 3 viruses (Bray et al., *Proc. Natl. Acad. Sci. USA* 88:10342–6, 1991; *J. Virol.* 70:3930–7, 1996).

Antigenic chimeric viruses have also been produced for single-stranded, negative-sense RNA viruses. For example, antigenic chimeric PIV1 vaccine candidates can be constructed according to the methods disclosed herein by substituting the full-length HN and F proteins of parainfluenza virus type 1 for those of PIV3 in an attenuated PIV3 vaccine candidate, and this recombinant is attenuated and protective against PIV1 challenge in experimental animals. Similarly, exemplary antigenic chimeric respiratory syncytial virus (RSV) vaccine candidates can be made in which one or more of the RSV F and G protective antigens, or antigenic determinant(s) thereof, of subgroup B virus are substituted for those in an attenuated RSV subgroup A virus yielding attenuated RSV subgroup B vaccine candidates. (See also, International Publication No. WO 97/06270; Collins et al., *Proc. Natl. Acad. Sci. USA* 92:11563–11567 (1995); U.S. patent application Ser. No. 08/892,403, filed Jul. 15, 1997 (corresponding to published International Application No. WO 98/02530 and priority U.S. Provisional Application Nos. 60/047,634, filed May 23, 1997, 60/046,141, filed May 9, 1997, and 60/021,773, filed Jul. 15, 1996); U.S. patent application Ser. No. 09/291,894, filed by Collins et al. on Apr. 13, 1999; U.S. Provisional Patent Application Ser. No. 60/129,006, filed Apr. 13, 1999; U.S. Provisional Patent Application Ser. No. 60/143,132, filed by Bucholz et al. on Jul. 9, 1999; and Whitehead et al., *J. Virol.* 73:9773–9780, 1999, each incorporated herein by reference). When the glycoprotein exchanges between the PIV1 and PIV3 viruses and between the RSV subgroup A and RSV subgroup B viruses were performed in a wild type virus background, the antigenic chimeric viruses replicated to wild type virus levels in vitro and in vivo. These findings indicate that a high level of compatibility exists between recipient and donor viruses and that only very little, if any, attenuation was achieved as a result of the process of chimerization. These findings with the PIV1 and PIV3 and the RSV A and B glycoprotein exchanges contrast strikingly in several ways with those between PIV2 and PIV3 disclosed herein.

In the present disclosure, viable recombinant virus in which the full-length PIV2 HN or F protein was used to replace those of PIV3 was not recovered in this instance, evidently attributable to incidental mutations introduced during cDNA construction, whereas this was successfully achieved for the PIV1-PIV3 glycoprotein exchange. This suggests that the PIV2 HN or F glycoprotein is poorly compatible with one or more of the PIV3 proteins encoded in the cDNA. Two viable PIV2-PIV3 chimeric viruses were obtained when chimeric HN and F ORFs rather than full-length PIV2 ORF were used to construct the full-length cDNA. One of these chimeric viruses contained chimeric HN and F glycoproteins in which the PIV2 ectodomain was fused to the PIV3 transmembrane and cytoplasmic tail region, and the other contained chimeric HN and F glycoproteins in which the PIV2 ectodomain and transmembrane region was fused to the PIV3 cytoplasmic tail region. Both rPIV3-2 recombinants possessed similar, although not xxxx identical, in vitro and in vivo phenotypes. Thus, it appeared that only the cytoplasmic tail of the HN or F glycoprotein of PIV3 was required for successful recovery of the PIV2-PIV3 chimeric viruses.

In previous studies directed to protein structure-function analysis, chimeric HN or F proteins have been constructed and expressed in vitro and have been used to map various functional domains of the proteins (Bousse et al., *Virology* 204:506–14, 1994; Deng et al., *Arch. Virol. Suppl.* 13:115–30, 1997; Deng, et al., *Virology* 253:43–54, 1999; Deng et al., *Virology* 209:457–69, 1995; Mebatsion et al., *J. Virol.* 69:1444–1451, 1995; Takimoto et al., *J. Virol.* 72:9747–54, 1998; Tanabayashi et al., *J. Virol.* 70:6112–6118, 1996; Tsurudome et al., *J. Gen. Virol.* 79:279–89, 1998; Tsurudome et al., *Virology* 213:190–203, 1995; Yao et al., *J. Virol.* 69:7045–53, 1995). In one report, a chimeric glycoprotein consisting of a measles virus F cytoplasmic tail fused to the transmembrane and ectodomains of the vesicular stomatitis virus G protein was inserted into a measles virus infectious clone in place of the measles virus F and HN virus glycoproteins (Spielhofer et al., *J. Virol.* 72:2150–9, 1998). A chimeric virus was obtained that was replication competent, but highly restricted in replication in vitro as indicated by delayed growth and by low virus yields indicating a high degree of attenuation in vitro. This finding is in marked contrast to the phenotype exhibited by recombinant PIV of the invention expressing chimeric glycoproteins, e.g., a PIV2-PIV3 chimera, which replicate efficiently in vitro.

The efficient replication of rPIV3-2 and other chimeric PIV viruses of the invention in vitro is an important property for a live attenuated vaccine candidate that is needed for large scale vaccine production. In contrast to rPIV3-2CT and rPIV3-2TM, rPIV3-1 was not attenuated in vivo. Thus, the chimerization of the HN and F proteins of PIV2 and PIV3 itself resulted in attenuation of replication in vivo, a novel finding for single-stranded, negative-sense RNA viruses. The mechanism for this host range restriction of replication in vivo is not known. Importantly, infection with these attenuated rPIV3-2CT and rPIV3-2TM vaccine candidates induced a high level of resistance to challenge with PIV2 indicating that the antigenic structure of the chimeric glycoproteins was largely or completely intact. Thus rPIV3-2CT and rPIV3-2TM function as live attenuated PIV2 candidate vaccine viruses, exhibiting a desirable balance between attenuation and immunogenicity in both AGMs and hamsters.

The attenuating effects of the PIV3-PIV2 chimerization of the F and HN glycoprotein are additive with that specified by the cp45 mutations. rPIV3-2 recombinants containing the cp45 mutations were highly attenuated in vivo and provided incomplete protection in hamsters against challenge with PIV2 and little protection in AGMs. This is in contrast to the finding with rPIV3-1cp45 which was satisfactorily attenuated in vivo and protected animals against challenge with PIV1. The combination of the independent, additive attenuating effects of the chimerization of PIV3-PIV2 glycoproteins and the 12 cp45 mutations appeared too attenuating in vivo. Clearly, if the rPIV3-2CT and rPIV3-2TM vaccine candidates are found to be insufficiently attenuated in humans, the cp45 attenuating mutations should be added incrementally rather than as a set of 12 to achieve a desired balance between attenuation and immunogenicity needed for a live attenuated PIV2 vaccine for use in humans. The findings presented herein thus identify a novel means to attenuate a paramyxovirus and provide the basis for evaluation of these PIV3-PIV2 chimeric live attenuated PIV2 vaccine candidates in humans. Importantly, the rPIV3-2CT or rPIV3-2TM viruses can also be used as vectors for other PIV antigens or for other viral protective antigens, e.g., the measles virus HA protein or immunogenic portions thereof.

The present invention overcomes the difficulties inherent in prior approaches to vector based vaccine development and provides unique opportunities for immunization of infants during the first year of life against a variety of human pathogens. Previous studies in developing live-attenuated PIV vaccines indicate that, unexpectedly, rPIVs and their attenuated and chimeric derivatives have properties which make them uniquely suited among the nonsegmented negative strand RNA viruses as vectors to express foreign proteins as vaccines against a variety of human pathogens. The skilled artisan would not have predicted that the human PIVs, which tend to grow substantially less well than the model nonsegmented negative strand viruses and which typically have been underrepresented with regard to molecular studies, would prove to have characteristics which are highly favorable as vectors. It is also surprising that the intranasal route of administration of these vaccines has proven a very efficient means to stimulate a robust local and systemic immune response against both the vector and the expressed heterologous antigen. Furthermore, this route provides additional advantages for immunization against heterologous pathogens which infect the respiratory tract or elsewhere. These properties of PIV vectors are described herein above using examples of rPIV3 vectors which bear (i) a major neutralization antigen of measles virus expressed as a separate gene in wild type and attenuated backgrounds or (ii) major neutralization antigens of hPIV1 in place of the PIV3 neutralization antigens which express in addition a major neutralization antigen of HPIV2. These rPIV vectors were constructed using wild type and attenuated backgrounds. In addition, the description herein demonstrates the ability to readily modify the level of attenuation of the PIV vector backbone. According to one of these methods, varying the length of genome inserts in a chimeric PIV of the invention allows for adjustment of the attenuation phenotype, an effect which was pronounced in attenuated viruses both which is only apparent in derivatives of wild type viruses using very long inserts.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited within the foregoing disclosure for economy of description. Each of these references are incorporated herein by reference in its entirety for all purposes.

What is claimed is:

1. An infectious chimeric parainfluenza virus (PIV) comprising a major nucleocapsid (N) protein, a nucleocapsid phosphoprotein (P), a large polymerase protein (L), and a human PIV (HPIV) background genome or antigenome that is modified to encode a chimeric glycoprotein comprising one or more structural domains, antigenic domains or epitopes of a glycoprotein of a first HPIV and one or more structural domains, antigenic domains or epitopes of a second heterologous, antigenically distinct HPIV.

2. The chimeric PIV of claim 1, wherein one or more heterologous genome segment(s) of the second, antigenically distinct HPIV encoding said one or more structural domains, antigenic domains or epitopes is/are substituted within the HPIV background genome or antigenome to encode said chimeric glycoprotein.

3. The chimeric PIV of claim 2, wherein said one or more heterologous genome segment(s) encode(s) one or more glycoprotein ectodomain(s) substituted for one or more corresponding glycoprotein ectodomain(s) in the background genome or antigenome.

4. The chimeric PIV of claim 2, wherein heterologous genome segments encoding both a glycoprotein ectodomain and transmembrane region are substituted for counterpart glycoprotein ecto- and transmembrane domains in the background genome or antigenome.

5. The chimeric PIV of claim 1, wherein said chimeric glycoprotein is selected from HPIV HN or F glycoproteins.

6. The chimeric PIV of claim 1, wherein the (HPIV) background genome or antigenome is modified to encode multiple chimeric glycoproteins.

7. The chimeric PIV of claim 1, wherein the HPIV background genome or antigenome is a partial HPIV3 genome or antigenome and the second, antigenically distinct HPIV is selected from HPIV1 or HPIV2.

8. The chimeric PIV of claim 7, wherein the HPIV background genome or antigenome is a partial HPIV3 genome or antigenome and the second, antigenically distinct HPIV is HPIV2.

9. The chimeric PIV of claim 8, wherein one or more glycoprotein ectodomain(s) of HPIV2 is/are substituted for one or more corresponding glycoprotein ectodomain(s) in the HPIV3 background genome or antigenome.

10. The chimeric PIV of claim 9, wherein both glycoprotein ectodomain(s) of HPIV FIN and F glycoproteins are substituted for corresponding HN and F glycoprotein ectodomains in the HPIV3 background genome or antigenome.

11. The chimeric PIV of claim 10, which is further modified to incorporate one or more and up to a full panel of attenuating mutations identified in HPIV3 JS cp45.

12. The chimeric PIV of claim 8, wherein PIV2 ectodomain and transmembrane regions of one or both HN and/or F glycoproteins is/are fused to one or more corresponding PIV3 cytoplasmic tail region(s).

13. The chimeric PIV of claim 12, wherein ectodomain and transmembrane regions of both PIV2 HN and F glycoproteins are fused to corresponding PIV3 HN and F cytoplasmic tail regions.

14. The chimeric PIV of claim 13, which is further modified to incorporate one or more and up to a full panel of attenuating mutations identified in HPIV3 JS cp45.

15. The chimeric PIV of claim 1, which is further modified to incorporate one or more and up to a full panel of attenuating mutations identified in HPIV3 JS cp45 selected from mutations specifying an amino acid substitution in the L protein at a position corresponding to Tyr942, Leu992, or Thr1558 of JS cp45; in the N protein at a position corresponding to residues Val96 or Ser 389 of JS cp45, in the C protein at a position corresponding to Ile96 of JS cp45, a nucleotide substitution in a 3' leader sequence of the chimeric virus at a position corresponding to nucleotide 23, 24, 28, or 45 of JS cp45, and/or a mutation in an N gene start sequence at a position corresponding to nucleotide 62 of JS cp45.

16. The chimeric PIV of claim 1, wherein a plurality of heterologous genes or genome segments encoding antigenic determinants of multiple heterologous PIVs are added to or incorporated within the partial or complete HPIV background genome or antigenome.

17. The chimeric PIV of claim 16, wherein said plurality of heterologous genes or genome segments encode antigenic determinants from both HPIV 1 and HPIV2 and are added to or incorporated within a partial or complete HPIV3 background genome or antigenome.

18. The chimeric PIV of claim 16, wherein the chimeric genome or antigenome encodes a chimeric glycoprotein having structural domains, antigenic domains or epitopes from two or more different HPIVs.

19. The chimeric PIV of claim 1, wherein the chimeric PIV genome or antigenome is attenuated by addition or incorporation of one gene or cis-acting regulatory element from a bovine PIV3 (BPIV3).

20. The chimeric PIV of claim 1, wherein the chimeric PIV genome or antigenome incorporates one or more heterologous, non-coding non-sense polynucleotide sequence(s).

21. The chimeric PIV of claim 1, wherein the chimeric genome or antigenome encodes a chimeric glycoprotein having structural domains, antigenic domains or epitopes from both HPIV3 JS and HPIV1 or HPIV2.

22. The chimeric PIV of claim 1, wherein the chimeric genome or antigenome is modified by introduction of an attenuating mutation involving an amino acid substitution of phenylalanine at position 456 of the HPIV3 L protein.

23. The chimeric PIV of claim 22, wherein phenylalanine at position 456 of the HPIV3 L protein is substituted by leucine.

24. The chimeric PIV of claim 1, wherein the chimeric genome or antigenome incorporates one or more heterologous gene(s) or genome segment(s) encoding one or more respiratory syncytial virus (RSV) F and/or G glycoprotein(s) or immunogenic domain(s), fragment(s), or epitope(s) thereof.

25. The chimeric PIV of claim, 1 which is a complete virus.

26. The chimeric PIV of claim 1 which is a subviral particle.

27. A method for stimulating the immune system of an individual to induce an immune response against one or more HPIVs which comprises administering to the individual an immunologically sufficient amount of the chimeric PIV of claim 1 combined with a physiologically acceptable carrier.

28. The method of claim 27, wherein the chimeric PIV is administered in a dose of $10^3$ to $10^7$ PFU.

29. The method of claim 27, wherein the chimeric PIV is administered to the upper respiratory tract.

30. The method of claim 27, wherein the chimeric PIV is administered by spray, droplet or aerosol.

31. The method of claim 27, wherein the background genome or antigenome is of human PIV3 (HPIV3) and the chimeric PIV elicits an immune response against HPIV 1 and/or HPIV2.

32. The method of claim 27, wherein the chimeric PIV elicits a polyspecific immune response against multiple human PIVs.

33. The method of claim 27, wherein a first, chimeric PIV and a second PIV are administered to said individual sequentially or simultaneously to elicit a polyspecific immune response.

34. The method of claim 33, wherein the second PIV is a second, chimeric PIV according to claim 1.

35. The method of claim 33, wherein the first, chimeric PIV and second PIV administered to said individual simultaneously in a mixture.

36. The method of claim 33, wherein the first and second chimeric PIVs comprise the same or different heterologous antigenic determinant(s).

37. The method of claim 33, wherein the first chimeric PIV elicits an immune response against HPIV3 and the second chimeric PIV elicits an immune response against HPIV 1 or HPIV2.

38. The method of claim 33, wherein the second chimeric PIV incorporates one or more heterologous gene(s) or genome segment(s) encoding one or more antigenic determinant(s) of respiratory syncytial virus (RSV).

39. The method of claim 38, wherein both the first and second chimeric PIVs elicit an immune response against RSV.

40. The method of claim 39, wherein the first chimeric PIV is administered to said individual initially and the second chimeric PIV is administered to said individual subsequently to provide an initial immune response against HPIV3 and a secondary immune response against HPIV1 or HPIV2 and to provide both initial and secondary immune responses against RSV.

41. The method of claim 33, wherein the first, chimeric PIV incorporates at least one and up to a full complement of attenuating mutations present within PIV3 JS cp45 selected from mutations specifying an amino acid substitution in the L protein at a position corresponding to Tyr942, Leu992, or Thr1558 of JS cp45; in the N protein at a position corresponding to residues Val96 or Ser389 of JS cp45, in the C protein at a position corresponding to Ile96 of JS cp45, a nucleotide substitution in a 3' leader sequence of the chimeric virus at a position corresponding to nucleotide 23, 24, 28, or 45 of JS cp45, and/or a mutation in an N gene start sequence at a position corresponding to nucleotide 62 of JS cp45.

42. An immunogenic composition to elicit an immune response against PIV comprising an immunogenically sufficient amount of the chimeric PIV of claim 1 in a physiologically acceptable carrier.

43. The immunogenic composition of claim 42, formulated in a dose of $10^3$ to $10^7$ PFU.

44. The immunogenic composition of claim 42, formulated for administration to the upper respiratory tract by spray, droplet or aerosol.

45. The immunogenic composition of claim 42, wherein the chimeric PIV elicits an immune response against one or more virus(es) selected from HPIV1, HPIV2 and HPIV3.

46. The immunogenic composition of claim 42, wherein the chimeric PIV elicits an immune response against HPIV3 and another virus selected from HPIV1, HPIV2, and respiratory syncytial virus (RSV).

47. The immunogenic composition of claim 42, further comprising a second, chimeric PIV according to claim 1.

48. The immunogenic composition of claim 47, wherein the first chimeric PIV elicits an immune response against HPIV3 and the second chimeric PIV elicits an immune response against HPIV 1 or HPIV2, and wherein both the first and second chimeric PIVs elicit an immune response against RSV.

49. An isolated polynucleotide comprising a chimeric PIV genome or antigenome which includes a human PIV (HPIV) background genome or antigenome modified to encode a chimeric glycoprotein comprising one or more structural domains, antigenic domains or epitopes of a first HPIV and one or more structural domains, antigenic domains or epitopes of a second heterologous, antigenically distinct HPIV.

50. The isolated polynucleotide of claim 49, wherein one or more heterologous genome segment(s) encoding the structural domains, antigenic domains, or epitopes of said second, antigenically distinct HPIV is/are substituted for one or more counterpart, genome segment(s) in the HPIV background genome or antigenome.

51. The isolated polynucleotide of claim 49, wherein, the chimeric genome or antigenome incorporates at least one and up to a full complement of attenuating mutations present within PIV3 JS cp45.

52. A method for producing an infectious attenuated chimeric PIV particle from one or more isolated polynucleotide molecules encoding said PIV, comprising:
expressing in a cell or cell-free lysate an expression vector comprising an isolated polynucleotide comprising a background genome or antigenome modified to encode a chimeric glycoprotein comprising one or more structural domains, antigenic domains or epitopes of a first HPIV and one or more structural domains, antigenic domains or epitopes of a second heterologous, antigenically distinct HPIV, and PIV N, P, and L proteins.

53. The method of claim 52, wherein the chimeric PIV genome or antigenome and the N, P, and L proteins are expressed by two or more different expression vectors.

54. An expression vector comprising an operably linked transcriptional promoter, a polynucleotide sequence which includes a background genome or antigenome modified to encode a chimeric glycoprotein comprising one or more structural domains, antigenic domains or epitopes of a first HPIV and one or more structural domains, antigenic domains or epitopes of a second heterologous, antigenically distinct HPIV, and a transcriptional terminator.

55. An infectious chimeric parainfluenza virus (PIV) comprising a major nucleocapsid (N) protein, a nucleocapsid phosphoprotein (P), a large polymerase protein (L), and a background human PIV genome or antigenome that is modified to comprise at least one open reading frame that encodes a chimeric glycoprotein incorporating into a first glycoprotein open reading frame of a first PIV at least one gene segment encoding one or more counterpart structural domains, antigenic domains or epitopes of a glycoprotein of a second heterologous, antigenically distinct PIV;
said at least one open reading frame that encodes a chimeric glycoprotein being inserted into the background PIV genome at one or more site(s) selected from the group consisting of a site between the P and M open reading frames, a site between the N and P open reading frames, a site between the HN and L open reading frames, and a site between the 3' leader sequence and the N open reading frame.

56. The infectious chimeric PIV of claim 55, in which one or more open reading frames encoding ectodomains of the heterologous glycoprotein are substituted for one or more counterpart open reading frames encoding ectodomains of the first glycoprotein.

57. The infectious chimeric PIV of claim 55 in which open reading frames encoding both an ectodomain and a transmembrane region of the heterologous glycoprotein are substituted for the counterpart open reading frames encoding an ectodomain and a transmembrane region of the first glycoprotein.

58. The infectious chimeric PIV of claim 55, in which open reading frames encoding an ectodomain and a transmembrane region of the heterologous glycoprotein are fused to open reading frames encoding a cytoplasmic tail region of the first glycoprotein.

59. The infectious chimeric PIV of claim 55, in which open reading frames encoding an ectodomain and a transmembrane region of HN or F or of both HN and F as the heterologous glycoprotein are fused to open reading frames encoding a cytoplasmic tail region of HN or F or of both HN and F, respectively, as the first glycoprotein.

60. The infectious chimeric PIV of claim 55, in which the recombinant genome or antigenome comprises a mutation producing an amino acid substitution of phenylalanine at position 456 of the HPIV L protein.

61. The chimeric PIV of claim 55, in which the recombinant genome or antigenome is further modified to incorporate one or more attenuating mutations selected from the group consisting of mutations specifying an amino acid substitution in the L protein at a position corresponding to Tyr942, Leu992, or Thr1558 of JS cp45; in the N protein at a position corresponding to residues Val96 or Ser389 of JS cp45, in the C protein at a position corresponding to Ile96 of JS cp45, a nucleotide substitution in a 3' leader sequence of the chimeric virus at a position corresponding to nucleotide 23, 24, 28, or 45 of JS cp45, and/or a mutation in an N gene start sequence at a position corresponding to nucleotide 62 of JS cp45.

62. An isolated nucleic acid molecule comprising a background human PIV genome or antigenome that is modified to comprise at least one open reading frame that encodes a chimeric glycoprotein incorporating into a first glycoprotein open reading frame of a first PIV at least one gene segment encoding one or more counterpart structural domains, antigenic domains or epitopes of a glycoprotein of a second heterologous, antigenically distinct PIV;
said at least one open reading frame that encodes a chimeric glycoprotein being inserted into the PIV background genome at one or more site(s) selected from the group consisting of a site between the P and M open reading frames, a site between the N and P open reading frames, a site between the HN and L open reading frames, and a site between the 3' leader sequence and the N open reading frame.

63. The isolated nucleic acid of claim 62, in which one or more open reading frames encoding ectodomains of the heterologous glycoprotein are substituted for one or more counterpart open reading frames encoding ectodomains of the first glycoprotein.

64. The isolated nucleic acid of claim 62, in which open reading frames encoding both an ectodomain and a transmembrane region of the heterologous glycoprotein are substituted for the counterpart open reading frames encoding an ectodomain and a transmembrane region of the first glycoprotein.

65. The isolated nucleic acid of claim 62, in which open reading frames encoding an ectodomain and a transmembrane region of the heterologous glycoprotein are fused to open reading frames encoding a cytoplasmic tail region of the first glycoprotein.

66. The isolated nucleic acid of claim 62, in which open reading frames encoding an ectodomain and a transmembrane region of HN or F or of both HN and F as the heterologous glycoprotein are fused to open reading frames encoding a cytoplasmic tail region of HN or F or of both HN and F, respectively, as the first glycoprotein.

67. The isolated nucleic acid of claim 62, in which the recombinant genome or antigenome comprises a mutation producing an amino acid substitution of phenylamine at position 456 of the HPIV L protein.

68. The isolated nucleic acid of claim 62, in which the recombinant genome or antigenome is further modified to incorporate one or more attenuating mutations selected from the group consisting of mutations specifying an amino acid substitution in the L protein at a position corresponding to Tyr942, Leu992, or Thr1558 of JS cp45; in the N protein at a position corresponding to residues Val96 or Ser389 of JS cp45, in the C protein at a position corresponding to Ile96 of JS cp45, a nucleotide substitution in a 3' leader sequence of the chimeric virus at a position corresponding to nucleotide 23, 24, 28, or 45 of JS cp45, and/or a mutation in an N gene start sequence at a position corresponding to nucleotide 62 of JS cp45.

69. An expression vector comprising the isolated nucleic acid of claim 62 operatively linked to a promoter operative in a mammalian cell or in vitro and to a transcription terminator sequence operative in a mammalian cell or in vitro.

70. An immunogenic composition comprising an immunologically sufficient amount of the infectious chimeric PIV of claim 55 and a physiologically acceptable carrier.

* * * * *